US012496310B2

(12) United States Patent
Scheinberg et al.

(10) Patent No.: US 12,496,310 B2
(45) **Date of Patent: *Dec. 16, 2025**

(54) COMPOSITIONS AND METHODS FOR ADOPTIVE CELL THERAPY

(71) Applicant: MEMORIAL SLOAN KETTERING CANCER CENTER, New York, NY (US)

(72) Inventors: David A. Scheinberg, New York, NY (US); Thomas J. Gardner, New York, NY (US); Derek S. Tan, New York, NY (US); Jonghan Lee, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 632 days.

This patent is subject to a terminal disclaimer.

(21) Appl. No.: 16/627,270

(22) PCT Filed: Jul. 2, 2018

(86) PCT No.: PCT/US2018/040640

§ 371 (c)(1),
(2) Date: Dec. 27, 2019

(87) PCT Pub. No.: WO2019/006468

PCT Pub. Date: Jan. 3, 2019

(65) Prior Publication Data

US 2020/0268794 A1 Aug. 27, 2020

Related U.S. Application Data

(60) Provisional application No. 62/527,936, filed on Jun. 30, 2017.

(51) Int. Cl.

| | |
|---|---|
| ***A61K 35/17*** | (2025.01) |
| ***A61K 31/7076*** | (2006.01) |
| ***A61K 40/11*** | (2025.01) |
| ***A61K 40/31*** | (2025.01) |
| ***A61K 40/42*** | (2025.01) |
| ***A61K 40/45*** | (2025.01) |
| ***A61K 40/46*** | (2025.01) |
| ***C07K 14/705*** | (2006.01) |
| ***C07K 16/08*** | (2006.01) |
| ***C07K 16/12*** | (2006.01) |
| ***C07K 16/30*** | (2006.01) |
| ***C07K 16/32*** | (2006.01) |
| *A61K 38/00* | (2006.01) |

(52) U.S. Cl.

CPC .......... *A61K 31/7076* (2013.01); *A61K 40/11* (2025.01); *A61K 40/31* (2025.01); *A61K 40/4211* (2025.01); *A61K 40/4243* (2025.01); *A61K 40/427* (2025.01); *A61K 40/45* (2025.01); *A61K 40/46* (2025.01); *C07K 14/70517* (2013.01); *C07K 16/30* (2013.01); *C07K 16/32* (2013.01); *A61K 38/00* (2013.01); *A61K 2239/31* (2023.05); *A61K 2239/59* (2023.05); *C07K 2317/622* (2013.01); *C07K 2319/03* (2013.01); *C07K 2319/33* (2013.01); *C12Y 304/17011* (2013.01); *C12Y 305/02006* (2013.01)

(58) Field of Classification Search

CPC ........ C07K 16/18; C07K 16/30; C07K 16/32; C07K 2317/622; C07K 2319/03; C07K 2319/33; C12Y 304/17011; C12Y 305/02006; A61K 35/17; A61K 2039/5158

See application file for complete search history.

(56) References Cited

U.S. PATENT DOCUMENTS

| | | | | |
|---|---|---|---|---|
| 5,426,029 | A | 6/1995 | Rittershaus et al. | |
| 5,925,529 | A * | 7/1999 | Coughlin | C07K 14/705 435/7.1 |
| 7,094,572 | B2 | 8/2006 | Ramanathan et al. | |
| 7,893,219 | B2 * | 2/2011 | Cassone | A61P 31/00 530/387.5 |
| 9,475,862 | B2 * | 10/2016 | Connors | A61K 45/06 |
| 11,028,143 | B2 * | 6/2021 | Zhao | A61K 39/12 |
| 12,178,830 | B2 * | 12/2024 | Scheinberg | C07H 19/16 |
| 12,241,097 | B2 * | 3/2025 | Scheinberg | C12N 5/0636 |
| 2003/0129749 | A1 * | 7/2003 | Gundersen | G01N 33/56972 435/372.3 |
| 2010/0310571 | A1 | 12/2010 | Cheung | |
| 2011/0301331 | A1 | 12/2011 | Glaser et al. | |
| 2016/0175359 | A1 | 6/2016 | Spencer et al. | |

(Continued)

FOREIGN PATENT DOCUMENTS

| | | | |
|---|---|---|---|
| CA | 2994829 | A1 | 2/2017 |
| CA | 2994969 | A1 | 2/2017 |
| CN | 106544365 | A | 3/2017 |

(Continued)

OTHER PUBLICATIONS

Paul, Fundamental Immunology, 3rd Edition, 1993, pp. 292-295.*

(Continued)

*Primary Examiner* — Hong Sang

(74) *Attorney, Agent, or Firm* — Foley & Lardner LLP

(57) ABSTRACT

Provided herein are compositions and methods for adoptive cell therapy comprising engineered immune cells that express an antigen-targeted chimeric antigen receptor and a prodrug converting enzyme for the treatment of inflammation, inflammatory diseases, or pathogenic infections.

7 Claims, 52 Drawing Sheets

Specification includes a Sequence Listing.

(56) References Cited

U.S. PATENT DOCUMENTS

2017/0010266 A1 1/2017 Rabbitts et al.

FOREIGN PATENT DOCUMENTS

| | | | | |
|---|---|---|---|---|
| EP | 2 609 932 | A2 | 7/2013 | |
| WO | WO-01/85960 | A1 | 11/2001 | |
| WO | WO-2014165707 | A2 * | 10/2014 | ............. A61K 35/17 |
| WO | WO-2015/121688 | A1 | 8/2015 | |
| WO | WO-2015140268 | A1 * | 9/2015 | ............. A61K 35/17 |
| WO | WO-2015/188119 | A1 | 12/2015 | |
| WO | WO-2016/201374 | A1 | 12/2016 | |
| WO | WO-2016/210293 | A1 | 12/2016 | |
| WO | WO-2017/027291 | A1 | 2/2017 | |
| WO | WO-2017178586 | A1 * | 10/2017 | ............. A61K 35/17 |
| WO | WO-2019/006467 | A1 | 1/2019 | |

OTHER PUBLICATIONS

Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Murphy et al. (Journal of Immunological Methods, vol. 463, p. 127-133, 2018.*
Zhao et al., Frontiers in Immunology, 2021, 12: 1-12.*
Cowen et al. Cancer Gene Therapy, 2002, 9:897-907.*
International Search Report and Written Opinion, PCT/US2018/040629, Memorial Sloan Kettering Cancer Center (Oct. 18, 2018).
International Search Report and Written Opinion, PCT/US2018/040633, Memorial Sloan Kettering Cancer Center (Oct. 18, 2018).
International Search Report and Written Opinion, PCT/US2018/040639, Memorial Sloan Kettering Cancer Center (Oct. 18, 2018).
International Search Report and Written Opinion, PCT/US2018/040640, Memorial Sloan Kettering Cancer Center (Oct. 22, 2018).
Szymczak et al., "Correction of Multi-Gene Deficiency in vivo Using a Single 'Self-Cleaving' 2A Peptide-Based Retroviral Vector," Nature Biotech., vol. 22, No. 5, 6 pages (May 2004).
Bourne Christopher et al: Mechanisms of Adoptive T Cell Micropharmacies11 , Molecular Therapy, vol. 28, No. 4, Suppl. 1, Apr. 28, 2020 (Apr. 28, 2020), p. 16.
Hedley D et al: "Carboxypeptidase G2-based gene-directed enzyme-prodrug therapy: a new weapon in the GDEPT armoury", Nature Reviews Cancer, vol. 7, No. 11, Nov. 2007 (Nov. 2007), pp. 870-879.
Kuehle J et al: "T cell-directed enzyme-prodrug therapy (TDEPT): CAR T cells engineered for tumour-restricted activation of cytotoxic prodrugs", Human Gene Therapy, vol. 28, No. 12, P072, Oct. 17, 2017 (Oct. 17, 2017),-Oct. 20, 2017 (Oct. 20, 2017), p. A38.
Lim W A & June C H: "The Principles of Engineering Immune Cells to Treat Cancer", Cell, vol. 168, No. 4, Feb. 9, 2017 (Feb. 9, 2017), pp. 724-740.
Niculescu-Duvaz D et al: "Self-Immolative 1-13 Nitrogen Mustards Prodrug Cleavable by Carboxypeptidase G2 (CPG2) Showing Large Cytotoxicity Differentials in GDEPT", Journal of Medicinal Chemistry, vol. 46, No. 9, Apr. 24, 2003 (Apr. 24, 2003) , pp. 1690-1705.
Chang Z L & Chen Y Y: "CARs: Synthetic Immunoreceptors for Cancer Therapy and Beyond", Trends in Molecular Medicine, vol. 23, No. 5, May 2017 (May 2017), pp. 430-450.
Patel et al: "T-cell therapies for HIV: Preclinical successes and current clinical strategies", Cytotherapy, vol. 18, No. 8, Aug. 2016 (Aug. 2016), pp. 931-942.
Ion Niculescu-Duvaz et al: "Self-Immolative Anthracycline Prodrugs for Suicide Gene Therapy", Journal of Medicinal Chemistry, vol. 42, No. 13, Jul. 1, 1999 (Jul. 1, 1999), pp. 2485-2489, XP055646443, US ISSN: 0022-2623, DOI: 10.1021/jm980696v *abstract*.
Marais et al. "A cell surface tethered enzyme improves efficiency in gene-directed enzyme prodrug therapy", Nat Biotechnol. Dec. 1997; 15(13):1373-7 (Year: 1997).
Roberge et al. "Construction and optimization of a CC49-based scFv-beta-lactamase fusion protein for ADEPT", Protein Eng Des Sel. Apr. 2006; 19(4):141-5. (Year: 2006).
Bourne C et al. "Mechanisms of Adoptive T-Cell Micropharmacies", Molecular Therapy, vol. 28, No. 4, Suppl. 1, Apr. 28, 2020 (Apr. 28, 2020), p. 16.
Jaffe J J et al: "Trypanocidal properties of 5'-O-sulfamoyladenosine, a close structural analog of nucleocidin", Experimental Parasitology, vol. 28, No. 3, Dec. 1970 (Dec. 1970), pp. 535-543.
Kuehle J et al: "T cell-directed enzyme-prodrug therapy (TDEPT): CAR T cells engineered for tumour-restricted activation of cytotoxic prodrugs", Human Gene Therapy, vol. 28, No. 12, P072, Oct. 17, 2017 (Oct. 17, 2017), p. A38.
Van de Vijver P et al: "Aminoacyl-tRNA Synthetase Inhibitors as Potent and Synergistic Immunosuppressants", Journal of Medicinal Chemistry, vol. 51, No. 10, May 2008 (May 2008), pp. 3020-3029.
Roellecke et al. "Optimized human CYP4B1 in combination with the alkylator prodrug 4-ipomeanol serves as a novel suicide gene system for adoptive T-cell therapies", Gene Ther. Jul. 2016 ;23(7):615-26 (Year: 2016).
Spooner et al. "In suicide gene therapy, the site of subcellular localization of the activating enzyme is more important than the rate at which it activates prod rug", J. Cancer Gene Therapy7.10: 1348-56 (Year: 2000).
Koroniak Lukasz et al: Synthesis and Characterization of an N-Acylsulfonamide Inhibitor of Human Asparagine Synthetase11 , Organic Letters, vol. 5, No. 12, May 9, 2003 (May 9, 2003), pp. 2033-2036, XP055848821.
Abate-Daga et al. "CAR models: next-generation CAR modifications for enhanced T-cell function", Mol Ther Oncolytics. 2016; 3: 16014. (Year: 2016).
Cowan et al., "Adenovirus vector-mediated delivery of the prodrug-converting enzyme carboxypeptidase G2 in a secreted or GPI-anchored form: High-level expression of this active conditional cytotoxic enzyme at the plasma membrane." Cancer Gene Therapy, 2002, 9:897-907 (Year: 2002).
Goodell et al., "CD34+ or CD34-: Does it Really Matter?" Blood, vol. 94, No. 8 Oct. 15, 1999: pp. 2545-2547 (Year: 1999).
Zhao et al., "Engineered TCR-T Cell immunotherapy in Anticancer Precision Medicine: Pros and Cons." Frontiers in Immunology, 2021, 12: 1-12 (Year: 2021).
Ali et al., "HIV-I-Specific Chimeric Antigen Receptors Based on Broadly Neutralizing Antibodies." J Vitrol 90: 6999-7006; publication date: May 25, 2016 (Year: 2016).
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111 :2129-2138, 1990 (Year: 1990).
Greenspan et al. 1999 Defining epitopes: It's not as easy as it seems; Nature Biotechnology, 17:936-937 (Year: 1999).
Kulmanov et al., "DeepGO: predicting protein functions from sequence and interactions using a deep ontology-aware classifier." Bioinformatics, 34(4), 2018, 660-668 (Year: 2018).
Miosge et al., "Comparison of predicted and actual consequences of missense mutations." Proc Natl Acad Sci US A Sep. 15, 2015;112(37):E5189-98 (Year: 2015).
Skolnick et al., "From genes to protein structure and function: novel applications of computational approaches in the genomic era." Trends Biotechnol. Jan. 2000; 18(1 ):34-9 (Year: 2000).
Appel et al., "Carboxypeptidases," Methods of Enzymatic Analysis (Second Edition), vol. 2, 1974, (3, pages).
Lindner, et al., "Chimeric Antigen Receptor Signaling: Functional Consequences and Design Implications," Sci Adv., 2020, Retrieved on May 6, 2020 (8, pages).
Phillippon, et al., "A Structure-Base Classification of class A ß-Lactamases, a Broadly Diverse Family of Enzymes," Clin Microbial Rev., 2015, vol. 29 Retrieved Jan. 2016, (29, pages).

(56) References Cited

OTHER PUBLICATIONS

Silverberg, et al., "Cumulative Incidence of Cancer Among Persons with HIV in North America Annals of Internal Medicine", vol. 163 No. 7, Retrieved on Oct. 10, 2015, (18, pages).
Stritzker, et al., "Prodrug Converting Enzyme Gene Delivery by L. monocytogenes," BMC Cancer, 2008, vol. 8 No. 94 (10, pages).

* cited by examiner

SEAKER cell (Synthetic Enzyme Activated Killer Cell)

inactive prodrug (X = O or NH)

active drug

Linkers

CO:

PAB-CO:

CO-PAB-CO:

TML-CO:

IND-CO:

Y = O, NH, $CH_2$, $CMe_2$

1a: AMS prodrug
1c: AMS

2a: ZD2767P (prodrug)
2c: ZD2767

3

MsCl
4: R = H
5: R = Ms

| *Drug name:* | AMS | ZD2767P | Erlotinib |
|---|---|---|---|
| *Drug class:* | Nucleoside analog | Nitrogen mustard | Kinase inhibitor |

FIG. 25

| Route | Group | Pretreatment | Analyte | Dose (mg/kg) | $T_{max}$ (hr) | $C_{max}$ (ng/mL) | $AUC_{last}$ (hr*ng/mL) | $AUC_{inf}$ (hr*ng/mL) | $T_{1/2}$ (hr) |
|---|---|---|---|---|---|---|---|---|---|
| IP | Group 1 | Probenecid | Glutamate AMS | 10 | 0.5 | 24997.27 | 32129.31 | 32221.26 | 0.49 |
| | | | AMS | - | 0.08 | 154.91 | 276.92 | 302.74 | - |
| | Group 2 | No pretreatment | Glutamate AMS | 10 | 0.08 | 17635.83 | 12039.35 | 12103.91 | 0.64 |
| | | | AMS | - | 0.08 | 43.54 | 23.77 | 25.84 | - |
| | **Group** | **Pretreatment** | **Analyte** | **Dose (mg/kg)** | **$T_{max}$ (hr)** | **$C_{max}$ (µM)** | **$AUC_{last}$ (hr* µM)** | **$AUC_{inf}$ (hr* µM)** | **$T_{1/2}$ (hr)** |
| | Group 1 | Probenecid | Glutamate AMS | 10 | 0.5 | 48.16 | 61.89 | 62.07 | 0.49 |
| | | | AMS | - | 0.08 | 0.45 | 0.8 | 0.87 | - |
| | Group 2 | No pretreatment | Glutamate AMS | 10 | 0.08 | 33.97 | 23.19 | 23.32 | 0.64 |
| | | | AMS | - | 0.08 | 0.13 | 0.07 | 0.07 | - |

COMPOSITIONS AND METHODS FOR ADOPTIVE CELL THERAPY

CROSS-REFERENCE TO RELATED APPLICATIONS

This application is a National Stage Application of PCT/US2018/040640, filed Jul. 2, 2018, which claims the benefit of and priority to U.S. Provisional Patent Application No. 62/527,936, filed Jun. 30, 2017, the entire contents of which are incorporated herein by reference.

STATEMENT OF GOVERNMENT SUPPORT

This invention was made with government support under AI073736, AI095692, AR068118, CA055349, CA023766, GM100477, and AI118224 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 1, 2018, is named 115872-0385 SL.txt and is 119,572 bytes in size.

BACKGROUND OF THE INVENTION

Adoptive and engineered T cell therapies, including chimeric antigen receptor (CAR) T cells, T cell receptor (TCR) engineered T cells, and antigen adopted T cells, have emerged recently as important therapies for cancer, inflammation and infectious diseases. First generation CARs were designed by fusing the scFv to the intracellular signaling domain of the CD3-ζ chain, whereas second generation CARs added CD28-CD80 costimulation in which the CD28 signaling domain was incorporated into the CAR construct (i.e.: "28ζ CAR") for improved T cell activation and efficacy. Resistance to the activity of these cells, relapse, and toxicity are still important hurdles to their success. Recent reports of significant toxicities and even deaths after CAR T cell therapy, and TCR T cell therapy, and the continuing incidence of GVHD with its associated short- and long-term morbidity and mortality, call for new methods to potentiate efficacy, and at the same time, to better control the various adoptive cell therapies.

SUMMARY OF THE INVENTION

Provided herein, in certain embodiments, are compositions and methods for adoptive cell therapy comprising engineered immune cells that express a prodrug converting enzyme and a receptor that binds to a target antigen. In some embodiments, the receptor is specific for an antigen found at a site of inflammation or pathogenic infection or a target tissue (e.g., bone marrow) or organ. In some embodiments, the receptor is a T cell receptor. In some embodiments, the receptor is a native receptor (e.g., a native T cell receptor). In some embodiments, the receptor is a non-native receptor (e.g., a non-native T cell receptor), for example, an engineered receptor, such as a chimeric antigen receptor (CAR). In some embodiments, the engineered immune cells comprise a prodrug converting enzyme and/or a nucleic acid encoding the prodrug converting enzyme. In some embodiments, the engineered immune cells comprise a chimeric antigen receptor and/or nucleic acid encoding the chimeric antigen receptor. In some embodiments, the prodrug converting enzyme is expressed on the surface of the immune cell. In some embodiments, the prodrug converting enzyme is fused to a transmembrane domain. In some embodiments, the transmembrane domain of the prodrug converting enzyme comprises a CD8 transmembrane domain. In some embodiments, the prodrug converting enzyme is attached to the surface of the cell by a GPI anchor. In some embodiments, the prodrug converting enzyme is secreted. In some embodiments, the nucleic acid encoding the prodrug converting enzyme comprises a leader sequence for secretion of the prodrug converting enzyme. In some embodiments, the prodrug converting enzyme is a carboxypeptidase (e.g., a *Pseudomonas* sp. Carboxypeptidase G2 (CPG2)). In some embodiments, the prodrug converting enzyme is a β-lactamase (e.g., an *Enterobacter cloacae* β-lactamase). In some embodiments, the nucleic acid encoding a prodrug converting enzyme is operably linked to a promoter. In some embodiments, the promoter is a constitutive promoter. In some embodiments, the promoter is a conditional promoter. In some embodiments, the conditional promoter is inducible by binding of the receptor (e.g., a CAR) to a target antigen. In some embodiments, the chimeric antigen receptor comprises (i) an extracellular antigen binding domain; (ii) a transmembrane domain; and (iii) an intracellular domain. In some embodiments, the target antigen selected from among an antigen from a pathogen, an inflammatory antigen, a bone marrow-specific antigen, stem cell specific antigen or hematopoietic-specific antigen. In some embodiments, the antigen from a pathogen is a bacterial, viral, or parasitic antigen. In some embodiments, the bacterial antigen is from a *Pasteurella*, Staphylococci, *Streptococcus, Escherichia coli, Pseudomonas* species, and *Salmonella* species bacteria. In some embodiments, the bacterial antigen is a capsule antigen or a cell wall antigen. In some embodiments, the bacterial antigen is a peptidoglycan antigen. In some embodiments, the viral antigen is derived from an HSV-1 or HSV-2 protein, a CMV protein, an HCV protein, an HPV protein or an HIV-1 protein. In some embodiments, the viral antigen is derived from an HSV-1 or HSV-2 protein selected from among gB, gD, gH, VP16, and VP22. In some embodiments, the viral antigen is derived from a CMV protein selected from among gB and gH. In some embodiments, the viral antigen is derived from an HCV E protein. In some embodiments, the viral antigen is derived from a HPV protein selected from among E6 and E7. In some embodiments, the viral antigen is derived from an HIV-1 protein selected from among gp120, gp41, gp160, gag, and pol. In some embodiments, the extracellular antigen binding domain binds to a bone marrow specific antigen. In some embodiments, the extracellular antigen binding domain binds to a bone marrow specific antigen. In some embodiments, the bone marrow specific antigen is a hematopoietic stem cell specific antigen. In some embodiments, the hematopoietic stem cell specific antigen is CD34. In some embodiments, the extracellular antigen binding domain comprises a single chain variable fragment (scFv). In some embodiments, the extracellular antigen binding domain comprises a human scFv. In some embodiments, the extracellular antigen binding domain comprises a signal peptide that is covalently joined to the N-terminus of the extracellular antigen-binding domain. In some embodiments, the transmembrane domain comprises a CD8 transmembrane domain. In some embodiments, the intracellular domain comprises a costimulatory domain. In some embodiments, the one or more costimulatory domains are selected from a CD28 costimulatory domain, a CD3ζ-chain, a 4-1BBL costimulatory domain, or any combination thereof. In some embodiments, the immune cell is a lymphocyte. In some embodiments, the lymphocyte is a T-cell, a B cell or a natural killer (NK) cell. In some embodiments, the T cell is a CD4+ T cell or a CD8+ T cell. In some embodiments, the immune cell is derived from an autologous donor or an allogenic donor.

Also provided are polypeptides comprising a prodrug converting enzyme and a chimeric antigen receptor. In some embodiments, the polypeptides further comprise a self-cleaving peptide located between the prodrug converting enzyme and the chimeric antigen receptor. In some embodiments, the self-cleaving peptide is a P2A self-cleaving peptide. In some embodiments, the prodrug converting enzyme is fused to a transmembrane domain. In some embodiments, the transmembrane domain of the prodrug converting enzyme comprises a CD8 transmembrane domain. In some embodiments, the prodrug converting enzyme comprises a leader sequence for secretion of the prodrug converting enzyme. In some embodiments, the prodrug converting enzyme is *Pseudomonas* sp. Carboxypeptidase G2 (CPG2) or *Enterobacter cloacae* β-lactamase. In some embodiments, the chimeric antigen receptor comprises (i) an antigen binding domain; (ii) a transmembrane domain; and (iii) an intracellular domain. In some embodiments, the antigen binding domain binds to an antigen from a pathogen or an inflammatory antigen. In some embodiments, the antigen binding domain comprises a single chain variable fragment (scFv). In some embodiments, the transmembrane domain comprises a CD8 transmembrane domain. In some embodiments, the intracellular domain comprises a one or more costimulatory domains. In some embodiments, the one or more costimulatory domains are selected from a CD28 costimulatory domain, a CD3ζ-chain, a 4-1BBL costimulatory domain, or any combination thereof.

Also provided are nucleic acids encoding any of polypeptides disclosed herein. In some embodiments, the nucleic acid encoding the polypeptide is operable linked to a promoter. In some embodiments, the promoter is a constitutive promoter. In some embodiments, the promoter is a conditional promoter. In some embodiments, the conditional promoter is inducible by the CAR binding to an antigen.

Also provided are vectors comprising any of nucleic acids disclosed herein. In some embodiments, the vector is a viral vector or a plasmid. In some embodiments, the vector is a retroviral vector.

Also provided are host cells comprising a polypeptide, a nucleic acid, or a vector disclosed herein.

Also provided are methods for treating an inflammation, an inflammatory disease, an autoimmune disease, or a pathogenic infection, in a subject in need thereof comprising administering an effective amount of any of the engineered immune cells provided herein. In some embodiments, the methods further comprise administering to the subject a prodrug that is converted to an active drug by the prodrug converting enzyme. In some embodiments, the methods further comprise administering to the subject a prodrug that is converted to an active drug by the prodrug converting enzyme. In some embodiments, the prodrug is administered subsequent to administration of the engineered immune cells. In some embodiments, the engineered immune cells are administered are administered intravenously, intraperitoneally, subcutaneously, or intramuscularly. In some embodiments, the autoimmune disease is selected from the group consisting of Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune ivmphoproliferative syndrome (ALPS), autoimmune thrombocytopenic purpura (ATP), Behcet's disease, cardiomyopathy, celiac sprue-dermatitis hepetiformis, chronic fatigue immune dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis—juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura, IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo, Wegener's granulomatosis, and any combination thereof. In some embodiments, the inflammation is due to an allergic or asthmatic condition. In some embodiments, the inflammation is due to an allogenic transplant or graft rejection (e.g., graft versus host disease (GVHD)).

In some embodiments, the methods further comprise administering a cytokine to the subject. In some embodiments, the cytokine is administered prior to, during, or subsequent to administration of the one or more engineered immune cells. In some embodiments, the cytokine is selected from a group consisting of interferon α, interferon β, interferon γ, complement C5a, IL-2, TNFalpha, CD40L, IL12, IL-23, IL15, IL17, CCL1, CCL11, CCL12, CCL13, CCL14-1, CCL14-2, CCL14-3, CCL15-1, CCL15-2, CCL16, CCL17, CCL18, CCL19, CCL19, CCL2, CCL20, CCL21, CCL22, CCL23-1, CCL23-2, CCL24, CCL25-1, CCL25-2, CCL26, CCL27, CCL28, CCL3, CCL3L1, CCL4, CCL4L1, CCL5, CCL6, CCL7, CCL8, CCL9, CCR10, CCR2, CCR5, CCR6, CCR7, CCR8, CCRL1, CCRL2, CX3CL1, CX3CR, CXCL1, CXCL10, CXCL11, CXCL12, CXCL13, CXCL14, CXCL15, CXCL16, CXCL2, CXCL3, CXCL4, CXCL5, CXCL6, CXCL7, CXCL8, CXCL9, CXCL9, CXCR1, CXCR2, CXCR4, CXCR5, CXCR6, CXCR7 and XCL2.

Also provided are methods for ablation therapy in a subject in need thereof comprising administering an effective amount of the engineered immune cells provide herein. In some embodiments the methods further comprise administering to the subject a prodrug that is converted to an active drug by the prodrug converting enzyme. In some embodiments, the prodrug is administered subsequent to administration of the engineered immune cells. In some embodiments, the ablation therapy is bone marrow ablation. In some embodiments, the ablation therapy is performed prior to hematopoietic stem cell transplant (HSCT) or bone marrow transplant (BMT) in the subject.

Also provided are methods for preparing immune cells for therapy, comprising isolating immune cells from a donor subject, transducing the immune cells (e.g., T cells) with a nucleic acid encoding a secreted or cell surface prodrug converting enzyme, and optionally, nucleic acid that encodes a receptor, e.g., a chimeric antigen receptor. In some embodiments, the immune cells isolated from the donor subject comprise one or more lymphocytes. In some embodiments, the lymphocytes comprise a T-cell, a B cell, and/or a natural killer (NK) cell. In some embodiments, the T cell is a CD4+ T cell or a CD8+ T cell. In some embodiments, the therapy is a therapy for an inflammation, an inflammatory disease, an autoimmune disease, or a pathogenic infection. In some embodiments, the therapy is a therapy for a rheumatologic disease. In some embodiments, the therapy is a therapy for treatment of graft versus host disease (GVHD).

Also provided are methods for treatment comprising isolating immune cells from a donor subject, transducing the immune cells with nucleic acid encoding a secreted or cell surface prodrug converting enzyme, and optionally, nucleic acid that encodes a receptor, e.g., a chimeric antigen receptor, and administering the transduced immune cells to a recipient subject. In some embodiments, the donor subject and the recipient subject are the same (i.e., autologous). In some embodiments, the donor subject and the recipient subject are different (i.e., allogenic). In some embodiments, the immune cells isolated from the donor subject comprise one or more lymphocytes. In some embodiments, the lymphocytes comprise a T-cell, a B cell, and/or a natural killer (NK) cell. In some embodiments, the T cell is a CD4+ T cell or a CD8+ T cell.

Also provided are uses of any of the engineered immune cells provided herein for treating an inflammation, an inflammatory disease, an autoimmune disease or a pathogenic infection or for an ablative therapy. In some embodiments, the engineered immune cells provided herein are used for treating a rheumatologic disease. In some embodiments, the engineered immune cells provided herein are used for treating graft versus host disease.

Also provided are uses of any of the engineered immune cells provided herein the preparation of a medicament for the treatment of an inflammation, an inflammatory disease, an autoimmune disease or a pathogenic infection or for an ablative therapy.

BRIEF DESCRIPTION OF THE DRAWINGS

FIG. 25 shows pharmacokinetic and biodistribution studies related to the glut-AMS prodrug conducted in Nod mice.

DETAILED DESCRIPTION OF THE INVENTION

Figure 1:
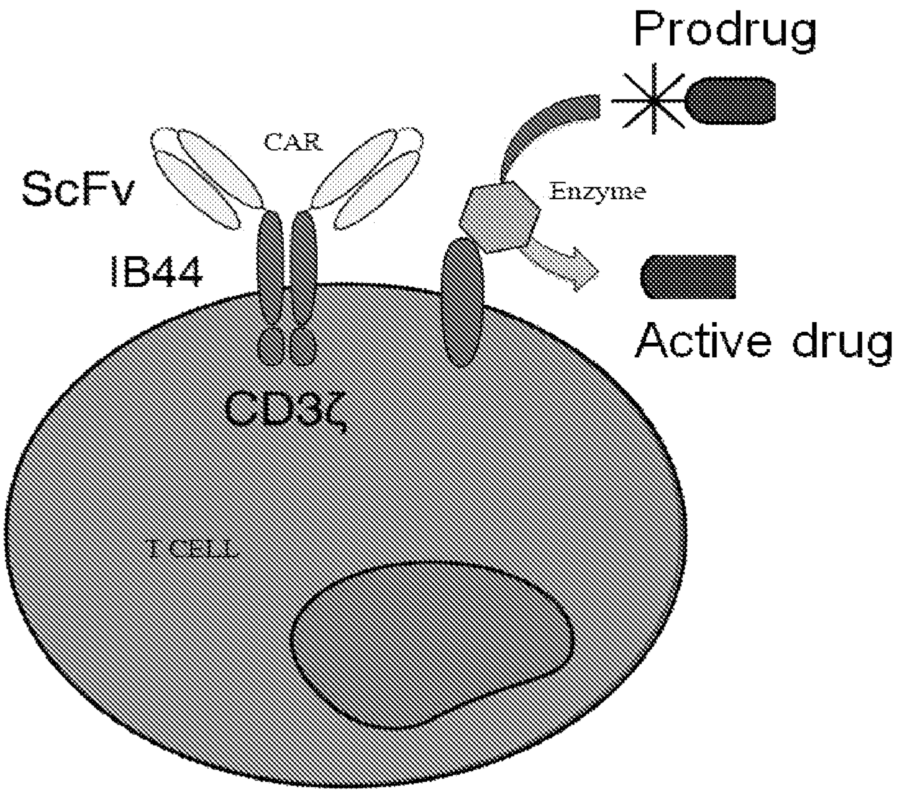
FIG. 1 provides an exemplary overview of the Synthetic Enzyme Activated Killer (SEAKER) Cell technology.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Definitions

Unless defined otherwise, all technical and scientific terms used herein have the meaning commonly understood by a person skilled in the art to which this disclosure belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

As used herein, the singular forms "a", "an" and "the" are intended to include the plural forms as well, unless the context clearly indicates otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl, and heteroaryl groups also include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi-, or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl, or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two, or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to $-C\equiv CH$, $-C\equiv CCH_3$, $-CH_2C\equiv CCH_3$, $-C\equiv CCH_2CH(CH_2CH_3)_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic, and tricyclic ring systems. Aryl groups may be substituted or unsubstituted. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). Representative substituted aryl groups may be mono-substituted (e.g., tolyl) or substituted more than once. For example, mono-substituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl, or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. Heterocyclyl groups may be substituted or unsubstituted. In some embodiments, the heterocyclyl group contains 1, 2, 3, or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated, and saturated ring systems, such as, for example, imidazolyl, and imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. The phrase includes heterocyclyl groups that have other groups, such as alkyl, oxo, or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Representative substituted heteroaryl groups may be substituted one or more times with various substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl, or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are heteroarylene groups, and so forth. Substituted groups having a single point of attachment to the compound of the present technology are not referred to using the "ene" designation. Thus, e.g., chloroethyl is not referred to herein as chloroethylene.

As used herein, the term "administration" of an agent to a subject includes any route of introducing or delivering the agent to a subject to perform its intended function. Administration can be carried out by any suitable route, including. but not limited to, intravenously, intramuscularly, intraperitoneally, subcutaneously, and other suitable routes as described herein. Administration includes self-administration and the administration by another.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells, at least about 10,000 cells, at least about 100,000 cells, at least about $1\times10^6$ cells, at least about $1\times10^7$ cells, at least about $1\times10^8$ cells, at least about $1\times10^9$ cells, at least about $1\times10^{10}$ cells, at least about $1\times10^{11}$ cells, at least about $1\times10^{12}$ cells, or more cells expressing similar or different phenotypes.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form and a second plurality of amino acids are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term "effective amount" or "therapeutically effective amount" refers to a quantity of an agent sufficient to achieve a desired therapeutic effect. In the context of therapeutic applications, the amount of a therapeutic peptide administered to the subject can depend on the type and severity of the infection and on the characteristics of the individual, such as general health, age, sex, body weight, and tolerance to drugs. It can also depend on the degree, severity, and type of disease. The skilled artisan will be able to determine appropriate dosages depending on these and other factors.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell.

The term "linker" refers to synthetic sequences (e.g., amino acid sequences) that connect or link two sequences, e.g., that link two polypeptide domains. In some embodiments, the linker contains 1, 2, 3, 4, 5, 6, 7, 8, 9, or 10 of amino acid sequences.

As used herein the term "immune cell" refers to any cell that plays a role in the immune response. Immune cells are of hematopoietic origin, and include lymphocytes, such as B cells and T cells; natural killer cells; myeloid cells, such as monocytes, macrophages, dendritic cells, eosinophils, neutrophils, mast cells, basophils, and granulocytes.

As used herein, the term "native immune cell" refers to an immune cell that naturally occurs in the immune system.

As used herein, the term "engineered immune cell" refers to an immune cell that is genetically modified.

The term "lymphocyte" refers to all immature, mature, undifferentiated, and differentiated white lymphocyte populations including tissue specific and specialized varieties. It encompasses, by way of non-limiting example, B cells, T cells, NKT cells, and NK cells. In some embodiments, lymphocytes include all B cell lineages including pre-B cells, progenitor B cells, early pro-B cells, late pro-B cells, large pre-B cells, small pre-B cells, immature B cells, mature B cells, plasma B cells, memory B cells, B-1 cells, B-2 cells, and anergic AN1/T3 cell populations.

As used herein, the term "T-cell" includes naïve T cells, CD4+ T cells, CD8+ T cells, memory T cells, activated T cells, anergic T cells, tolerant T cells, chimeric B cells, and antigen-specific T cells.

As used herein "adoptive cell therapeutic composition" refers to any composition comprising cells suitable for adoptive cell transfer. In exemplary embodiments, the adoptive cell therapeutic composition comprises a cell type selected from a group consisting of a tumor infiltrating lymphocyte (TIL), TCR (i.e. heterologous T-cell receptor) modified lymphocytes and CAR (i.e. chimeric antigen receptor) modified lymphocytes. In another embodiment, the adoptive cell therapeutic composition comprises a cell type selected from a group consisting of T-cells, CD8+ cells, CD4+ cells, NK-cells, delta-gamma T-cells, regulatory T-cells and peripheral blood mononuclear cells. In another embodiment, TILs, T-cells, CD8+ cells, CD4+ cells, NK-cells, delta-gamma T-cells, regulatory T-cells or peripheral blood mononuclear cells form the adoptive cell therapeutic composition. In one embodiment, the adoptive cell therapeutic composition comprises T cells.

As used herein "tumor-infiltrating lymphocytes" or TILs refer to white blood cells that have left the bloodstream and migrated into a tumor.

As used herein, "allogeneic" refers to a graft derived from, a different animal of the same species. As used herein, "xenogeneic" refers to a graft derived from an animal of a different species.

As used herein, "auto-antigen" refers any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

As used herein, "autoimmune disease" means a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barre syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others. As used herein, the term "autologous" is meant to refer to any material derived from the same individual to whom it is later to be re-introduced into the individual.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983)). The antibodies of the invention comprise whole native antibodies, monoclonal antibodies, human antibodies, humanized antibodies, camelised antibodies, multispecific antibodies, bispecific antibodies, chimeric antibodies, Fab, Fab', single chain V region fragments (scFv), single domain antibodies (e.g., nanobodies and single domain camelid antibodies), $V_{NAR}$ fragments, Bi-specific T-cell engager (BiTE) antibodies, minibodies, disulfide-linked Fvs (sdFv), and anti-idiotypic (anti-Id) antibodies, intrabodies, fusion polypeptides, unconventional antibodies and antigen-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA, and IgY), class (e.g., IgG1, IgG2, IgG3, IgG4, IgA1, and IgA2), or subclass.

In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant ($C_H$) region. The heavy chain constant region is comprised of three domains, CHI, CH2, and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Cl q) of the classical complement system. As used herein interchangeably, the terms "antigen-binding portion", "antigen-binding fragment", or "antigen-binding region" of an antibody, refer to the region or portion of an antibody that binds to the antigen and which confers antigen specificity to the antibody; fragments of antigen-binding proteins, for example, antibodies includes one or more fragments of an antibody that retain the ability to specifically bind to an antigen (e.g., an peptide/HLA complex). It has been shown that the antigen-binding function of an antibody can be performed by fragments of a full-length antibody. Examples of antigen-binding portions encompassed within the term "antibody fragments" of an antibody include a Fab fragment, a monovalent fragment consisting of the $V_L$, $V_H$, $C_L$ and CHI domains; a $F(ab)_2$ fragment, a bivalent fragment comprising two Fab fragments linked by a disulfide bridge at the hinge region; a Fd fragment consisting of the $V_H$ and CHI domains; a Fv fragment consisting of the $V_L$ and $V_H$ domains of a single arm of an antibody; a dAb fragment (Ward et al., *Nature* 341: 544-546 (1989)), which consists of a $V_H$ domain; and an isolated complementarity determining region (CDR).

Antibodies and antibody fragments can be wholly or partially derived from mammals (e.g., humans, non-human primates, goats, guinea pigs, hamsters, horses, mice, rats, rabbits and sheep) or non-mammalian antibody producing animals (e.g., chickens, ducks, geese, snakes, and urodele amphibians). The antibodies and antibody fragments can be produced in animals or produced outside of animals, such as from yeast or phage (e.g., as a single antibody or antibody fragment or as part of an antibody library).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., *Science* 242:423-426 (1988); and Huston et al., *Proc. Natl. Acad. Sci.* 85: 5879-5883 (1988). These antibody fragments are obtained using conventional techniques known to those of ordinary skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., about 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. In certain embodiments, the linker comprises amino acids having the sequence set forth in SEQ ID NO: 21 as provided below.

(SEQ ID NO: 21)
GGGGSGGGGSGGGGS

In certain embodiments, the nucleic acid sequence encoding the amino acid sequence of SEQ ID NO: 21 is set forth in SEQ ID NO: 22, which is provided below:

(SEQ ID NO: 22)
ggcggcggcggatctggaggtggtggctcaggtggcggaggctcc

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (*Proc. Nat. Acad. Sci. USA,* 85:5879-5883 (1988)). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., *Hybridoma* (*Larchmt*) 27(6):455-51 (2008); Peter et al., *J Cachexia Sarcopenia Muscle* (2012); Shieh et al., *J Imunol* 183(4): 2277-85 (2009); Giomarelli et al., *Thromb Haemost* 97(6): 955-63 (2007); Fife eta., *J Clin Invst* 116(8):2252-61 (2006); Brocks et al., *Immunotechnology* 3(3): 173-84 (1997); Moosmayer et al., *Ther Immunol* 2(10):31-40 (1995) Agonistic scFvs having stimulatory activity have been described (see, e.g., Peter et al., *J Biol Chem* 25278(38):36740-7 (2003); Xie et al., *Nat Biotech* 15(8):768-71 (1997); Ledbetter et al., *Crit Rev Immunol* 17(5-6):427-55 (1997); Ho et al., *Bio Chim Biophys Acta* 1638(3):257-66 (2003)).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "$F(ab')_2$" refers to an antibody fragment generated by pepsin digestion of whole IgG antibodies, wherein this fragment has two antigen binding (ab') (bivalent) regions, wherein each ($ab^1$) region comprises two separate amino acid chains, a part of a H chain and a light (L) chain linked by an S—S bond for binding an antigen and where the remaining H chain portions are linked together. A "$F(ab')_2$" fragment can be split into two individual Fab' fragments.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. Sequences of Proteins of Immunological Interest, Fifth Edition, U.S. Department of Health and Human Services, NIH Publication No. 91-3242(1991)).

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes (e.g., either monovalent or multivalent). Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay). Nucleic acid molecules useful in the presently disclosed subject matter include any nucleic acid molecule that encodes a polypeptide or a fragment thereof. In certain embodiments, nucleic acid molecules useful in the presently disclosed subject matter include nucleic acid molecules that encode an antibody or an antigen-binding portion thereof. Such nucleic acid molecules need not be 100% identical with an endogenous nucleic acid sequence, but will typically exhibit substantial identity. Polynucleotides having "substantial homology" or "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger, *Methods Enzymol.* 152:399 (1987); Kimmel, A. R. *Methods Enzymol.* 152:507 (1987)).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% w/v formamide, and more preferably at least about 50% w/v formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In certain embodiments, hybridization will occur at 30° C. in 750 mM NaCl, 75 mM trisodium citrate, and 1% w/v SDS. In certain embodiments, hybridization will occur at 37° C. in 500 mM NaCl, 50 mM trisodium citrate, 1% w/v SDS, 35% w/v formamide, and 100 μg/ml denatured salmon sperm DNA (ssDNA). In certain embodiments, hybridization will occur at 42° C. in 250 mM NaCl, 25 mM trisodium citrate, 1% w/v SDS, 50% w/v formamide, and 200 μg ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In certain embodiments, wash steps will occur at 25° C. in 30 mM NaCl, 3 mM trisodium citrate, and 0.1% w/v SDS. In certain embodiments, wash steps will occur at 42° C. in 15 mM NaCl, 1.5 mM trisodium citrate, and 0.1% w/v SDS. In certain embodiments, wash steps will occur at 68° C. in 15 mM NaCl, 1.5 mM trisodium citrate, and 0.1% w/v SDS. Additional variations on these conditions will be readily apparent to those skilled in the art. Hybridization techniques are well known to those skilled in the art and are described, for example, in Benton and Davis (*Science* 196: 180 (1977)); Grunstein and Rogness (*Proc. Natl. Acad. Sci., USA* 72:3961 (1975)); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

The terms "substantially homologous" or "substantially identical" mean a polypeptide or nucleic acid molecule that exhibits at least 50% or greater homology or identity to a reference amino acid sequence (for example, any one of the amino acid sequences described herein) or nucleic acid sequence (for example, any one of the nucleic acid sequences described herein). For example, such a sequence is at least about 60%, about 65%, about 70%, about 75%, about 80%, about 85%, about 90%, about 95% or about 99% homologous or identical at the amino acid level or nucleic acid to the sequence used for comparison (e.g., a wild-type, or native, sequence). In some embodiments, a substantially homologous or substantially identical polypeptide contains one or more amino acid amino acid substitutions, insertions, or deletions relative to the sequence used for comparison. In some embodiments, a substantially homologous or substantially identical polypeptide contains one or more non-natural amino acids or amino acid analogs, including, D-amino acids and retroinverso amino, to replace homologous sequences.

Sequence homology or sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between $e^{-3}$ and $^{e-100}$ indicating a closely related sequence.

As used herein, the term "analog" refers to a structurally related polypeptide or nucleic acid molecule having the function of a reference polypeptide or nucleic acid molecule.

As used herein, the term "a conservative sequence modification" refers to an amino acid modification that does not significantly affect or alter the binding characteristics of the presently disclosed CAR (e.g., the extracellular antigen-binding domain of the CAR) comprising the amino acid sequence. Conservative modifications can include amino acid substitutions, additions, and deletions. Modifications can be introduced into the human scFv of the presently disclosed CAR by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, and histidine; negatively-charged amino acids include aspartic acid and glutamic acid; and neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (1) above) using the functional assays described herein. In certain embodiments, no more than one, no more than two, no more than three, no more than four, no more than five residues within a specified sequence or a CDR region are altered.

As used herein, the term "ligand" refers to a molecule that binds to a receptor. In particular, the ligand binds a receptor on another cell, allowing for cell-to-cell recognition and/or interaction.

As used herein, the term, "co-stimulatory signaling domain," or "co-stimulatory domain", refers to the portion of the CAR comprising the intracellular domain of a costimulatory molecule. Co-stimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD28 and 4-1BB, other costimulatory domains are contemplated for use with the CARs described herein. The inclusion of one or more co-stimulatory signaling domains can enhance the efficacy and expansion of T cells expressing CAR receptors. The intracellular signaling and co-stimulatory signaling domains can be linked in any order in tandem to the carboxyl terminus of the transmembrane domain.

As used herein, the term "chimeric co-stimulatory receptor" or "CCR" refers to a chimeric receptor that binds to an antigen and provides co-stimulatory signals, but does not provide a T-cell activation signal.

As used herein, regulatory region of a nucleic acid molecule means a cis-acting nucleotide sequence that influences expression, positively or negatively, of an operatively linked gene. Regulatory regions include sequences of nucleotides that confer inducible (i.e., require a substance or stimulus for increased transcription) expression of a gene. When an inducer is present or at increased concentration, gene expression can be increased. Regulatory regions also include sequences that confer repression of gene expression (i.e., a substance or stimulus decreases transcription). When a repressor is present or at increased concentration gene expression can be decreased. Regulatory regions are known to influence, modulate or control many in vivo biological activities including cell proliferation, cell growth and death, cell differentiation and immune modulation. Regulatory regions typically bind to one or more trans-acting proteins, which results in either increased or decreased transcription of the gene.

Particular examples of gene regulatory regions are promoters and enhancers. Promoters are sequences located around the transcription or translation start site, typically positioned 5' of the translation start site. Promoters usually are located within 1 Kb of the translation start site, but can be located further away, for example, 2 Kb, 3 Kb, 4 Kb, 5 Kb or more, up to and including 10 Kb. Enhancers are known to influence gene expression when positioned 5' or 3' of the gene, or when positioned in or a part of an exon or an intron. Enhancers also can function at a significant distance from the gene, for example, at a distance from about 3 Kb, 5 Kb, 7 Kb, 10 Kb, 15 Kb or more.

Regulatory regions also include, but are not limited to, in addition to promoter regions, sequences that facilitate translation, splicing signals for introns, maintenance of the correct reading frame of the gene to permit in-frame translation of mRNA and, stop codons, leader sequences and fusion partner sequences, internal ribosome binding site (IRES) elements for the creation of multigene, or polycistronic, messages, polyadenylation signals to provide proper polyadenylation of the transcript of a gene of interest and stop codons, and can be optionally included in an expression vector.

As used herein, "operably linked" with reference to nucleic acid sequences, regions, elements or domains means that the nucleic acid regions are functionally related to each other. For example, nucleic acid encoding a leader peptide can be operably linked to nucleic acid encoding a polypeptide, whereby the nucleic acids can be transcribed and translated to express a functional fusion protein, wherein the leader peptide effects secretion of the fusion polypeptide. In some instances, the nucleic acid encoding a first polypeptide (e.g., a leader peptide) is operably linked to nucleic acid encoding a second polypeptide and the nucleic acids are transcribed as a single mRNA transcript, but translation of the mRNA transcript can result in one of two polypeptides being expressed. For example, an amber stop codon can be located between the nucleic acid encoding the first polypeptide and the nucleic acid encoding the second polypeptide, such that, when introduced into a partial amber suppressor cell, the resulting single mRNA transcript can be translated to produce either a fusion protein containing the first and second polypeptides, or can be translated to produce only the first polypeptide. In another example, a promoter can be operably linked to nucleic acid encoding a polypeptide, whereby the promoter regulates or mediates the transcription of the nucleic acid.

As used herein, "synthetic," with reference to, for example, a synthetic nucleic acid molecule or a synthetic gene or a synthetic peptide refers to a nucleic acid molecule or polypeptide molecule that is produced by recombinant methods and/or by chemical synthesis methods. As used herein, production by recombinant means by using recombinant DNA methods means the use of the well-known methods of molecular biology for expressing proteins encoded by cloned DNA.

As used herein, "expression" refers to the process by which polypeptides are produced by transcription and translation of polynucleotides. The level of expression of a polypeptide can be assessed using any method known in art, including, for example, methods of determining the amount of the polypeptide produced from the host cell. Such methods can include, but are not limited to, quantitation of the polypeptide in the cell lysate by ELISA, Coomassie blue staining following gel electrophoresis, Lowry protein assay and Bradford protein assay.

As used herein, a "host cell" is a cell that is used in to receive, maintain, reproduce and amplify a vector. A host cell also can be used to express the polypeptide encoded by the vector. The nucleic acid contained in the vector is replicated when the host cell divides, thereby amplifying the nucleic acids.

As used herein, a "vector" is a replicable nucleic acid from which one or more heterologous proteins can be expressed when the vector is transformed into an appropriate host cell. Reference to a vector includes those vectors into which a nucleic acid encoding a polypeptide or fragment thereof can be introduced, typically by restriction digest and ligation. Reference to a vector also includes those vectors that contain nucleic acid encoding a polypeptide. The vector is used to introduce the nucleic acid encoding the polypeptide into the host cell for amplification of the nucleic acid or for expression/display of the polypeptide encoded by the nucleic acid. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art.

As used herein, a vector also includes "virus vectors" or "viral vectors." Viral vectors are engineered viruses that are operatively linked to exogenous genes to transfer (as vehicles or shuttles) the exogenous genes into cells.

As used herein, an "expression vector" includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, the term "disease" refers to any condition or disorder that damages or interferes with the normal function of a cell, tissue, or organ. Examples of diseases include inflammatory diseases or pathogen infection of cell.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the engineered immune cells administered.

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "immunoresponsive cell" refers to a cell that functions in an immune response or a progenitor, or progeny thereof.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "isolated cell" refers to a cell that is separated from the molecular and/or cellular components that naturally accompany the cell.

As used herein, the term "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or polypeptide of the presently disclosed subject matter is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "secreted" is meant a polypeptide that is released from a cell via the secretory pathway through the endoplasmic reticulum, Golgi apparatus, and as a vesicle that transiently fuses at the cell plasma membrane, releasing the proteins outside of the cell. Small molecules, such as drugs, can also be secreted by diffusion through the membrane to the outside of cell.

As used herein, the term "specifically binds" or "specifically binds to" or "specifically target" is meant a polypeptide or fragment thereof that recognizes and binds a biological molecule of interest (e.g., a polypeptide), but which does not substantially recognize and bind other molecules in a sample, for example, a biological sample, which includes or expresses a target antigen.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

Overview

Adoptive transfer of chimeric antigen receptor (CAR) T cells has been shown to be an effective therapy for B-cell ALL and other hematopoietic cancers. More recently, CAR T cell therapies are being employed to treat inflammatory and infectious diseases. These strategies take advantage of the cytotoxic and regulatory functions of the immune cells. CD8 and CD4 T lymphocytes can be generated for recognition of viral, fungal, bacterial, and parasitic antigens, and allow the lymphocytes to target sites of active infection. For treatment of inflammation and autoimmune disease, regulatory lymphocytes can be generated for recognition of self-antigens responsible for autoimmune and inflammatory diseases and can target the lymphocytes to sites of inflammation. Provided herein are engineered immune cells, including compositions comprising engineered immune cells and methods of use thereof, engineered to constitutively or conditionally express a prodrug converting enzyme that converts prodrug forms of cytotoxic or other therapeutic drugs at the cell surface or into the targeted site. (FIG. 1). In some embodiments, the engineered immune cells additionally express a chimeric antigen receptor for delivering the immune cell to the target site. These engineered immune cells are interchangeably called herein Synthetic Enzyme Activated Killer (SEAKER) cells. Without intending to be bound by theory, the local release of potent drugs at the target site is expected to overcome the micro-environmental immune resistance to the T cells, and the escape by antigen loss variants as the drug is antigen independent, not suppressed by other cells, and may diffuse locally. The methods provided herein allow for modular use of a wide range of drugs depending on the desired application. The drugs can also synergize with the direct immune-based cytotoxic effects of the engineered immune cells, e.g., CAR T cells. Selective synthesis of the drug at the target site by the engineered immune cells also reduces systemic toxicity of the administered drugs.

Given their excellent targeting ability, the engineered immune cells provided herein can be used in any therapy requiring delivery of a cytotoxic or therapeutic molecule to a target site. For example, in addition to targeting tumors and sites of infection or inflammation, the engineered immune cells provided herein can also be used for ablative therapies, such as normal stem cell ablation for hematopoietic stem cell transplantation (HSCT) or bone marrow transplant (BMT). In some embodiments, engineered immune cells can be generated that express a receptor (e.g., a CAR) specific for a stem cell-specific marker, such as CD34+. The engineered immune cells expressing the receptor are administered to the patient and are targeted to the bone marrow. Once localized prodrugs of cytotoxic ablative drugs can be administered to effect localize ablation at the target site with minimal toxicity.

The engineered immune cells described herein can be employed in combination with a wide variety of prodrugs. Methods for making prodrugs are provided herein and are known in art. In some embodiments, the active drug of the prodrug is a cytotoxic chemotherapeutic drug. Cytotoxic chemotherapeutic drugs can be non-targeted or targeted. Exemplary non-targeted cytotoxic therapies as well as prodrugs forms of the compounds are provided herein or known in the art and include, for example, mustards, methotrexate, doxorubicin, nucleosides, and AMS. Exemplary targeted chemotherapies as well as prodrugs forms of the compounds are provided herein or known in the art and include, for example, erlotinib, dasatinib, and tyrosine kinase inhibitors. In addition, as described herein, prodrugs of antiviral, antimicrobial, antifungal, or antiparasitic agents can be used. Further, as described herein, prodrugs of anti-inflammatory or immunomodulatory drugs can be used.

Prior methods to effect local distribution of prodrug converting enzymes have included antibody-directed enzyme prodrug therapy (ADEPT). ADEPT was conceived as a means to leverage enzyme catalysis to generate high local concentrations of a cytotoxic drug at target sites. ADEPT was an alternative to traditional antibody—drug conjugates (ADCs), which are constrained by the number of conjugation sites on the antibody. Typically, ADCs deliver only about one to four drug molecules per antibody. By comparison, ADEPT relies on monoclonal antibody (mAb)-mediated delivery of a chemically-conjugated activating enzyme (i.e., a prodrug converting enzyme) to the target site, where the antibody binds to a target specific antigen. A non-toxic prodrug is then administered systemically, which is cleaved by the enzyme/antibody conjugate locally to synthesize the cytotoxic drug at the target site. The ADEPT approach provided several advantages over the traditional ADC, namely scheduled control and stopping of the prodrug, rapid diffusion the small prodrug and drug versus a mAb, enzymatically-driven local increases in drug concentration, and possible killing of antigen loss variants in the vicinity. However, toxicity is still an issue with ADEPT due to persistence of the enzyme/antibody conjugate in the blood. In addition, achieving a good therapeutic index is difficult due the poor target-to-blood ratio of the enzyme carried by the antibody. In fact, the ADEPT and ADC approaches have limited efficacy given that about 0.5% or less of the injected dose of antibody is typically found at the target site in a human, and the remaining 99.5% or more is elsewhere in the body.

As described herein, the engineered immune cells provided herein are can be used to deliver prodrug therapies to other sites of disease or sites requiring therapy. For example, the engineered immune cells can be used to deliver antimicrobial and antiviral agents for the treatment of pathogenic infection at target sites of infection. Accordingly, in some embodiments, the engineered immune cells are delivered for the treatment of pathogenic infection, such as, for example microbial or viral infection. In some embodiments, the engineered immune cells are delivered for the treatment of a viral infection, such as CMV, HSV, or HPV. In some embodiments, the engineered immune cells are delivered for the treatment of a bacterial infection, such as tuberculosis (TB). For targeting to site of infection, the engineered immune cells express a receptor that binds to a target antigen at the target site or can be modified to express a receptor, such as a chimeric antigen receptor, that binds to a target antigen at the target site. In some embodiments, the target antigen is microbial or viral antigen.

In another example, the engineered immune cells can be used to deliver anti-inflammatory agents to target sites of inflammation. Accordingly, in some embodiments, the engineered immune cells are delivered for the treatment of inflammation or inflammatory disease, such as autoimmune or rheumatologic diseases. In some embodiments, the engineered immune cells are delivered for the treatment of allogenic transplant or graft rejection (e.g., graft versus host disease (GVHD)).

In exemplary embodiments, the engineered immune cells provided herein express a T-cell receptor (TCR) or other cell-surface ligand that binds to a target antigen, such as an antigen from a pathogen or inflammatory antigen, and a prodrug converting enzyme. In some embodiments, the T cell receptor is a wild-type, or native, T-cell receptor. In some embodiments, the T cell receptor is a chimeric T-cell receptor (CAR).

In exemplary embodiments provided herein, the engineered immune cells provided herein express a T-cell receptor (TCR) (e.g., a CAR) or other cell-surface ligand that binds to an inflammatory antigen or an antigen from a pathogen, such as a microbial, viral, fungal or parasitic antigen.

The engineered immune cells (e.g., CAR T cells) provided herein that express an antigen receptor, e.g., a chimeric antigen receptor, in combination with a prodrug converting enzyme provide numerous advantages over the existing ADEPT and ADC technologies. A non-exhaustive list of these advantages includes, for example: 1) The ability of the engineered immune cells (e.g., CAR T cells) to significantly increase the quantity activating enzyme (e.g., 100 times or more) at the target site, such as an inflammatory site or site of pathogenic infection. This is because the engineered immune cells contain nucleic acid encoding the prodrug converting enzyme for expression of numerous copies of the enzyme by the cell. In addition, the engineered immune cells will proliferate extensively (e.g., 100 times or more) when it encounters the target antigen at the target site, thus significantly increasing production of the enzyme. 2) The prodrug can be administered after the engineered immune cells (e.g., CAR T cells) are reaching peak numbers at the target site, which can lower the systemic exposure to the drug and ensure maximal localized conversion of the prodrug. 3) The engineered immune cells (e.g., CAR T cells) can be easily generated by in vitro transduction of immune cells with nucleic acid encoding the chimeric antigen and the prodrug converting enzyme. Thus, in contrast to ADEPT or ADC, there is no difficult-to-manufacture chemical conjugate. 4) The engineered immune cells (e.g., CAR T cells) can also have additive or synergistic activity of its own (e.g. cytotoxic or regulatory). Further, the activity of the engineered immune cells (e.g., CAR T cells) can be adjusted by selection of co-stimulatory molecules include in the chimeric antigen receptor. 5) Gated conditional expression of the prodrug converting enzyme can be employed to allow better control of toxicity. 6) If the drug-mediated cytotoxic (e.g., pathogen killing) or therapeutic effect only is needed and/or CAR T mediated killing is not desired, the engineered immune cells (e.g., CAR T cells) can be further modified to engineer out the T cell-mediated inflammatory responses (e.g., cytokine release), which are responsible for much of the toxicity seen in humans.

Prodrugs and Prodrug Converting Enzymes

The engineered immune cells (e.g., CAR T cells) provided herein express at least one prodrug converting enzyme that converts a prodrug into an active drug. In some embodiments, the prodrug converting enzyme is expressed on the surface of the engineered immune cell. In some embodiments, the prodrug converting enzyme is secreted by the engineered immune cell. The enzyme can be any enzyme which is capable of converting a prodrug into an active drug and which is not normally expressed on the surface of a cell (e.g., a mammalian cell, such as a human cell) or released into the circulation.

In some embodiments, the prodrug converting enzyme will convert the prodrug into an active drug by removing a protecting group from the prodrug. In some embodiments, the protecting group will be cleaved as a whole from the prodrug. In some embodiments, the enzyme cleaves or alters part of the protecting group, resulting in a partially cleaved or altered protecting group which is unstable, resulting in spontaneous removal of the remainder of the group.

Figure 2A:
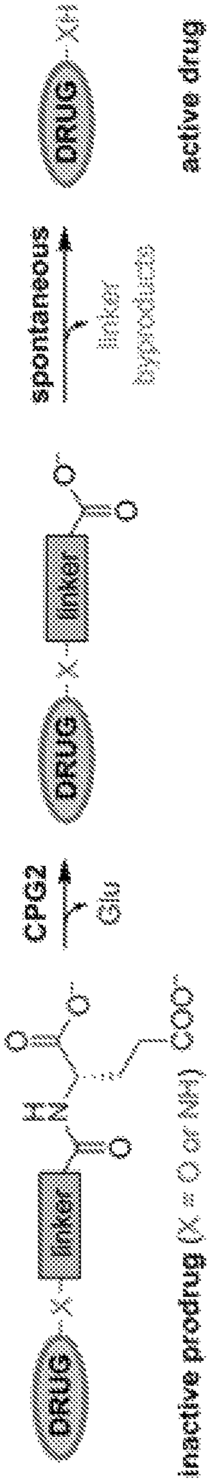
FIG. 2 illustrates an exemplary scheme for the production of CPG2-labile glutamate prodrugs. (a) Inactive prodrugs undergo cleavage of glutamate (blue) by CPG2 then spontaneous decomposition of linker (gray) to unmask active drug (red). (b) Various self-immolative linkers that can be used to tune prodrug stability and cleavage rates based on electronic and steric considerations. (c) Prodrug variants 1a ("P-AMS") and 2a of the cytotoxic sulfamoyladenosine ("AMS"; 1c) and nitrogen mustard ZD2767 (2c), respectively. (d) Synthetic precursors. (e) A prodrug variant of erlotinib (6a) with an alkyl PAB linker to avoid spontaneous hydrolysis of conventional amide-based linkers (cf. N,N-diarylamide). (CO=carbonyl linker; PAB=p-aminobenzyl linker; TML=trimethyl lock linker; IND=indanone-forming linker).
Figure 2B:
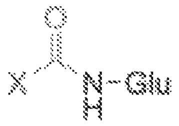
Figure 2B:
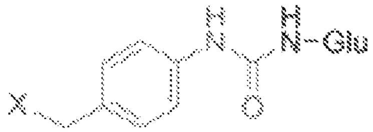
Figure 2B:
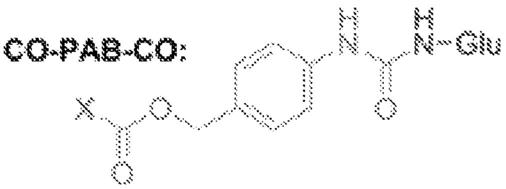
Figure 2B:
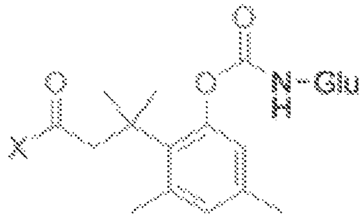
Figure 2B:
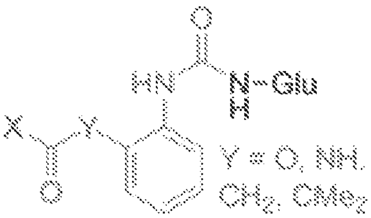

In some embodiments, the prodrug converting enzyme is a non-mammalian enzyme. Suitable non-mammalian enzymes include bacterial enzymes. Bacterial enzymes include carboxypeptidases, such as carboxypeptidase G2 (CPG2), which is a bacterial hydrolase enzyme isolated from *Pseudomonas* sp. RS-16 based on its ability to cleave N-linked glutamate from folate derivatives (*Pseudomonas* γ-glutamylhydrolase EC3.4.22.12, as disclosed in WO88/07378 and Levy and Goldstein, *J. Biol. Chem.* 242:2933 (1967)). CPG2 is specific for cleavage between an aromatic N-acyl moiety and glutamate, and has been used extensively in ADEPT strategies, including several systems that advanced to human clinical trials for cancer. In some embodiments, active drugs can be masked as glutamate prodrugs by coupling to amine or alcohol moieties in the drug (FIG. 2*a*), via various self-immolative linkers that undergo spontaneous decomposition to inert byproducts after glutamate hydrolysis (FIG. 2*b*). In certain embodiments, the prodrug converting enzyme is CPG2. In some embodiments, CPG2 comprises the sequence set forth in SEQ ID NO: 1, which is a secreted form of CPG2 including the leader sequence for secretion. In some embodiments, CPG2 comprises the sequence set forth in SEQ ID NO: 3, which is a CPG2 polypeptide without the leader sequence of SEQ ID NO:1 and optimized for human expression. In some embodiments, CPG2 comprises the sequence set forth in SEQ ID NO: 5, which is an exemplary secreted form of CPG2 including the leader sequence for secretion and optimized for human expression. In some embodiments, CPG2 comprises the sequence set forth in SEQ ID NOS: 7 or 40, which are exemplary transmembrane forms of CPG2 optimized for human expression with a CD8 leader sequence (e.g., SEQ ID NO: 11), a transmembrane portion and a CD8 intracellular portion with a disrupted Lyk binding domain (e.g., SEQ ID NO: 15).

In some embodiments, the prodrug converting enzyme is a β-lactamase, such as an *Enterobacter cloacae* β-lactamase. β-Lactamase (EC 3.5.2.6) is a serine protease produced by various bacteria; it catalyzes the hydrolysis of the β-lactam moiety in penicillin and other similar β-lactam antibiotics to β-amino acid. β-lactamase is highly selective to the β-lactam containing compounds. Cephalosporin has been widely utilized as the core of β-lactamase-activated prodrugs due to its ability of releasing the drug from C3' position following the cleavage of β-lactam ring by β-lactamase. In some embodiments, β-Lactamase comprises the sequence set forth in SEQ ID NO: 43, which is a secreted form of β-Lactamase including the leader sequence for secretion. In some embodiments, β-Lactamase comprises the sequence set forth in SEQ ID NO: 44, which is a β-Lactamase polypeptide without the leader sequence of SEQ ID NO:43 and optimized for human expression. In some embodiments, β-Lactamase comprises the sequence set forth in SEQ ID NO: 45, which is an exemplary secreted form of β-Lactamase including the leader sequence for secretion and optimized for human expression. In some embodiments, β-Lactamase comprises the sequence set forth in SEQ ID NOS: 46 or 47, which are exemplary transmembrane forms of β-Lactamase optimized for human expression with a CD8 leader sequence (e.g., SEQ ID NO: 11), a transmembrane portion and optionally, a CD8 intracellular portion with a disrupted Lyk binding domain (e.g., SEQ ID NO: 15).

Examples of other suitable non-mammalian enzymes include nitroreductases, such as an *E. coli* nitroreductase as disclosed in WO93/08288, thymidine kinase (tk), including viral tk such as VZV or HSV tk, β-glucosidase, β-glucoronidase, penicillin V amidase, penicillin G amidase and cytosine deaminase.

In some embodiments, the enzyme is a mammalian enzyme which does not naturally occur in a human. In some embodiments, the enzyme is a human enzyme which is not normally accessible to the prodrug, is expressed in limited quantities outside of cells, is expressed in a compartment that is not reached by the prodrug, is expressed by a cell that can be killed by the prodrug activation but is not essential to the patient, and/or is expressed by a cell that is resistant to the active drug or not killed by the active drug. This includes, for example, enzymes from other species as well as mammalian enzymes which are altered in a manner which is selective for the prodrug. In some embodiment, the alteration means that the conversion of the prodrug to an active drug by the natural enzyme will be at a rate one or more orders of magnitude less than the rate at which the altered enzyme operates. Altered enzymes can be made by standard recombinant DNA techniques, e.g., by cloning the enzyme, determining its gene sequence and altering the gene sequence by methods such as site-directed mutagenesis. In some embodiments, the prodrug converting enzyme is carboxypeptidase A, or a mutant thereof, e.g. a T268G mutant of carboxypeptidase A.

For expression of the secreted prodrug converting enzymes or transmembrane prodrug converting enzymes, eukaryotic based expression systems (e.g., plasmid or viral-based systems, such as retroviral transduction) are employed. For secretion or transmembrane expression, a signal peptide is included at the N-terminus of protein. The signal sequence or leader can be a peptide sequence (about 5, about 10, about 15, about 20, about 25, or about 30 amino acids long) present at the N-terminus of newly synthesized proteins that directs their entry to the secretory pathway. In certain embodiments, the signal peptide is covalently joined to the N-terminus of the prodrug converting enzyme (e.g., a CPG2 enzyme or a β-Lactamase). In certain embodiments, the signal peptide comprises a CPG2 signal sequence or a β-Lactamase signal sequence. In certain embodiments, the signal peptide comprises a CPG2 signal sequence comprising amino acids having the sequence set forth in SEQ ID NO: 9 as provided below.

(SEQ ID NO: 9)
MRPSIHRTAIAAVLATAFVAGT.

The nucleotide sequence encoding the amino acid sequence of SEQ ID NO: 9 is set forth in SEQ ID NO: 10, which is provided below:

(SEQ ID NO: 10)
atgcgaccgagtatccacagaacagcaatagctgctgtgcttgcaacagcg tttgtagcgggcacg In certain embodiments, the signal peptide comprises a CD8 signal polypeptide comprising amino acids having the sequence set forth in SEQ ID NO: 11 as provided below.

(SEQ ID NO: 11)
MALPVTALLLPLALLLHAARP

The nucleotide sequence encoding the amino acid sequence of SEQ ID NO: 11 is set forth in SEQ ID NO: 12, which is provided below:

(SEQ ID NO: 12)
atggccctgccagtaacggctctgctgctgccacttgctctgctcctccat gcagccaggcct.

For cell surface expression of the prodrug converting enzyme, the expressed protein is anchored to the cell membrane. In some embodiments, the prodrug converting enzyme comprises a transmembrane domain. In some embodiments, the transmembrane domain is covalently attached to the C-terminus of the CPG2 enzyme or β-lactamase. In some embodiments, the transmembrane domain is covalently attached to the N-terminus of the CPG2 enzyme or β-lactamase. In some embodiments, the transmembrane domain is CD8 transmembrane domain. In some embodiments, the transmembrane domain comprises a transmembrane spanning portion. In some embodiments, the membrane-spanning portion comprises the following sequence:

(SEQ ID NO: 38)
IYIWAPLAGTCGVLLLSLVIT

In some embodiments, the CD8 transmembrane domain also comprise an intracellular portion having the amino acid sequence: LYCNHRNRRRVCKCPRPVVKSGDKPSLSARYV (SEQ ID NO: 13).

In some embodiments, the CD8 transmembrane domain comprise an intracellular portion in which the natural Lyk binding domain is disrupted to uncouple the endogenous function of CD8 from the CPG2 or β-lactamase molecule. For example, in some embodiments, the CD8 transmembrane domain portion with disrupted Lyk binding domain has the following sequence: LYCNHRNRRRVGGGRPVVKSGDKPSLSARYV (SEQ ID NO: 15)

In some embodiments, the transmembrane CPG2 enzyme has the following amino acid sequence, which includes a signal peptide that is removed during processing in the endoplasmic reticulum:

(SEQ ID NO: 40)
MALPVTALLLPLALLLHAARPALAQKRDNVLFQAATDEQPAVIKTLEKLVN

IETGTGDAEGIAAAGNFLEAELKNLGFTVTRSKSAGLVVGDNIVGKIKGRG

GKNLLLMSHMDTVYLKGILAKAPFRVEGDKAYGPGIADDKGGNAVILHTLK

LLKEYGVRDYGTITVLFNTDEEKGSFGSRDLIQEEAKLADYVLSFEPTSAG

DEKLSLGTSGIAYVQVQITGKASHAGAAPELGVNALVEASDLVLRTMNIDD

KAKNLRFQWTIAKAGQVSNIIPASATLNADVRYARNEDFDAAMKTLEERAQ

QKKLPEADVKVIVTRGRPAFNAGEGGKKLVDKAVAYYKEAGGTLGVEERTG

GGTDAAYAALSGKPVIESLGLPGFGYHSDKAEYVDISAIPRRLYMAARLIM

DLGAGKYPYDVPDYAGGGIYIWAPLAGTCGVLLLSLVITLYCNHRNRRRVG

GGRPVVKSGDKPSLSARYV.

In some alternative embodiments, a construct for expression of a CPG2 enzyme comprises a CPG2 without a signal peptide.

In some embodiments, the transmembrane β-lactamase enzyme has the following amino acid sequence, which includes a signal peptide that is removed during processing in the endoplasmic reticulum:

(SEQ ID NO: 47)
MALPVTALLLPLALLLHAARPTPVSEKQLAEVVANTITPLMAAQSVPGMAV

AVIYQGKPHYYTFGKADIAANKPVTPQTLFELGSISKTFTGVLGGDAIARG

EISLDDAVTRYWPQLTGKQWQGIRMLDLATYTAGGLPLQVPDEVTDNASLL

RFYQNWQPQWKPGTTRLYANASIGLFGALAVKPSGMPYEQAMTTRVLKPLK

LDHTWINVPKAEEAHYAWGYRDGKAVRVSPGMLDAQAYGVKTNVQDMANWV

WMANMAPENVADASLKQGIALAQSRYRIGSMYQGLGWEMLNWPVEANTVVE

GSDSKVALAPLPVAEVNPPAPPVKASWVHKTGSTGGFGAYVAFIPEKQIGI

-continued

```
VMLANTSYPNPARVEAAYHILEALQYPYDVPDYAGGGLYCNHRNRRRVCKC

PRPVVKSGDKPSLSARYV.
```

In some alternative embodiments, a construct for expression of a β-lactamase enzyme comprises a β-lactamase without a signal peptide.

In some embodiments, the CPG2 or β-lactamase enzyme is attached to the cell surface via a glycosylphosphatidylinositol (GPI)-linker. Glypiated (GPI-linked) proteins contain a cleavable, hydrophobic amino-terminal signal sequence that targets the protein to the lumen of the endoplasmic reticulum (ER) and a cleavable, carboxy-terminal signal sequence that directs GPI anchoring. The GPI-anchoring signal consists of a hydrophobic region separated from the GPI-attachment site (w-site) by a hydrophilic spacer region. (See e.g. Galian et al. (2012) *J Biol Chem.* 11; 287(20): 16399-16409).

Because the expressed secreted or transmembrane prodrug converting enzymes are processed through the Golgi apparatus and endoplasmic reticulum, they can become glycosylated, which may lead in a reduction in activity of the enzyme compared to its non-glycosylated form. Accordingly, in some embodiments, prodrug converting enzymes is altered from its native sequence by substitution, deletion or insertion at one or more (e.g., two, three or four) glycosylation sites. For example, within the primary amino acid sequence of CPG2, there are three such consensus glycosylation motifs, located at residues Asn 222, Asn 264 and Asn 272 of SEQ ID NO: 1. In some embodiments, one or more of these glycosylation sites is altered to remove the glycosylation site. In some embodiments, one or more of Asn 222, Asn 264 and Asn 272 is removed. In some embodiments, one or more of Asn 222, Asn 264 and Asn 272 is substituted with leucine or glutamine (see, e.g., SEQ ID NOS: 3, 5, 7, and 40 which represent exemplary CPG2 polypeptides for expression).

In some embodiments, at least 1, 2, 3, 4, 5, 6, 7, 8, 9, 10 or more glycosylation sites in the prodrug converting enzyme are substituted. In some embodiments, 1, 2, 3, 4, 5 or more amino acids are deleted or inserted at or near the consensus glycosylation site. Typically, the alteration will be such that the enzyme retains its ability to convert a prodrug to an active drug at substantially the same rate as the unchanged, non-glycosylated enzyme. In this context, “substantially unchanged,” is within 1 order of magnitude, such as from about 2-fold less activity to 2, 3, 4, 5, 6, 7, 8, 9, or 10-fold or more activity.

In some embodiments, the enzyme is altered by truncation, substitution, deletion or insertion relative to its native form so as long as the activity of the enzyme is substantially unchanged as defined above. For example, in some embodiments small truncations in the N- and/or C-terminal sequence (e.g., about 1- to about 20 amino acids) relative to the native full-length sequence are employed. In some embodiments, such truncations are needed to link the polypeptide to the various other signal sequences or peptides as described herein. The activity of the altered enzyme can be measured in suitable model systems which can be prepared in routine ways known in the art.

A prodrug for use in the system is selected to be compatible with the prodrug converting enzyme, i.e., such that the enzyme will be capable of converting the prodrug into an active drug. In some embodiments, the active drug is a cytotoxic drug. In some embodiments, the active drug is a cytotoxic chemotherapeutic drug that is effective for the treatment of inflammatory and autoimmune diseases. In some embodiments, the toxicity of the prodrug to the patient being treated will be at least one order of magnitude less toxic to the patient than the active drug. In some embodiments, the active drug is several, e.g., 2, 3, 4, 5, or more orders of magnitude more toxic. Suitable prodrugs include prodrugs of cytotoxic chemotherapeutic drugs including, but not limited to, nitrogen mustards, methotrexate, doxorubicin, nucleosides, AMS, targeted cytotoxic therapies, such as erlotinib, dasatinib, tk inhibitors, and other compounds such as those described in WO88/07378, WO89/10140, WO90/02729, WO91/03460, EP-A-540 263, WO94/02450, WO95/02420 or WO95/03830, which are incorporated herein by reference. In some embodiments, the cytotoxic drug is selected from the group consisting of azathioprine, cyclophosphamide, mycophenolate mofetil, cyclosporine A, methotrexate, chlorambucil, or a combination thereof. In some embodiments, where the prodrug converting enzyme is CPG2, the prodrug is a CPG2-labile glutamate prodrug. In some embodiments, where the prodrug converting enzyme is β-lactamase, the prodrug is a β-lactamase-labile β-lactam prodrug.

In some embodiments, the prodrug is a prodrug form of an anti-inflammatory agent. In some embodiments, the prodrug is a prodrug form of a non-steroidal anti-inflammatory agent. Exemplary non-steroidal anti-inflammatory agents include, but are not limited to, aspirin, arthopan, celecoxib, diclofenac, etodolac, fenprofen, flurbiprofen, ibuprofen, ketoprofen, meclofamate, meloxicam, nabumetone, naproxen, oxaprozin, piroxicam, rofecoxib, sulindac, tolmetin, acetaminophen, or a combination thereof. In some embodiments, the prodrug is a prodrug form of a corticosteroid, such as, but not limited to, triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, or a combination thereof. In some embodiments, the prodrug is a prodrug form of a immunosuppressive agent, such as, but not limited to, azathioprine, cyclophosphamide, mycophenolate mofetil, cyclosporine A, methotrexate, chlorambucil, or a combination thereof.

In some embodiments, where the target site is a site of pathogenic infection, the prodrug is a prodrug form of an antiviral, antimicrobial, antifungal, or antiparasitic agents. In some embodiments, prodrug is a prodrug form of an antimicrobial, including antibiotics, cephalosporins, penicillins, erythromycins, and tetracyclines. Exemplary antibiotics include, but are not limited to, ceftazidime, cefepime, imipenem, aminoglycoside, vancomycin and antipseudomonal β-lactam. In some embodiments, prodrug is a prodrug form of an antiviral agent. Exemplary antiviral agents include, but are not limited to, cidofovir, alkoxyalkyl esters of cidofovir (CDV), cyclic CDV, and (S)-9-(3-hydroxy-2 phosphonylmethoxypropyl)adenine, 5-(dimethoxymethyl)-2'-deoxyuridine, isatin-beta-thiosemicarbazone, N-methanocarbathymidine, brivudine, 7-deazaneplanocin A, ST-246, Gleevec, 2'-beta-fluoro-2',3'-dideoxyadenosine, indinavir, nelfinavir, ritonavir, nevirapine, AZT, ddl, ddC, ganciclovir, acyclovir, ST-246, Gleevec, ribavirin, interferon, zidovudine, amantadine hydrochloride, and combinations thereof. In some embodiments, prodrug is a prodrug form of an antifungal agent. Exemplary antifungal agents include, but are not limited to, amphotericin B, dapsone, fluconazole, flucytosine, griseofulvin, itraconazole, ketoconazole, miconazole, clotrimazole, nystatin, and combinations thereof.

Exemplary prodrugs include a compound of Formula I (I)

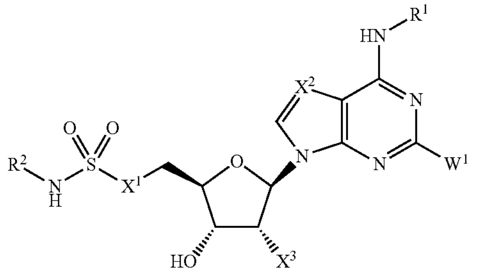

or a zwitterion, pharmaceutically acceptable salt, and/or solvate thereof, where $X^1$ is O or NH; $X^2$ is N or CH; $X^3$ is OH or H; $W^1$ is H or NH—$R^3$; two of $R^1$, $R^2$, and $R^3$ are H and the remaining $R^1$, $R^2$, and $R^3$ is

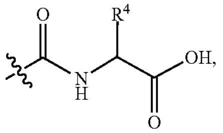

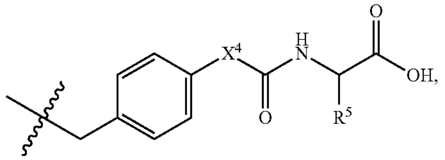

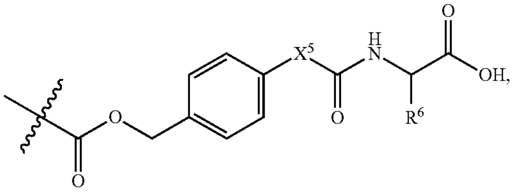

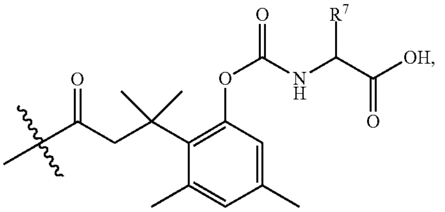

or

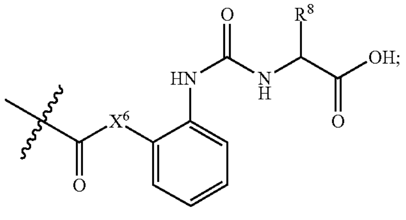

$X^4$ and $X^5$ are each independently O or NH; $X^6$ is O, NH, $CH_2$, or $C(Me)_2$; $R^4$, $R^5$, $R^6$, $R^7$, and $R^8$ are each independently H, $-(CH_2)_3-NH(NH)-NH_2$, $-(CH_2)_3-NH_2$, $-(CH_2)_4-NH_2$, $-CH_2-C(O)OH$, $-(CH_2)_2-C(O)OH$,

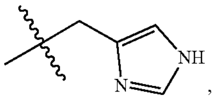

, or

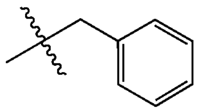

.

In particular, it may be that two of $R^1$, $R^2$, and $R^3$ are H and the remaining $R^1$, $R^2$, and $R^3$ is

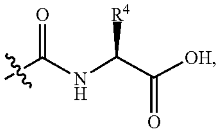

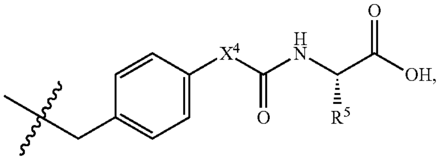

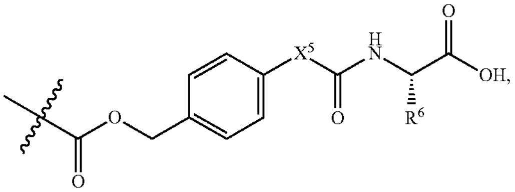

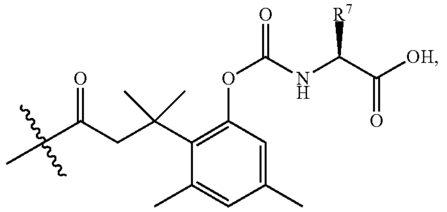

or

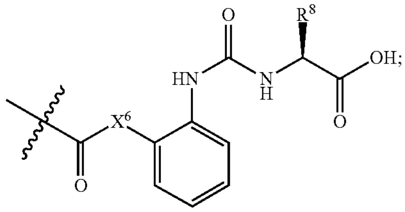

and $R^4$, $R^5$, $R^6$, $R^7$, and $R^8$ are each independently $-(CH_2)_3-NH(NH)-NH_2$, $-(CH_2)_3-NH_2$, $-(CH_2)_4-NH_2$, $-CH_2-C(O)OH$, $-(CH_2)_2-C(O)OH$,

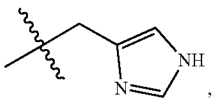

, or

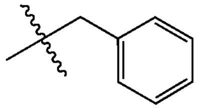

.

Exemplary prodrugs useful in the present technology also include a compound of Formula II (II)

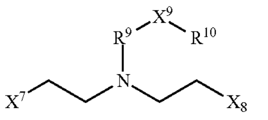

or a zwitterion, pharmaceutically acceptable salt, and/or solvate thereof, where $X^7$ and $X^8$ are each independently Cl, Br, I, O—$S(O)_2CH_3$, or O—$S(O)_2$-tolyl; $X^9$ is —C(O)—O, —C(O)—NH, O, or NH; $R^9$ is a bond, alkylene, arylene, aralkylene, heteroarylene, or heteroaralkylene; and $R^{10}$ is

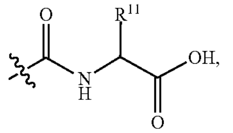

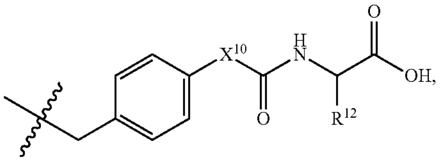

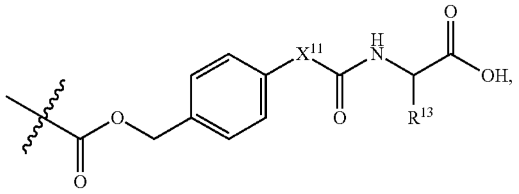

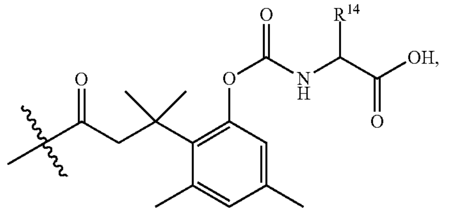

or

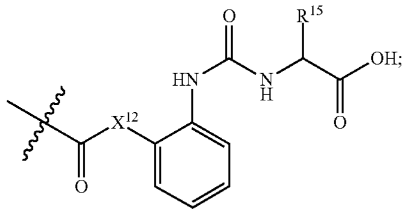

$X^{10}$ and $X^{11}$ are each independently O or NH; $X^{12}$ is O, NH, $CH_2$, or $C(Me)_2$; $R^{11}$, $R^{12}$, $R^{13}$, $R^{14}$, and $R^{15}$ are each independently H, —$(CH_2)_3$—NH(NH)—$NH_2$, —$(CH_2)_3$—$NH_2$, —$(CH_2)_4$—$NH_2$, —$CH_2$—C(O))OH, —$(CH_2)_2$—C(O)OH,

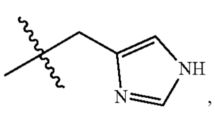

, or

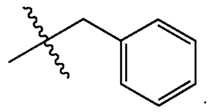

.

In particular, $R^{10}$ may be

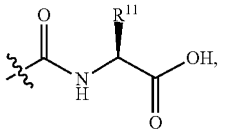

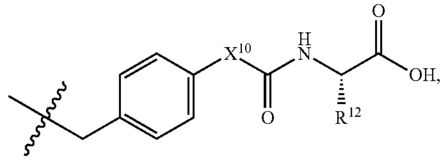

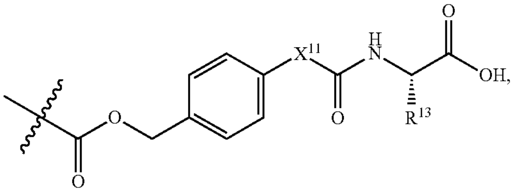

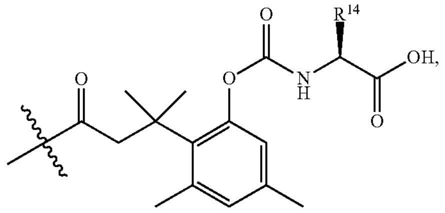

or

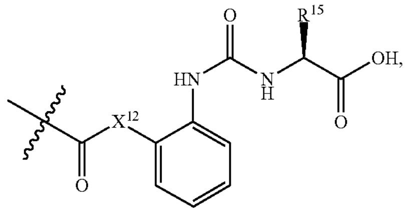

where $R^{11}$, $R^{12}$, $R^{13}$, $R^{14}$, and $R^{15}$ are each independently —$(CH_2)_3$—NH(NH)—$NH_2$, —$(CH_2)_3$—$NH_2$, —$(CH_2)_4$—$NH_2$, —$CH_2$—C(O)OH, —$(CH_2)_2$—C(O)OH,

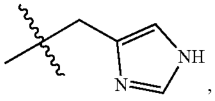

, or

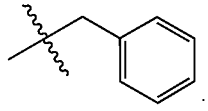

.

In any embodiment herein, it may be that when $X^9$ is —C(O)—O, $R^{10}$ is

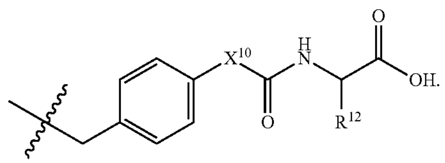

In any embodiment herein, it may be that when $X^9$ is —C(O)—O, $R^{10}$ is

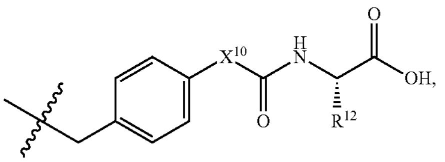

and $R^{12}$ is $-(CH_2)_3-NH(NH)-NH_2$, $-(CH_2)_3-NH_2$, $-(CH_2)_4-NH_2$, $-CH_2-C(O)OH$, $-(CH_2)_2-C(O)OH$,

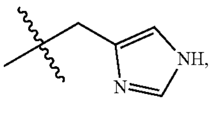

or

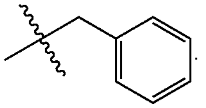

The prodrug compound of Formula II may be a compound of any one of Formulas IIa-IIe (IIa)

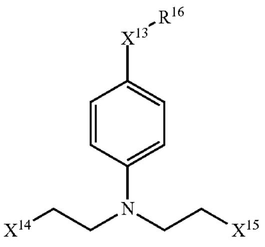

(IIb)

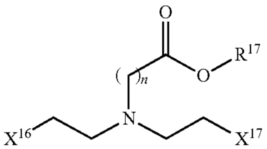

(IIc)

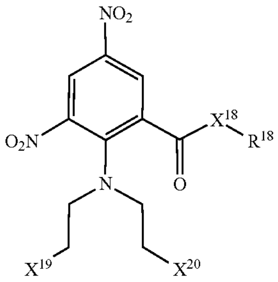

(IId)

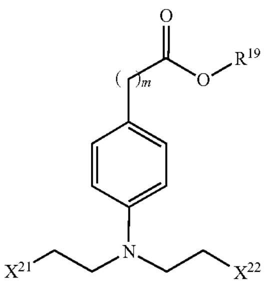

-continued (IIe)

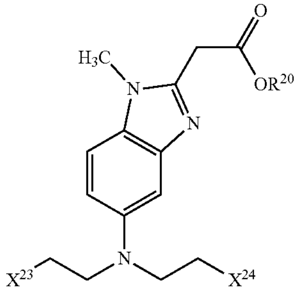

or a zwitterion, pharmaceutically acceptable salt, and/or solvate thereof, where $X^{13}$ and $X^{18}$ are each independently O or NH; $X^{14}$, $X^{15}$, $X^{16}$, $X^{17}$, $X^{19}$, $X^{20}$, $X^{21}$, $X^{22}$, $X^{23}$ are each independently Cl, Br, I, $O-S(O)_2CH_3$, or $O-S(O)_2$-tolyl; n and m are each independently 0, 1, 2, 3, 4, or 5; $R^{16}$, $R^{17}$, $R^{18}$, $R^{19}$, and $R^{20}$ are each independently

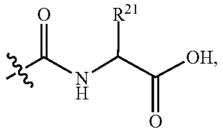

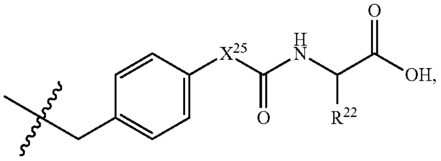

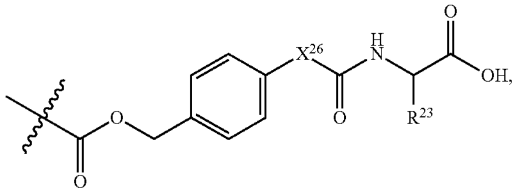

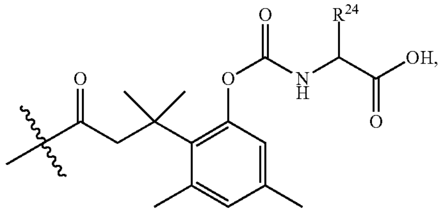

or

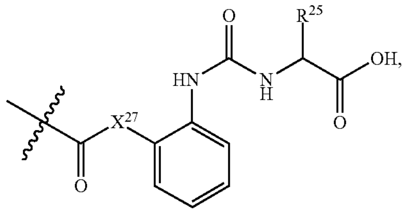

$X^{25}$ and $X^{26}$ are each independently O or NH; $X^{27}$ is O, NH, $CH_2$, or $C(Me)_2$; $R^{21}$, $R^{22}$, $R^{23}$, $R^{24}$, and $R^{25}$ are each independently H, $-(CH_2)_3-NH(NH)-NH_2$, $-(CH_2)_3-NH_2$, $-(CH_2)_4-NH_2$, $-CH_2-C(O)OH$, $-(CH_2)_2-C(O)OH$,

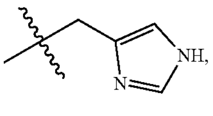
or
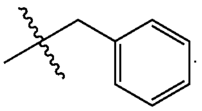

In any embodiment herein, $R^{16}$, $R^{17}$, $R^{18}$, $R^{19}$, and $R^{20}$ may each independently be

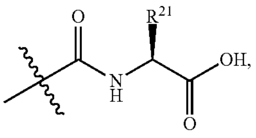

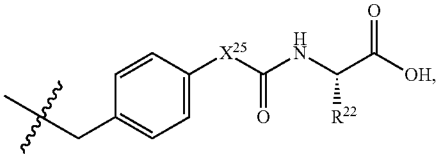

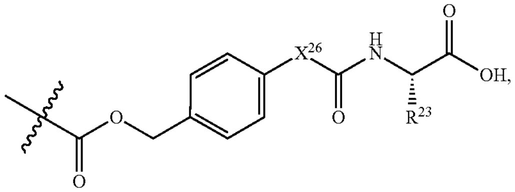

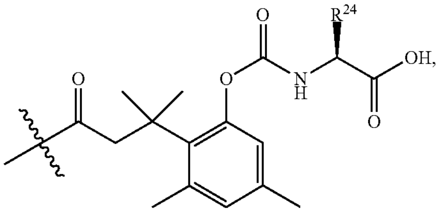

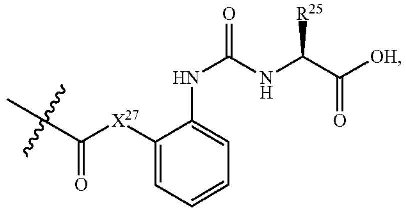

where $R^{21}$, $R^{22}$, $R^{23}$, $R^{24}$, and $R^{25}$ are each independently H, $-(CH_2)_3-NH(NH)-NH_2$, $-(CH_2)_3-NH_2$, $-(CH_2)_4-NH_2$, $-CH_2-C(O)OH$, $-(CH_2)_2-C(O)OH$,

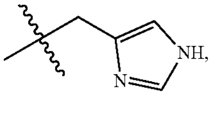
or
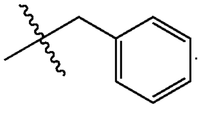

The prodrug compound of Formula II may be a compound of Formula IIf or Formula IIg (IIf)

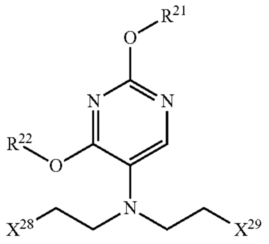

(IIg)

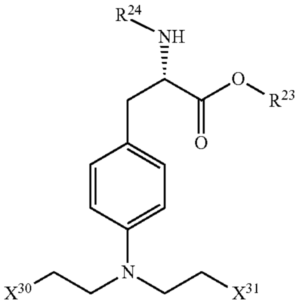

or a zwitterion, pharmaceutically acceptable salt, and/or solvate thereof, where; $X^{28}$, $X^{29}$, $X^{30}$, and $X^{31}$ are each independently Cl, Br, I, $O-S(O)_2CH_3$, or $O-S(O)_2$-tolyl; one of $R^{21}$ and $R^{22}$ is H and one of $R^{23}$ and $R^{24}$ is H and the remaining $R^{21}$ and $R^{22}$ (for Formula IIf) and $R^{23}$ and $R^{24}$ (for Formula IIg) are each independently

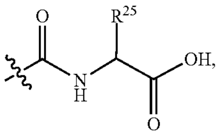

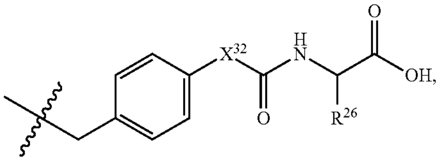

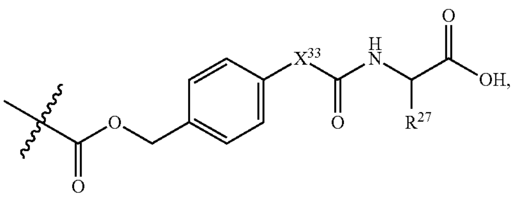

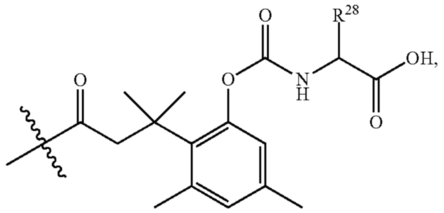
or

-continued

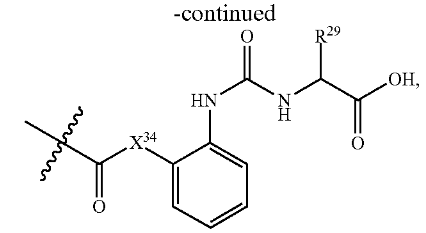

where $X^{32}$ and $X^{33}$ are each independently O or NH; $X^{34}$ is O, NH, $CH_2$, or $C(Me)_2$; $R^{25}$, $R^{26}$, $R^{27}$, $R^{28}$, and $R^{29}$ are each independently H, $—(CH_2)_3—NH(NH)—NH_2$, $—(CH_2)_3—NH_2$, $—(CH_2)_4—NH_2$, $—CH_2—C(O)OH$, $—(CH_2)_2—C(O)OH$,

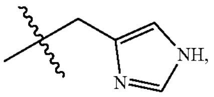 or 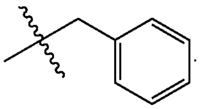

In any embodiment herein, one of $R^{21}$ and $R^{22}$ is H and one of $R^{23}$ and $R^{24}$ is H and the remaining $R^{21}$ and $R^{22}$ (for Formula IIf) and $R^{43}$ and $R^{44}$ (for Formula IIg) may each independently

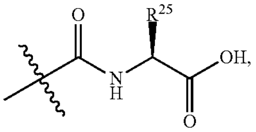

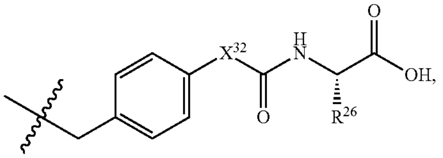

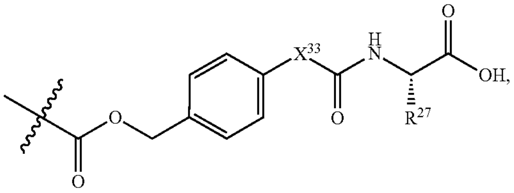

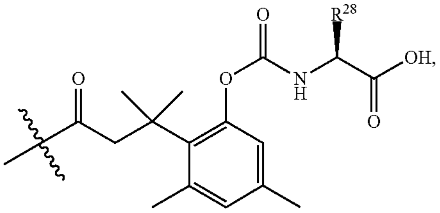 or

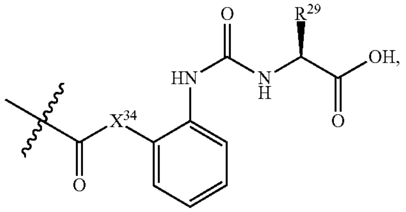

where $R^{25}$, $R^{26}$, $R^{27}$, $R^{28}$, and $R^{29}$ are each independently $—(CH_2)_3—NH(NH)—NH_2$, $—(CH_2)_3—NH_2$, $—(CH_2)_4—NH_2$, $—CH_2—C(O)OH$, $—(CH_2)_2—C(O)OH$,

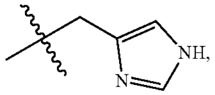 or 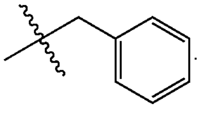

Exemplary prodrugs useful in the present technology further include prodrugs of erlotinib, such as a compound of Formula III (III)

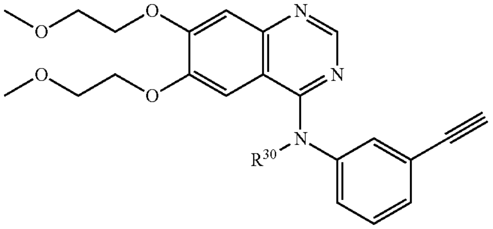

or a zwitterion, pharmaceutically acceptable salt, and/or solvate thereof, where $R^{30}$ is

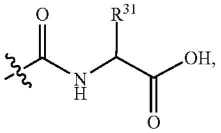

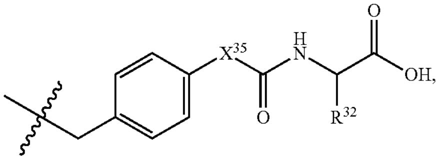

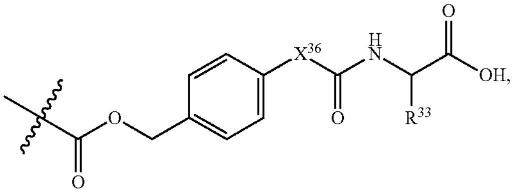

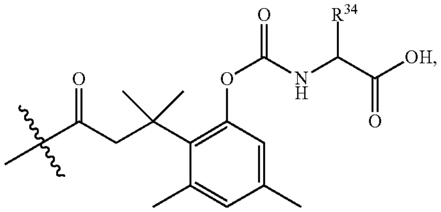 or

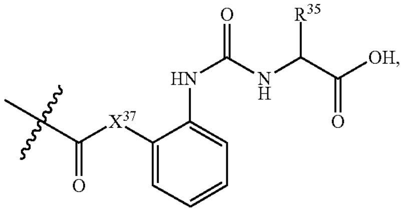

where $X^{35}$ and $X^{36}$ are each independently O or NH; $X^{37}$ is O, NH, $CH_2$, or $C(Me)_2$; $R^{31}$, $R^{32}$, $R^{33}$, $R^{34}$, and $R^{35}$ are each independently H, $—(CH_2)_3—NH(NH)—NH_2$, $—(CH_2)_3—NH_2$, $—(CH_2)_4—NH_2$, $—CH_2—C(O)OH$, $—(CH_2)_2—C(O)OH$,

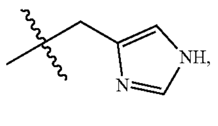
or
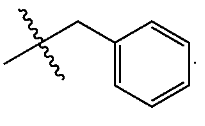

In particular, $R^{30}$ may be

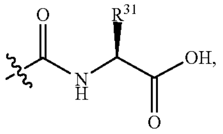

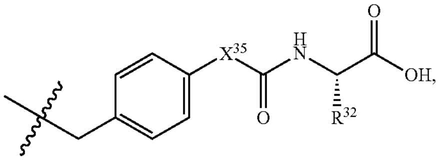

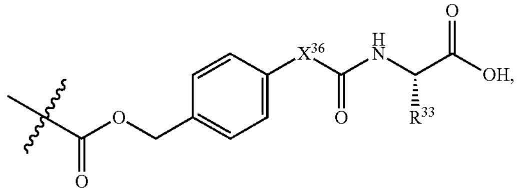

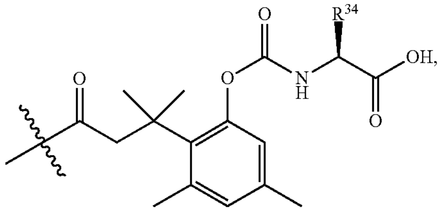
or

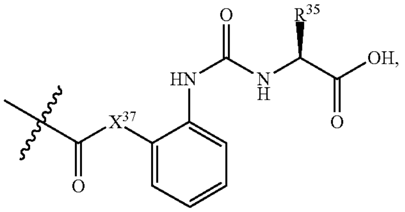

where $R^{31}$, $R^{32}$, $R^{33}$, $R^{34}$, and $R^{35}$ are each independently $-(CH_2)_3-NH(NH)-NH_2$, $-(CH_2)_3-NH_2$, $-(CH_2)_4-NH_2$, $-CH_2-C(O)OH$, $-(CH_2)_2-C(O)OH$,

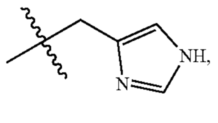
or
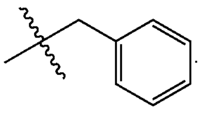

Pharmaceutically acceptable salts of compounds described herein include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^-$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

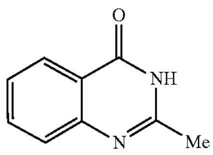

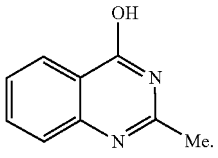

As another example, guanidines may exhibit the following isomeric forms in protic organic solution, also referred to as tautomers of each other:

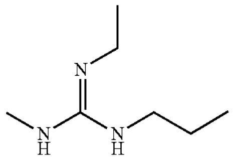

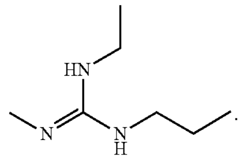

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

The prodrug compounds taught herein can be modified based on the selection of the prodrug converting enzyme expressed. Non-limiting examples of other prodrug systems that can be used in combination with the present technology are described in the art for carboxypeptidase A (e.g., prodrugs utilizing a phenylalanine mask, described e.g., in Vitols et al. *Cancer Res.* 55(3):478-81 (1995) and Deckert et al. *Int J Oncol.* 24(5):1289-95 (2004)); glucosidases (e.g., prodrugs utilizing a glycoside mask, described e.g., in Tietze et al. *J Med Chem.* 52(2):537-43 (2009) and Tietze et al. *Chem Eur J.* 17(6):1922-9 (2001)); β-lactamase (e.g., prodrugs utilizing a cephalosporin mask, described, e.g., in Kerr et al. *Bioconjugate Chem.* 9(2):255-9 (1998) and Zhou et al. *OncoTargets Ther.* 7:535-41 (2014)); and nitroreductases (e.g., prodrugs utilizing a nitro→amine mask, described, e.g., in Williams et al. *Biochem J.* 471(2):131-53 (2015).

The prodrug compounds taught herein can be employed in any method or use requiring a prodrug compound. For example, any clinical application that employs an enzyme that can cleave the prodrugs provided herein to the active drug can use the provided prodrug compounds. Such methods and uses are not limited to the methods and uses described herein. For example, the prodrug compounds taught herein are not limited to use with the engineered immune cells (e.g., SEAKER cells) and related technologies provided herein. In some embodiments, the prodrug compounds provided herein are converted into an active drug by any suitable prodrug converting enzyme intracellularly (e.g. a suitable prodrug converting enzyme transduced into a cell or expressed by a cell). In some embodiments, the prodrug compounds provided herein are converted into an active drug by any suitable prodrug converting enzyme extracellularly. In some embodiments, the prodrug compounds are converted into an active drug by any suitable prodrug converting enzyme conjugated to ligand. In some embodiments, the ligand is an antibody. In some embodiments, the prodrug compounds are employed in combination with a directed enzyme prodrug therapy (DEPT). In some embodiments, the directed enzyme prodrug therapy is an antibody-directed enzyme prodrug therapy (ADEPT), a gene-directed enzyme prodrug therapy (GDEPT), a virus-directed enzyme prodrug therapy (VDEPT), a lectin-directed Enzyme-Activated Prodrug Therapy (LEAPT), polymer-directed enzyme prodrug therapy (PDEPT), clostridia-directed enzyme prodrug therapy (CDEPT) or any combination thereof.

Targeting Ligands and Target Antigens

In some embodiments, the engineered immune cells provided herein express a T-cell receptor (TCR) or other cell-surface ligand that binds to a target antigen. The antigen can be any antigen that is present or expressed at a target site. In some embodiments, the target antigen is an antigen, such as an antigen from a pathogen, or an inflammatory antigen. The cell-surface ligand can be any molecule that directs an immune cell to a target site (e.g., a site of pathogenic infection or a site of inflammation). Exemplary cell surface ligands include, for example endogenous receptors, engineered receptors, or other specific ligands to achieve targeting of the immune cell to a target site. In some embodiments, the receptor is a T cell receptor. In some embodiments, the T cell receptor is a wild-type, or native, T-cell receptor that binds to a target antigen. In some embodiments, the receptor, e.g. a T cell receptor, is non-native receptor (e.g., not endogenous to the immune cells). In some embodiments, the receptor is a chimeric antigen receptor (CAR), for example, a T cell CAR, that binds to a target antigen.

In some embodiments, the target antigen is an antigen from a pathogen. Antigens can be derived from a wide variety of pathogens, including viruses, bacteria, fungi, plants, protozoans and other parasites. In some embodiments, the target antigen is an antigen from a pathogen presented in the context of an MEW molecule. In some embodiments, the MEW protein is a MHC class I protein. In some embodiments, the MEW Class I protein is an HLA-A, HLA-B, or HLA-C molecules. In some embodiments, target antigen is an antigen from a pathogen presented in the context of an HLA-A2 molecule.

In some embodiments, the target antigen is a bacterial antigen. Exemplary bacterial antigens are derived from organisms that cause diphtheria, tetanus, pertussis, meningitis, and other pathogenic states, including, without limitation, antigens derived from *Corynebacterium diphtherias, Clostridium tetani, Bordetella pertussis, Neisseria meningitides*, including serotypes Meningococcus A, B, C, Y and WI35 (MenA, B, C, Y and WI35), *Haemophilus* influenza type B (Hib), and *Helicobacter pylori*. Examples of bacterial antigens include capsule antigens (e.g., protein or polysaccharide antigens such as CP5 or CP8 from the *S. aureus* capsule); cell wall antigens, including outer membrane antigens, such as peptidoglycan (e.g., mucopeptides, glycopeptides, mureins, muramic acid residues, and glucose amine residues) polysaccharides, teichoic acids (e.g., ribitol teichoic acids and glycerol teichoic acids), phospholipids, hopanoids, and lipopolysaccharides (e.g., the lipid A or O-polysaccharide moieties of bacteria such as *Pseudomonas aeruginosa* serotype O11); plasma membrane components including phospholipids, hopanoids, and proteins; proteins and peptidoglycan found within the periplasm; fimbrae antigens, pili antigens, flagellar antigens, and S-layer antigens. *S. aureus* antigens can be a serotype 5 capsular antigen, a serotype 8 capsular antigen, and antigen shared by serotypes 5 and 8 capsular antigens, a serotype 336 capsular antigen, protein A, coagulase, clumping factor A, clumping factor B, a fibronectin binding protein, a fibrinogen binding protein, a collagen binding protein, an elastin binding protein, a MHC analogous protein, a polysaccharide intracellular adhesion, alpha hemolysin, beta hemolysin, delta hemolysin, gamma hemolysin, Panton-Valentine leukocidin, exfoliative toxin A, exfoliative toxin B, V8 protease, hyaluronate lyase, lipase, staphylokinase, LukDE leukocidin, an enterotoxin, toxic shock syndrome toxin-1, poly-N-succinyl beta-1-6 glucosamine, catalase, beta-lactamase, teichoic acid, peptidoglycan, a penicillin binding protein, chemotaxis inhibiting protein, complement inhibitor, Sbi, and von Willebrand factor binding protein.

In some embodiments, the target antigen is a viral antigen. In some embodiments, the target antigen is derived from adenoviridae (e.g. adenovirus), papovaviridae (papillomavirus, HPV-1), parvoviridae, herpesviridae (e.g., herpes simplex virus (HSV-1, HSV-2), varicella-zoster virus (VSV), cytomegalovirus (CMV), Epstein-Barr virus (EBV)), poxviridae (e.g. smallpox virus, cow pox virus, sheep pox virus, orf virus, monkey pox virus, vaccinia virus), hepadnaviridae (e.g., hepatitis B virus), anelloviridae, reoviridae, picornaviridae (e.g., enterovirus, rhinovirus, hepatovirus, cardiovirus, aphthovirus, poliovirus, parechovirus, erbovirus, kobuvirus, teschovirus, coxsackie), caliciviridae (e.g., Norwalk virus), togaviridae (e.g., rubella virus, dengue virus), arenaviridae, flaviviridae (e.g., dengue virus, hepatitis C virus, yellow fever virus), orthomyxoviridae (e.g., influenza virus types A, B and C), paramyxoviridae (e.g., mumps virus, measles virus, respiratory syncytial virus (RSV)), bunyaviridae, rhabodoviridae (e.g., rabies virus), filoviridae (e.g., Ebola virus, Marburg virus), coronaviridae, bornaviridae, arteriviridae, hepeviridae (e.g., hepatitis e virus), and retroviradae (e.g., HTLV-I, HTLV-II, HIV-1, HIV-2, simian immunodeficiency virus (SIV)). In some embodiments the target antigen is derived from a capsid protein or an envelope protein. In some embodiments the target antigen is derived from a protein expressed in an infected cell. In some embodiments the target antigen is derived from an HSV-1 or HSV-2 protein, such as gB, gD, gH, VP16 and VP22. In some embodiments the target antigen is derived from a CMV protein, such as gB and gH. In some embodiments the target antigen is derived from a HCV protein, such as E1 (also known as E). In some embodiments the target antigen is derived from an HPV protein, such as E6 and E7. In some embodiments the target antigen is derived from an HIV-1 protein, such as gp120, gp41, gp160, gag and pol.

In some embodiments, the target antigen is a parasitic antigen. Examples of parasitic antigens include those derived from organisms causing malaria and Lyme disease.

In some embodiments, the target antigen is an autoantigen. Exemplary autoantigens, include, but are not limited to, acetylcholine receptor, actin, adenine nucleotide translocator, adrenoceptor, aromatic L-amino acid decarboxylase, asialoglycoprotein receptor, bactericidal/permeability increasing protein (BPi), calcium sensing receptor, cholesterol side chain cleavage enzyme, collagen type IV-chain, cytochrome P450 2D6, desmin, desmoglein-1, desmoglein-3, F-actin, GM-gangliosides, glutamate decarboxylase, glutamate receptor, H/K ATPase, 17-hydroxylase, 21-hydroxylase, IA-2 (ICAS12), insulin, insulin receptor, intrinsic factor type 1, leucocyte function antigen 1, myelin associated glycoprotein, myelin basic protein, myelin oligodendrocyte protein, myosin, P80-coilin, pyruvate dehydrogenase complex E2 (PDC-E2), sodium iodide symporter, SOX-10, thyroid and eye muscle shared protein, thyroglobulin, thyroid peroxidase, thyrotropin receptor, tissue transglutaminase, transcription coactivator p75, tryptophan hydroxylase, tyrosinase, tyrosine hydroxylase, ACTH, aminoacyl-tRNA-histidyl synthetase, cardiolipin, carbonic anhydrase II, centromere associated proteins, DNA-dependent nucleosome-stimulated ATPase, fibrillarin, fibronectin, glucose 6 phosphate isomerase, beta 2-glycoprotein I, golgin (95, 97, 160, 180), heat shock proteins, hemidesmosomal protein 180, histone H2A, H2B, keratin, IgE receptor, Ku-DNA protein kinase, Ku-nucleoprotein, La phosphoprotein, myeloperoxidase, proteinase 3, RNA polymerase I-III, signal recognition protein, topoisomerase I, tubulin, vimentin, myelin associated oligodendrocyte basic protein (MOBP), proteolipid protein, oligodendrocyte specific protein (OSP/Claudin 11), cyclic nucleotide 3' phosphodiesterase (CNPase), BP antigen 1 (BPAG1-e), transaldolase (TAL), human mitochondrial autoantigens PDC-E2 (Novo 1 and 2), OGDC-E2 (Novo 3), and BCOADC-E2 (Novo 4), bullous pemphigoid (BP)180, laminin 5 (LN5), DEAD-box protein 48 (DDX48) and insulinoma-associated antigen-2.

In some embodiments, the target antigen is associated with a particular target tissue or target organ. In some embodiments, the target antigen is expressed by one or more cells or one or more cell types in a target tissue or target organ. In some embodiments, the target antigen is found in the extracellular matrix or non-cell portion of the target tissue or target organ.

In some embodiments, the target antigen is an inflammatory antigen. In some embodiments, the inflammatory antigen is a multiple sclerosis antigen or a joint-associated antigen. Exemplary multiple sclerosis-associated antigens include, but are not limited to, to myelin basic protein (MBP), myelin associated glycoprotein (MAG), myelin oligodendrocyte protein (MOG), proteolipid protein (PLP), oligodendrocyte myelin oligoprotein (OMGP), myelin associated oligodendrocyte basic protein (MOBP), oligodendrocyte specific protein (OSP/Claudin 11), heat shock proteins, oligodendrocyte specific proteins (OSP), NOGO A, glycoprotein Po, peripheral myelin protein 22 (PMP22), 2'3'-cyclic nucleotide 3'-phosphodiesterase (CNPase). Exemplary joint-associated antigens include, but are not limited to, citrulline-substituted cyclic and linear filaggrin peptides, collagen type II peptides, human cartilage glycoprotein 39 (HCgp39) peptides, HSP, heterogeneous nuclear ribonucleoprotein (hnRNP) A2 peptides, hnRNP Bl, hnRNP D, Ro60/52, HSP60, 65, 70 and 90, BiP, keratin, vimentin, fibrinogen, collagen type I, III, IV and V peptides, annexin V, Glucose 6 phosphate isomerase (GPI), acetyl-calpastatin, pyruvate dehydrogenase (PDH), aldolase, topoisomerase I, snRNP, PARP, Scl-70, Scl-100, phospholipid antigen including anionic cardiolipin and phosphatidylserine, neutrally charged phosphatidylethanolamine and phosphatidylcholine, matrix metalloproteinase, fibrillin, and aggrecan. In some embodiments, the inflammatory antigen is a proinflammatory cytokine or chemokine. In some embodiments, the inflammatory antigen is IL-1$\alpha$, IL-1$\beta$, IL-2, IL-6, IL-7, IL-8, IL-11, MCP-1, MCP-3, MCP-5, MIP-1$\beta$, MIP-2, MIP-3$\beta$, RANTES, TNF$\alpha$, VEGF or CD40 ligand. In some embodiments, the inflammatory antigen is a cluster of differentiation antigen (a “CD antigen”). Exemplary CD antigens that can be employed for targeting are provided, for example, in Engel et al., *J Immunol* 195:4555-4563 (2015) (see e.g., Table 1), which is incorporated by reference herein in its entirety.

In some embodiments, the target antigen is a stem cell-specific marker. In some embodiments, the stem cell-specific marker expressed by cells in the bone marrow. Exemplary bone marrow and stem cell specific markers that can be employed for targeting are provided, for example, in Wilson et al., *Nature Reviews Immunology* 6: 93-106 (2006) and Boxall et al., *Stem Cells International Volume* 2012 (2012) (see e.g., Tables 1 and 2), which are incorporated by reference herein in their entirety. In some embodiments, the stem cell-specific marker is CD34.

Chimeric Antigen Receptors

In some embodiments, the engineered immune cells provided herein express at least one chimeric antigen receptor (CAR). CARs are engineered receptors, which graft or confer a specificity of interest onto an immune effector cell. For example, CARs can be used to graft the specificity of a monoclonal antibody onto an immune cell, such as a T cell.

In some embodiments, transfer of the coding sequence of the CAR is facilitated by nucleic acid vector, such as a retroviral vector.

There are currently three generations of CARs. In some embodiments, the engineered immune cells provided herein express a "first generation" CAR. "First generation" CARs are typically composed of an extracellular antigen binding domain (e.g., a single-chain variable fragment (scFv)) fused to a transmembrane domain fused to cytoplasmic/intracellular domain of the T cell receptor (TCR) chain. "First generation" CARs typically have the intracellular domain from the CD3ζ chain, which is the primary transmitter of signals from endogenous TCRs. "First generation" CARs can provide de novo antigen recognition and cause activation of both $CD4^+$ and $CD8^+$ T cells through their CD3ζ chain signaling domain in a single fusion molecule, independent of HLA-mediated antigen presentation.

In some embodiments, the engineered immune cells provided herein express a "second generation" CAR. "Second generation" CARs add intracellular domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-IBB) and activation (e.g., CD3ζ). Preclinical studies have indicated that "Second Generation" CARs can improve the activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL).

In some embodiments, the engineered immune cells provided herein express a "third generation" CAR. "Third generation" CARs comprise those that provide multiple co-stimulation (e.g., CD28 and 4-1BB) and activation (e.g., CD3ζ).

In accordance with the presently disclosed subject matter, the CARs of the engineered immune cells provided herein comprise an extracellular antigen-binding domain, a transmembrane domain and an intracellular domain.

Extracellular Antigen Binding Domain of a CAR

In certain embodiments, the extracellular antigen-binding domain of a CAR specifically binds a target site antigen, such as an antigen from a pathogen, or an inflammatory antigen. In certain embodiments, the extracellular antigen-binding domain is derived from a monoclonal antibody (mAb) that binds to a target antigen. In some embodiments, the extracellular antigen-binding domain comprises an scFv. In some embodiments, the extracellular antigen-binding domain comprises a Fab, which is optionally crosslinked. In a some embodiments, the extracellular binding domain comprises a $F(ab)_2$. In some embodiments, any of the foregoing molecules are comprised in a fusion protein with a heterologous sequence to form the extracellular antigen-binding domain. In certain embodiments, the extracellular antigen-binding domain comprises a human scFv that binds specifically to a target antigen. In certain embodiments, the scFv is identified by screening scFv phage library with a target antigen-Fc fusion protein.

In certain embodiments, the extracellular antigen-binding domain of a presently disclosed CAR has a high binding specificity and high binding affinity to a target antigen (e.g., a an antigen from a pathogen or an inflammatory antigen). For example, in some embodiments, the extracellular antigen-binding domain of the CAR (embodied, for example, in a human scFv or an analog thereof) binds to a particular target antigen with a dissociation constant ($K_d$) of about $1\times10^{-5}$ M or less. In certain embodiments, the $K_d$ is about $5\times10^{-6}$ M or less, about $1\times10^{-6}$ M or less, about $5\times10^{-7}$ M or less, about $1\times10^{-7}$ M or less, about $5\times10^{-8}$ M or less, about $1\times10^{-8}$ M or less, about $5\times10^{-9}$ or less, about $4\times10^{-9}$ or less, about $3\times10^{-9}$ or less, about $2\times10^{-9}$ or less, or about $1\times10^{-9}$ M or less. In certain non-limiting embodiments, the $K_d$ is from about $3\times10^{-9}$ M or less. In certain non-limiting embodiments, the $K_d$ is from about $3\times10^{-9}$ to about $2\times10^{-7}$.

Binding of the extracellular antigen-binding domain (embodiment, for example, in a human scFv or an analog thereof) of a presently disclosed antigen-targeted CAR can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or a scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the extracellular antigen-binding domain of the antigen-targeted CAR is labeled with a fluorescent marker. Non-limiting examples of fluorescent markers include green fluorescent protein (GFP), blue fluorescent protein (e.g., EBFP, EBFP2, Azurite, and mKalamal), cyan fluorescent protein (e.g., ECFP, Cerulean, and CyPet), and yellow fluorescent protein (e.g., YFP, Citrine, Venus, and YPet). In certain embodiments, the human scFv of a presently disclosed antigen-targeted CAR is labeled with GFP.

In some embodiments, the extracellular antigen-binding domain of the expressed CAR binds to target antigen that is expressed by a cell found at the target site, such as a microbial cell, a parasite, a cell infected with a pathogen, or an inflammatory cell. In some embodiments, the extracellular antigen-binding domain of the expressed CAR binds to target antigen that is expressed on the surface of a cell. In some embodiments, the extracellular antigen-binding domain of the expressed CAR binds to target antigen that is expressed on the surface of a cell in combination with an MEW protein. In some embodiments, the MHC protein is a MHC class I protein. In some embodiments, the MHC Class I protein is an HLA-A, HLA-B, or HLA-C molecules. In some embodiments, the extracellular antigen-binding domain of the expressed CAR binds to target antigen that is expressed on the surface of a cell not in combination with an MHC protein.

In certain embodiments, the extracellular antigen-binding domain (e.g., human scFv) comprises a heavy chain variable region and a light chain variable region, optionally linked with a linker sequence, for example a linker peptide (e.g., SEQ NO:21), between the heavy chain variable region and the light chain variable region. In certain embodiments, the extracellular antigen-binding domain is a human scFv-Fc fusion protein or full length human IgG with $V_H$ and $V_L$ regions.

In certain embodiments, the extracellular antigen-binding domain comprises a human scFv that binds to a CD19 antigen. In some embodiments, the scFv comprises a polypeptide having an amino acid sequence of SEQ ID NO: 19.

(SEQ ID NO: 19)

MALPVTALLLPLALLLHAEVKLQQSGAELVRPGSSVKISCKASGYAFSSYW

MNWVKQRPGQGLEWIGQIYPGDGDTNYNGKFKGQATLTADKSSSTAYMQLS

GLTSEDSAVYFCARKTISSVVDFYFDYWGQGTTVTVSSGGGGSGGGGSGGG

GSDIELTQSPKFMSTSVGDRVSVTCKASQNVGTNVAWYQQKPGQSPKPLIY

SATYRNSGVPDRFTGSGSGTDFTLTITNVQSKDLADYFCQQYNRYPYTSGG

GTKLEIKR

In some embodiments, the scFv comprises a polypeptide having an amino acid sequence that is at least 80%, at least 85%, at least 90%, or at least 95% identical to SEQ ID NO: 19. For example, the scFv comprises a polypeptide having an amino acid sequence that is about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 19.

In some embodiments, the scFv is encoded by a nucleic acid having a nucleic acid sequence of SEQ ID NO: 20.

(SEQ ID NO: 20)

ATGGCTCTCCCAGTGACTGCCCTACTGCTTCCCCTAGCGCTTCTCCTGCAT

GCAGAGGTGAAGCTGCAGCAGTCTGGGGCTGAGCTGGTGAGGCCTGGGTCC

TCAGTGAAGATTTCCTGCAAGGCTTCTGGCTATGCATTCAGTAGCTACTGG

ATGAACTGGGTGAAGCAGAGGCCTGGACAGGGTCTTGAGTGGATTGGACAG

ATTTATCCTGGAGATGGTGATACTAACTACAATGGAAAGTTCAAGGGTCAA

GCCACACTGACTGCAGACAAATCCTCCAGCACAGCCTACATGCAGCTCAGC

GGCCTAACATCTGAGGACTCTGCGGTCTATTTCTGTGCAAGAAAGACCATT

AGTTCGGTAGTAGATTTCTACTTTGACTACTGGGGCCAAGGGACCACGGTC

ACCGTCTCCTCAGGTGGAGGTGGATCAGGTGGAGGTGGATCTGGTGGAGGT

GGATCTGACATTGAGCTCACCCAGTCTCCAAAATTCATGTCCACATCAGTA

GGAGACAGGGTCAGCGTCACCTGCAAGGCCAGTCAGAATGTGGGTACTAAT

GTAGCCTGGTATCAACAGAAACCAGGACAATCTCCTAAACCACTGATTTAC

TCGGCAACCTACCGGAACAGTGGAGTCCCTGATCGCTTCACAGGCAGTGGA

TCTGGGACAGATTTCACTCTCACCATCACTAACGTGCAGTCTAAAGACTTG

GCAGACTATTTCTGTCAACAATATAACAGGTATCCGTACACGTCCGGAGGG

GGGACCAAGCTGGAGATCAAACGG

In some embodiments, the scFv is encoded by a nucleic acid having a nucleic acid sequence that is at least 80%, at least 85%, at least 90%, or at least 95% identical to SEQ ID NO: 20. In some embodiments, the scFv is encoded by a nucleic acid having a nucleic acid sequence of SEQ ID NO: 20. In some embodiments, the scFv is encoded by a nucleic acid having a nucleic acid sequence that is about 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 20.

In certain non-limiting embodiments, an extracellular antigen-binding domain of the presently disclosed CAR can comprise a linker connecting the heavy chain variable region and light chain variable region of the extracellular antigen-binding domain. As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In certain embodiments, the linker comprises amino acids having the sequence set forth in SEQ ID NO: 21. In certain embodiments, the nucleotide sequence encoding the amino acid sequence of SEQ ID NO: 21 is set forth in SEQ ID NO: 22.

In addition, the extracellular antigen-binding domain can comprise a leader or a signal peptide that directs the nascent protein into the endoplasmic reticulum. Signal peptide or leader can be essential if the CAR is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway. In certain embodiments, the signal peptide is covalently joined to the N-terminus of the extracellular antigen-binding domain. In certain embodiments, the signal peptide comprises a CD8 signal polypeptide comprising amino acids having the sequence set forth in SEQ ID NO: 11 as provided below.

(SEQ ID NO: 11)

MALPVTALLLPLALLLHAARP

The nucleotide sequence encoding the amino acid sequence of SEQ ID NO: 11 is set forth in SEQ ID NO: 12, which is provided below:

(SEQ ID NO: 12)

atggccctgccagtaacggctctgctgctgccacttgctctgctcctccat gcagccaggcct

Transmembrane Domain of a CAR

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3ζ polypeptide, a CD4 polypeptide, a 4-IBB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (e.g., a transmembrane peptide not based on a protein associated with the immune response), or a combination thereof.

In certain embodiments, the transmembrane domain of a presently disclosed CAR comprises a CD28 polypeptide. The CD28 polypeptide can have an amino acid sequence that is at least about 85%, about 90%, about 95%, about 96%, about 97%, about 98%, about 99% or 100% homologous to the sequence having a NCBI Reference No: PI0747 or NP006130 (SEQ ID NO: 24), or fragments thereof, and/or may optionally comprise up to one or up to two or up to three conservative amino acid substitutions. In certain embodiments, the CD28 polypeptide can have an amino acid sequence that is a consecutive portion of SEQ ID NO: 24 which is at least 20, or at least 30, or at least 40, or at least 50, and up to 220 amino acids in length. Alternatively or additionally, in non-limiting various embodiments, the CD28 polypeptide has an amino acid sequence of amino acids 1 to 220, 1 to 50, 50 to 100, 100 to 150, 114 to 220, 150 to 200, or 200 to 220 of SEQ ID NO: 24. In certain embodiments, the CAR of the presently disclosed comprises a transmembrane domain comprising a CD28 polypeptide, and an intracellular domain comprising a co-stimulatory signaling region that comprises a CD28 polypeptide. In certain embodiments, the CD28 polypeptide comprised in the transmembrane domain and the intracellular domain has an amino acid sequence of amino acids 114 to 220 of SEQ ID NO: 24.

SEQ ID NO: 24 is provided below:

(SEQ ID NO: 24)
MLRLLLALNLFPSIQVTGNKILVKQSPMLVAYDNALSCKYSYNLFSREFRA

SLHKGLDSAVEVCWYGNYSQQLQVYSKTGFNCDGKLGNESVTFYLQNLYQT

DIYFCKIEVMYPPPYLDNEKSNGTIIHVKGKHLCPSPLFPGPSKPFWVLVW

GGVLACYSLLVTVAFIIFWVRSKRSRLLHSDYMNMTPRRPGPTRKHYQPYA

PPRDFAAYRS

In accordance with the presently disclosed subject matter, a "CD28 nucleic acid molecule" refers to a polynucleotide encoding a CD28 polypeptide. In certain embodiments, the CD28 nucleic acid molecule encoding the CD28 polypeptide comprised in the transmembrane domain and the intracellular domain (e.g., the co-stimulatory signaling region) of the presently disclosed CAR (amino acids 114 to 220 of SEQ ID NO: 24) comprises nucleic acids having the sequence set forth in SEQ ID NO: 25 as provided below.

(SEQ ID NO: 25)
attgaagttatgtatcctcctccttacctagacaatgagaagagcaatgga accattatccatgtgaaagggaaacacctttgtccaagtcccctatttccc ggaccttctaagcccttttgggtgctggtggtggttggtggagtcctggct tgctatagcttgctagtaacagtggcctttattattttctgggtgaggagt aagaggagcaggctcctgcacagtgactacatgaacatgactccccgccgc cccgggcccacccgcaagcattaccagccctatgccccaccacgcgacttc gcagcctatcgctcc In certain embodiments, the transmembrane domain comprises a CD8 polypeptide. The CD8 polypeptide can have an amino acid sequence that is at least about 85%, about 90%, about 95%, about 96%, about 97%, about 98%, about 99% or about 100%) homologous to SEQ ID NO: 26 (homology herein may be determined using standard software such as BLAST or FASTA) as provided below, or fragments thereof, and/or may optionally comprise up to one or up to two or up to three conservative amino acid substitutions. In certain embodiments, the CD8 polypeptide can have an amino acid sequence that is a consecutive portion of SEQ ID NO: 26 which is at least 20, or at least 30, or at least 40, or at least 50, and up to 235 amino acids in length. Alternatively or additionally, in non-limiting various embodiments, the CD8 polypeptide has an amino acid sequence of amino acids 1 to 235, 1 to 50, 50 to 100, 100 to 150, 150 to 200, or 200 to 235 of SEQ ID NO: 26.

(SEQ ID NO: 26)
MALPVTALLLPLALLLHAARPSQFRVSPLDRTWNLGETVELKCQVLLSNPT

SGCSWLFQPRGAAASPTFLLYLSQNKPKAAEGLDTQRFSGKRLGDTFVLTL

-continued

SDFRRENEGYYFCSALSNSIMYFSHFVPVFLPAKPTTTPAPRPPTPAPTIA

SQPLSLRPEACRPAAGGAVHTRGLDFACDIYIWAPLAGTCGVLLLSLVITL

YCNHRNRRRVCKCPRPWKSGDKPSLSARYV

In accordance with the presently disclosed subject matter, a "CD8 nucleic acid molecule" refers to a polynucleotide encoding a CD8 polypeptide.

In certain non-limiting embodiments, a CAR can also comprise a spacer region that links the extracellular antigen-binding domain to the transmembrane domain. The spacer region can be flexible enough to allow the antigen-binding domain to orient in different directions to facilitate antigen recognition while preserving the activating activity of the CAR. In certain non-limiting embodiments, the spacer region can be the hinge region from IgG1, the $CH_2CH_3$ region of immunoglobulin and portions of CD3, a portion of a CD28 polypeptide (e.g., SEQ ID NO: 24), a portion of a CD8 polypeptide (e.g., SEQ ID NO: 26), a variation of any of the foregoing which is at least about 80%, at least about 85%>, at least about 90%, or at least about 95% homologous thereto, or a synthetic spacer sequence. In certain non-limiting embodiments, the spacer region may have a length between about 1-50 (e.g., 5-25, 10-30, or 30-50) amino acids.

Intracellular Domain of a CAR

In certain non-limiting embodiments, an intracellular domain of the CAR can comprise a CD3ζ polypeptide, which can activate or stimulate a cell (e.g., a cell of the lymphoid lineage, e.g., a T cell). CD3ζ comprises 3 ITAMs, and transmits an activation signal to the cell (e.g., a cell of the lymphoid lineage, e.g., a T cell) after antigen is bound. The CD3ζ polypeptide can have an amino acid sequence that is at least about 85%, about 90%, about 95%, about 96%, about 97%, about 98%, about 99% or about 100% homologous to the sequence having a NCBI Reference No: NP_932170 (SEQ ID No: 48), or fragments thereof, and/or may optionally comprise up to one or up to two or up to three conservative amino acid substitutions. In non-limiting certain embodiments, the CD3ζ polypeptide can have an amino acid sequence that is a consecutive portion of SEQ ID NO: 27 which is at least 20, or at least 30, or at least 40, or at least 50, and up to 164 amino acids in length. Alternatively or additionally, in non-limiting various embodiments, the CD3ζ polypeptide has an amino acid sequence of amino acids 1 to 164, 1 to 50, 50 to 100, 100 to 150, or 150 to 164 of SEQ ID NO: 27. In certain embodiments, the CD3ζ polypeptide has an amino acid sequence of amino acids 52 to 164 of SEQ ID NO: 27.

SEQ ID NO: 27 is provided below:

(SEQ ID NO: 27)
MKWKALFTAAILQAQLPITEAQSFGLLDPKLCYLLDGILFIYGVILTALFL

RVKFSRSADAPAYQQGQNQLYNELNLGRREEYDVLDKRRGRDPEMGGKPQR

NERKNPQEGLYLQKDKMAEAYSEIGMKGERRRGKGHDGLYQGLSTATKDTY

DALHMQALPPR

In certain embodiments, the CD3ζ polypeptide has the amino acid sequence set forth in SEQ ID NO: 28, which is provided below:

(SEQ ID NO: 28)
RVKFSRSAEPPAYQQGQNQLYNELNLGRREEYDVLDKRRGRDPEMGGKPRR

KNPQEGLYNELQKDKMAEAYSEIGMKGERRRGKGHDGLYQGLSTATKDTYD

ALHMQALPPR

In accordance with the presently disclosed subject matter, a "CD3ζ nucleic acid molecule" refers to a polynucleotide encoding a CD3ζ polypeptide. In certain embodiments, the CD3ζ nucleic acid molecule encoding the CD3ζ polypeptide (SEQ ID NO: 28) comprised in the intracellular domain of the presently disclosed CAR comprises a nucleotide sequence as set forth in SEQ ID NO: 29 as provided below.

(SEQ ID NO: 29)
agagtgaagttcagcaggagcgcagagcccccgcgtaccagcagggccag aaccagctctataacgagctcaatctaggacgaagagaggagtacgatgtt ttggacaagagacgtggccgggaccctgagatgggggaaagccgagaagg aagaaccctcaggaaggcctgtacaatgaactgcagaaagataagatggcg gaggcctacagtgagattgggatgaaaggcgagcgccggaggggcaagggg cacgatggcctttaccagggtctcagtacagccaccaaggacacctacgac gcccttcacatgcaggccctgccccctcgcg In certain non-limiting embodiments, an intracellular domain of the CAR further comprises at least one signaling region. The at least one signaling region can include a CD28 polypeptide, a 4-IBB polypeptide, an OX40 polypeptide, an ICOS polypeptide, a DAP-10 polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof.

In certain embodiments, the signaling region is a co-stimulatory signaling region.

In certain embodiments, the co-stimulatory signaling region comprises at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-IBB polypeptide, an OX40 polypeptide, an ICOS polypeptide, a DAP-10 polypeptide, or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands, include, but are not limited to CD80, CD86, CD70, OX40L, 4-1BBL, CD48, TNFRSF14, and PD-L1. As one example, a 4-1BB ligand (i.e., 4-1BBL) may bind to 4-1BB (also known as "CD 137") for providing an intracellular signal that in combination with a CAR signal induces an effector cell function of the CAR$^+$ T cell. CARs comprising an intracellular domain that comprises a co-stimulatory signaling region comprising 4-1BB, ICOS or DAP-10 are disclosed in U.S. Pat. No. 7,446,190, which is herein incorporated by reference in its entirety. In certain embodiments, the intracellular domain of the CAR comprises a co-stimulatory signaling region that comprises a CD28 polypeptide. In certain embodiments, the intracellular domain of the CAR comprises a co-stimulatory signaling region that comprises two co-stimulatory molecules: CD28 and 4-1BB or CD28 and OX40.

4-IBB can act as a tumor necrosis factor (TNF) ligand and have stimulatory activity. The 4-IBB polypeptide can have an amino acid sequence that is at least about 85%, about 90%, about 95%, about 96%, about 97%, about 98%, about 99% or 100% homologous to the sequence having a NCBI Reference No: P41273 or NP_001552 (SEQ ID NO: 30) or fragments thereof, and/or may optionally comprise up to one or up to two or up to three conservative amino acid substitutions.

SEQ ID NO: 30 is provided below:

(SEQ ID NO: 30)
MGNSCYNIVATLLLVLNFERTRSLQDPCSNCPAGTFCDNNRNQICSPCPPN

SFSSAGGQRTCDICRQCKGVFRTRKECSSTSNAECDCTPGFHCLGAGCSMC

EQDCKQGQELTKKGCKDCCFGTFNDQKRGICRPWTNCSLDGKSVLGTKERD

WCGPSPADLSPGASSVTPPAPAREPGHSPQIISFFLALTSTALLFLLFFLT

LRFSWKRGRKKLLYIFKQPFMRPVQTTQEEDGCSCRFPEEEEGGCEL

In accordance with the presently disclosed subject matter, a "4-IBB nucleic acid molecule" refers to a polynucleotide encoding a 4-IBB polypeptide.

An OX40 polypeptide can have an amino acid sequence that is at least about 85%, about 90%, about 95%, about 96%, about 97%, about 98%, about 99% or 100% homologous to the sequence having a NCBI Reference No: P43489 or NP 003318 (SEQ ID NO: 31), or fragments thereof, and/or may optionally comprise up to one or up to two or up to three conservative amino acid substitutions.

SEQ ID NO: 31 is provided below:

(SEQ ID NO: 31)
MCVGARRLGRGPCAALLLLGLGLSTVTGLHCVGDTYPSNDRCCHECRPGNG

MVSRCSRSQNTVCRPCGPGFYNDWSSKPCKPCTWCNLRSGSERKQLCTATQ

DTVCRCRAGTQPLDSYKPGVDCAPCPPGHFSPGDNQACKPWTNCTLAGKHT

LQPASNSSDAICEDRDPPATQPQETQGPPARPITVQPTEAWPRTSQGPSTR

PVEVPGGRAVAAILGLGLVLGLLGPLAILLALYLLRRDQRLPPDAHKPPGG

GSFRTPIQEEQADAHSTLAKI

In accordance with the presently disclosed subject matter, an "OX40 nucleic acid molecule" refers to a polynucleotide encoding an OX40 polypeptide.

An ICOS polypeptide can have an amino acid sequence that is at least about 85%, about 90%, about 95%, about 96%, about 97%, about 98%, about 99% or 100% homologous to the sequence having a NCBI Reference No: NP_036224 (SEQ ID NO: 32) or fragments thereof, and/or may optionally comprise up to one or up to two or up to three conservative amino acid substitutions.

SEQ ID NO: 32 is provided below:

(SEQ ID NO: 32)
MKSGLWYFFLFCLRIKVLTGEINGSANYEMFIFHNGGVQILCKYPDIVQQF

KMQLLKGGQILCDLTKTKGSGNTVSIKSLKFCHSQLSNNSVSFFLYNLDHS

HANYYFCNLSIFDPPPFKVTLTGGYLHIYESQLCCQLKFWLPIGCAAFVWC

ILGCILICWLTKKKYSSSVHDPNGEYMFMRATAKKSRLTDVTL

In accordance with the presently disclosed subject matter, an "ICOS nucleic acid molecule" refers to a polynucleotide encoding an ICOS polypeptide.

CTLA-4 is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion, enhanced the endogenous anti-tumor response albeit, in the clinical setting, with significant unforeseen toxicities.

CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif able to bind PI3K, PP2A and SHP-2 and one proline-rich motif able to bind SH3 containing proteins. One role of CTLA-4 in inhibiting T cell responses seem to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

In accordance with the presently disclosed subject matter, a CTLA-4 polypeptide can have an amino acid sequence that is at least about 85%, about 90%, about 95%, about 96%, about 97%, about 98%, about 99% or about 100% homologous to UniProtKB/Swiss-Prot Ref. No.: P16410.3 (SEQ ID NO: 33) (homology herein may be determined using standard software such as BLAST or FASTA) or fragments thereof, and/or may optionally comprise up to one or up to two or up to three conservative amino acid substitutions.

SEQ ID NO: 33 is provided below:

```
                                      (SEQ ID NO: 33)
MACLGFQRHKAQLNLATRTWPCTLLFFLLFIPVFCKAMHVAQPAWLASSRG

IASFVCEYASPGKATEVRVTVLRQADSQVTEVCAATYMMGNELTFLDDSIC

TGTSSGNQLTIQGLRAMDTGLYICKVELMYPPPYYLGIGNGTQIYVIDPEP

CPDSDFLLWILAAVSSGLFFYSFLLTAVSLSKMLKKRSPLTTGVYVKMPPT

EPECEKQFQPYFIPIN
```

In accordance with the presently disclosed subject matter, a "CTLA-4 nucleic acid molecule" refers to a polynucleotide encoding a CTLA-4 polypeptide.

PD-1 is a negative immune regulator of activated T cells upon engagement with its corresponding ligands PD-L1 and PD-L2 expressed on endogenous macrophages and dendritic cells. PD-1 is a type I membrane protein of 268 amino acids. PD-1 has two ligands, PD-L1 and PD-L2, which are members of the B7 family. The protein's structure comprises an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, that PD-1 negatively regulates TCR signals. SHP-I and SHP-2 phosphatases bind to the cytoplasmic tail of PD-1 upon ligand binding. Upregulation of PD-L1 is one mechanism tumor cells may evade the host immune system. In pre-clinical and clinical trials, PD-1 blockade by antagonistic antibodies induced anti-tumor responses mediated through the host endogenous immune system. In accordance with the presently disclosed subject matter, a PD-1 polypeptide can have an amino acid sequence that is at least about 85%, about 90%, about 95%, about 96%, about 97%, about 98%, about 99% or about 100% homologous to NCBI Reference No: NP_005009.2 (SEQ ID NO: 34) or fragments thereof, and/or may optionally comprise up to one or up to two or up to three conservative amino acid substitutions.

SEQ ID NO: 34 is provided below:

```
                                      (SEQ ID NO: 34)
MQIPQAPWPVVWAVLQLGWRPGWFLDSPDRPWNPPTFSPALLWTEGDNATF

TCSFSNTSESFVLNWYRMSPSNQTDKLAAFPEDRSQPGQDCRFRVTQLPNG

RDFHMSVVRARRNDSGTYLCGAISLAPKAQIKESLRAELRVTERRAEVPTA

HPSPSPRPAGQFQTLVVGWGGLLGSLVLLVWVLAVICSRAARGTIGARRTG

QPLKEDPSAVPVFSVDYGELDFQWREKTPEPPVPCVPEQTEYATIVFPSGM

GTSSPARRGSADGPRSAQPLRPEDGHCSWPL
```

In accordance with the presently disclosed subject matter, a "PD-1 nucleic acid molecule" refers to a polynucleotide encoding a PD-1 polypeptide.

Lymphocyte-activation protein 3 (LAG-3) is a negative immune regulator of immune cells. LAG-3 belongs to the immunoglobulin (Ig) superfamily and contains 4 extracellular Ig-like domains. The LAG3 gene contains 8 exons. The sequence data, exon/intron organization, and chromosomal localization all indicate a close relationship of LAG3 to CD4. LAG3 has also been designated CD223 (cluster of differentiation 223).

In accordance with the presently disclosed subject matter, a LAG-3 polypeptide can have an amino acid sequence that is at least about 85%, about 90%, about 95%, about 96%, about 97%, about 98%, about 99% or about 100% homologous to UniProtKB/Swiss-Prot Ref. No.: P18627.5 (SEQ ID NO: 35) or fragments thereof, and/or may optionally comprise up to one or up to two or up to three conservative amino acid substitutions.

SEQ ID NO: 35 is provided below:

```
                                      (SEQ ID NO: 35)
MWEAQFLGLLFLQPLWVAPVKPLQPGAEVPWWAQEGAPAQLPCSPTIPLQD

LSLLRRAGVTWQHQPDSGPPAAAPGHPLAPGPHPAAPSSWGPRPRRYTVLS

VGPGGLRSGRLPLQPRVQLDERGRQRGDFSLWLRPARRADAGEYRAAVHLR

DRALSCRLRLRLGQASMTASPPGSLRASDWVILNCSFSRPDRPASVHWFRN

RGQGRVPVRESPHHHLAESFLFLPQVSPMDSGPWGCILTYRDGFNVSIMYN

LTVLGLEPPTPLTVYAGAGSRVGLPCRLPAGVGTRSFLTAKWTPPGGGPDL

LVTGDNGDFTLRLEDVSQAQAGTYTCHIHLQEQQLNATVTLAIITVTPKSF

GSPGSLGKLLCEVTPVSGQERFVWSSLDTPSQRSFSGPWLEAQEAQLLSQP

WQCQLYQGERLLGAAVYFTELSSPGAQRSGRAPGALPAGHLLLFLILGVLS

LLLLVTGAFGFHLWRRQWRPRRFSALEQGIHPPQAQSKIEELEQEPEPEPE

PEPEPEPEPEPEQL
```

In accordance with the presently disclosed subject matter, a "LAG-3 nucleic acid molecule" refers to a polynucleotide encoding a LAG-3 polypeptide. Natural Killer Cell Receptor 2B4 (2B4) mediates non-MHC restricted cell killing on NK cells and subsets of T cells. To date, the function of 2B4 is still under investigation, with the 2B4-S isoform believed to be an activating receptor, and the 2B4-L isoform believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

In accordance with the presently disclosed subject matter, a 2B4 polypeptide can have an amino acid sequence that is at least about 85%, about 90%, about 95%, about 96%, about 97%, about 98%, about 99% or about 100% homologous to UniProtKB/Swiss-Prot Ref. No.: Q9BZW8.2 (SEQ ID NO: 36) or fragments thereof, and/or may optionally comprise up to one or up to two or up to three conservative amino acid substitutions.

SEQ ID NO: 36 is provided below:

```
                                        (SEQ ID NO: 36)
MLGQWTLILLLLLKVYQGKGCQGSADHWSISGVPLQLQPNSIQTKVDSIAW

KKLLPSQNGFHHILKWENGSLPSNTSNDRFSFIVKNLSLLIKAAQQQDSGL

YCLEVTSISGKVQTATFQVFVFESLLPDKVEKPRLQGQGKILDRGRCQVAL

SCLVSRDGNVSYAWYRGSKLIQTAGNLTYLDEEVDINGTHTYTCNVSNPVS

WESHTLNLTQDCQNAHQEFRFWPFLVIIVILSALFLGTLACFCVWRRKRKE

KQSETSPKEFLTIYEDVKDLKTRRNHEQEQTFPGGGSTIYSMIQSQSSAPT

SQEPAYTLYSLIQPSRKSGSRKRNHSPSFNSTIYEVIGKSQPKAQNPARLS

RKELENFDVYS
```

In accordance with the presently disclosed subject matter, a "2B4 nucleic acid molecule" refers to a polynucleotide encoding a 2B4 polypeptide.

B- and T-lymphocyte attenuator (BTLA) expression is induced during activation of T cells, and BTLA remains expressed on Th1 cells but not Th2 cells. Like PD1 and CTLA4, BTLA interacts with a B7 homolog, B7H4. However, unlike PD-1 and CTLA-4, BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human $CD8^+$ cancer-specific T cells. BTLA has also been designated as CD272 (cluster of differentiation 272).

In accordance with the presently disclosed subject matter, a BTLA polypeptide can have an amino acid sequence that is at least about 85%>, about 90%, about 95%, about 96%, about 97%, about 98%, about 99% or about 100% homologous to UniProtKB/Swiss-Prot Ref. No.: Q7Z6A9.3 (SEQ ID NO: 37) or fragments thereof, and/or may optionally comprise up to one or up to two or up to three conservative amino acid substitutions.

SEQ ID NO: 37 is provided below:

```
                                        (SEQ ID NO: 37)
MKTLPAMLGTGKLFWVFFLIPYLDIWNIHGKESCDVQLYIKRQSEHSILAG

DPFELECPVKYCANRPHVTWCKLNGTTCVKLEDRQTSWKEEKNISFFILHF
```

-continued

```
EPVLPNDNGSYRCSANFQSNLIESHSTTLYVTDVKSASERPSKDEMASRPW

LLYRLLPLGGLPLLITTCFCLFCCLRRHQGKQNELSDTAGREINLVDAHLK

SEQTEASTRQNSQVLLSETGIYDNDPDLCFRMQEGSEVYSNPCLEENKPGI

VYASLNHSVIGPNSRLARNVKEAPTEYASICVRS
```

In accordance with the presently disclosed subject matter, a "BTLA nucleic acid molecule" refers to a polynucleotide encoding a BTLA polypeptide.

Exemplary CAR and Prodrug Converting Enzyme Constructs

In certain embodiments, the CAR and prodrug converting enzyme are expressed as single polypeptide linked by a self-cleaving linker, such as a P2A linker. In certain embodiments, the CAR and prodrug converting enzyme are expressed as two separate polypeptides.

In certain embodiments, the CAR comprises an extracellular antigen-binding region that comprises a human scFv that specifically binds to a target antigen (e.g., an antigen from a pathogen or an inflammatory antigen), a transmembrane domain comprising a CD28 polypeptide, and an intracellular domain comprising a CD3ζ polypeptide and a co-stimulatory signaling region that comprises a 4-1BB polypeptide, as shown in FIG. 3. As shown in FIG. 3, the CAR also comprises a signal peptide or a leader covalently joined to the N-terminus of the extracellular antigen-binding domain. The signal peptide comprises amino acids having the sequence set forth in SEQ ID NO: 11. In certain embodiments, the human scFv is selected from the group consisting of an anti-CD19 scFv, and anti-WT1 scFv, and anti-PRAME scFv. In certain embodiments, the human scFv is an anti-CD19 scFv comprising the amino acid set forth in SEQ ID NO: 19.

In some embodiments, the nucleic acid encoding the CAR and the prodrug converting enzyme (e.g., CPG2 or β-lactamase) is operably linked an inducible promoter. In some embodiments, the nucleic acid encoding the CAR and the prodrug converting enzyme (e.g., CPG2 or β-lactamase) is operably linked a constitutive promoter. In some embodiments, the nucleic acid encoding the CAR and the nucleic acid encoding prodrug converting enzyme (e.g., CPG2 or β-lactamase) are operably linked to two separate promoters. In some embodiments, the nucleic acid encoding the CAR is operably linked a constitutive promoter and the prodrug converting enzyme (e.g., CPG2 or β-lactamase) is operably linked an constitutive promoter. In some embodiments, the nucleic acid encoding the CAR is operably linked a constitutive promoter and the prodrug converting enzyme (e.g., CPG2 or β-lactamase) is operably linked an inducible promoter.

In some embodiments, the inducible promoter is a synthetic Notch promoter that is activatable in a CAR T cell, where the intracellular domain of the CAR contains a transcriptional regulator that is released from the membrane when engagement of the CAR with the target antigen induces intramembrane proteolysis (see, e.g. Morsut et al., *Cell* 164(4): 780-791 (2016). Accordingly, transcription of the prodrug converting enzyme is induce upon binding of the engineered immune cell with the target antigen.

The presently disclosed subject matter also provides isolated nucleic acid molecules encoding the CAR/prodrug converting enzyme constructs described herein or a functional portion thereof. In certain embodiments, the isolated nucleic acid molecule encodes an anti-CD19-targeted CAR comprising a human scFv that specifically binds to a human CD19 polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and a CPG2 or β-lactamase polypeptide fused to a signal peptide and a transmembrane domain comprising a CD8 polypeptide (see, e.g., FIG. 3A and exemplary constructs set forth in SEQ ID NOS: 48-51).

Figure 3A:
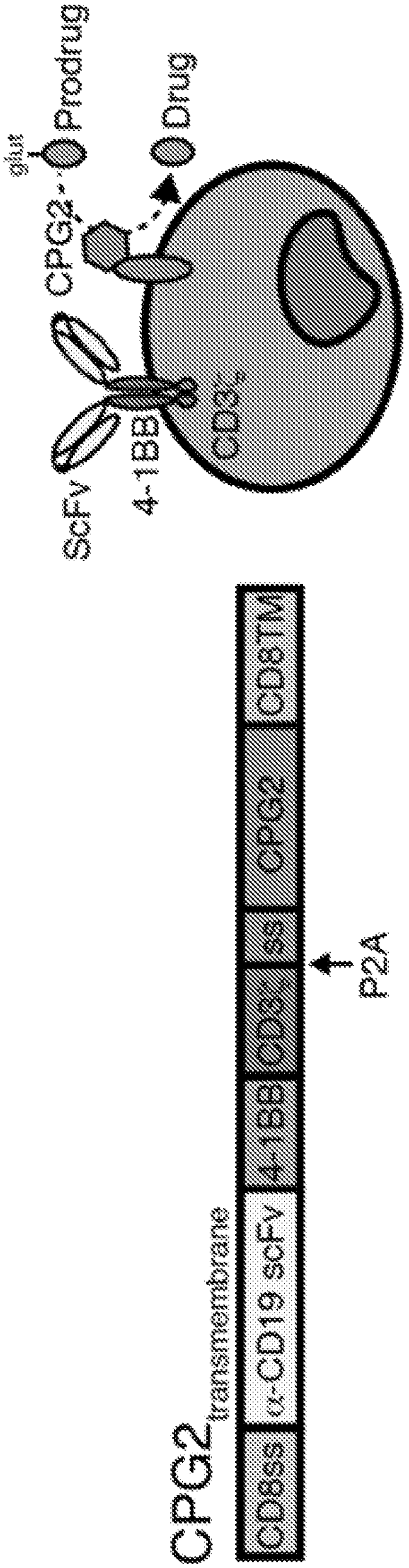
FIG. 3 provides a schematic depiction of exemplary SEAKER constructs. In exemplary embodiments of the SEAKER cell technology, a glutamated prodrug is administered systemically but activated to its cytotoxic form only at sites of CAR-T cell accumulation. (A) $CPG2_{transmembrane}$ expresses a CPG2 enzyme tethered to the surface of the CAR-T cell through the CD8 transmembrane region. (B) $CPG2_{secreted}$ expresses a CPG2 enzyme that is secreted directly into the surrounding environment. These exemplary CAR-T cells express an antigen-specific scFv coupled to the 4-1BB costimulatory molecule and CD3ζ chain. A self-cleaving P2A peptide sequence permits co-translational cleavage of the polyprotein. (C) An exemplary $CPG2_{inducible}$ CAR-T cell utilizes a syn-notch system to activate expression of a secreted form of CPG2 only upon engagement with a target antigen.
Figure 3B:
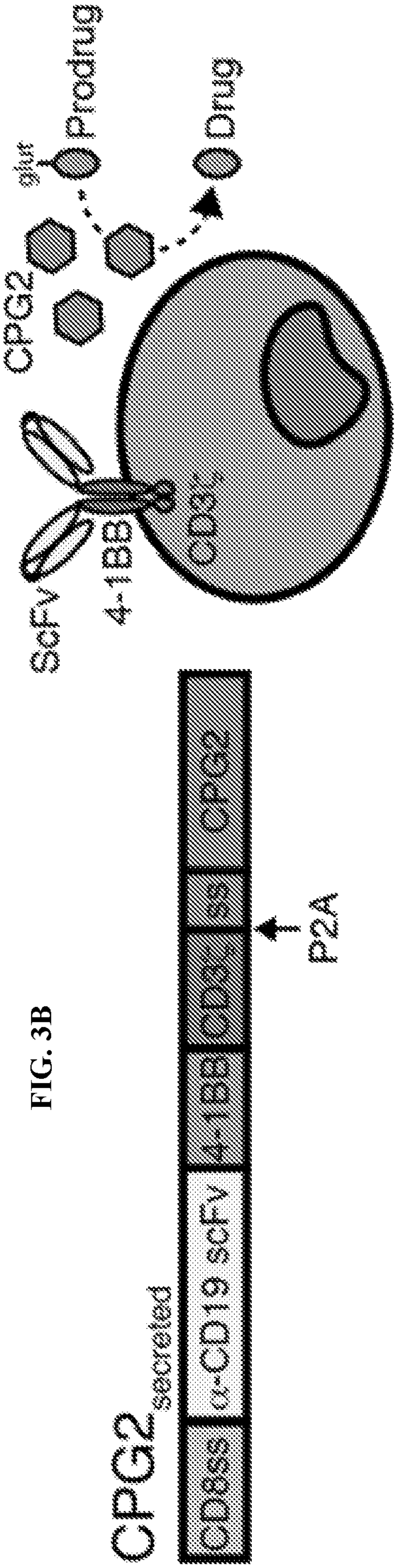

In certain embodiments, the isolated nucleic acid molecule encodes an anti-CD19-targeted CAR comprising a human scFv that specifically binds to a human CD19 polypeptide, a transmembrane domain comprising a CD8 polypeptide, and an intracellular domain comprising a CD3ζ polypeptide and a co-stimulatory signaling region comprising a 4-1BB polypeptide, a P2A self-cleaving peptide, and a CPG2 or β-lactamase polypeptide fused to a signal peptide (see, e.g., FIG. 3B).

In certain embodiments, the isolated nucleic acid molecule encodes an anti-CD19-targeted CAR comprising a human scFv that specifically binds to a human CD19 polypeptide fused to a synthetic Notch transmembrane domain and an intracellular cleavable transcription factor (see, e.g., FIG. 3C) In certain embodiments, the isolated nucleic acid molecule encodes a CPG2 or β-lactamase enzyme inducible by release of the transcription factor of a synthetic Notch system.

In certain embodiments, the isolated nucleic acid molecule encodes a functional portion of a presently disclosed CAR constructs. As used herein, the term "functional portion" refers to any portion, part or fragment of a CAR, which portion, part or fragment retains the biological activity of the targeted CAR (the parent CAR). For example, functional portions encompass the portions, parts or fragments of an antigen-targeted CAR that retains the ability to recognize a target cell, to treat a disease, e.g., inflammatory disease or a pathogenic infection, to a similar, same, or even a higher extent as the parent CAR. In certain embodiments, an isolated nucleic acid molecule encoding a functional portion of an antigen-targeted CAR can encode a protein comprising, e.g., about 10%, about 20%, about 25%, about 30%, about 35%, about 40%, about 45%, about 50%, about 55%, about 60%, about 65%, about 70%, about 75%, about 80%, about 85%, about 90%, and about 95%, or more of the parent CAR.

Immune Cells

The presently disclosed subject matter provides engineered immune cells expressing a prodrug converting enzyme and a T-cell receptor (e.g., a CAR) or other ligand that comprises an extracellular antigen-binding domain, a transmembrane domain and an intracellular domain, where the extracellular antigen-binding domain specifically binds a target antigen, e.g., a an antigen from a pathogen or an inflammatory antigen as described above. In certain embodiments immune cells can be transduced with a presently disclosed CAR/prodrug converting enzyme constructs such that the cells express the CAR and the prodrug converting enzyme. The presently disclosed subject matter also provides methods of using such cells for the treatment of an inflammation, an inflammatory disease, or pathogenic infection. The engineered immune cells of the presently disclosed subject matter can be cells of the lymphoid lineage or myeloid lineage. The lymphoid lineage, comprising B, T, and natural killer (NK) cells, provides for the production of antibodies, regulation of the cellular immune system, detection of foreign agents in the blood, detection of cells foreign to the host, and the like. Non-limiting examples of immune cells of the lymphoid lineage include T cells, Natural Killer (NK) cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., TEM cells and TEMRA cells, Regulatory T cells (also known as suppressor T cells), Natural killer T cells, Mucosal associated invariant T cells, and γδ T cells. Cytotoxic T cells (CTL or killer T cells) are a subset of T lymphocytes capable of inducing the death of infected cells. In certain embodiments, the CAR-expressing T cells express Foxp3 to achieve and maintain a T regulatory phenotype.

Natural killer (NK) cells can be lymphocytes that are part of cell-mediated immunity and act during the innate immune response. NK cells do not require prior activation in order to perform their cytotoxic effect on target cells.

The engineered immune cells of the presently disclosed subject matter can express an extracellular antigen-binding domain (e.g., a human scFv, a Fab that is optionally cross-linked, or a $F(ab)_2$) that specifically binds to an inflammatory antigen, for the treatment of an inflammation or an inflammatory disease. Such engineered immune cells can be administered to a subject (e.g., a human subject) in need thereof for the treatment of the inflammation or inflammatory disease. In some embodiments, the immune cell is a lymphocyte, such as a T cell, a B cell or a natural killer (NK) cell. In certain embodiments, the engineered immune cell is a T cell. The T cell can be a $CD4^+$ T cell or a $CD8^+$ T cell. In certain embodiments, the T cell is a $CD4^+$ T cell. In certain embodiments, the T cell is a $CD8^+$ T cell.

The engineered immune cells of the presently disclosed subject matter can express an extracellular antigen-binding domain (e.g., a human scFv, a Fab that is optionally cross-linked, or a $F(ab)_2$) that specifically binds to an antigen from a pathogen, for the treatment of infectious disease (e.g., a pathogenic infection, such as a viral, bacterial or parasitic infection). Such engineered immune cells can be administered to a subject (e.g., a human subject) in need thereof for the treatment of the infectious disease (e.g., a pathogenic infection, such as a viral, bacterial or parasitic infection). In certain embodiments, the immune cell is a T cell. The T cell can be a $CD4^+$ T cell or a CD8 T cell. In certain embodiments, the T cell is a $CD4^+$ T cell. In certain embodiments, the T cell is a $CD8^+$ T cell.

A presently disclosed engineered immune cells can further include at least one recombinant or exogenous co-stimulatory ligand. For example, a presently disclosed engineered immune cells can be further transduced with at least one co-stimulatory ligand, such that the engineered immune cells co-expresses or is induced to co-express the antigen-targeted CAR and the at least one co-stimulatory ligand. The interaction between the antigen-targeted CAR and at least one co-stimulatory ligand provides a non-antigen-specific signal important for full activation of an immune cell (e.g., T cell). Co-stimulatory ligands include, but are not limited to, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, without limitation, nerve growth factor (NGF), CD40L (CD40L)/CD 154, CD137L/4-1BBL, TNF-a, CD134L/OX40L/CD252, CD27L/CD70, Fas ligand (FasL), CD30L/CD153, tumor necrosis factor beta (TNFP)/lymphotoxin-alpha (LTa), lymphotoxin-beta O-Tβ), CD257/B cell-activating factor (B AFF)/Blys/THANK/Tall-1, glucocorticoid-induced TNF Receptor ligand (GITRL), and T F-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, but are not limited to, CD80 and CD86, both ligands for CD28, PD-L1/(B7-H1) that ligands for PD-1. In certain embodiments, the at least one co-stimulatory ligand is selected from the group consisting of 4-1BBL, CD80, CD86, CD70, OX40L, CD48, TNFRSF14, PD-L1, and combinations thereof. In certain embodiments, the engineered immune cell comprises one recombinant co-stimulatory ligand that is 4-1BBL. In certain embodiments, the engineered immune cell comprises two recombinant co-stimulatory ligands that are 4-1BBL and CD80. CARs comprising at least one co-stimulatory ligand are described in U.S. Pat. No. 8,389,282, which is incorporated by reference in its entirety.

Furthermore, a presently disclosed engineered immune cells can further comprise at least one exogenous cytokine. For example, a presently disclosed engineered immune cell can be further transduced with at least one cytokine, such that the engineered immune cells secretes the at least one cytokine as well as expresses the antigen-targeted CAR. In certain embodiments, the at least one cytokine is selected from the group consisting of IL-2, IL-3, IL-6, IL-7, IL-11, IL-12, IL-15, IL-17, and IL-21. In certain embodiments, the cytokine is IL-12.

The engineered immune cells can be generated from peripheral donor lymphocytes, e.g., those disclosed in Sadelain, M., et al., *Nat Rev Cancer* 3:35-45 (2003) (disclosing peripheral donor lymphocytes genetically modified to express CARs), in Morgan, R. A. et al., *Science* 314: 126-129 (2006) (disclosing peripheral donor lymphocytes genetically modified to express a full-length tumor antigen-recognizing T cell receptor complex comprising the α and β heterodimer), in Panelli et al. *J Immunol* 164:495-504 (2000); Panelli et al. *J Immunol* 164:4382-4392 (2000) (disclosing lymphocyte cultures derived from tumor infiltrating lymphocytes (TILs) in tumor biopsies), and in Dupont et al. *Cancer Res* 65:5417-5427 (2005); Papanicolaou et al. *Blood* 102:2498-2505 (2003) (disclosing selectively in v/Yro-expanded antigen-specific peripheral blood leukocytes employing artificial antigen-presenting cells (AAPCs) or pulsed dendritic cells). The engineered immune cells (e.g., T cells) can be autologous, non-autologous (e.g., allogeneic), or derived in vitro from engineered progenitor or stem cells.

In certain embodiments, a presently disclosed engineered immune cells (e.g., T cells) expresses from about 1 to about 5, from about 1 to about 4, from about 2 to about 5, from about 2 to about 4, from about 3 to about 5, from about 3 to about 4, from about 4 to about 5, from about 1 to about 2, from about 2 to about 3, from about 3 to about 4, or from about 4 to about 5 vector copy numbers per cell of a presently disclosed antigen-targeted CAR and/or prodrug converting enzyme.

For example, the higher the CAR expression level in an engineered immune cell, the greater cytotoxicity and cytokine production the engineered immune cell exhibits. An engineered immune cell (e.g., T cell) having a high antigen-targeted CAR expression level can induce antigen-specific cytokine production or secretion and/or exhibit cytotoxicity to a tissue or a cell having a low expression level of antigen-targeted CAR, e.g., about 2,000 or less, about 1,000 or less, about 900 or less, about 800 or less, about 700 or less, about 600 or less, about 500 or less, about 400 or less, about 300 or less, about 200 or less, about 100 or less of antigen binding sites/cell. Additionally or alternatively, the cytotoxicity and cytokine production of a presently disclosed engineered immune cell (e.g., T cell) are proportional to the expression level of the target antigen in a target tissue or a target cell. For example, the higher the expression level of target antigen (e.g., an antigen from a pathogen, or an inflammatory antigen) in the target, the greater cytotoxicity and cytokine production the engineered immune cell exhibits.

As described herein, the co-expression of prodrug converting enzyme increases the cytotoxic effect in the CAR T cells by converting a prodrug into an active drug at the target site. In certain embodiments, an engineered immune cells of the present disclosure exhibits a cytotoxic effect against target antigen-expressing cells (e.g., target antigen expressing cell or cell infected with a pathogen) that is at least about 2-times, about 3-times, about 4-times, about 5-times, about 6-times, about 7-times, about 8-times, about 9-times, about 10-times, about 20-times, about 30-times, about 40-times, about 50-times, about 60-times, about 70-times, about 80-times, about 90-times, or about 100-times, the cytotoxic effect in the absence of the prodrug converting enzyme.

The unpurified source of immune cells may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-immune cell initially. Monoclonal antibodies are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g., plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

In some embodiments, the engineered immune cells comprise one or more additional modifications. For example, in some embodiments, the engineered immune cells comprise and express (is transduced to express) an antigen recognizing receptor that binds to a second antigen that is different than selected target antigen. The inclusion of an antigen recognizing receptor in addition to a presently disclosed CAR on the engineered immune cell can increase the avidity of the CAR or the engineered immune cell comprising thereof on a targeted cell, especially, the CAR is one that has a low binding affinity to a particular target antigen, e.g., a $K_d$ of about $2\times10^{-8}$M or more, about $5\times10^{-8}$ M or more, about $8\times10^{-8}$ M or more, about $9\times10^{-8}$ M or more, about $1\times10^{-7}$ M or more, about $2\times10^{-7}$ M or more, or about $5\times10^{-7}$ M or more.

In certain embodiments, the antigen recognizing receptor is a chimeric co-stimulatory receptor (CCR). CCR is described in Krause, et al., *J. Exp. Med.* 188(4):619-626 (1998), and US20020018783, the contents of which are incorporated by reference in their entireties. CCRs mimic co-stimulatory signals, but unlike, CARs, do not provide a T-cell activation signal, e.g., CCRs lack a CD3ζ polypeptide. CCRs provide co-stimulation, e.g., a CD28-like signal, in the absence of the natural co-stimulatory ligand on the antigen-presenting cell. A combinatorial antigen recognition, i.e., use of a CCR in combination with a CAR, can augment T-cell reactivity against the dual-antigen expressing T cells, thereby improving selective target site delivery, e.g., targeting to a site of inflammation or pathogenic infection. Kloss et al., describe a strategy that integrates combinatorial antigen recognition, split signaling, and, critically, balanced strength of T-cell activation and costimulation to generate T cells that eliminate target cells that express a combination of antigens while sparing cells that express each antigen individually (Kloss et al., *Nature Biotechnology* 31(1):71-75 (2013)). With this approach, T-cell activation requires CAR-mediated recognition of one antigen, whereas costimulation is independently mediated by a CCR specific for a second antigen. To achieve target site (e.g., a site of pathogenic infection or a site of inflammation) selectivity, the combinatorial antigen recognition approach diminishes the efficiency of T-cell activation to a level where it is ineffective without rescue provided by simultaneous CCR recognition of the second antigen. In certain embodiments, the CCR comprises an extracellular antigen-binding domain that binds to an antigen different than selected target antigen, a transmembrane domain, and a co-stimulatory signaling region that comprises at least one co-stimulatory molecule, including, but not limited to, CD28, 4-1BB, OX40, ICOS, PD-1, CTLA-4, LAG-3, 2B4, and BTLA. In certain embodiments, the co-stimulatory signaling region of the CCR comprises one co-stimulatory signaling molecule. In certain embodiments, the one co-stimulatory signaling molecule is CD28. In certain embodiments, the one co-stimulatory signaling molecule is 4-IBB. In certain embodiments, the co-stimulatory signaling region of the CCR comprises two co-stimulatory signaling molecules. In certain embodiments, the two co-stimulatory signaling molecules are CD28 and 4-IBB. A second antigen is selected so that expression of both selected target antigen and the second antigen is restricted to the targeted cells. Similar to a CAR, the extracellular antigen-binding domain can be a scFv, a Fab, a $F(ab)_2$; or a fusion protein with a heterologous sequence to form the extracellular antigen-binding domain. In certain embodiments, the CCR comprises a scFv that binds to CD 138, transmembrane domain comprising a CD28 polypeptide, and a co-stimulatory signaling region comprising two co-stimulatory signaling molecules that are CD28 and 4-IBB.

In certain embodiments, the antigen recognizing receptor is a truncated CAR. A "truncated CAR" is different from a CAR by lacking an intracellular signaling domain. For example, a truncated CAR comprises an extracellular antigen-binding domain and a transmembrane domain, and lacks an intracellular signaling domain. In accordance with the presently disclosed subject matter, the truncated CAR has a high binding affinity to the second antigen expressed on the targeted cells. The truncated CAR functions as an adhesion molecule that enhances the avidity of a presently disclosed CAR, especially, one that has a low binding affinity to target antigen, thereby improving the efficacy of the presently disclosed CAR or engineered immune cell (e.g., T cell) comprising thereof. A presently disclosed T cell comprises or is transduced to express a presently disclosed CAR targeting a target antigen (e.g., a an antigen from a pathogen, or an inflammatory antigen) and a truncated CAR targeting a second target antigen.

In some embodiments, the engineered immune cells are further modified to suppress expression of one or more genes. In some embodiments, the engineered immune cells are further modified via genome editing. Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20050064474; 20060063231; 201000218264; 20120017290; 20110265198; 20130137104; 20130122591; 20130177983 and 20130177960, the disclosures of which are incorporated by reference in their entireties. These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. In some embodiments, the engineered immune cells are modified to disrupt or reduce expression of an endogenous T-cell receptor gene (see, e.g. WO 2014153470, which is incorporated by reference in its entirety). In some embodiments, the engineered immune cells are modified to result in disruption or inhibition of PD1, PDL-1 or CTLA-4 (see, e.g. U.S. Patent Publication 20140120622), or other immunosuppressive factors known in the art (Wu et al. (2015) *Oncoimmunology* 4(7): e1016700, Mahoney et al. (2015) *Nature Reviews Drug Discovery* 14, 561-584).

Vectors

Many expression vectors are available and known to those of skill in the art and can be used for expression of polypeptides provided herein. The choice of expression vector will be influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vector in the cells.

Vectors also can contain additional nucleotide sequences operably linked to the ligated nucleic acid molecule, such as, for example, an epitope tag such as for localization, e.g. a hexa-his tag or a myc tag, hemagglutinin tag or a tag for purification, for example, a GST fusion, and a sequence for directing protein secretion and/or membrane association.

Expression of the antibodies or antigen-binding fragments thereof can be controlled by any promoter/enhancer known in the art. Suitable bacterial promoters are well known in the art and described herein below. Other suitable promoters for mammalian cells, yeast cells and insect cells are well known in the art and some are exemplified below. Selection of the promoter used to direct expression of a heterologous nucleic acid depends on the particular application and is within the level of skill of the skilled artisan. Promoters which can be used include but are not limited to eukaryotic expression vectors containing the SV40 early promoter (Bernoist and Chambon, *Nature* 290:304-310(1981)), the promoter contained in the 3' long terminal repeat of Rous sarcoma virus (Yamamoto et al., *Cell* 22:787-797(1980)), the herpes thymidine kinase promoter (Wagner et al., *Proc. Natl. Acad. Sci. USA* 75: 1441-1445 (1981)), the regulatory sequences of the metallothionein gene (Brinster et al., *Nature* 296:39-42 (1982)); prokaryotic expression vectors such as the β-lactamase promoter (Jay et al., *Proc. Natl. Acad. Sci. USA* 75:5543 (1981)) or the tac promoter (DeBoer et al., *Proc. Natl. Acad. Sci. USA* 50:21-25(1983)); see also "Useful Proteins from Recombinant Bacteria": in *Scientific American* 242:79-94 (1980)); plant expression vectors containing the nopaline synthetase promoter (Herrera-Estrella et al., *Nature* 505:209-213(1984)) or the cauliflower mosaic virus 35S RNA promoter (Gardner et al., *Nucleic Acids Res.* 9:2871(1981)), and the promoter of the photosynthetic enzyme ribulose bisphosphate carboxylase (Herrera-Estrella et al., *Nature* 510: 1 15-120(1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., *Cell* 55:639-646 (1984); Ornitz et al., *Cold Spring Harbor Symp. Quant. Biol.* 50:399-409 (1986); MacDonald, *Hepatology* 7:425-515 (1987)); insulin gene control region which is active in pancreatic beta cells (Hanahan et al., *Nature* 515: 115-122 (1985)), immunoglobulin gene control region which is active in lymphoid cells (Grosschedl et al., *Cell* 55:647-658 (1984); Adams et al., *Nature* 515:533-538 (1985); Alexander et al., *Mol. Cell Biol.* 7: 1436-1444 (1987)), mouse mammary tumor virus control region which is active in testicular, breast, lymphoid and mast cells (Leder et al., *Cell* 15:485-495 (1986)), albumin gene control region which is active in liver (Pinckert et al., *Genes and Devel.* 1:268-276 (1987)), alpha-fetoprotein gene control region which is active in liver (Krumlauf et al., *Mol. Cell. Biol.* 5:1639-403 (1985)); Hammer et al., *Science* 255:53-58 (1987)), alpha-1 antitrypsin gene control region which is active in liver (Kelsey et al., *Genes and Devel.* 7:161-171 (1987)), beta globin gene control region which is active in myeloid cells (Magram et al., *Nature* 515:338-340 (1985)); Kollias et al., *Cell* 5:89-94 (1986)), myelin basic protein gene control region which is active in oligodendrocyte cells of the brain (Readhead et al., *Cell* 15:703-712 (1987)), myosin light chain-2 gene control region which is active in skeletal muscle (Shani, *Nature* 514:283-286 (1985)), and gonadotrophic releasing hormone gene control region which is active in gonadotrophs of the hypothalamus (Mason et al., *Science* 254: 1372-1378 (1986)).

In addition to the promoter, the expression vector typically contains a transcription unit or expression cassette that contains all the additional elements required for the expression of the antibody, or portion thereof, in host cells. A typical expression cassette contains a promoter operably linked to the nucleic acid sequence encoding the antibody chain and signals required for efficient polyadenylation of the transcript, ribosome binding sites and translation termination. Additional elements of the cassette can include enhancers. In addition, the cassette typically contains a transcription termination region downstream of the structural gene to provide for efficient termination. The termination region can be obtained from the same gene as the promoter sequence or can be obtained from different genes.

Some expression systems have markers that provide gene amplification such as thymidine kinase and dihydrofolate reductase. Alternatively, high yield expression systems not involving gene amplification are also suitable, such as using a baculovirus vector in insect cells, with a nucleic acid sequence encoding a germline antibody chain under the direction of the polyhedron promoter or other strong baculovirus promoter.

Any methods known to those of skill in the art for the insertion of DNA fragments into a vector can be used to construct expression vectors containing a nucleic acid encoding any of the polypeptides provided herein. These methods can include in vitro recombinant DNA and synthetic techniques and in vivo recombinants (genetic recombination). The insertion into a cloning vector can, for example, be accomplished by ligating the DNA fragment into a cloning vector which has complementary cohesive termini. If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can contain specific chemically synthesized nucleic acids encoding restriction endonuclease recognition sequences.

Exemplary plasmid vectors useful to produce the polypeptides provided herein contain a strong promoter, such as the HCMV immediate early enhancer/promoter or the MHC class I promoter, an intron to enhance processing of the transcript, such as the HCMV immediate early gene intron A, and a polyadenylation (poly A) signal, such as the late SV40 polyA signal.

Genetic modification of engineered immune cells (e.g., T cells, NK cells) can be accomplished by transducing a substantially homogeneous cell composition with a recombinant DNA or RNA construct. The vector can be a retroviral vector (e.g., gamma retroviral), which is employed for the introduction of the DNA or RNA construct into the host cell genome. For example, a polynucleotide encoding the antigen-targeted CAR and the prodrug converting enzyme can be cloned into a retroviral vector and expression can be driven from its endogenous promoter, from the retroviral long terminal repeat, or from an alternative internal promoter.

Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide antigen-targeted CAR and the prodrug converting enzyme expressing cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. *Mol. Cell. Biol.* 5:431-437 (1985)); PA317 (Miller, et al. *Mol. Cell. Biol.* 6:2895-2902(1986)); and CRIP (Danos, et al. *Proc. Natl. Acad. Sci. USA* 85:6460-6464 (1988)). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. *Blood* 80: 1418-1422 (1992), or culturing with viral supernatant alone or concentrated vector stocks with or without appropriate growth factors and polycations, e.g., by the method of Xu, et al. *Exp. Hemat.* 22:223-230 (1994); and Hughes, et al. *J. Clin. Invest.* 89: 1817 (1992).

Transducing viral vectors can be used to express a co-stimulatory ligand and/or secretes a cytokine (e.g., 4-1BBL and/or IL-12) in an engineered immune cell. Preferably, the chosen vector exhibits high efficiency of infection and stable integration and expression (see, e.g., Cayouette et al., *Human Gene Therapy* 8:423-430 (1997); Kido et al., *Current Eye Research* 15:833-844 (1996); Bloomer et al., *Journal of Virology* 71:6641-6649, 1997; Naldini et al., *Science* 272:263 267 (1996); and Miyoshi et al., *Proc. Natl. Acad. Sci. U.S.A.* 94: 10319, (1997)). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, *Human Gene Therapy* 15-14, (1990); Friedman, *Science* 244: 1275-1281 (1989); Eglitis et al., *BioTechniques* 6:608-614, (1988); Tolstoshev et al., *Current Opinion in Biotechnology* 1:55-61 (1990); Sharp, *The Lancet* 337: 1277-1278 (1991); Cornetta et al., *Nucleic Acid Research and Molecular Biology* 36:311-322 (1987); Anderson, *Science* 226:401-409 (1984); Moen, *Blood Cells* 17:407-416 (1991); Miller et al., *Biotechnology* 7:980-990 (1989); Le Gal La Salle et al., *Science* 259:988-990 (1993); and Johnson, *Chest* 107:77S-83S (1995)). Retroviral vectors are particularly well developed and have been used in clinical settings (Rosenberg et al., *N. Engl. J. Med* 323:370 (1990); Anderson et al., U.S. Pat. No. 5,399,346).

In certain non-limiting embodiments, the vector expressing a presently disclosed antigen-targeted CAR is a retroviral vector, e.g., an oncoretroviral vector.

Non-viral approaches can also be employed for the expression of a protein in cell. For example, a nucleic acid molecule can be introduced into a cell by administering the nucleic acid in the presence of lipofection (Feigner et al., *Proc. Nat'l. Acad. Sci. U.S.A.* 84:7413, (1987); Ono et al., *Neuroscience Letters* 17:259 (1990); Brigham et al., *Am. J. Med. Sci.* 298:278, (1989); Staubinger et al., *Methods in Enzymology* 101:512 (1983)), asialoorosomucoid-polylysine conjugation (Wu et al., *Journal of Biological Chemistry* 263: 14621 (1988); Wu et al., *Journal of Biological Chemistry* 264: 16985 (1989)), or by micro-injection under surgical conditions (Wolff et al., *Science* 247: 1465 (1990)). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g., Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g., the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes. VI. Polypeptides and Analogs and Polynucleotides Also included in the presently disclosed subject matter are extracellular antigen-binding domains that specifically binds to a target antigen (e.g., an antigen from a pathogen, or an inflammatory antigen) (e.g., an scFv (e.g., a human scFv), a Fab, or a $(Fab)_2$), CD3ζ, CD8, CD28, etc. polypeptides or fragments thereof, and polynucleotides encoding thereof that are modified in ways that enhance their cytotoxic when expressed in an engineered immune cell. The presently disclosed subject matter provides methods for optimizing an amino acid sequence or a nucleic acid sequence by producing an alteration in the sequence. Such alterations may comprise certain mutations, deletions, insertions, or post-translational modifications. The presently disclosed subject matter further comprises analogs of any naturally-occurring polypeptide of the presently disclosed subject matter. Analogs can differ from a naturally-occurring polypeptide of the presently disclosed subject matter by amino acid sequence differences, by post-translational modifications, or by both.

Analogs of the presently disclosed subject matter can generally exhibit at least about 85%, about 90%, about 91%, about 92%, about 93%, about 94%, about 95%, about 96%, about 97%), about 98%, about 99% or more identity or homology with all or part of a naturally-occurring amino, acid sequence of the presently disclosed subject matter. The length of sequence comparison is at least about 5, about 10, about 15, about 20, about 25, about 50, about 75, about 100 or more amino acid residues. Again, in an exemplary approach to determining the degree of identity, a BLAST program may be used, with a probability score between $e^{-3}$ and $e^{-100}$ indicating a closely related sequence. Modifications comprise in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the presently disclosed subject matter by alterations in primary sequence. These include genetic variants, both natural and induced (for example, resulting from random mutagenesis by irradiation or exposure to ethanemethyl sulfate or by site-specific mutagenesis as described in Sambrook, Fritsch and Maniatis, Molecular Cloning: A Laboratory Manual (2nd ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., beta (β) or gamma (γ) amino acids.

In addition to full-length polypeptides, the presently disclosed subject matter also provides fragments of any one of the polypeptides or peptide domains of the presently disclosed subject matter. A fragment can be at least about 5, about 10, about 13, or about 15 amino acids. In some embodiments, a fragment is at least about 20 contiguous amino acids, at least about 30 contiguous amino acids, or at least about 50 contiguous amino acids. In some embodiments, a fragment is at least about 60 to about 80, about 100, about 200, about 300 or more contiguous amino acids. Fragments of the presently disclosed subject matter can be generated by methods known to those of ordinary skill in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the presently disclosed subject matter. Such analogs may exceed the physiological activity of the original polypeptide. Methods of analog design are well known in the art, and synthesis of analogs can be carried out according to such methods by modifying the chemical structures such that the resultant analogs increase the activity of the original polypeptide when expressed in an engineered immune cell. These chemical modifications include, but are not limited to, substituting alternative R groups and varying the degree of saturation at specific carbon atoms of a reference polypeptide. The protein analogs can be relatively resistant to in vivo degradation, resulting in a more prolonged therapeutic effect upon administration. Assays for measuring functional activity include, but are not limited to, those described in the Examples below.

In accordance with the presently disclosed subject matter, the polynucleotides encoding an extracellular antigen-binding domain that specifically binds to target antigen (e.g., an antigen from a pathogen or an inflammatory antigen) (e.g., an scFv (e.g., a human scFv), a Fab, or a $(Fab)_2$), CD3, CD8, CD28) can be modified by codon optimization. Codon optimization can alter both naturally occurring and recombinant gene sequences to achieve the highest possible levels of productivity in any given expression system. Factors that are involved in different stages of protein expression include codon adaptability, mRNA structure, and various cis-elements in transcription and translation. Any suitable codon optimization methods or technologies that are known to ones skilled in the art can be used to modify the polynucleotides of the presently disclosed subject matter, including, but not limited to, OptimumGene™, Encor optimization, and Blue Heron.

Administration

Engineered immune cells expressing the antigen-targeted CAR and a prodrug converting enzyme of the presently disclosed subject matter can be provided systemically or directly to a subject for treating or preventing an inflammation, an inflammatory disease or a pathogenic infection. In certain embodiments, engineered immune cells are directly injected into an organ of interest (e.g., an organ affected by inflammation or pathogenic infection). Alternatively or additionally, the engineered immune cells are provided indirectly to the organ of interest, for example, by administration into the circulatory system or lymphatic system. Expansion and differentiation agents can be provided prior to, during or after administration of cells and compositions to increase production of T cells in vitro or in vivo.

Engineered immune cells of the presently disclosed subject matter can be administered in any physiologically acceptable vehicle, systemically or regionally, normally intravascularly, intraperitoneally, intrathecally, or intrapleurally, although they may also be introduced into bone or other convenient site where the cells may find an appropriate site for regeneration and differentiation (e.g., thymus). In certain embodiments, at least $1\times10^5$ cells can be administered, eventually reaching $1\times10^{10}$ or more. In certain embodiments, at least $1\times10^6$ cells can be administered. A cell population comprising engineered immune cells can comprise a purified population of cells. Those skilled in the art can readily determine the percentage of engineered immune cells in a cell population using various well-known methods, such as fluorescence activated cell sorting (FACS). The ranges of purity in cell populations comprising engineered immune cells can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art (e.g., a decrease in purity may require an increase in dosage). The engineered immune cells can be introduced by injection, catheter, or the like. If desired, factors can also be included, including, but not limited to, interleukins, e.g., IL-2, IL-3, IL 6, IL-11, IL-7, IL-12, IL-15, IL-21, as well as the other interleukins, the colony stimulating factors, such as G-, M- and GM-CSF, interferons, e.g., γ-interferon.

In certain embodiments, compositions of the presently disclosed subject matter comprise pharmaceutical compositions comprising engineered immune cells expressing an antigen-targeted CAR and a prodrug converting enzyme with a pharmaceutically acceptable carrier. Administration can be autologous or non-autologous. For example, engineered immune cells expressing an antigen-targeted CAR and a prodrug converting enzyme and compositions comprising thereof can be obtained from one subject, and administered to the same subject or a different, compatible subject. Peripheral blood derived T cells of the presently disclosed subject matter or their progeny (e.g., in vivo, ex vivo or in vitro derived) can be administered via localized injection, including catheter administration, systemic injection, localized injection, intravenous injection, or parenteral administration. When administering a pharmaceutical composition of the presently disclosed subject matter (e.g., a pharmaceutical composition comprising engineered immune cells expressing an antigen-targeted CAR), it can be formulated in a unit dosage injectable form (solution, suspension, emulsion).

Formulations

Engineered immune cells expressing an antigen-targeted CAR and prodrug converting enzyme and compositions comprising thereof can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions of the presently disclosed subject matter, e.g., a composition comprising engineered immune cells, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the presently disclosed subject matter, however, any vehicle, diluent, or additive used would have to be compatible with the engineered immune cells of the presently disclosed subject matter.

The compositions can be isotonic, i.e., they can have the same osmotic pressure as blood and lacrimal fluid. The desired isotonicity of the compositions of the presently disclosed subject matter may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the engineered immune cells as described in the presently disclosed subject matter. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the engineered immune cells of the presently disclosed subject matter is the quantity of cells necessary to achieve an optimal effect. The quantity of cells to be administered will vary for the subject being treated. In certain embodiments, from about $10^2$ to about $10^{12}$, from about $10^3$ to about $10^{11}$, from about $10^4$ to about $10^{10}$, from about $10^5$ to about $10^9$, or from about $10^6$ to about $10^8$ engineered immune cells of the presently disclosed subject matter are administered to a subject. More effective cells may be administered in even smaller numbers. In some embodiments, at least about $1\times10^8$, about $2\times10^8$, about $3\times10^8$, about $4\times10^8$, about $5\times10^8$, about $1\times10^9$, about $5\times10^9$, about $1\times10^{10}$, about $5\times10^{10}$, about $1\times10^{11}$, about $5\times10^{11}$, about $1\times10^{12}$ or more engineered immune cells of the presently disclosed subject matter are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art. Generally, prodrugs are administered at doses that are non-toxic or tolerable to the patient. In some embodiments, the prodrug is administered at an amount that is about 10 to about 1000 times higher than that possible for the active drug. A suitable dose of prodrug can be from about 0.1 to 200 mg/Kg, such as about from 10 to 100 mg/Kg per patient per day or from 5 to 2000 mg/$m^2$ (e.g., 200 mg/$m^2$).

The skilled artisan can readily determine the amount of cells and optional additives, vehicles, and/or carrier in compositions and to be administered in methods of the presently disclosed subject matter. Typically, any additives (in addition to the active cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation Methods for Therapy For treatment, the amount of the engineered immune cells provided herein administered is an amount effective in producing the desired effect. An effective amount can be provided in one or a series of administrations of the engineered immune cells provided herein. An effective amount can be provided in a bolus or by continuous perfusion. For adoptive immunotherapy using antigen-specific T cells, cell doses in the range of about $10^6$ to about $10^{10}$ are typically infused. Co-expression of the prodrug converting enzyme as disclosed herein, may permit lower doses of the engineered immune cells to be administered, e.g., about $10^4$ to about $10^8$. Upon administration of the engineered immune cells into the subject, the engineered immune cells are induced that are specifically directed against one target antigen (e.g., an antigen from a pathogen, or an inflammatory antigen). "Induction" of T cells can include inactivation of antigen-specific T cells such as by deletion or anergy. Inactivation is particularly useful to establish or reestablish tolerance such as in autoimmune disorders. The engineered immune cells of the presently disclosed subject matter can be administered by any methods known in the art, including, but not limited to, pleural administration, intravenous administration, subcutaneous administration, intranodal administration, intrathecal administration, intrapleural administration, intraperitoneal administration, and direct administration to the thymus. In certain embodiments, the engineered immune cells and the compositions comprising thereof are administered by direct injection into the lymph nodes of the patient, directly into the inflammatory site or directly into the transplanted organ. In certain embodiments, the engineered immune cells and the compositions comprising thereof are intravenously administered to the subject in need. Methods for administering cells for adoptive cell therapies, including, for example, donor lymphocyte infusion and CAR T cell therapies, and regimens for administration are known in the art and can be employed for administration of the engineered immune cells provided herein.

The presently disclosed subject matter provides various methods of using the engineered immune cells (e.g., T cells, e.g., CAR T cells) provided herein, expressing an antigen-targeted receptor (e.g., a CAR) and a prodrug converting enzyme. The presently disclosed subject matter further provides, in some embodiments, methods for treating or preventing inflammation or an autoimmune or inflammatory disease by administering an effective amount of the engineered immune cells followed by administration of a cytotoxic or therapeutic prodrug.

In some embodiments, the engineered immune cells provided herein are employed for ablative therapy, such as normal stem cell ablation prior to hematopoietic stem cell transplantation (HSCT) or bone marrow transplant (BMT). In some embodiments, an effective amount of engineered immune cells that express a receptor (e.g., a CAR) specific for a stem cell-specific marker, such as CD34 are administered to the patient followed by administration of a cytotoxic ablative prodrug to effect localize ablation at the target site.

In some embodiments, the engineered immune cells and the prodrug are administered at different times. For example, in some embodiments, the engineered immune cells are administered and then the prodrug is administered. In some embodiments, the prodrug is administered 1 hour, 2 hours, 3 hours, 4 hours, 5 hours, 6 hours, 7 hours, 8 hours, 9 hours, 10 hours, 11 hours, 12 hours, 18 hours, 24 hours, 30 hours, 26 hours, 48 hours or longer after the administration of the engineered immune cells.

Additionally, the presently disclosed subject matter provides methods of increasing immune-activating cytokine production in response to a pathogen in a subject. In one non-limiting example, the method comprises administering the presently disclosed engineered immune cell to the subject. The immune-activating cytokine can be granulocyte macrophage colony stimulating factor (GM-CSF), IFN-a, IFN-β, IFN-γ, TNF-a, IL-2, IL-3, IL-6, IL-1 1, IL-7, IL-12, IL-15, IL-21, interferon regulatory factor 7 (IRF7), and combinations thereof. In certain embodiments, the engineered immune cells including an antigen-specific CAR of the presently disclosed subject matter increase the production of GM-CSF, IFN-γ, and/or TNF-a.

In some embodiments, an antigen-targeted CAR provided herein is administered for the treatment of inflammation or an inflammatory disease. In some embodiments, the antigen-targeted CAR is administered for the treatment of an autoimmune disease. In some embodiment, the autoimmune disease is selected from the group consisting of Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune ivmphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis—juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura, IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo, Wegener's granulomatosis, and any combination thereof. In some embodiments, an antigen-targeted CAR provided herein is administered for the treatment of an allergic or asthmatic condition. In some embodiments, an antigen-targeted CAR provided herein is administered for the treatment an allogenic transplant or graft rejection.

In some embodiments, an antigen-targeted CAR is administered for the treatment of a pathogenic infection. In some embodiments, an antigen-targeted CAR is administered for the treatment of a viral infection. Exemplary viruses include, but are not limited to, adenoviridae (e.g. adenovirus), papovaviridae (papillomavirus, HPV-1), parvoviridae, herpesviridae (e.g., herpes simplex virus (HSV-1, HSV-2), varicella-zoster virus (VSV), cytomegalovirus (CMV), Epstein-Barr virus (EBV)), poxviridae (e.g. smallpox virus, cow pox virus, sheep pox virus, orf virus, monkey pox virus, vaccinia virus), hepadnaviridae (e.g., hepatitis B virus), anelloviridae, reoviridae, picornaviridae (e.g., enterovirus, rhinovirus, hepatovirus, cardiovirus, aphthovirus, poliovirus, parechovirus, erbovirus, kobuvirus, teschovirus, coxsackie), caliciviridae (e.g., Norwalk virus), togaviridae (e.g., rubella virus, dengue virus), arenaviridae, flaviviridae (e.g., dengue virus, hepatitis C virus, yellow fever virus), orthomyxoviridae (e.g., influenza virus types A, B and C), paramyxoviridae (e.g., mumps virus, measles virus, respiratory syncytial virus (RSV)), bunyaviridae, rhabodoviridae (e.g., rabies virus), filoviridae (e.g., Ebola virus, Marburg virus), coronaviridae, bornaviridae, arteriviridae, hepeviridae (e.g., hepatitis e virus), and retroviradae (e.g., HTLV-I, HTLV-II, HIV-1, HIV-2, simian immunodeficiency virus (SIV)).

In some embodiments, an antigen-targeted CAR is administered for the treatment of a bacterial infection. Exemplary bacteria include, but are not limited to, *Pasteurella*, Staphylococci, *Streptococcus, Escherichia coli, Pseudomonas species*, and *Salmonella* species. Specific examples of infectious bacteria include but are not limited to, *Helicobacter pyloris, Borelia burgdorferi, Legionella pneumophilia, Mycobacteria* sps (e.g., *M. tuberculosis, M. avium, M. intracellulare, M. kansaii, M. gordonae*). *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus antracis, corynebacterium, diphtherias, corynebacterium* sp., *Erysipelothrix rhusiopathiae, Clostridium perfringens, Clostridium tetani, Enterobacter aerogenes, Klebsiella pneumoniae, Pasturella mxdtocida, Bacteroides* sp., *Fusobacterium nucleatum, Streptobacillus moniliformis, Treponema pallidium, Treponema pertenue, Leptospira, Rickettsia*, and *Actinomyces israelii*.

In some embodiments, an antigen-targeted CAR is administered for the treatment of a fungal infection, parasite infection, or protozoal infection.

Further modifications can be introduced to the antigen-targeted CAR-expressing engineered immune cells (e.g., T cells) to avert or minimize the risks of immunological complications (known as "malignant T-cell transformation"), e.g., graft versus-host disease (GvHD), or when healthy tissues express the same target antigens as the target cells, leading to outcomes similar to GvFID. Modification of the engineered immune cells can include engineering a suicide gene into the antigen-targeted CAR-expressing T cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T cell elimination by administering anti-EGFR monoclonal antibody (e.g., cetuximab). EGFRt can be covalently joined to the C-terminus of the intracellular domain of the antigen-targeted CAR. The suicide gene can be included within the vector comprising nucleic acids encoding the presently disclosed antigen-targeted CARs. In this way, administration of a prodrug designed to activate the suicide gene (e.g., a prodrug (e.g., API 903 that can activates iCasp-9) during malignant T-cell transformation (e.g., GVHD) triggers apoptosis in the suicide gene-activated CAR-expressing T cells. The incorporation of a suicide gene into the a presently disclosed antigen-targeted CAR gives an added level of safety with the ability to eliminate the majority of CART cells within a very short time period. A presently disclosed engineered immune cell (e.g., a T cell) incorporated with a suicide gene can be pre-emptively eliminated at a given time point post CAR T cell infusion, or eradicated at the earliest signs of toxicity.

Articles of Manufacture and Kits

The presently disclosed subject matter provides kits for the treatment or prevention of an inflammation, an inflammatory disease, or a pathogenic infection. In certain embodiments, the kit comprises a therapeutic or prophylactic composition containing an effective amount of an engineered immune cell comprising an antigen-targeted receptor (e.g., a CAR) and prodrug converting enzyme in unit dosage form. In particular embodiments, the cells further expresses at least one co-stimulatory ligand. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the engineered immune cell can be provided together with instructions for administering the engineered immune cell to a subject having or at risk of developing an inflammation, an inflammatory disease, or a pathogenic infection. The instructions will generally include information about the use of the composition for the treatment or prevention of an inflammation, an inflammatory disease, or a pathogenic infection. In other embodiments, the instructions include at least one of the following: description of the therapeutic agent; dosage schedule and administration for treatment or prevention of an inflammation, an inflammatory disease, or a pathogenic infection or symptoms thereof; precautions; warnings; indications; counter-indications; overdose information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the compositions, and assay, screening, and therapeutic methods of the invention, and are not intended to limit the scope of what the inventors regard as their invention.

Example 1

Figure 2C:
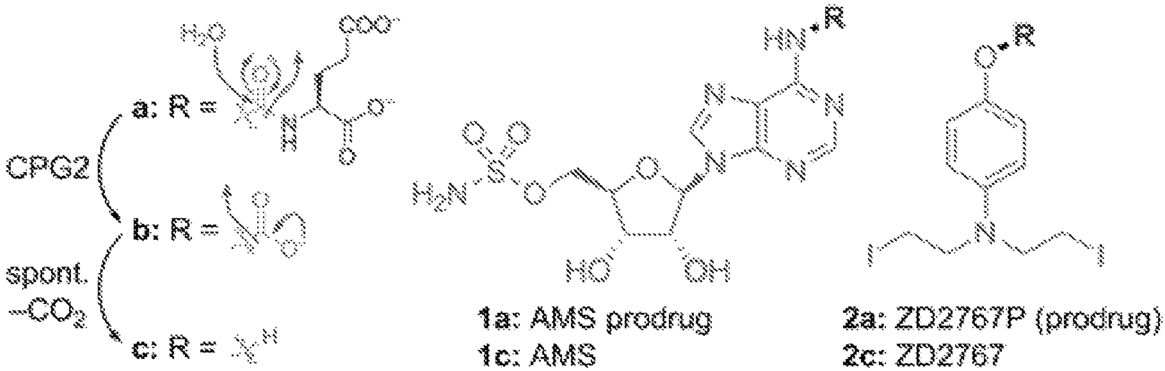
Figure 2D:
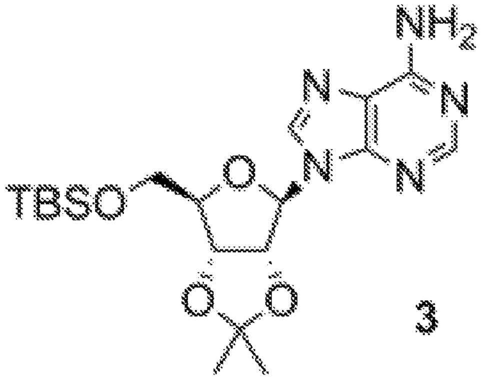
Figure 2D:
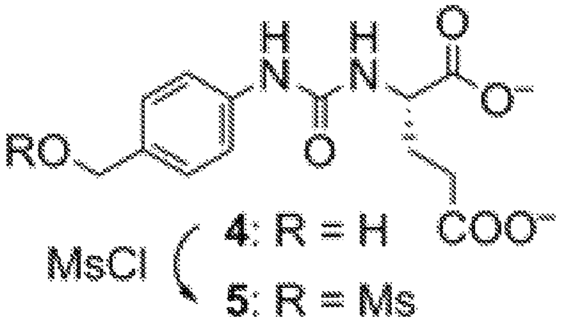

Synthesis of Prodrugs of Cytotoxic and Targeted Small Molecules for Use with SEAKER Cells This example describes the synthesis of exemplary prodrugs based on sulfamoyladenosine (AMS) (structure 1c) (FIG. 2*c*) for cleavage by the bacterial hydrolase enzyme CPG2. AMS is a close analog of nucleocidin and a potent cytotoxic molecule (HepG2 $IC_{50}$=9 nM). A detailed structure—activity relationship (SAR) study was performed, which indicated that cytotoxicity of AMS is dramatically reduced or eliminated by substitution at the 6-amino ($Me_2$, >500 μM) C2 (Ph, ≈500 μM), C8 (n-Pr, >250 μM), or sulfamate positions (salicyl, >500 μM). Based on these SAR data, AMS prodrug 1a ("P-AMS"; FIG. 2*c*) was synthesized from 2',3'-O-isopropylidene-5'-O-TBS-adenosine (structure 3, FIG. 2*d*) by 6-N-acylation with CDI-activated bis-O-t-Bu-glutamate (30%), desilylation (TBAF), sulfamoylation ($H_2NSO_2Cl$, DMA), and acetonide hydrolysis (TFA, $H_2O$, 15% over 3 steps). Two alternative N-sulfamate-linked prodrugs (not shown) attached via CO-PAB-CO and TML-CO linkers were synthesized (FIG. 2*b*). A more detailed discussion of the P-AMS synthesis and the synthesis of the N-sulfamate-linked prodrug attached via a TML-CO linker ("Trimethyllock-AMS") is provided below in this example. As an alternative cytotoxic using a known chemotherapeutic, the mustard prodrug ZD2767P (structure 2a, FIG. 2*c*) was also synthesized as previously reported (Springer et al., *J Med Chem.* 37(15):2361-70(1994) and Niculescu-Duvaz et al., *Tetrahedron Lett.* 46(40):6919-22 (2005)).

Figure 2E:
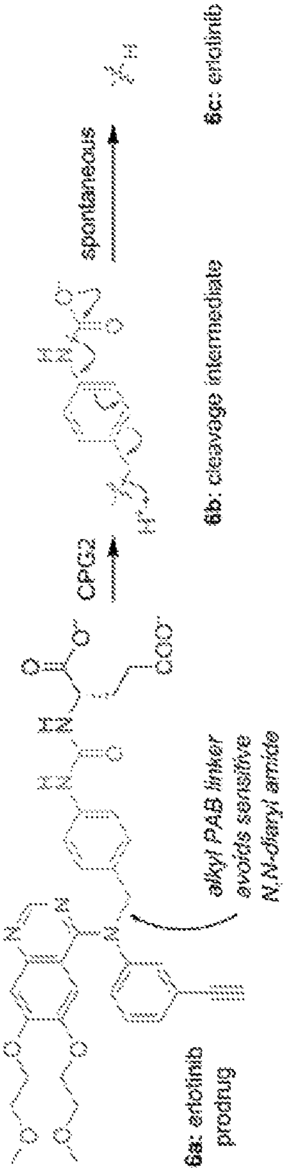

As an example of a targeted therapy approach, an erlotinib prodrug (structure 6a, FIG. 2*e*) was also designed. To avoid potential hydrolytic instability of an N,N-diarylamide (cf. CO or CO-PAB-CO linkers), a N-benzyl linker (PAB-CO) that undergo spontaneous elimination after glutamate cleavage was synthesized. Similar 1,6-elimination of a p-aminobenzyl quaternary ammonium salt has been demonstrated (Staben et al. *Nat Chem.* 8(12):1112-9 (2016). The synthesis was achieved by conversion of the known benzyl alcohol (structure 4, FIG. 2*d*) to the corresponding mesylate (MsCl) (structure 5, FIG. 2*d*), N-alkylation of erlotinib (25% over 2 steps), and deprotection of the t-Bu esters (TFA, $CH_2Cl_2$, 3%, unoptimized). A more detailed discussion and characterization of this erlotinib prodrug synthesis is provided below in this example.

The in vitro cytotoxicity of AMS (structure 1c) and its prodrug variant (structure 1a) was tested against a variety of cell lines using a CellTitre Glo® assay (Promega, Madison, WI). As expected, AMS is highly cytotoxic to HEK293T (kidney, IC50=666 nM), HL 60 (leukemia; 70 nM), Jurkat (T cell; 18 nM), and primary T-cells (66 nM), while prodrug 1a is non-toxic (IC50>1,000 nM; SI selectivity index up to >56). Moreover, co-treatment with the prodrug and supernatant from CPG2-transfected HEK293T cells (see Example 3) led to cytotoxicity approaching that of the free drug (50 nM), consistent with CPG2-mediated cleavage of the prodrug to release the active parent drug. Similar results were obtained with the mustard prodrug ZD2767P (structure 2a) (IC50=1.7 μM with CPG2 supernatant). In contrast, AMS prodrug 1a was not activated by HEK293T cells expressing CPG intracellularly, which likely attributed to poor cell-penetrance of the prodrug due to the free bis-anionic gluatamate moiety.

In vitro cytotoxicity of AMS-related structures was also assessed to determine the modifications of AMS that alter cytotoxicity. The in vitro cytotoxicity of each of these AMS-related structures was tested against both hepatocellular carcinoma HepG2 and normal human fibroblast MRCS cell lines using a CellTitre Glo® assay (Promega, Madison, WI) The modifications and results are provided in Table 1 below.

TABLE 1

| | Shorthand ref (MSK ref) | X | $R^1$ | $R^2$ | $IC_{50}$, HepG2 (μM) | $IC_{50}$, MRC5 (μM) |
|---|---|---|---|---|---|---|
| 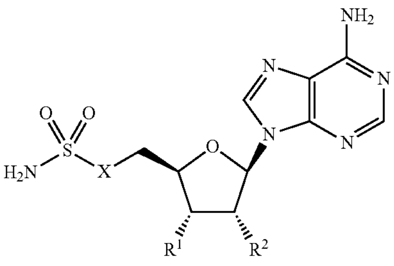 | AMS (lcsTan1) | O | —OH | —OH | 0.009 | 0.030 |
| | AMSN (lcsTan12) | NH | —OH | —OH | 0.36 | 0.39 |
| | 2'-deoxy-AMS (lcsTan13) | O | —OH | —H | <1 0.55 | <1 0.48 |
| | 3'-deoxy-AMS (lcsTan14) | O | —H | —OH | >5 ~500 | >5 ~100 |

TABLE 1-continued

| | Shorthand ref (MSK ref) | | | | IC$_{50}$, HepG2 (μM) | IC$_{50}$, MRC5 (μM) |
|---|---|---|---|---|---|---|
| | | R$^1$ | R$^2$ | R$^3$ | | |
| 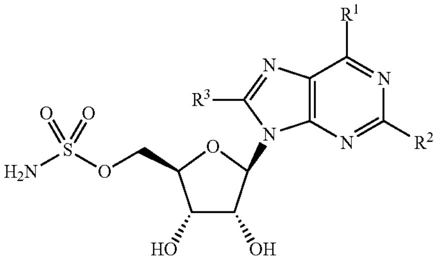 | 6-desN-AMS (lcsTan18) | —H | —H | —H | <1<br>0.16 | <1<br>0.13 |
| | 6-NHMe-AMS (lcsTan4) | —NHMe | —H | —H | 1.8 | 0.9 |
| | 6-NMe2-AMS (lcsTan22) | —NMe$_2$ | —H | —H | >500 | >500 |
| | 6-NCyp-AMS (lcsTan5) | —NHCyp | —H | —H | 10.9 | 7.2 |
| | 6-OMe-AMS (lcsTan21) | —OCH$_3$ | —H | —H | 141 | 129 |
| | 2-NH$_2$-AMS<br>(lcsTan19) | —NH$_2$ | —NH$_2$ | —H | <1<br>1.75 | <1<br>1.17 |
| | 2-phenyl-AMS (lcsTan6) | —NH$_2$ | —Ph | —H | ~500 | >500 |
| | 2-CCPh-AMS (lcsTan7) | —NH$_2$ | —CCPh | —H | 20.7 | 13.4 |
| | 2-NHPh-AMS (lcsTan8) | —NH$_2$ | —NHPh | —H | >500 | 123.5 |
| | 8-Cl-AMS (lcsTan17) | —NH$_2$ | —H | —Cl | <1<br>4.51 | 3.2<br>3.51 |
| | 8-propyl-AMS (lcsTan20) | —NH$_2$ | —H | -propyl | >250<br>>500 | >250<br>>500 |
| | | B | R | | | |
| 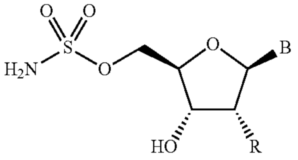 | IMS (lcsTan2) | 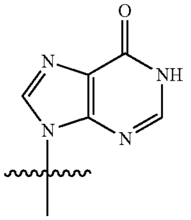 [SMILES: *n1cnc2c(=O)[nH]cnc21] | —OH | | >500 | >500 |
| | GMS (lcsTan3) | 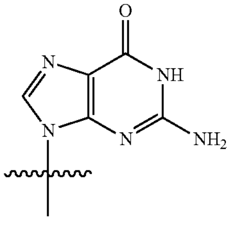 [SMILES: *n1cnc2c(=O)[nH]c(N)nc21] | —OH | | >500 | >500 |
| | Tubericidin-MS (lcsTan23) | 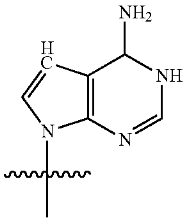 [SMILES: *n1ccc2c1N=CNC2N] | —OH | | 1.7<br>0.018 | <0.015<br>0.005 |
| | l'-homo-AMS, n = 1 (lcsTan15) | 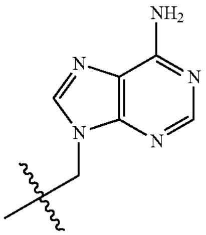 [SMILES: *Cn1cnc2c(N)ncnc21] | —OH | | >500 | >500 |

TABLE 1-continued
| Shorthand ref (MSK ref) | | | $IC_{50}$, HepG2 (μM) | $IC_{50}$, MRC5 (μM) |
|---|---|---|---|---|
| l'-homo-AMS, n = 2 (lcsTan16) | 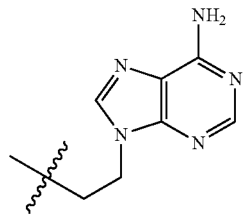 [SMILES: *CCn1cnc2c(N)ncnc21] | —OH | >500 | >500 |
| CMS (lcsTan11) | 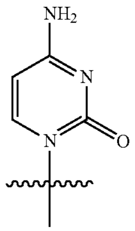 | —OH | >500 | >500 |
| UMS (lcsTan10) | 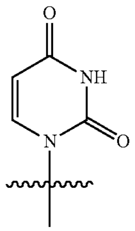 | —OH | >500 | >500 |
| TMS (lcsTan9) | 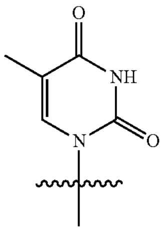 [SMILES: *n1cc(C)c(=O)[nH]c1=O] | —H | >500 | >500 |

Surprisingly, while most modifications resulted in a marked decrease in cytotoxicity, several compounds continued to possess sufficient cytotoxic activity for utility in the present technology. For example, AMSN, 2'-deoxy-AMS, 6-desN-AMS, 2-NH2-AMS, and Tubericidin-MS are each well-disposed for generation of prodrugs and use in the present technology.

Representative Synthesis and Examples of ProDrug Compounds of Formula I

Synthesis and Characterization of P-AMS

Synthesis of the prodrug compound P-AMS is summarized in Scheme 1 below (where P-AMS is also referred to as S5) and further detailed thereafter.

Scheme 1.

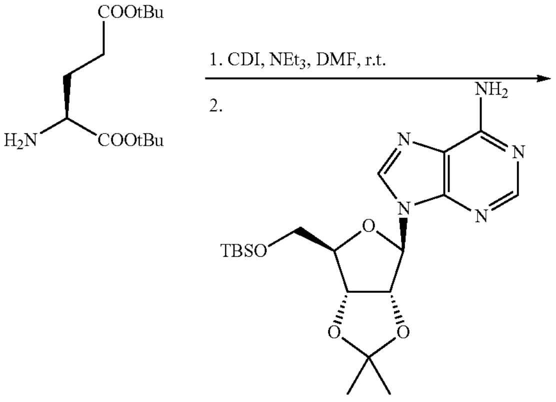

S1

NAH, DMF, r.t.

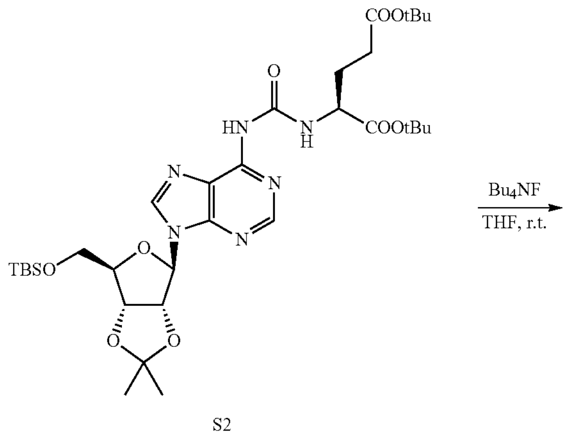

S2

35%

-continued

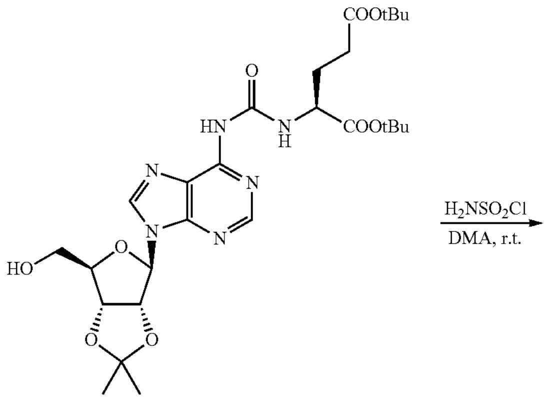

S3

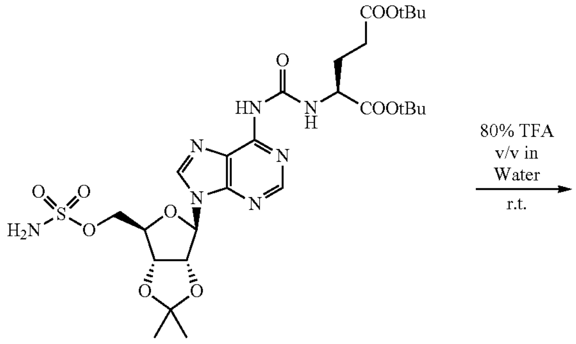

S4

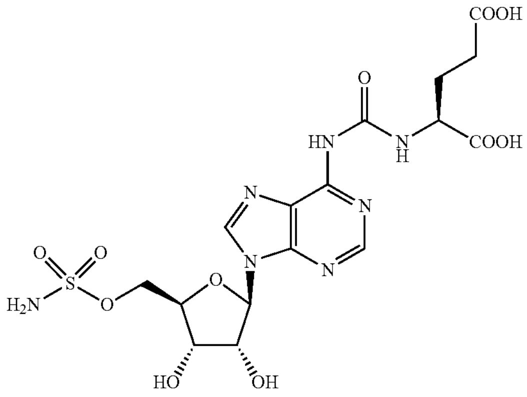

S5

15% over three steps di-tert-butyl ((9-((3aR,4R,6R,6aR)-6-(((tert-butyldimethylsilyl)oxy) methyl)-2,2-dimethyltetrahydrofuro[3,4-d][1,3]dioxol-4-yl)-9H-purin-6-yl)carbamoyl)-L-glutamate) (S2)

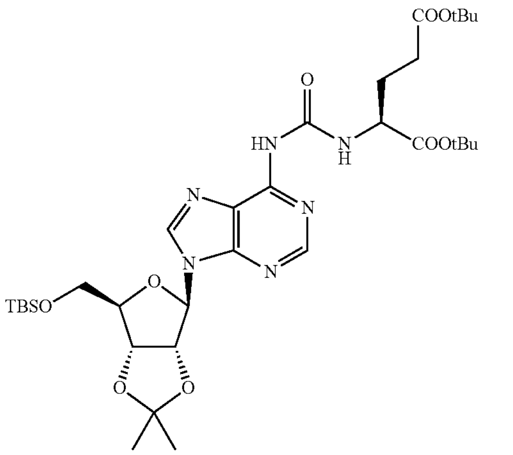

S1 was prepared as described in Somu, R. V.; Boshof, H.; Qiao, C.; Bennett, E. M.; Barry, C. E.; Aldrich, C. C. *J. Med. Chem.* 2006, 49 (1), 31-34. In a 25 mL round bottom flask at 25° C., (S)-di-tertbutyl glutamate (300 mg, 1.16 mmol, 1.0 equiv) was suspended in 8 mL anhyd DMF. 1,1'-Carbonyldiimidazole (CDI, 187 mg, 1.16 mmol, 1 equiv) was added in one portion, and the mixture was stirred for 1 h. Separately, a solution of S1 (828 mg, 1.96 mmol, 1.7 equiv) in anhyd DMF (4 mL) was added 60% NaH in mineral oil (117.8 mg, 2.95 mmol, 2.6 equiv) for 15 min. This separate adenosine mixture was added dropwise to the CDI activated glutamate mixture at 25° C. The reaction was stirred at 25° C. overnight for an additional 16-20 h, until complete conversion had occurred as judged by LC-MS. The mixture was then quenched with satd aq NaCl. The aqueous mixture was extracted with ethyl acetate (3×20 mL), and the combined organic extracts were dried over $MgSO_4$, filtered, and concentrated by rotary evaporation to afford the crude product as a yellow oil. Purification by silica flash chromatography (3:1 hexanes/EtOAc to 1:1 hexanes/EtOAc) yielded product S2 (286 mg, 35%) as a light yellow oil. TLC: $R_f$ 0.35 (1:1 hexanes/EtOAc). $^1$H-NMR (500 MHz, $CDCl_3$): δ 9.91 (d, 1H, J=8.0), 8.61 (s, 1H), 8.19 (s, 1H), 7.94 (s, 1H), 6.20 (s, 1H), 5.23 (dd, 1H, J=10, 5.2), 4.94 (dd, 1H, J=10, 4.9), 4.61 (q, 1H, 4.6), 3.89 (dd, 1H, J=8.8, 4.0), 3.77 (dd, 1H, J=8.7, 3.9), 3.33 (dd, 1H, J=7.9, 5.2), 2.42 (m, 2H), 2.26 (m, 1H), 2.09 (m, 1H), 1.64 (s, 3H), 1.50 (s, 9H), 1.43 (s, 9H), 1.41 (s, 3H), 0.83 (s, 9H), 0.01 (dd, 6H, J=1.6). $^{13}$C-NMR (126 MHz, $CDCl_3$): δ 206.8, 172.0, 171.0, 153.3, 151.3, 150.0, 120.8, 114.1, 91.9, 87.5, 85.1, 82.1, 81.5, 80.5, 77.2, 63.6, 60.3, 53.4, 31.6, 30.9, 28.3, 28.0, 27.2, 25.8, 25.3, 21.0, 18.3, 14.2, −5.5. ESI-MS m/z (rel int): (pos) 707.4 ([M+H]$^+$, 100).

di-tert-butyl ((9-((3aR,4R,6R,6aR)-6-(hydroxymethyl)-2,2-dimethyltetrahydrofuro[3,4-d][1,3]dioxol-4-yl)-9H-purin-6-yl)carbamoyl)-L-glutamate (S3)

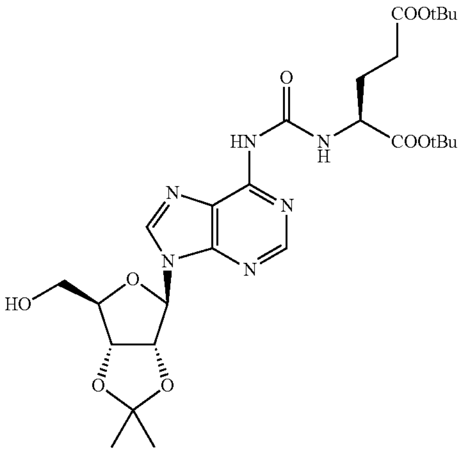

In a 50 mL round bottom flask at 25° C., S2 (286 mg, 404 μmol, 1.0 equiv) was suspended in 15 mL THF. 1M TBAF in THF (0.88 mL, 0.88 mmol, 2.2 equiv) was added in one portion, and the mixture was stirred for 1 h at 25° C. The mixture was then quenched with satd aq NaCl. The aqueous mixture was extracted with ethyl acetate (3×20 mL), dried over $MgSO_4$, filtered, and concentrated by rotary evaporation to afford the crude product (274 mg) as a yellow oil. Crude product was carried over to the next step without further purification.

Crude $^1$H-NMR (500 MHz, $CDCl_3$) δ 8.57 (s, 1H), 8.41 (s, 1H), 6.01 (d, J=4.0 Hz, 1H), 5.43 (s, 1H), 5.18 (dd, J=5.9, 4.1 Hz, 1H), 5.05 (d, J=5.9 Hz, 1H), 4.56 (dt, J=7.9, 3.9 Hz, 1H), 4.53 (s, 1H), 3.95 (d, J=1.8 Hz, 0H), 3.94-3.91 (m, 1H), 3.77 (d, J=12.6 Hz, 1H), 3.42 (s, 2H), 3.34-3.27 (m, 1H), 2.43-2.27 (m, 2H), 2.27-2.17 (m, 1H), 2.10-2.00 (m, 1H), 1.61 (s, 3H), 1.60 (s, 3H), 1.48 (s, 9H), 1.38 (s, 9H). ESI-MS m/z (rel int): (pos) 593.3 ([M+H]$^+$, 100).

di-tert-butyl ((9-((3aR,4R,6R,6aR)-2,2-dimethyl-6-((sulfamoyloxy) methyl) tetrahydrofuro[3,4-d][1,3] dioxol-4-yl)-9H-purin-6-yl)carbamoyl)-L-glutamate (S4)

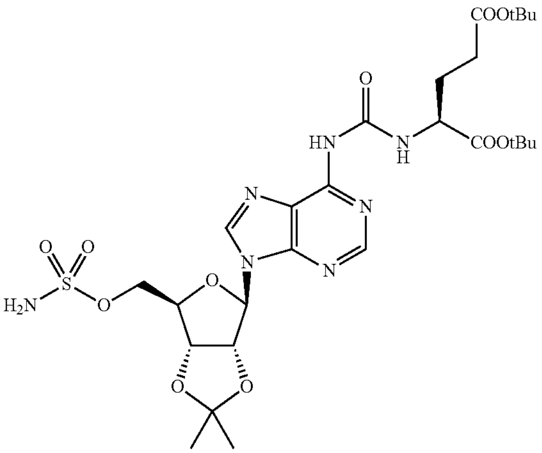

In a 25 mL round bottom flask at 0° C., S3 (274.4 mg, 462 μmol, 1.0 equiv) was suspended in 10 mL anhyd DMA. Sulfamoyl chloride (133.4 mg, 1.156 mmol, 2.5 equiv) was added in one portion, and the mixture was stirred for 1 h warming to 25° C. The mixture was then quenched with satd aq $NaHCO_3$. The aqueous mixture was extracted with ethyl acetate (3×15 mL), dried over $MgSO_4$, filtered, and concentrated by rotary evaporation to afford the crude product (310 mg) as a yellow oil. Crude product was carried to next step without further purification. Crude $^1$H-NMR (500 MHz, $CDCl_3$) δ 8.24 (s, 1H), 8.20 (s, 1H), 5.94 (d, J=2.8 Hz, 1H), 5.04 (dd, J=6.1, 2.8 Hz, 1H), 4.77 (dd, J=6.2, 2.6 Hz, 1H), 4.29-4.18 (m, 2H), 4.02 (dd, J=10.9, 4.4 Hz, 1H), 3.97 (dd, J=10.8, 4.6 Hz, 1H), 3.72 (q, J=7.1 Hz, 2H), 2.11-1.84 (m, 3H), 1.65 (s, 6H), 1.14 (s, 9H), 1.05 (s, 9H). ESI-MS m/z (rel int): (pos) 672.3 ([M+H]$^+$, 100).

((9-((2R,3R,4S,5R)-3,4-dihydroxy-5-((sulfamoyloxy)methyl)tetrahydrofuran-2-yl)-9H-purin-6-yl)carbamoyl)-L-glutamic acid (S5)

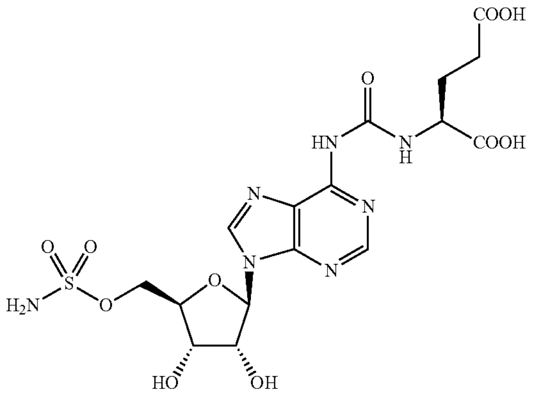 [SMILES: NS(=O)(=O)OC[C@H]1O[C@@H](n2cnc3c(NC(=O)N[C@@H](CCC(=O)O)C(=O)O)ncnc32)[C@H](O)[C@@H]1O]

In a 25 mL round bottom flask at 25° C., S4 (310.3 mg, 462 μmol, 1.0 equiv) was suspended in 22.5 mL 80% aq TFA solution. The reaction was stirred at 25° C. for an additional overnight for 5-6 h, until complete conversion had occurred as judged by LC-MS. The mixture was then quenched with 10 mL MeOH, and azeotroped through for a total of three times. The crude mixture was then purified through prep-HPLC and lyophilized overnight to yield S4 (36.7 mg, 70.6 μmol, 15% over three steps) as a white powder. $^1$H-NMR (500 MHz, Methanol-$d_4$): δ 8.67 (s, 1H), 8.56 (s, 1H), 6.20 (d, J=4.9 Hz, 1H), 4.75 (t, J=5.0 Hz, 1H), 4.63 (dd, J=7.9, 5.2 Hz, 1H), 4.46 (dd, J=8.0, 3.0 Hz, 2H), 4.43-4.35 (m, 2H), 2.59-2.44 (m, 2H), 2.37 (dq, J=13.6, 7.5, 7.0 Hz, 1H), 2.16 (dq, J=14.4, 7.6 Hz, 1H). 7 exchangeable H not observed. $^{13}$C-NMR (126 MHz, Methanol-$d_4$): 176.3, 174.6, 173.5, 155.5, 151.9, 150.3, 144.0, 121.3, 90.5, 83.8, 75.7, 71.8, 69.6, 54.0, 49.5, 31.0, 28.4. ESI-MS m/z (rel int): (pos) 520.2 ([M+H]$^+$, 100).

Synthesis and Characterization of Trimethyllock-AMS

Synthesis of the prodrug compound Trimethyllock-AMS is summarized in Scheme 2 below (where Trimethyllock-AMS is also referred to as S13) and further detailed thereafter.

Scheme 2.

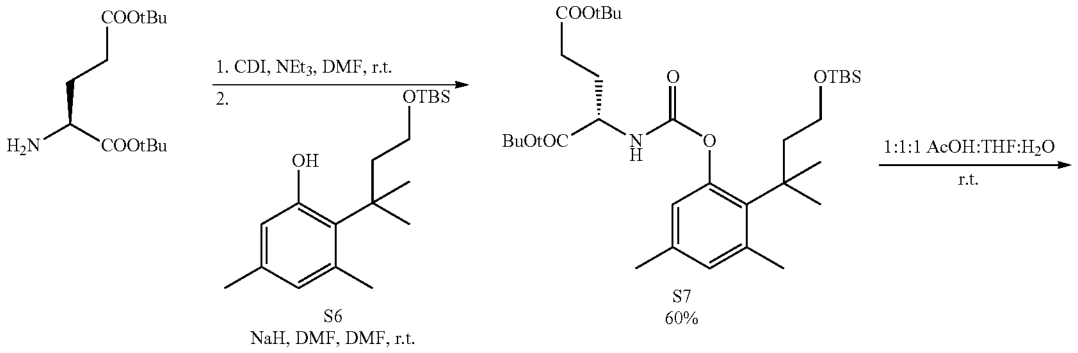

-continued
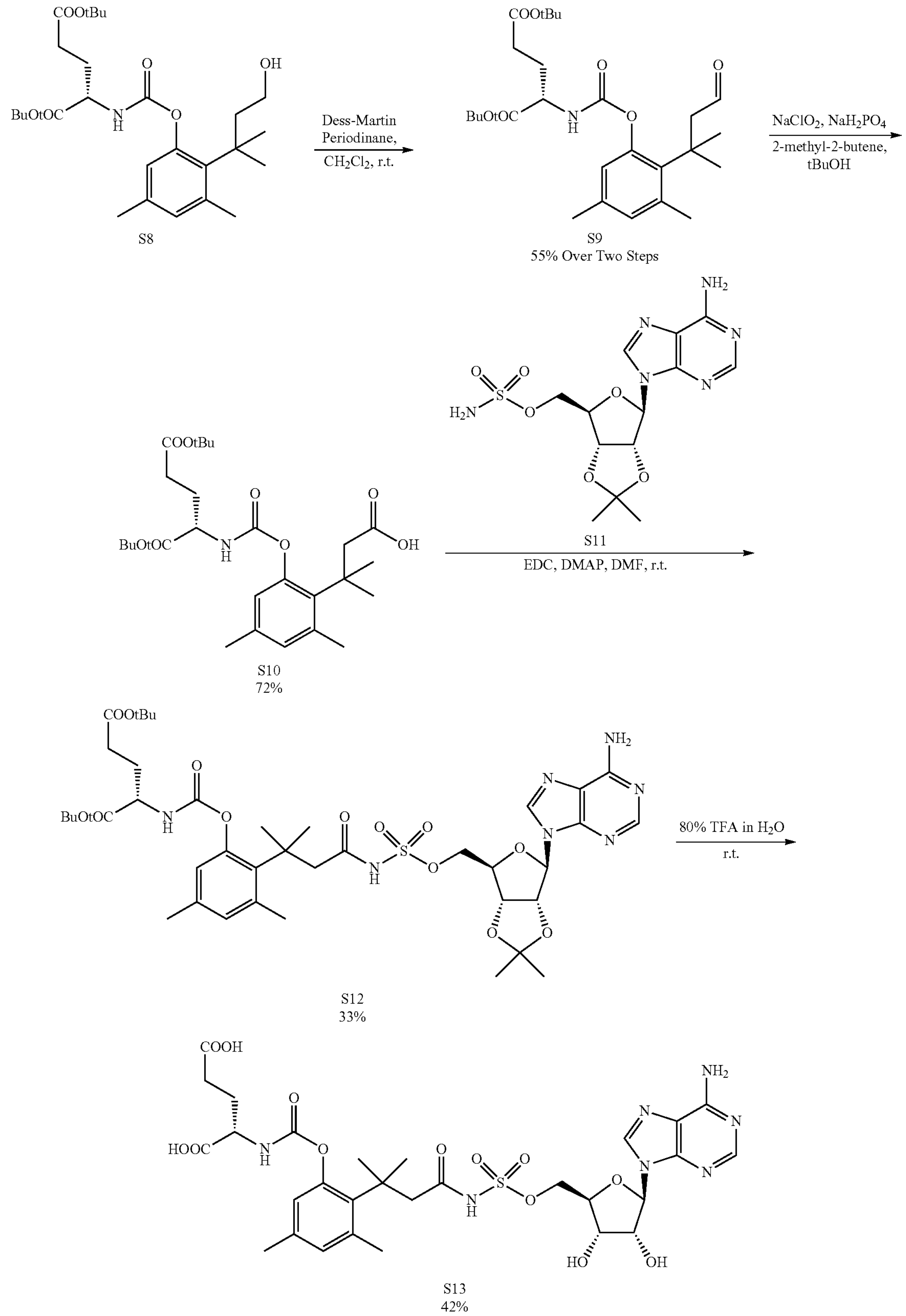

di-tert-butyl ((2-(4-((tert-butyldimethylsilyl)oxy)-2-methylbutan-2-yl)-3,5-dimethylphenoxy)carbonyl)-L-glutamate (S7)

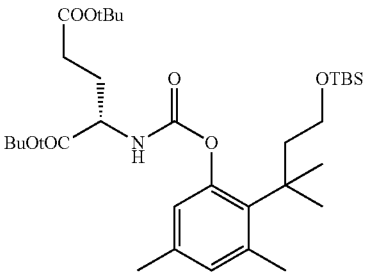

S6 was synthesized as described in Wang, B.; Gangwar, S.; Pauletti, G. M.; Siahaan, T. J.; Borchardt, R. T.; *J. Org. Chem.* 1997, 62, 1363-1367. In a 50 mL round bottom flask at 25° C., L-di-tertbutyl glutamate (1.12 g, 4.32 mmol, 1.0 equiv) was suspended in 10.79 mL anhyd DMF. 1,1'-Carbonyldiimidazole (CDI, 770 mg, 4.75 mmol, 1.1 equiv) and triethylamine (662 μL, 4.75 mmol, 1.1 equiv) was added in one portion, and the mixture was stirred for 1 h. Separately, S6 (1.04 g, 3.24 mmol, 0.75 equiv) was suspended in anhyd DMF (10.8 mL) and added 60% NaH in mineral oil (173 mg, 4.32 mmol, 1.0 equiv) for 15 min. This separate S6 mixture was added dropwise to the CDI activated glutamate mixture at 25° C. The reaction was stirred at 25° C. for overnight for an additional 17-20 h, until complete conversion had occurred as judged by TLC. The mixture was then quenched with satd aq NaCl, diluted with 50 mL ethyl acetate. The organic layer was then extracted, washed with satd aq NaCl (1×30 mL) followed by water (2×30 mL). The aqueous layers were then combined and extracted with ethyl acetate (2×30 mL). All organic layers were then combined, dried over $MgSO_4$, filtered, and concentrated by rotary evaporation to afford the crude product as a yellow oil. Purification by silica flash chromatography (9:1 hexanes/EtOAc to 3:1 hexanes/EtOAc) yielded product S7 (1.16 g, 60%) as a yellow oil.

TLC: $R_f$ 0.46 (3:1 hexanes/EtOAc). $^1$H-NMR (500 MHz, $CDCl_3$): δ 6.77 (s, 1H), 6.63 (s, 1H), 5.67 (d, J=8.2 Hz, 1H), 3.50 (t, J=7.5 Hz, 2H), 2.50 (s, 3H), 2.46-2.25 (m, 2H), 2.21 (s, 3H), 2.04 (t, J=7.5 Hz, 2H), 2.01-1.92 (m, 1H), 1.49 (s, 13H), 1.45 (s, 9H), 0.84 (s, 9H), −0.03 (s, 6H). $^{13}$C NMR (126 MHz, $CDCl_3$) δ 155.6, 137.5, 135.7, 128.9, 126.6, 116.5, 61.8, 45.0, 39.4, 32.0, 28.0, 25.5, 20.2, 18.3, −5.3. ESI-MS m/z (rel int): (pos) 608.5 ([M+H]$^+$, 100).

di-tert-butyl ((2-(4-hydroxy-2-methylbutan-2-yl)-3,5-dimethylphenoxy)carbonyl)-L-glutamate (S8)

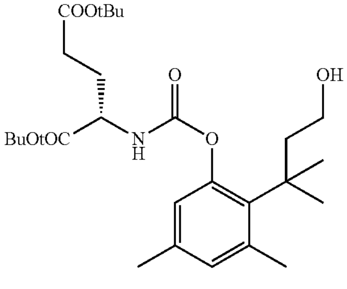

In a 50 mL round bottom flask at 25° C., S7 (1.159 g, 1.906 mmol, 1.0 equiv) was suspended in 12 mL 1:1 v:v THF:$H_2O$ solution. 12 mL of acetic acid was added, and the reaction was stirred at 25° C. for an additional 3 h, until complete conversion had occurred as judged by LC-MS. The mixture was then concentrated by rotary evaporator, and toluene (10 mL) was added to the mixture and concentrated by rotary evaporator. Azeotroping with toluene was repeated for a total of three times. Crude product S8 (941 mg) was carried to next step without further purification. Crude $^1$H-NMR (500 MHz, $CDCl_3$) δ 6.73 (s, 1H), 6.59 (s, 1H), 6.23 (d, J=8.1 Hz, 1H), 4.23 (m, 1H), 3.47 (td, J=7.3, 6.4, 3.3 Hz, 2H), 2.45 (s, 3H), 2.38-2.27 (m, 2H), 2.16 (s, 3H), 2.07-2.00 (m, 1H), 1.99 (s, 3H), 1.96-1.91 (m, 1H), 1.90 (s, 3H), 1.44 (s, 9H), 1.42 (s, 9H). Crude $^{13}$C NMR (126 MHz, $CDCl_3$) δ 172.5, 171.2, 155.6, 137.6, 135.9, 129.0, 128.5, 126.6, 125.2, 116.2, 82.7, 81.2, 61.3, 54.3, 44.9, 39.4, 31.8, 28.0, 25.9, 25.5, 20.2. ESI-MS m/z (rel int): (pos) 494.4 ([M+H]$^+$, 100).

di-tert-butyl ((2-(4-hydroxy-2-methylbutan-2-yl)-3,5-dimethylphenoxy)carbonyl)-L-glutamate (S9)

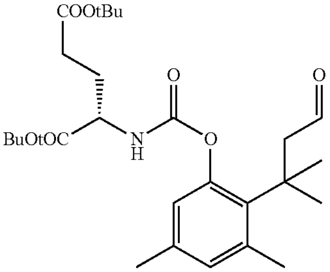

In a 50 mL round bottom flask at 0° C., Crude S8 (941 mg, 1.906 mmol, 1.0 equiv) was suspended in 19 mL $CH_2Cl_2$. Dess-Martin periodinane (1.78 g, 4.19 mmol, 2.2 equiv) was added and stirred warming to 25° C. for 17 h. The mixture was then concentrated by rotary evaporator, and purified directly by s and toluene (10 mL) was added to the mixture and concentrated by rotary evaporator. Purification by silica flash chromatography (3:1 hexanes/EtOAc) yielded product S10 (513 mg, 55% over two steps) as a light yellow oil.

TLC: $R_f$ 0.27 (3:1 hexanes/EtOAc). $^1$H-NMR (500 MHz, $CDCl_3$): δ 9.52 (t, J=2.6 Hz, 1H), 6.78 (s, 1H), 6.64 (s, 1H), 5.85 (d, J=8.1 Hz, 1H), 4.27 (dt, J=8.1, 4.0 Hz, 2H), 2.80 (s, 2H), 2.48 (s, 3H), 2.42-2.27 (m, 2H), 2.19 (s, 3H), 2.17-2.08 (m, 1H), 1.98-1.88 (m, 1H), 1.55 (s, 6H), 1.54 (s, 3H), 1.45 (s, 9H), 1.42 (s, 9H). $^{13}$C-NMR (126 MHz, $CDCl_3$): δ 203.7, 172.2, 170.9, 154.4, 153.2, 152.8, 149.3, 137.7, 136.8, 135.0, 133.0, 132.5, 94.3, 82.6, 81.0, 68.4, 64.7, 56.9, 54.2, 49.2, 38.9, 38.8, 38.2, 31.6, 28.1, 27.5, 27.2, 25.7, 25.5, 22.6, 20.8, 20.3, 15.2. ESI-MS m/z (rel int): (pos) 493.2 ([M+H]$^+$, 100).

(S)-3-(2-(((1,5-di-tert-butoxy-1,5-dioxopentan-2-yl) carbamoyl)oxy)-4,6-dimethylphenyl)-3-methylbutanoic acid (S10)

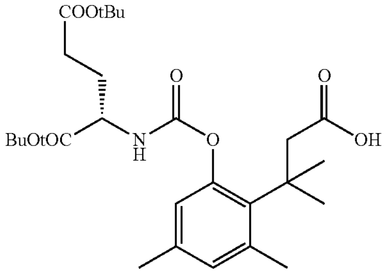

In a 50 mL round bottom flask at 0° C., Crude S9 (513 mg, 1.04 mmol, 1.0 equiv) was suspended in 12 mL 1:1 $H_2O$: 2-methyl-2-butene. $NaH_2PO_4$ (264 mg, 2.2 mmol, 2.1 equiv), tBuOH (48.7 mg, 0.657 mmol, 0.63 equiv), and $NaClO_2$ (416 mg, 3.685 mmol, 3.5 equiv) was added sequentially and stirred warming to 25° C. for 22 h. The mixture was then quenched with sat aq $NH_4Cl$, and the pH of the mixture was then adjusted to ~3 with 1M aq HCl. The mixture was then washed with ethyl acetate (3×10 mL), and the combined organic layers were then washed with brine (2×20 mL). The organic layers were then concentrated by rotary evaporator. Purification by silica flash chromatography (3:1 hexanes/EtOAc to 1:1 hexanes/EtOAc) yielded product S10 (384 mg, 72%) as a light yellow oil. TLC: $R_f$ 0.15 (1:1 hexanes/EtOAc). $^1$H-NMR (500 MHz, $CDCl_3$) δ 6.76 (s, 1H), 6.63 (s, 1H), 5.96 (d, J=8.2 Hz, 1H), 4.28 (td, J=8.3, 4.9 Hz, 2H), 2.90-2.74 (m, 2H), 2.49 (s, 3H), 2.45-2.26 (m, 2H), 2.19 (s, 3H), 2.15 (m 1H), 1.99-1.91 (m, 1H), 1.57 (s, 3H), 1.56 (s, 3H), 1.46 (s, 9H), 1.43 (s, 9H). $^{13}$C-NMR (126 MHz, $CDCl_3$) δ 176.4, 172.0, 170.9, 154.6, 149.3, 137.7, 136.0, 133.6, 132.1, 123.0, 82.3, 80.7, 60.3, 54.1, 48.0, 38.6, 31.4, 31.2, 27.9, 27.4, 25.1, 20.9, 20.1, 14.0. ESI-MS m/z (rel int): (pos) 508.3 ([M+H]$^+$, 100).

di-tert-butyl ((2-(4-(((((3aR,4R,6R,6aR)-6-(6-amino-9H-purin-9-yl)-2,2-dimethyltetrahydrofuro[3,4-d][1,3]dioxol-4-yl)methoxy)sulfonyl)amino)-2-methyl-4-oxobutan-2-yl)-3,5-dimethylphenoxy)carbonyl)-L-glutamate (S12)

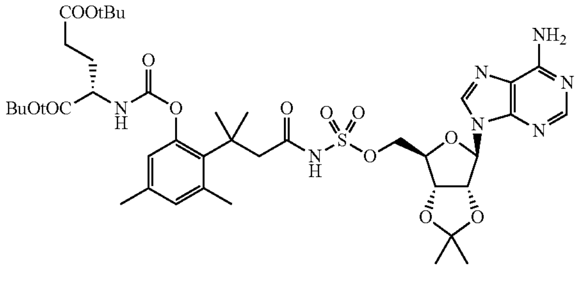

S11 was synthesized as discussed in Moreau, C.; et al. *J. Med. Chem.* 2013, 56, 10079-10102. In a 25 mL round bottom flask at 25° C., S10 (307 mg, 0.605 mmol, 1.0 equiv) was suspended in 6 mL anhyd DMF. To the solution was then added EDCI (140 mg, 0.904 mmol, 3.2 equiv), and DMAP (110 mg, 0.904 mmol, 3.1 equiv) for 20 min. Separately, S11 (111 mg, 0.287 mmol, 1 equiv) was then suspended in 6 mL anyd DMF and then added dropwise to the S10 mixture. The reaction was then stirred overnight under 25° C. for 18 h. The mixture was then diluted with 9 mL ethyl acetate, washed with satd aq $NH_4Cl$ (3×10 mL) and satd aq $NaHCO_3$ (3×10 mL), and the organic layer was then dried with $MgSO_4$. Purification by silica flash chromatography (5% MeOH in $CH_2Cl_2$ to 10% MeOH in $CH_2Cl_2$) yielded semi-pure product S12 (83 mg, 33%) as a transparent oil. TLC: $R_f$ 0.44 (10% MeOH in $CH_2Cl_2$). Crude $^1$H-NMR (500 MHz, $CDCl_3$): δ 7.38-7.28 (m, 5H), 5.60 (m, 2H), 4.63 (m, 1H), 4.58 (s, 2H), 4.36 (t, 1H, J=5.6), 3.49 (dd, 1H, J=9.5, 3.7), 3.44 (dd, 1H, J=9.6, 7.9), 3.34 (s, 3H), 3.32 (s, 3H), 2.68 (d, 1H, J=2.5), 2.52 (m, 1H), 2.38 (m, 1H). Crude $^{13}$C-NMR (125 MHz. $CDCl_3$): δ 137.9, 131.0, 128.5-127.5 (Ar), 103.8, 73.6, 73.4, 66.7, 53.5, 53.2, 31.8. ESI-MS m/z (rel int): (pos) 876.1 ([M+H]$^+$, 100).

((2-(4-(((((2R,3S,4R,5R)-5-(6-amino-9H-purin-9-yl)-3,4-dihydroxytetrahydrofuran-2-yl)methoxy) sulfonyl)amino)-2-methyl-4-oxobutan-2-yl)-3,5-dimethylphenoxy)carbonyl)-L-glutamic acid (S13)

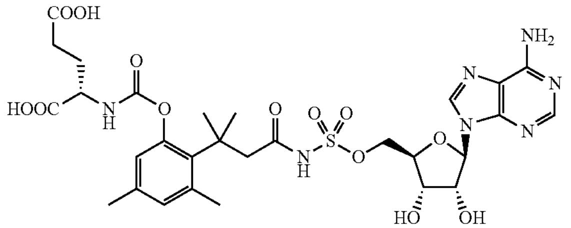 [SMILES: Cc1cc(C)c(C(C)(C)CC(=O)NS(=O)(=O)OC[C@H]2O[C@@H](n3cnc4c(N)ncnc43)[C@H](O)[C@@H]2O)c(OC(=O)N[C@@H](CCC(=O)O)C(=O)O)c1]

In a 10 mL glass vial at 25° C., S12 (20 mg, 22.8 μmol, 1.0 equiv) was suspended in 456 μL 80% aq TFA. The reaction was then stirred under 25° C. for 2 h. The mixture was then diluted with 5 mL $H_2O$, azeotroped TFA with toluene (3×5 mL) through concentration by the rotary evaporator. Purification by prep-HPLC and lyophilization yielded product S13 (6.95 mg, 42%) as a white powder. $^1$H-NMR (500 MHz, Methanol-$d_4$) δ 8.41 (s, 1H), 8.29 (s, 1H), 6.73 (d, J=2.0 Hz, 1H), 6.63 (s, 1H), 6.07 (s, 1H), 4.57 (t, J=5.1 Hz, 1H), 4.31 (dd, J=9.4, 4.9 Hz, 1H), 4.22 (dt, J=9.7, 3.7 Hz, 4H), 2.85 (d, J=15.3 Hz, 1H), 2.77 (d, J=15.3 Hz, 1H), 2.52 (t, J=7.4 Hz, 3H), 2.48 (s, 3H), 2.37-2.24 (m, 1H), 2.15 (s, 3H), 2.09-1.97 (m, 1H), 1.60 (d, J=3.0 Hz, 6H). 7 exchangeable H not observed. ESI-MS m/z (rel int): (pos) 724.3 ([M+H]$^+$, 100).

Representative Synthesis and Examples of ProDrug Compounds of Formula II

As noted above, the mustard prodrug ZD2767P (structure 2a, FIG. 2*c*) was synthesized as previously reported (Springer et al., *J Med Chem.* 37(15):2361-70(1994) and Niculescu-Duvaz et al., *Tetrahedron Lett.* 46(40):6919-22 (2005)). Based on the present disclosure, including in regard to the representative syntheses of prodrug compounds of Formulas I & III, a person of ordinary skill in the art is well-enabled to generate compounds of Formula II. Further guidance towards synthesis of compounds of Formula II may be found in Niculescu-Duvaz et al., *J. Med. Chem.* 47(10):2651-58 (2004), Niculescu-Duvaz et al., *J. Med. Chem.* 46(9):1690-705 (2003), Springer et al., *J. Med. Chem.* 38(26):5051-65, and Springer et al., *Eur J Cancer* 27(11):1361-66(1991) (each of which is incorporated herein by reference), as well as references cited in each therein.

Representative Synthesis and Examples of ProDrug Compounds of Formula III

Synthesis and Characterization of Glu-PABA-Erlotinib

Synthesis of a representative prodrug of erlotinib, Glu-PABA-erlotinib (S17), is summarized in Scheme 3 below and further detailed thereafter.

Scheme 3.

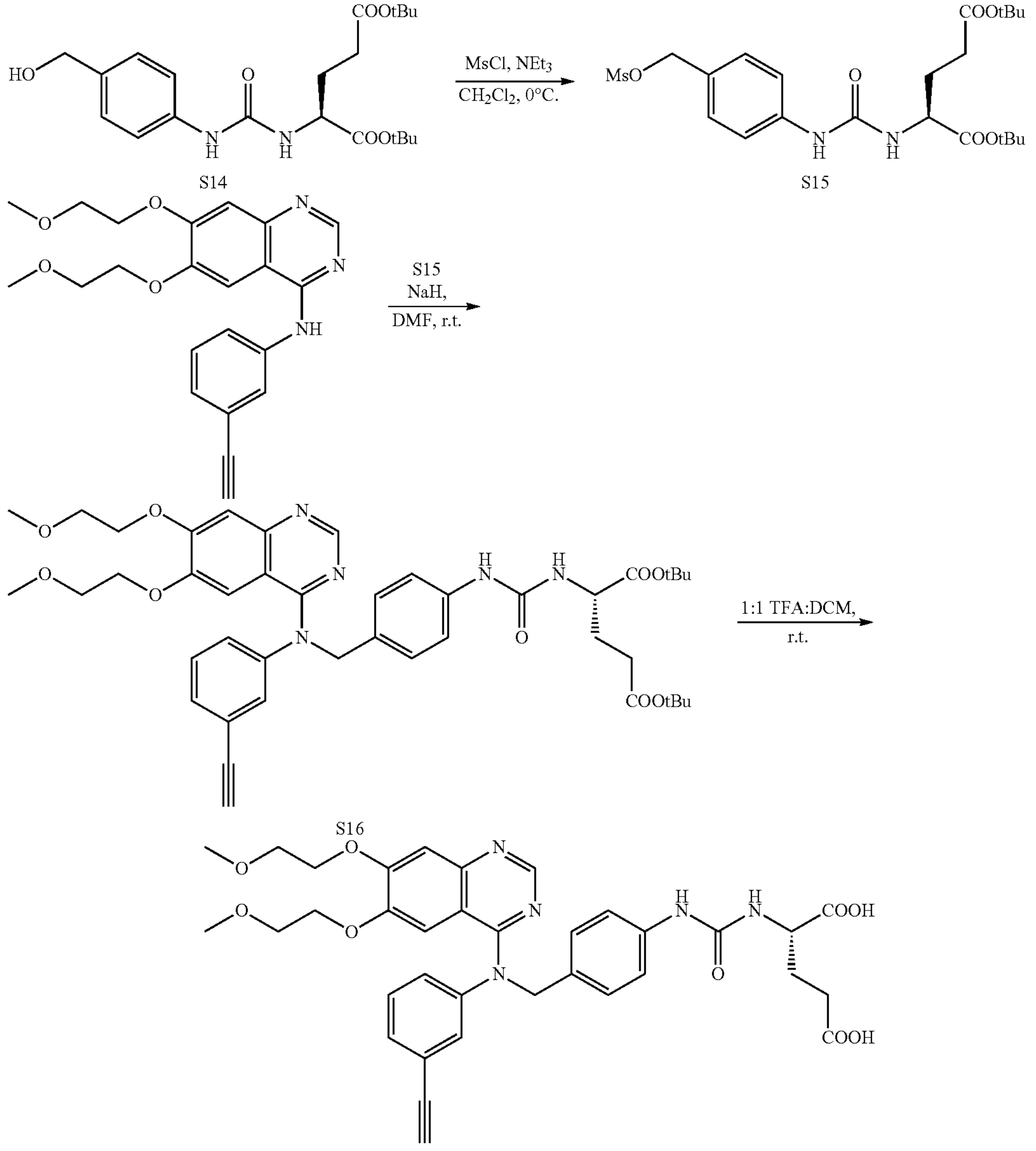

S14

S15

S16

S17

3% over two steps di-tert-butyl ((4-(((methylsulfonyl)oxy)methyl)phenyl)carbamoyl)-L-glutamate (S15)

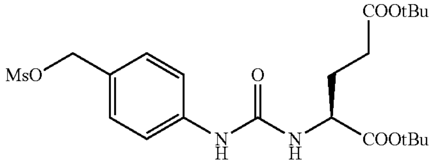

S14 was synthesized as discussed in Niculescu-Duvaz, D.; et al. *J. Med. Chem.* 1998, 41, 5297-5309. In a 15 mL round bottom flask at 0° C., S14 (90 mg, 220 μmol, 1.0 equiv) was suspended in 2.2 mL anhyd $CH_2Cl_2$. Triethylamine (61 μL, 441 μmol, 2 equiv) and methanesulfonyl chloride (34 μL, 441 μmol, 2 equiv) were added and the reaction was stirred at 0° C. for an additional 2 h until judged by completion through TLC. The mixture was then diluted by 5 mL $CH_2Cl_2$, and the organic layers was washed with water (1×10 mL). The aqueous layer was then washed with $CH_2Cl_2$ (3×10 mL), and the combined organic extracts were then concentrated by rotary evaporator. The crude product was azeotroped (3×5 mL) and placed on high vacuum for 1 h. Crude product S15 (107 mg) was unstable and carried to next step without further purification. TLC: $R_f$ 0.80 (1:1 hexanes/EtOAc). Crude $^1H$ NMR: (500 MHz, $CDCl_3$) δ 7.34 (m, Hz, 2H), 7.24-6.85 (m, 2H), 3.66 (s, 3H), 2.42-2.27 (m, 2H), 2.13-2.03 (m, 1H), 1.89 (m, 1H), 1.40 (s, 9H).

di-tert-butyl ((4-((((6,7-bis(2-methoxyethoxy)quinazolin-4-yl)(3-ethynylphenyl)amino)methyl)phenyl)carbamoyl)-L-glutamate (S16)

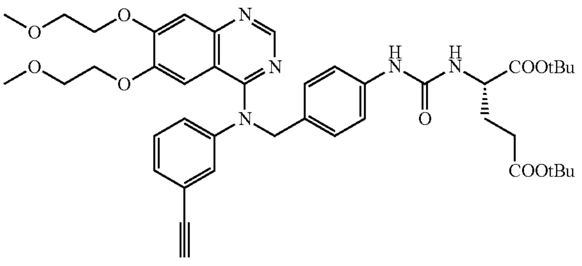

In a 15 mL round bottom flask at 0° C., erlotinib (72 mg, 184 μmol, 1.0 equiv) was suspended in 1.8 mL anhyd DMF and added 60% NaH in mineral oil (11 mg, 275 μmol, 1.5 equiv) for 5 min. Separately, S15 (107 mg, 220 μmol, 1.2 equiv, assumed 100% pure) was suspended in 1.8 mL anhyd DMF, cooled to 0° C., and added dropwise to erlotinib mixture at 0° C. The resulting was stirred for an additional 30 min at 0° C., until complete conversion had occurred as judged by LC-MS. The mixture was then quenched with 1 mL water, and the aqueous layers were then washed with ethyl acetate (3×5 mL). The combined organic extracts were then concentrated by rotary evaporator, placed on high vacuum, and carried to the next step as a crude product S16 (11.1 mg) without further purification. ESI-MS m/z (rel int): (pos) 784.7 ($[M+H]^+$, 100).

((4-((((6,7-bis(2-methoxyethoxy)quinazolin-4-yl)(3-ethynylphenyl)amino)methyl)phenyl)carbamoyl)-L-glutamic acid (S17)

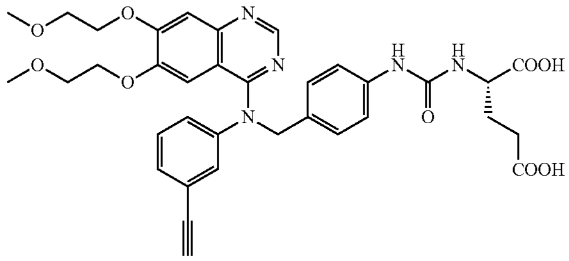 [SMILES: C#Cc1cccc(N(Cc2ccc(NC(=O)N[C@@H](CCC(=O)O)C(=O)O)cc2)c2ncnc3cc(OCCOC)c(OCCOC)cc23)c1]

In a 10 mL glass vial at 25° C., crude compound S16 (11.1 mg, 14.1 μmol, 1.0 equiv, assumed 100% pure) was suspended in 950 μL 1:1 TFA:$CH_2Cl_2$ solution. The reaction was stirred for 1 h until complete conversion had occurred as judged by LC-MS. The mixture was then azeotroped with MeOH (3×3 mL), concentrated by rotary evaporator, and purified through prep-HPLC to yield product S17 (0.43 mg, 3.5% yield over two steps) as a white powder. $^1$H NMR (500 MHz, Methanol-$d_4$) δ 8.79 (s, 1H), 7.58-7.40 (m, 4H), 7.32-7.21 (m, 8H), 7.17 (s, 1H), 6.42 (s, 1H), 5.52 (s, 2H), 4.37 (dd, J=8.4, 5.1 Hz, 1H), 4.32-4.27 (m, 3H), 3.84-3.77 (m, 3H), 3.65 (s, 1H), 3.52 (d, J=5.2 Hz, 8H), 3.41 (s, 3H), 3.35 (s, 3H), 2.42 (m, 6.7 Hz, 2H), 2.25-2.13 (m, 1H), 2.02-1.89 (m, 1H). ESI-MS m/z (rel int): (pos) 672.4 ($[M+H]^+$, 100).

Example 2

Methods of Testing Prodrug Candidates

Candidate prodrugs for use with selected prodrug converting enzymes can be tested through in vitro assays with filtering at each step to achieve a Target Product Profile (Table 2).

TABLE 2

| Parameter | Accept | Ideal |
|---|---|---|
| CPG2 kindlics ($k_{cat}/K_m$, $S^{-1}\mu M^{-1}$) | ≥1 | ≥10 |
| drug activity ($IC_{50}$, nM) | ≤1,000 | ≤100 |
| prodrug Selectivity Index (SI, told) | ≥10 | ≥100 |
| prodrug activation ($IC_{60}$ pro/free, fold) | ≤20 | ≤5 |
| aqueous solubility PH 7.4 (logS, M) | ≥−5 | ≥−4 |
| plasma stability ($t_{1/2}$) | ≥2 | ≥4 h |
| microsomal stability ($t_{1/2}$) | ≥0.5 h | ≥4 h |
| plasma protein binding | ≤95% | ≤75% |

These results can be used to design improved prodrugs. The kinetics (Km, kcat) of CPG2-mediated prodrug cleavage is determined using recombinant, purified CPG2 (Jeyaharan et al. *Protein Expr Purif.* 127:44-52 (2016)). The reaction is monitored based on decreased UV absorbance, as described previously for ZD2767P (Springer et al., *J Med Chem.* 37(15):2361-70 (1994) and Springer et al., *J Med Chem.* 38(26):5051-65 (1995)) and methotrexate (Sherwood et al., *Eur J Biochem.* 148(3):447-53(1985)). Prodrug stability is confirmed in physiologic conditions. Prodrugs with kcat/Km≥1 s-1 μM-1 (ideally≥10) are advanced.

The cytotoxicity of each prodrug/drug pair can be tested in antigen-positive tumor cell lines, including HL 60 (leukemia), Jurkat (T cell), MDA 231 (breast), OVCAR (ovarian), SW480 (colon), SET2 (AML), as well as MDR variants and primary cancer cells. Pairs with drug activity ≤1 M (e.g., ≤100 nM) and SI≥10 (e.g., ≥100) are advanced.

The prodrug cytotoxicity in the presence of purified CPG2 and supernatant from CPG2-secreting HEK293T cells is also tested. The prodrug and unmasked dependent drug are quantified by LC MS/MS. Prodrugs with IC50 within 20-fold of free drug (e.g., 5-fold) are advanced.

The drug and prodrug activity in HEK293T cells expressing secreted, surface-associated, and intracellular CPG2 are also tested. Prodrugs with IC50 within 20-fold of free drug (e.g., 5-fold) are advanced.

The prodrugs are also tested for in vitro ADME (absorption, distribution, metabolism, and excretion) properties: e.g., solubility at pH 7.4, mouse/human plasma/whole blood stability, mouse/human microsomal stability (±NADPH, ±UDPGA), mouse/human plasma protein binding. Prodrugs with acceptable in vitro properties are advanced to in vivo evaluation.

Example 3

Construction of Cells Expressing a Chimeric Antigen Receptor

This Example describes the construction of a cell that comprises a CAR (e.g., with an antigen-binding domain specific for CD19, WT1, or PRAME). In this exemplary embodiment, CPG2 is engineered to have a transmembrane domain and localizes to the extracellular side of the cell membrane, where it can hydrolyze and activate prodrugs that come in contact with the cell into active drugs (e.g., prodrugs of Example 1, which are hydrolyzed into active cytotoxic drugs). The activation of the drug enhances cytolytic action locally at the site where the CAR T cell is targeted via the antigen binding domain.

The CD19 CAR T cells and WT1 CAR T cells have been made and initial publications on the methods to create them and to characterize their activity are described (Brentjens et al., *Sci. Trans. Med.* 5(177):177ra38 (2013), Pegram et al. *Leukemia* 29(2):415-22 (2015)). The PRAME-reactive CAR T cell will be made and characterized similarly.

The mammalian optimized CD19, WT1 and PR20 ($PRAME^{300-309}$) scFv sequences were utilized to generate the antigen binding domain of the CARs. The variable heavy and light chains of the scFv are connected via a $(Gly4Ser)_3$ linker. A leader peptide (e.g., a CD8 signal sequence) was added to the N-terminus of the scFv for localization. In alternative embodiments, a c-Myc tag can be added to allow detection of the CAR by flow cytometry. A CD8 transmembrane domain follows the antigen binding domain. On the cytoplasmic side of the CAR, 4-1BB was used as a costimulatory element due to the increased persistence of 4-1BB CART cells (Oka et al. *PNAS.* 101:13885-90 (2004)). The CAR can be optimized to include a spacer domain upstream of the CD8 transmembrane domain if desired. The nucleic acid encoding the CAR was cloned into an SFG retroviral vector containing the 4-1BB signaling and CD3t activation domains, forming a second generation CAR (Brentjens et al. *Clin Cancer Res.* 13(18 Pt 1):5426-35 (2007)). A clinical grade construct, without the c-Myc tag, can also be generated, for which an anti-idiotype mAb to allow detection of the CAR can be generated.

Stable HEK293T viral producing cell lines were generated, subcloned and used to transduce primary human T cells as described previously (Curran et al. *American Society of Gene Therapy* 23(4):769-78 (2015)). Following transduction, CAR expression was verified by flow cytometry, using an anti-idiotype antibody to detect the anti-CD19 ScFv.

For co-expression of the CPG2 enzyme, nucleic acid encoding the carboxypeptidase CPG2 enzyme was cloned into the CAR vector as described in Example 5.

Example 4

Generation of Transmembrane and Secreted CPG2 Constructs and Characterization of Expressed CPG2

This example describes the generation of transmembrane and secreted forms of CPG and their characterization when expressed in bacteria or mammalian cells. The transmembrane form of CPG2 encodes a CD8 signal sequence (MALPVTALLLPLALLLHAARP (SEQ ID NO: 11) at the 5' terminus of the CPG2 encoding sequence and at its 3' terminus, the sequence derived from the transmembrane domain of CD8 to permit membrane anchoring and extracellular exposure of the enzyme (FIG. 3A).

The gene encoding the CPG2 enzyme was initially cloned into the pET151 vector using the pET151 Directional TOPO® expression system, which incorporates an N-terminal 6× His tag (Invitrogen). For bacterial expression, the endogenous signal sequence was removed to facilitate protein isolation (see Jeyaharan et al., *Protein Expression and Purification* (2016)). Removal of signal sequence allowed expression of a soluble CPG2 species.

The amino acid sequence used for CPG2 (without start Met and leader signal sequence) is as follows: ALAQKRDNVLFQAATDEQPAVIKTLEKLVNIETGTG-DAEGIAAAGNFLEAELKNLGF TVTRSKSAGLVVGD-NIVGKIKGRGGKNLLLMSHMDTVYLKGILAKAP-FRVEGDKAY GPGIADDKGG-NAVILHTLKLLKEYGVRDYGTITVLFNT-DEEKGSFGSRDLIQEEAKLA DYVLSFEPT-SAGDEKLSLGTSGIAYVQVQITGKASHAGAAPE-LGVNALVEASDLVLR TMNIDDKAKNLRFQWTIAK-AGQVSNIIPASATLNADVR-YARNEDFDAAMKTLEERA QQKKLPEADVKVIVTR-GRPAFNAGEGGKKLVDKAVAYYKEAGGTLGVEE-RTGGGT DAAYAAL SGKPVIESLGLPGFGYHSD-KAEYVDISAIPRRLYMAARLIMDLGAGK (SEQ ID NO: 3, CPG2 without leader sequence and optimized for human expression)

Two variants of the of the transmembrane CPG2 construct were generated. One construct includes a CD8 signal sequence, the CPG2 sequence, an optional HA tag, a CD8-membrane-spanning portion and a CD8 intracellular portion.

CD8 signal sequence:

(SEQ ID NO: 11)
MALPVTALLLPLALLLHAARP

CD8-membrane-spanning portion:

(SEQ ID NO: 38)
IYIWAPLAGTCGVLLLSLVIT

CD8 intracellular domain amino acid sequence:

(SEQ ID NO: 13)
LYCNHRNRRRVCKCPRPVVKSGDKPSLSARYV

The full CPG-CD8 TM sequence is as follows:

(SEQ ID NO: 40)
```
MALPVTALLLPLALLLHAARPALAQKRDNVLFQAATDEQPAVIKTLEKLVN
IETGTGDAEGIAAAGNFLEAELKNLGFTVTRSKSAGLVVGDNIVGKIKGRG
GKNLLLMSHMDTVYLKGILAKAPFRVEGDKAYGPGIADDKGGNAVILHTLK
LLKEYGVRDYGTITVLFNTDEEKGSFGSRDLIQEEAKLADYVLSFEPTSAG
DEKLSLGTSGIAYVQVQITGKASHAGAAPELGVNALVEASDLVLRTMNIDD
KAKNLRFQWTIAKAGQVSNIIPASATLNADVRYARNEDFDAAMKTLEERAQ
QKKLPEADVKVIVTRGRPAFNAGEGGKKLVDKAVAYYKEAGGTLGVEERTG
GGTDAAYAALSGKPVIESLGLPGFGYHSDKAEYVDISAIPRRLYMAARLIM
DLGAGKYPYDVPDYAGGGIYIWAPLAGTCGVLLLSLVITLYCNHRNRRRVG
GGRPVVKSGDKPSLSARYV
```

The second construct is identical to the sequence above except that the natural Lyk binding domain is disrupted to uncouple the endogenous function of CD8 from the CPG molecule. CD8 transmembrane domain portion with disrupted Lyk binding domain:

(SEQ ID NO: 15)
LYCNHRNRRRVGGGRPVVKSGDKPSLSARYV

For the secreted form of CPG2, a CPG2 signal sequence (MRPSIHRTAIAAVLATAFVAGT (SEQ ID NO: 9) was inserted at the 5' terminus of the CPG2 encoding sequence (FIG. 3B) to facilitate secretion.

Figure 4A:
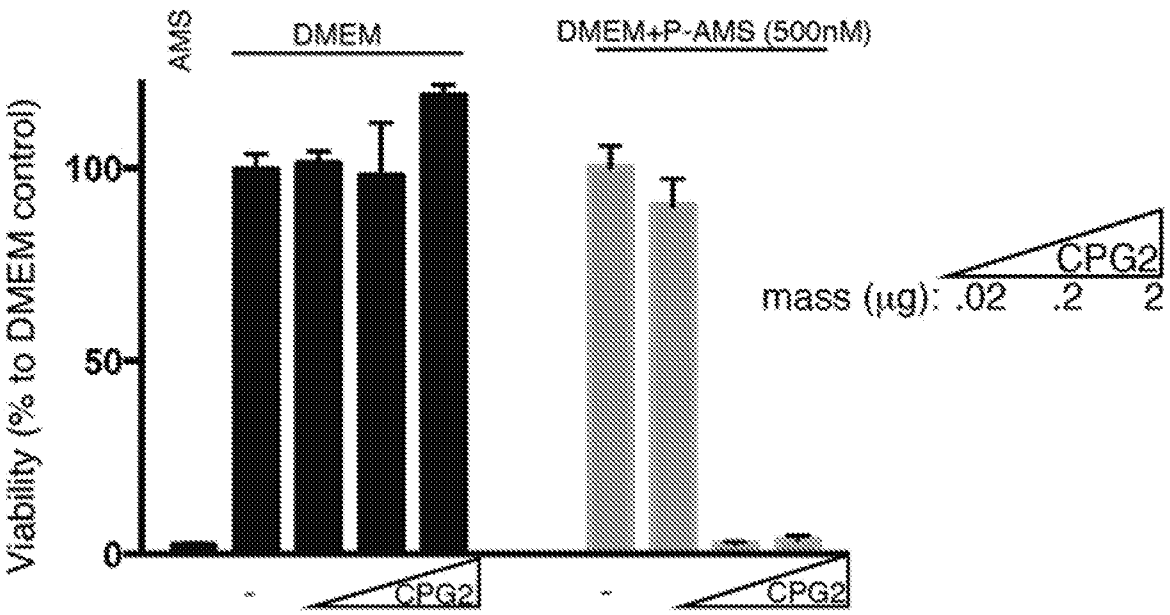
FIG. 4 provides exemplary data showing activation of P-AMS (see FIG. 2) by recombinant CPG2 expressed and purified from *E. coli*. (A) Human Jurkat T cells were incubated with or without P-AMS in the presence of increasing concentration of purified CPG2. Cell viability was measured at 48 hours by CellTitre-Glo luminescence. (B) Recombinant CPG2 was exposed to various concentrations of glutamated AMS prodrug. Following incubation at 37° C. (0.5, 1, 2, and 4 hr.), the reaction was combined with Amplex® Red (converts free glutamate to a fluorescent species) and fluorescent emission was analyzed using a fluorescence multiwell plate scanner. The data indicate that at high concentrations (~10 μM), the majority of the prodrug is converted within 1 hour.
Figure 4B:
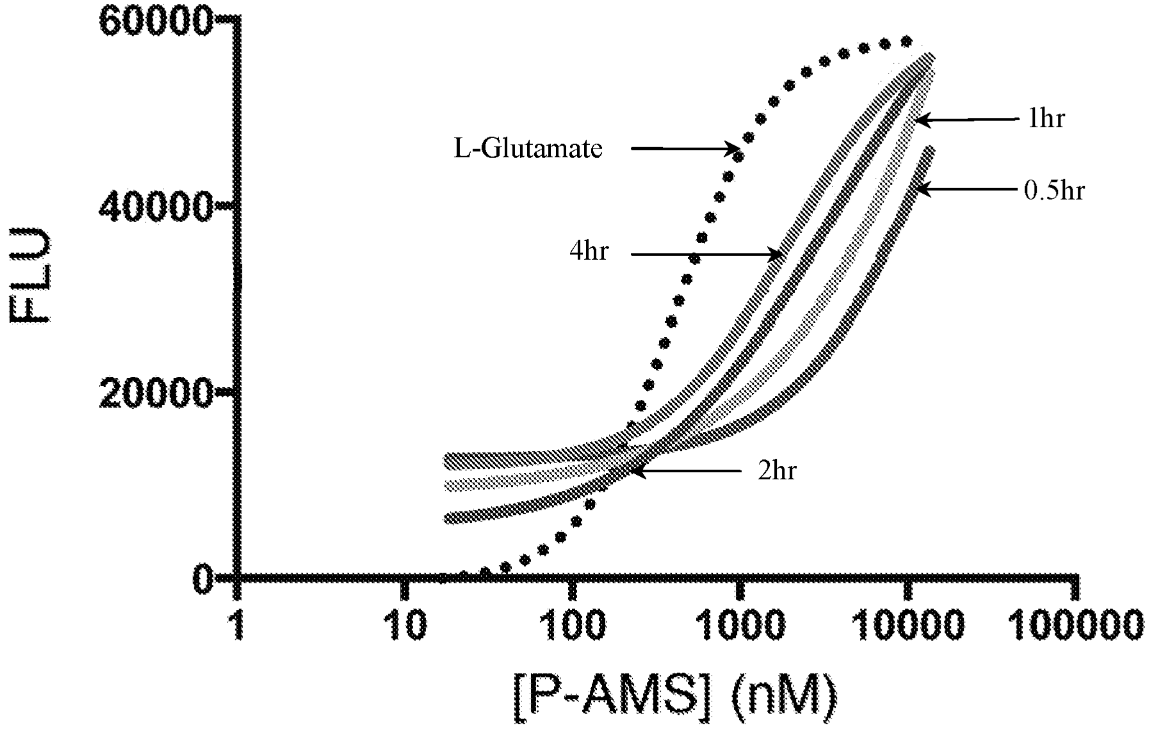

The CPG2-pET151 vector was transformed into BL21 star *E. coli* cells and induced with IPTG. Bacteria were homogenized in a French Press and purified by affinity chromatography over Ni++ beads using standard protocols. Imidazole was exchanged via PBS dialysis and protein was purified via desalting spin columns. The expressed and purified CPG2 was assayed to confirm that the active enzyme was a potent converter of glutamated prodrugs. FIG. 4A shows that the initial bacterially produced CPG2 is highly active. Pro-AMS was activated by recombinant CPG2 in vitro. Human Jurkat T cells were incubated with or without P-AMS in the presence of increasing concentration of purified CPG2. Cell viability of the Jurkat cells was measured at 48 hours by CellTitre-Glo® luminescence. Studies to detect free glutamate in solution indicated that most glutamate cleavage occurs within one hour in vitro. (FIG. 4B) Similar enzyme kinetics will be used to assess the characteristics of the enzyme activity for each of the prodrugs similarly. This PK is done in order to optimize expression and if necessary, optimize the prodrugs. These studies also allow assessment of susceptibility of target cells and normal cells in vivo.

Transient expression studies in eukaryotic cells were carried out by cloning the CPG2 variants the pcDNA3.1+ vector (Invitrogen) which utilizes the CMV promoter for eukaryotic expression. Expression studies were performed using Lipofectamine® to transfect in HEK293T cells.

Figure 5:
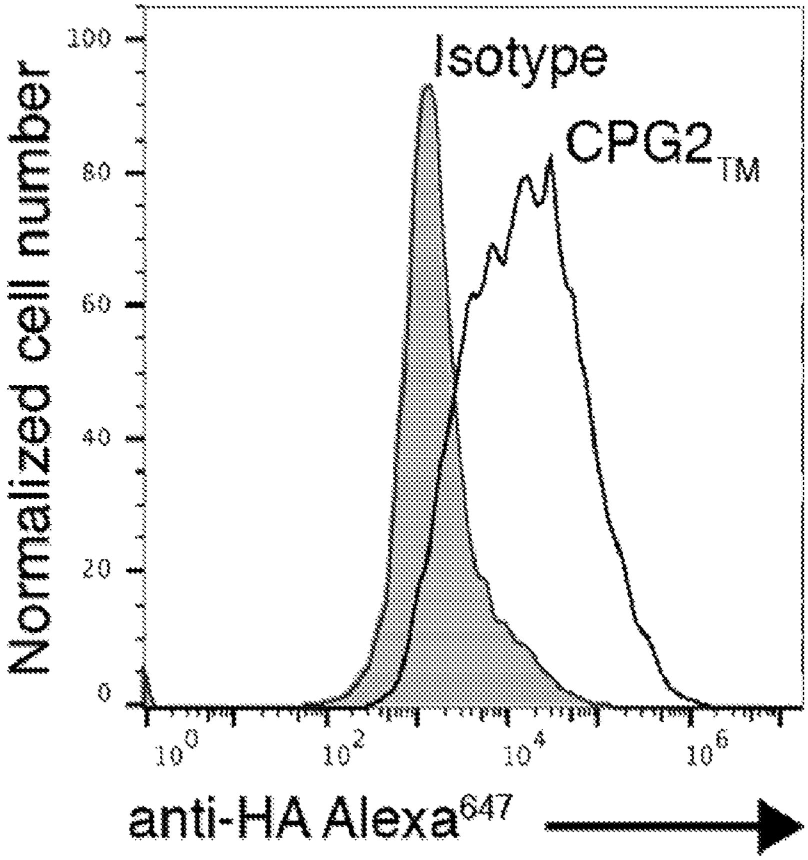
FIG. 5 provides exemplary data showing surface expression of a membrane-anchored CPG2. HEK293T cells transfected with a membrane-tethered CPG2 (CPG2TM) expressing a hemagglutinin tag were exposed to surface staining with an anti-HA antibody and compared to cells stained with isotype control antibody.

The CPG2 expression vector was then transduced into HEK293T cells to characterize the appropriate expression and activity of the transmembrane form. FIG. 4 demonstrates surface expression of a membrane-anchored CPG2. HEK293T cells transfected with a membrane-tethered CPG2 ($CPG2_{TM}$) expressing a hemagglutinin (HA) tag. The cells were exposed to surface staining with an anti-HA antibody and compared to cells stained with isotype control antibody (FIG. 5).

Figure 6:
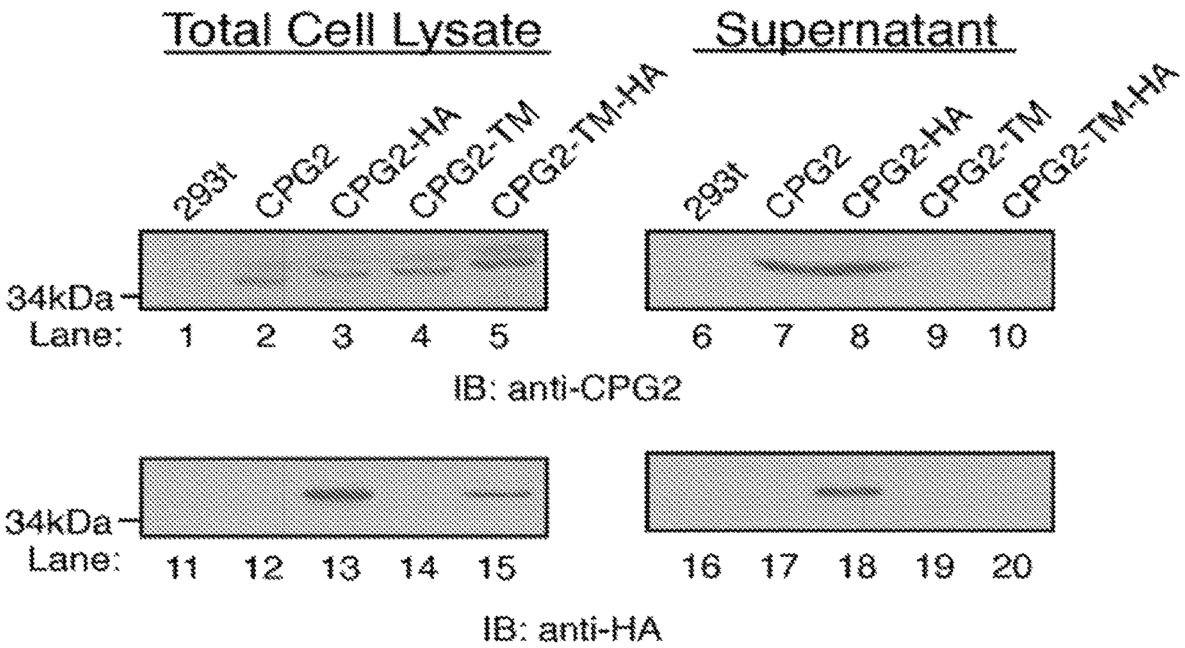
FIG. 6 provides exemplary data showing expression of CPG2 in mammalian cells. Human embryonic kidney (293t) cells transfected with constructs encoding a secreted form of CPG2 (CPG2) and a membrane bound CPG2 (CPG2-TM) with or without hemagglutinin (HA) tags were assayed for CPG2 expression by immunoblot of total cell lysates (Lanes 1-5, 11-15), or cell supernatant (Lanes 1-10, 16-20) for CPG2 (top row) or HA (bottom row).

FIG. 6 demonstrates localization of the various CPG constructs, either transmembrane or secreted form, by comparing HEK293T total cell lysates (FIG. 6, left) to detect the transmembrane form versus the supernatant (FIG. 6, right) for the secreted form.

Figure 7:
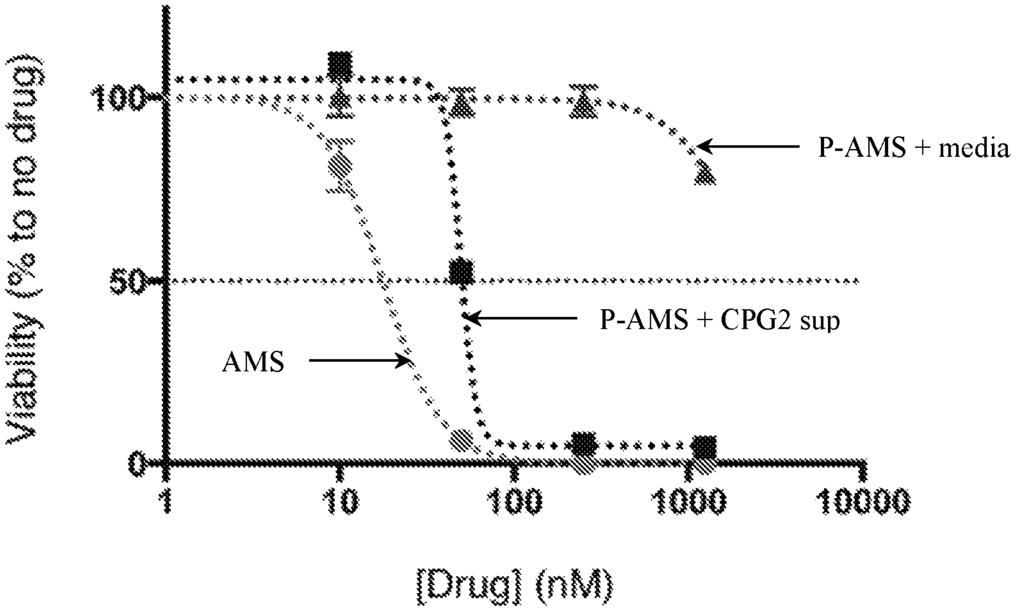
FIG. 7 provides exemplary data showing that cell-secreted CPG2 activates an AMS prodrug. Jurkat T cells were exposed to increasing concentrations of AMS (red circle) or P-AMS with media alone (blue triangle) or supernatant from CPG2-secreting 293t cells (black square). Cell viability was measured at 48 hours by CellTitre-Glo luminescence.

FIG. 7 demonstrates that the secreted form of the CPG2 expressed in HEK293T cells has enzymatic activity in vitro. Jurkat T cells were exposed to increasing concentrations of AMS (circle) or Pro-AMS with media alone (triangle) or supernatant from CPG2-secreting HEK293T cells (square). Cell viability was measured at 48 hours by CellTitre-Glo® luminescence assay. As shown in FIG. 7, increasing amount of the prodrug with the CPG2 supernatant resulted in a significant decrease in cell viability that was comparable to the AMS prodrug at around 100 nM, whereas control media did not.

Figure 8:
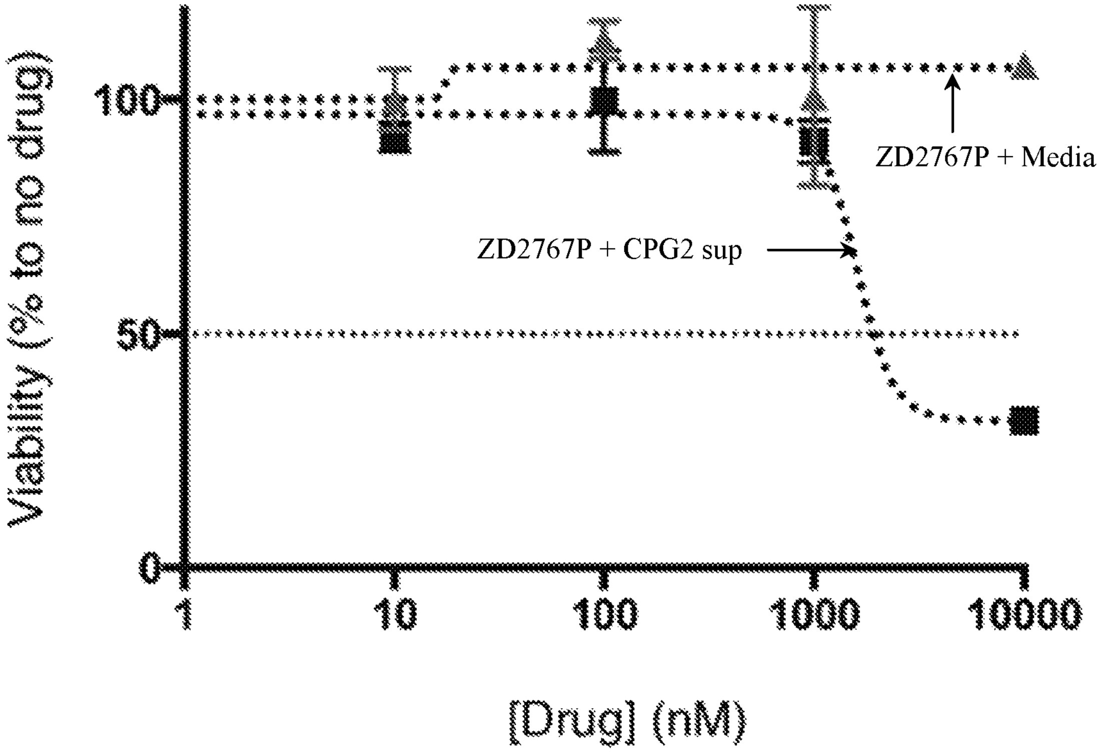
FIG. 8 provides exemplary data showing that cell-secreted CPG2 activates a Mustard prodrug. Jurkat T cells were exposed to increasing concentrations of ZD2767P with media (blue triangle) or supernatant from CPG2-secreting 293t cells (black square). Cell viability was measured at 48 hours by CellTitre-Glo luminescence.

FIG. 8 further demonstrates that the secreted form of the CPG2 expressed in HEK293T cells has enzymatic activity in vitro. Jurkat T cells were exposed to increasing concentrations of ZD2767P with media alone (triangle) or supernatant from CPG2-secreting HEK293T cells (square). Cell viability was measured at 48 hours by CellTitre-Glo® luminescence assay. As shown in FIG. 8, increasing amounts of the prodrug with the CPG2 supernatant resulted in a significant decrease in cell viability, whereas control media did not.

HEK293T cell lines expressing stably-integrated CPG2 variants were also generated using the retroviral pLGPW vector (a modified vector derived from pLHCX (Addgene) which drives GFP expression from the 5'LTR promoter, and CPG2 expression from the CMV promoter. Retrovirus was generated by transfection of the retroviral vector and VSVg glycoprotein for pseudotyping in gp293 packaging cells (Clontech).

Figure 9A:
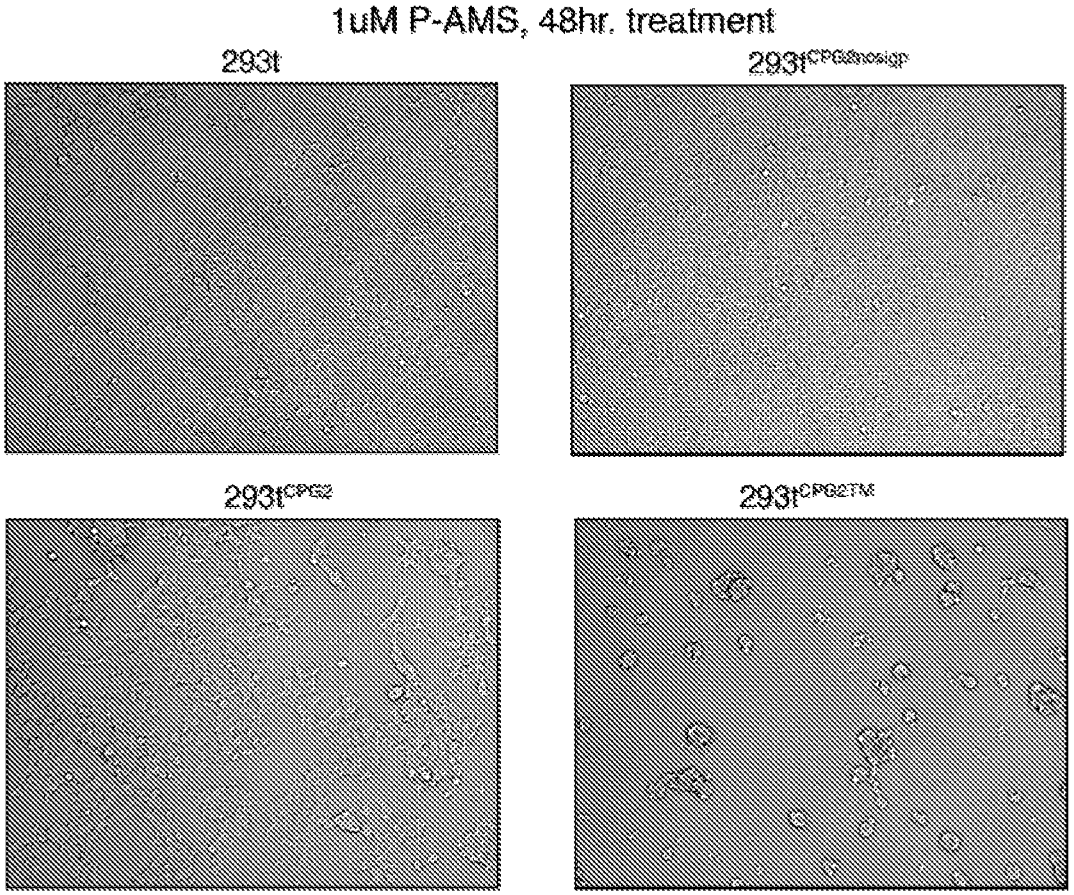
FIG. 9 provides exemplary data showing that that cell-secreted and transmembrane CPG2 expressed in stably transfected cells activates an AMS prodrug. Expression of CPG2 without a signal peptide (CPG2nosigp) was employed as a control. 293t cells stably transfected with CPG2 variants were exposed to P-AMS (1 μM) for 48 hours and analyzed by bright field microscopy (FIG. 9A). Cells were exposed to varying concentrations of P-AMS and cell viability was analyzed at 48 hr post treatment (FIG. 9B).
Figure 9B:
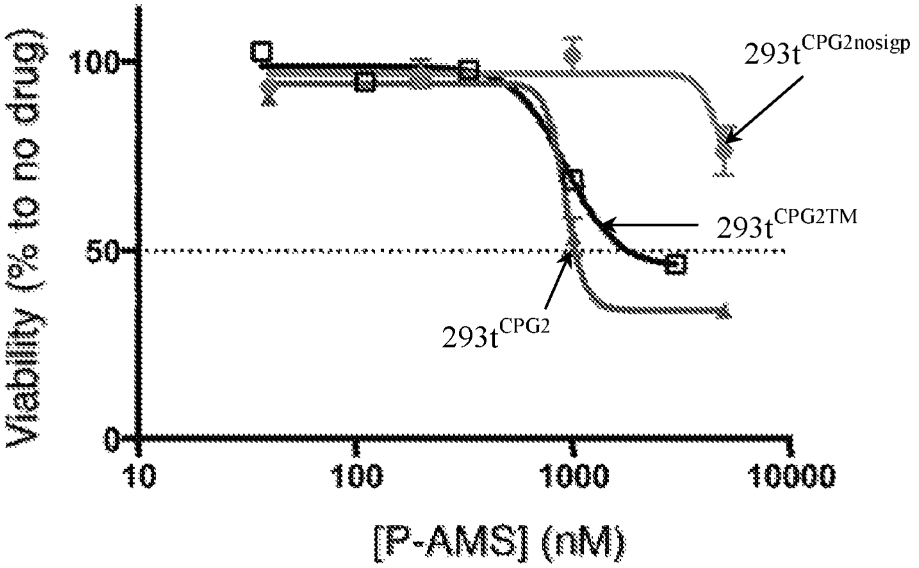

FIG. 9 demonstrates cell-secreted and transmembrane CPG2 expressed in stably transfected HEK293T cells activates an AMS prodrug. Expression of CPG2 without a signal peptide (CPG2nosigp) was employed as a control. HEK293t cells stably transfected with CPG2 variants were exposed to P-AMS (1 μM) for 48 hours and analyzed by bright field microscopy (FIG. 9A). Cells were exposed to varying concentrations of P-AMS and cell viability was analyzed at 48 hr post treatment (FIG. 9B). The cell-secreted and transmembrane CPG2 each induced significant cell death whereas the control construct did not.

Example 5

Construction of SEAKER Cells that Comprise a CD19, WT1, or PRAME CAR T in Combination with a CPG2 Enzyme To generate the CPG2-secreting and CPG2-transmembrane SEAKER variants of the CAR T cells described in Example 3, the nucleic acid encoding CPG2 enzyme, either secreted or transmembrane form, respectively, was cloned and inserted downstream of the CD3-ζ chain of the CAR, separated by a self-cleaving P2A peptide sequence which generates an independent CPG2 protein (FIGS. 3A, B).

Constructs were generated using the Gibson Assembly strategy (NEB) to insert the CPG constructs into existing SFG retroviral vectors expressing the CD19 ScFv. In brief, anti-CD19 SFG vectors (19-1BBz and 19-28z) were linearized downstream of the CD3ζ sequence and a fragment containing the P2A sequence followed by the CPG variant were inserted (see, e.g., SEQ ID NOS: 48 and 49).

The CAR-CPG2 constructs were transduced into HEK293T cells to characterize the expression and secretion of the secretory form in the cell supernatant and the enzymatic activity in vitro. The secreted forms showed significant activity in activating the cytotoxic drug of P-AMS and ZD2767P prodrugs as demonstrated in Example 4. The transmembrane form is also active.

In addition to the transmembrane and secreted form of CPG2, a conditionally expressed form of the CPG enzyme is also constructed using the synthetic Notch inducible system (FIG. 3C) (see e.g., Kloss et al., *Nature biotechnology* 31(1):71-5 (2013); Lim et al. *Cell* 168(4):724-40 (2017); and Roybal et al. *Cell* 164(4):770-9 (2016)). This format gates expression of CPG2 (secreted or in the membrane) only upon engagement of the target of the primary CAR. Thus, the CPG2 enzyme selectively activates the prodrug only upon contact with target cells, which further enhances specificity and is expected to reduce potential toxicity, both locally and systemically. The kinetics of drug formation from prodrug, the potency of the SEAKER construct, and the off-target effects on antigen negative cells are assessed.

Example 6

Characterization of Primary T Cells and T Cell Lines Transduced with SEAKER Cell Retroviral Constructs Encoding Anti-CD19 CAR and CPG2

Figure 10:
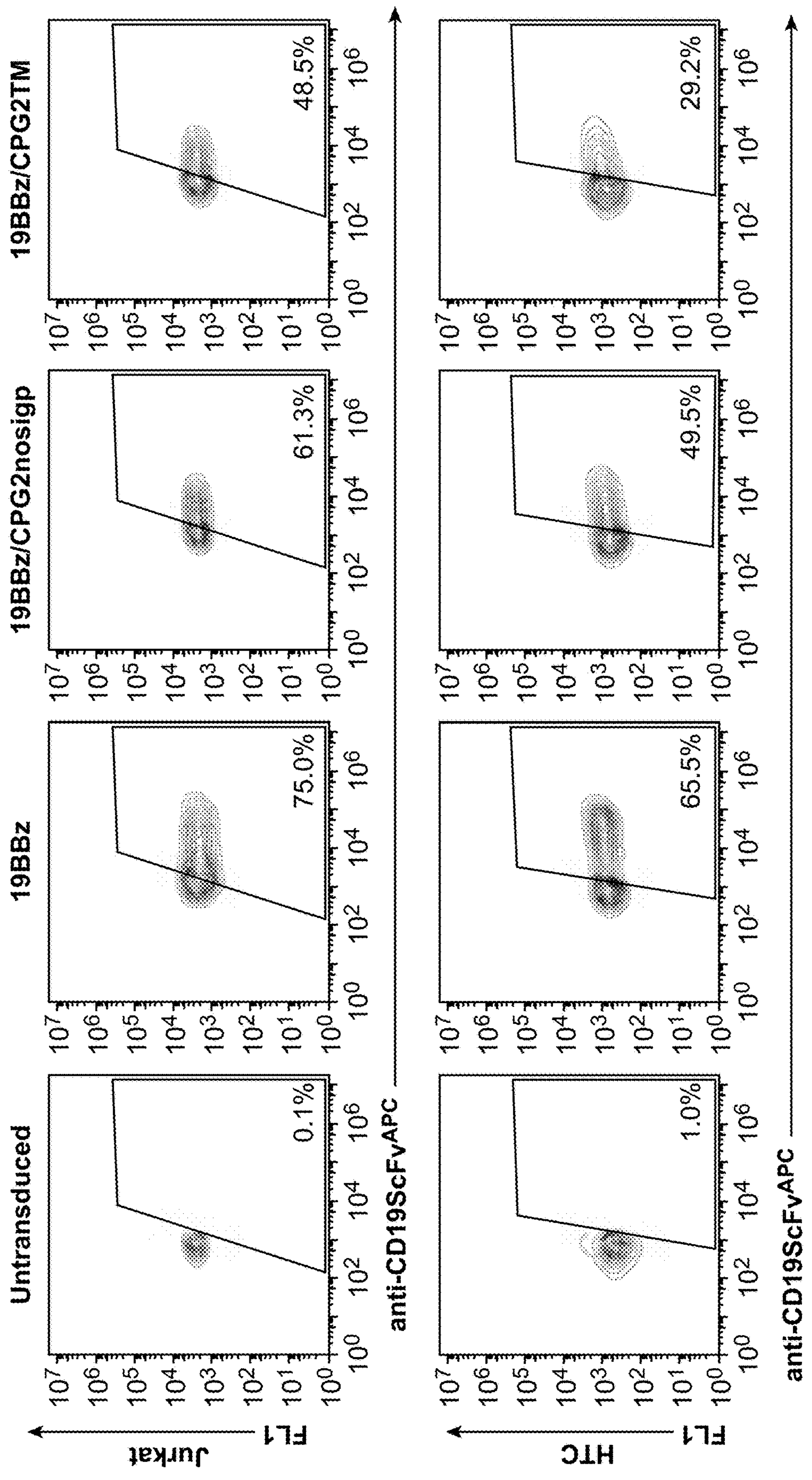
FIG. 10 provides exemplary data showing expression of the anti-CD19 CAR in a human T cell line, Jurkat, and primary human T cells following retroviral transduction of constructs encoding the anti-CD19 CAR in combination with the transmembrane or secreted forms of CPGS. A human T cell line, Jurkat (top panel) and primary human T cells (bottom panel) were transduced with retrovirus encoding an anti-CD19 CAR with 4-1BB costimulatory element (BBz) and either a CPG gene with no signal peptide (CPGnosigp) or a CPG transmembrane gene as described above. Transduction levels were assessed by staining for anti-CD19 ScFv expression on the cell surface demonstrating that the CAR protein is expressed on the cell surface of the engineered immune cell.

The retroviral constructs encoding the anti-CD19 CAR and CPG2 enzymes described above were then introduced into T cell lines (e.g., Jurkat) and primary T cells to measure expression of the chimeric antigen receptor (CAR) and CPG2 and characterize their activity. Jurkat cells and primary human T cells were transduced with retrovirus encoding the anti-CD19 CAR with the 4-1BB costimulatory element alone (19BBz) or with either CPGnosigp (no signal peptide control) or CPGTM (transmembrane) genes. Transduction levels were assessed by staining for anti-CD19 ScFv expression on the cell surface and flow cytometry. FIG. 10 demonstrates that the CAR protein is expressed on the cell surface of the engineered immune cells that express the CPG2 enzyme.

Figure 11:
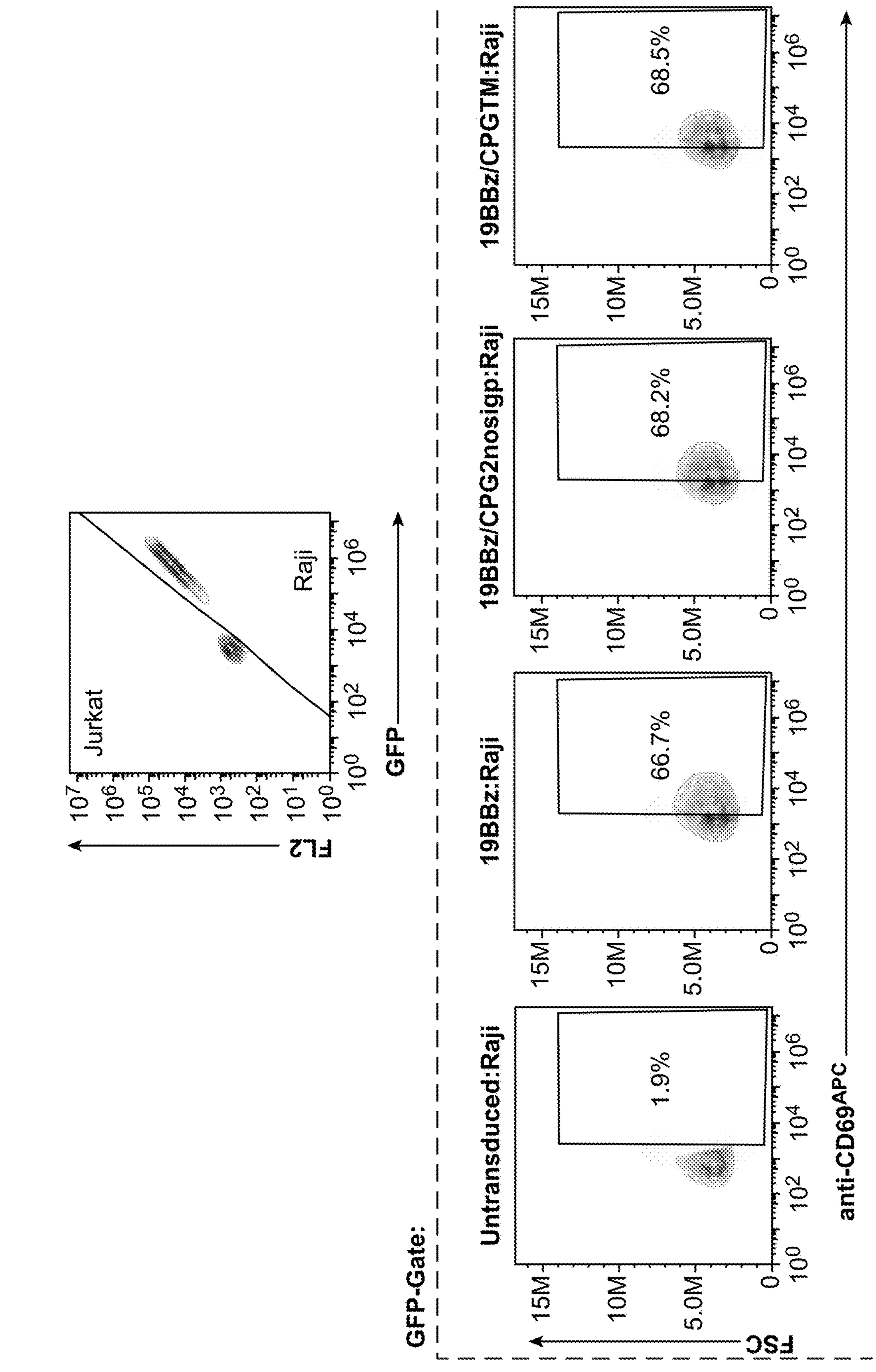
FIG. 11 provides exemplary data showing the activity of Human Jurkat T cells expressing an anti-CD19 CAR with 4-1BB costimulatory element (BBz) and either a CPG gene with no signal peptide (CPGnosigp) or a CPG transmembrane gene as described above. Human Jurkat T cells transduced with 19BBz/CPG retrovirus were co-cultured with a GFP+ Raji (human Burkitt's lymphoma) target cell line for 24 hours (1:1 ratio) and flow cytometry analysis. Jurkat and Raji cells were differentiated by GFP expression (left panel). Activation of Jurkat cells was examined by assessing CD69 expression in GFP-negative cells (right panel).
Figure 12A:
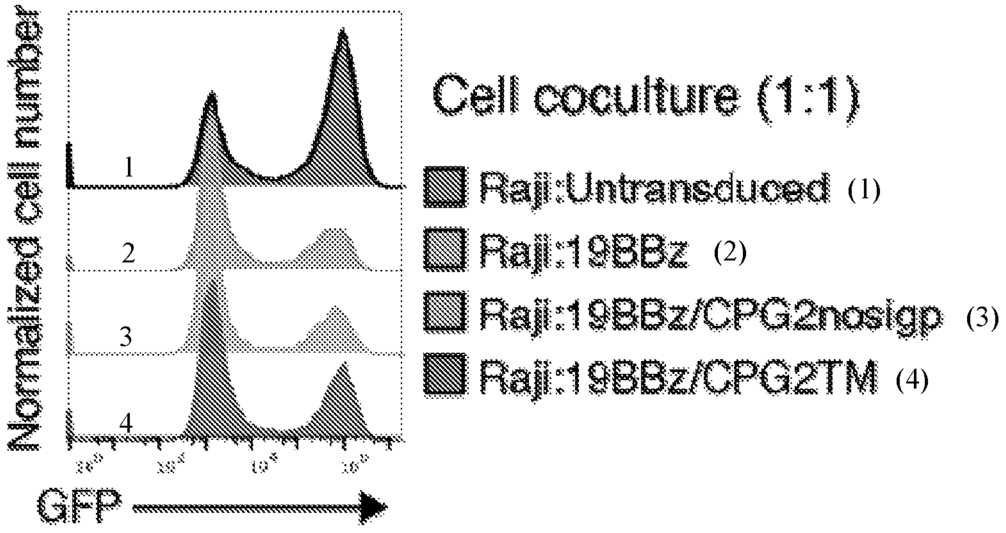
FIG. 12 provides exemplary data showing the activity of non-transduced primary human T cells and transduced human primary human T cells expressing an anti-CD19 CAR with 4-1BB costimulatory element (BBz) and either a CPG gene with no signal peptide (CPGnosigp) or a CPG transmembrane gene as described above. Primary non-transduced human T cells and transduced 19BBz and 19BBz/CPG CAR-T cells were co-cultured at a 1:1 ratio with GFP+ Raji cells. Following a 48-hour incubation cells were analyzed by flow cytometry (A) and % GFP+ cells was calculated (B). The increase in GFP negative cells (signifying the various CAR T cells prepared) to the same levels with both traditional CAR T and the 2 different SEAKER cells show the SEAKER cells are of comparable activity to traditional CARs FIG. 13 provides exemplary data showing expression of anti-CD19 CAR and a secreted CPG2. Primary human T cells were transduced with retrovirus encoding an anti-CD19 CAR with 4-1BB costimulatory element (19BBz) and either a CPG gene with no signal peptide (CPGnosigp) or a secreted form of the CPG gene with the signal peptide as described above. Cell supernatants from human CAR-T cells encoding 19BBZ or 19BBz/CPG constructs were analyzed for CPG2 expression by immunoblot.
Figure 12B:
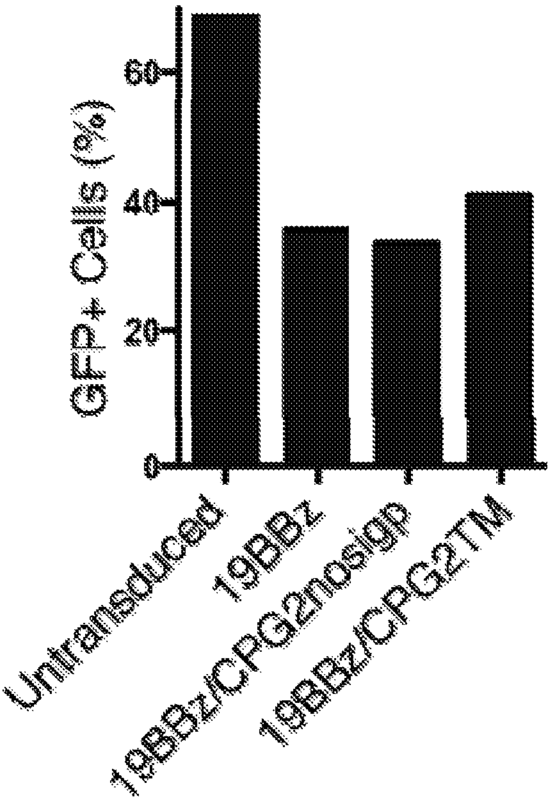

The activity of Human Jurkat T cells expressing an anti-CD19 CAR with 4-1BB costimulatory element (BBz) and either a CPG gene with no signal peptide (CPGnosigp) or a CPG transmembrane gene was also assessed. Human Jurkat T cells transduced with 19BBz/CPG retrovirus were co-cultured with a GFP+ Raji (human Burkitt's lymphoma) cancer target cell line for 24 hours (1:1 ratio) and flow cytometry analysis. Jurkat and Raji cells were differentiated by GFP expression (left panel). Activation of Jurkat cells was examined by assessing CD69 expression in GFP-negative cells (right panel). FIG. 11 shows that the CAR T cells recognize and are activated by the target cancer cells, as evidenced by increased CD69 expression, demonstrating that the pathways are functional in the SEAKER cell.

In a separate experiment, the activity of primary human T cells expressing an anti-CD19 CAR with 4-1BB costimulatory element (BBz) and either a CPG gene with no signal peptide (CPGnosigp) or a CPG transmembrane gene was also assessed. Primary human T cells and human 19BBz and 19BBz/CPG CAR-T cells were co-cultured at a 1:1 ratio with GFP+ Raji cells. Following a 48-hour incubation cells were analyzed by flow cytometry (A) and % GFP+ cells was calculated (B). The increase in GFP negative cells (signifying the various CAR T cells prepared) to the same levels with both traditional CAR T and the 2 different SEAKER cells show the SEAKER cells are of comparable activity to traditional CARs.

Figure 13:
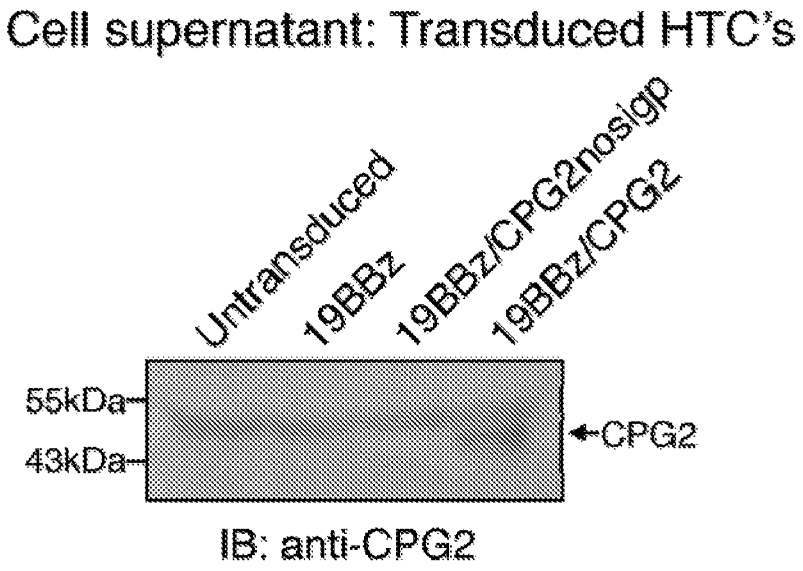

Human T cells transduced with a retroviral construct for secreted CPG2 were also analyzed. Cell supernatant from human CAR-T cells encoding 19BBZ, 19BBz/CPG or control 19BBz/CPGnosigp constructs were analyzed for CPG2 expression by immunoblot. As shown in FIG. 13, the CPG2-secreting SEAKER cell immunoblot showed that the enzyme is found in the supernatant fluid showing that the cell is actively secreting the CPG2 enzyme. The SEAKER cell that has CPG2 without a signal sequence (CPG3nosigp) does not secrete the enzyme.

Example 7

CAR T Cells for Ablation Therapy

CAR T cells for ablation therapy can be generated using the methods provide herein, e.g., according to the methods in the working Examples above or known in the art. In one example, the chimeric antigen receptor is engineered to contain an antigen-binding domain that is specific for a hematopoietic stem cell marker. In one example, the chimeric antigen receptor is engineered to contain an antigen-binding domain that is specific for CD34. A retroviral construct (e.g., an SFG retroviral vector) is generated for the expression of the CAR. Nucleic acid encoding an scFv from an antibody that binds to CD34 is fused at the 5' end (relative to the coding sequence) to a nucleic acid encoding a CD8 signal sequence and at the 3' end, to nucleic acid encoding a CD8 transmembrane domain and 4-1BB signaling and CD3ζ activation domains. The CAR is further linked via nucleic acid encoding a PP2A self-cleaving peptide to a CPG2 or β-lactamase transmembrane form comprising a CD8 transmembrane domain as exemplified in FIG. 3.

T cells are isolated from a patient that is about to receive a hematopoietic stem cell transplant or a bone marrow transplant. The isolated T cells are transduced with the retroviral construct and administered to the patient via intravenous infusion. The T cells are expected to localize to the bone marrow of the patient. Following administration of the CAR T cells, the patient is administered a cytotoxic prodrug that can be cleaved into an active cytotoxic drug by the CPG2 or β-lactamase enzyme. It is expected that release of the cytotoxic drug in the bone marrow will result in localized ablation of the cells, including progenitor hematopoietic stem cells in the bone marrow.

Example 8

CAR T Cells for the Treatment of Viral Infection

CAR T cells for treatment of a viral infection in a patient can be generated using the methods provide herein, e.g., according to the methods in the working Examples above or known in the art. In one example, the chimeric antigen receptor is engineered to contain an antigen-binding domain that is specific for a viral antigen of the virus that has infected the patient. A retroviral construct (e.g., an SFG retroviral vector) is generated for the expression of the CAR. Nucleic acid encoding an scFv from an antibody that binds to the viral antigen is fused at the 5' end (relative to the coding sequence) to a nucleic acid encoding a CD8 signal sequence and at the 3' end, to nucleic acid encoding a CD8 transmembrane domain and 4-1BB signaling and CD3ζ activation domains. The CAR is further linked via nucleic acid encoding a PP2A self-cleaving peptide to a CPG2 or β-lactamase transmembrane form comprising a CD8 transmembrane domain as exemplified in FIG. 3.

T cells are isolated from a patient suffering from a viral infection. The isolated T cells are transduced with the retroviral construct and administered to the patient via intravenous infusion. The T cells are expected to localize to sites of active viral infection in the patient. Following administration of the CAR T cells, the patient is administered antiviral prodrug that can be cleaved into an active drug by the CPG2 or β-lactamase enzyme. It is expected that release of the antiviral drug at the site of infection will result in localized elimination of virally infected cells. It is also expected that treatment of the viral infection is significantly improved compared to treatment of the patient with the antiviral drug alone.

Example 9

CAR T Cells for the Treatment of Bacterial Infection

CAR T cells for treatment of a bacterial infection in a patient can be generated using the methods provide herein, e.g., according to the methods in the working Examples above or known in the art. In one example, the chimeric antigen receptor is engineered to contain an antigen-binding domain that is specific for a bacterial antigen of the bacteria that has infected the patient. In one example, the chimeric antigen receptor is engineered to contain an antigen-binding domain that is specific for a bacterial antigen. A retroviral construct (e.g., an SFG retroviral vector) is generated for the expression of the CAR. Nucleic acid encoding an scFv from an antibody that binds to the bacterial antigen is fused at the 5' end (relative to the coding sequence) to a nucleic acid encoding a CD8 signal sequence and at the 3' end, to nucleic acid encoding a CD8 transmembrane domain and 4-1BB signaling and CD3ζ activation domains. The CAR is further linked via nucleic acid encoding a PP2A self-cleaving peptide to a CPG2 or β-lactamase transmembrane form comprising a CD8 transmembrane domain as exemplified in FIG. 3.

T cells are isolated from a patient suffering from a bacterial infection. The isolated T cells are transduced with the retroviral construct and administered to the patient via intravenous infusion. The T cells are expected to localize to sites of active bacterial infection in the patient. Following administration of the CAR T cells, the patient is administered antimicrobial prodrug that can be cleaved into an active drug by the CPG2 or β-lactamase enzyme. It is expected that release of the antimicrobial drug at the site of infection will result in localized elimination of the bacteria. It is also expected that treatment of the antimicrobial infection is significantly improved compared to treatment of the patient with the antimicrobial drug alone.

Example 10

CAR T Cells for the Treatment of Inflammation

CAR T cells for treatment of inflammation in a patient suffering from inflammation or an inflammatory disorder can be generated using the methods provide herein, e.g., according to the methods in the working Examples above or known in the art. In one example, the chimeric antigen receptor is engineered to contain an antigen-binding domain that is specific for an inflammatory antigen. A retroviral construct (e.g., an SFG retroviral vector) is generated for the expression of the CAR. Nucleic acid encoding an scFv from an antibody that binds to the inflammatory antigen is fused at the 5' end (relative to the coding sequence) to a nucleic acid encoding a CD8 signal sequence and at the 3' end, to nucleic acid encoding a CD8 transmembrane domain and 4-1BB signaling and CD3ζ activation domains. The CAR is further linked via nucleic acid encoding a PP2A self-cleaving peptide to a CPG2 or β-lactamase transmembrane form comprising a CD8 transmembrane domain as exemplified in FIG. 3.

T cells are isolated from a patient suffering from inflammation or an inflammatory disorder. The isolated T cells are transduced with the retroviral construct and administered to the patient via intravenous infusion. The T cells are expected to localize to sites of inflammation in the patient. Following administration of the CAR T cells, the patient is administered anti-inflammatory prodrug that can be cleaved into an active drug by the CPG2 or β-lactamase enzyme. It is expected that release of the anti-inflammatory drug at the site of inflammation will result in localized elimination of the inflammation. It is also expected that treatment of the inflammation is significantly improved compared to treatment of the patient with the anti-inflammatory drug alone.

Example 11

Figure 14A:
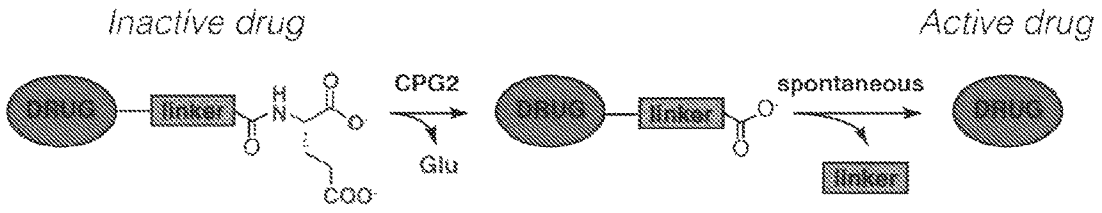
FIG. 14A provides a schematic of glutamate prodrug cleavage and linker decay leading to active drug synthesis following exposure to CPG2.
Figure 14B:
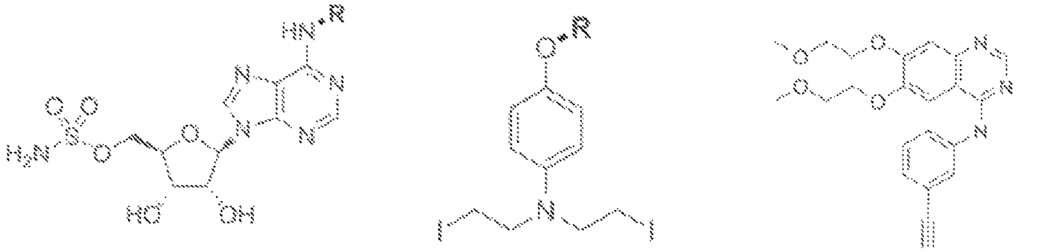
FIG. 14B provides a schematic of the 3 classes of prodrug compounds synthesized for use with the CPG2 enzyme platform.

This example describes the generation of transmembrane and secreted forms of CPG and/or Beta-lactamase and their characterization when expressed in mammalian cells. In this exemplary embodiment, several cytotoxic drugs were synthesized carrying a terminal glutamate masking residue linked via a self-immolating moiety that decays following glutamate cleavage to result in formation of the active cytotoxin (FIG. 14A). These prodrugs included the masked forms of the nucleoside analog AMS (glut-AMS), the alkylating nitrogen mustard (ZDP275), and the targeted kinase inhibitor Erlotinib (glut-erlotinib) (FIG. 14B). $IC_{50}$ values were generated for each pair of drugs against a panel of cancer cell lines and primary cell lines to determine the effective therapeutic indices that could be achieved with the new prodrug platforms.

Figure 14C:
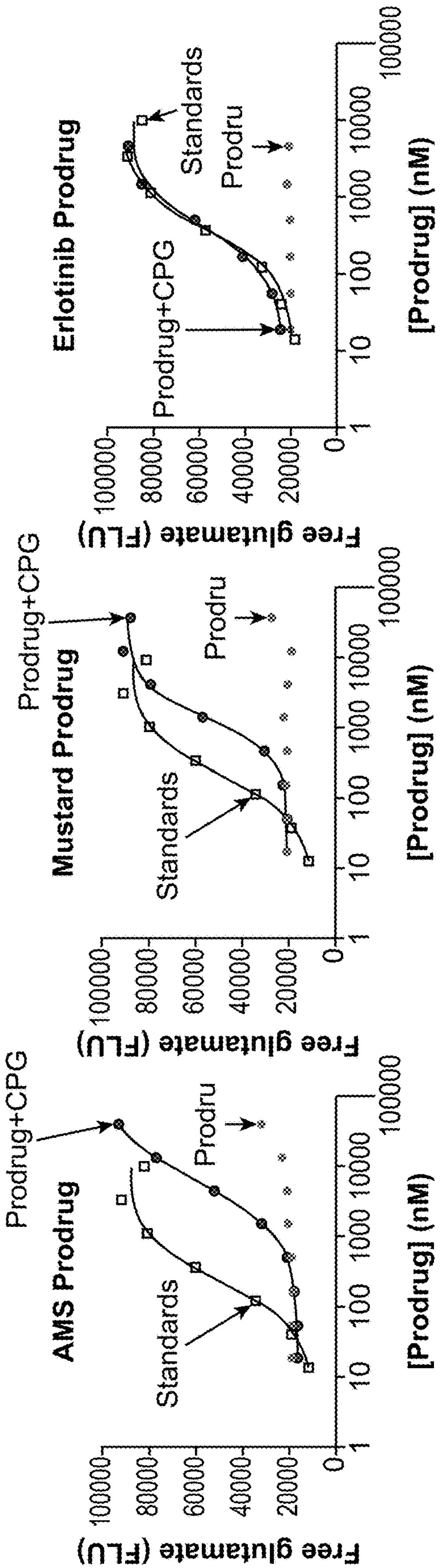
FIG. 14C shows an Ampex Red assay demonstrating release of free glutamate from prodrug compounds upon incubation with recombinant CPG2 enzyme.
Figure 14D:
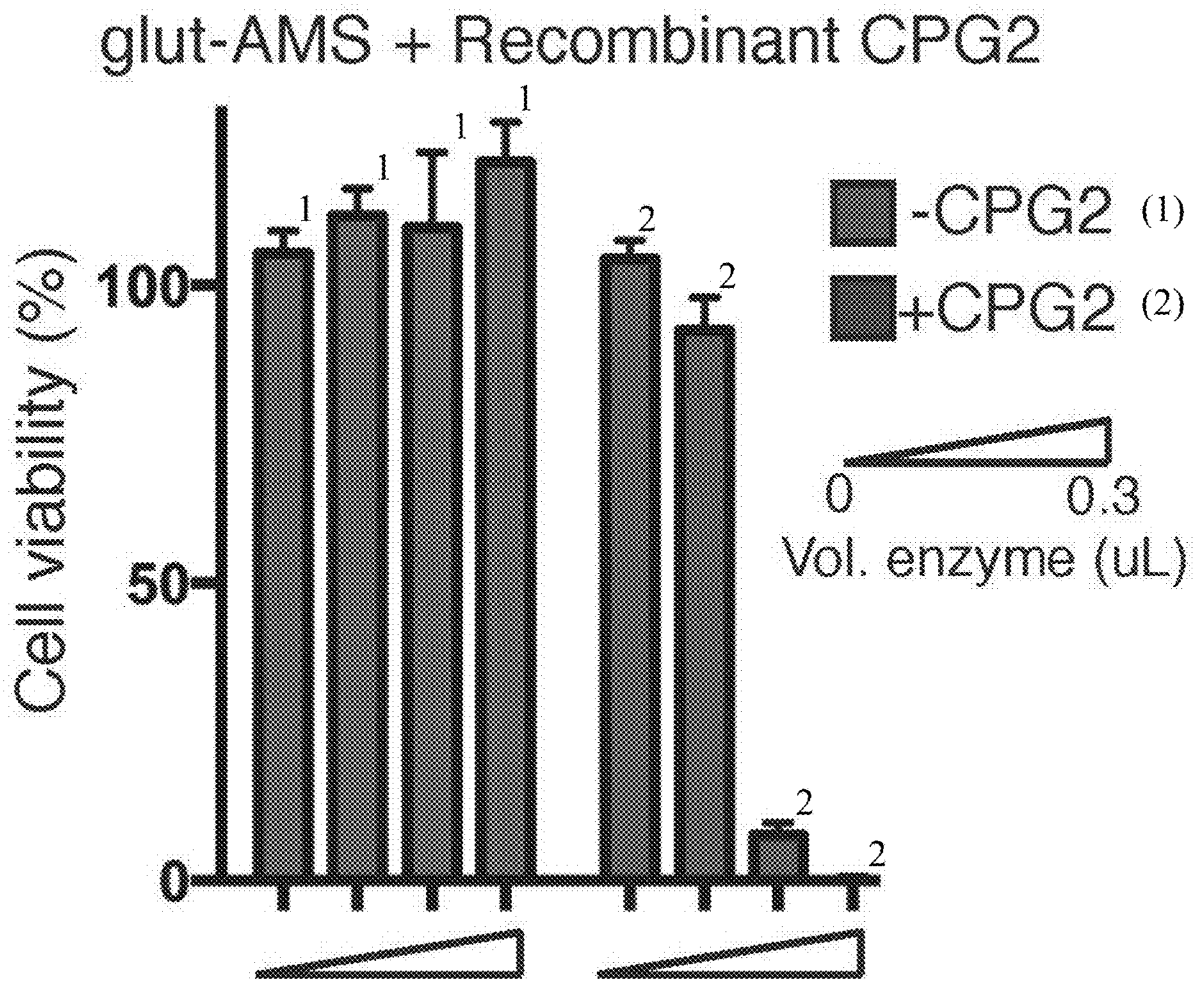
FIG. 14D shows a Cell Titer-Glo viability assay of SET2 cells incubated in 3 μM AMS-glut with or without recombinant CPG2.
Figure 14E:
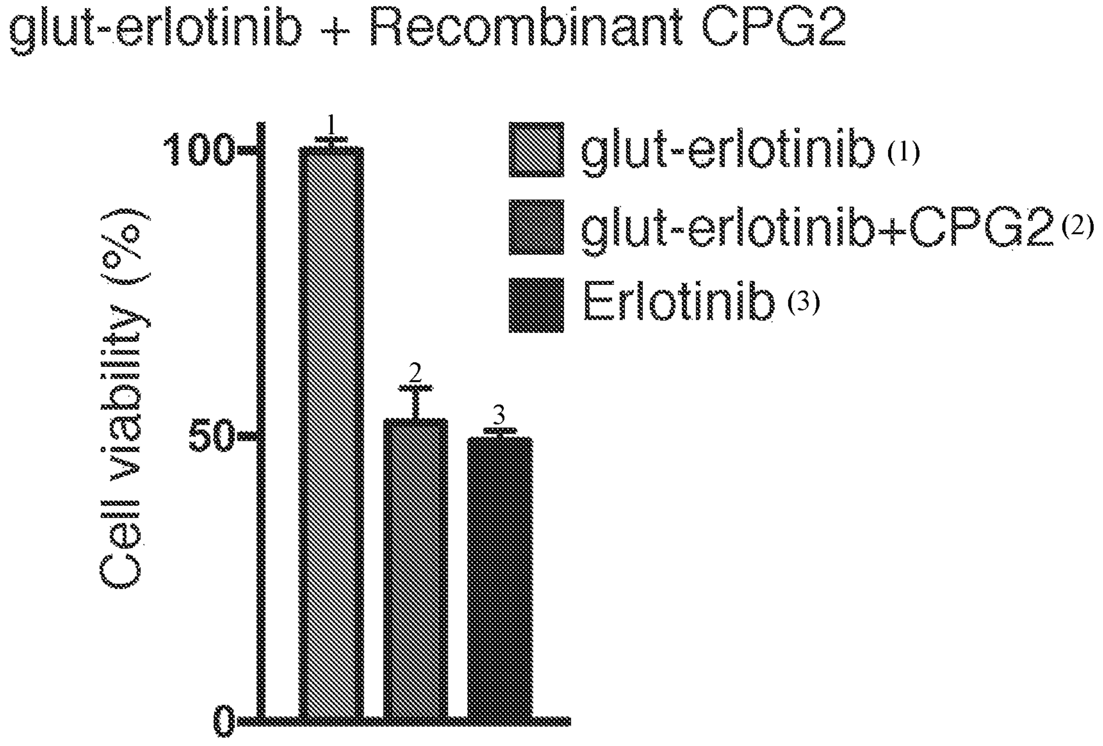
FIG. 14E shows a Cell Titer-Glo viability assay of SET2 cells incubated in 1 μM Erlotinib-glut with or without recombinant CPG2.
Figure 14F:
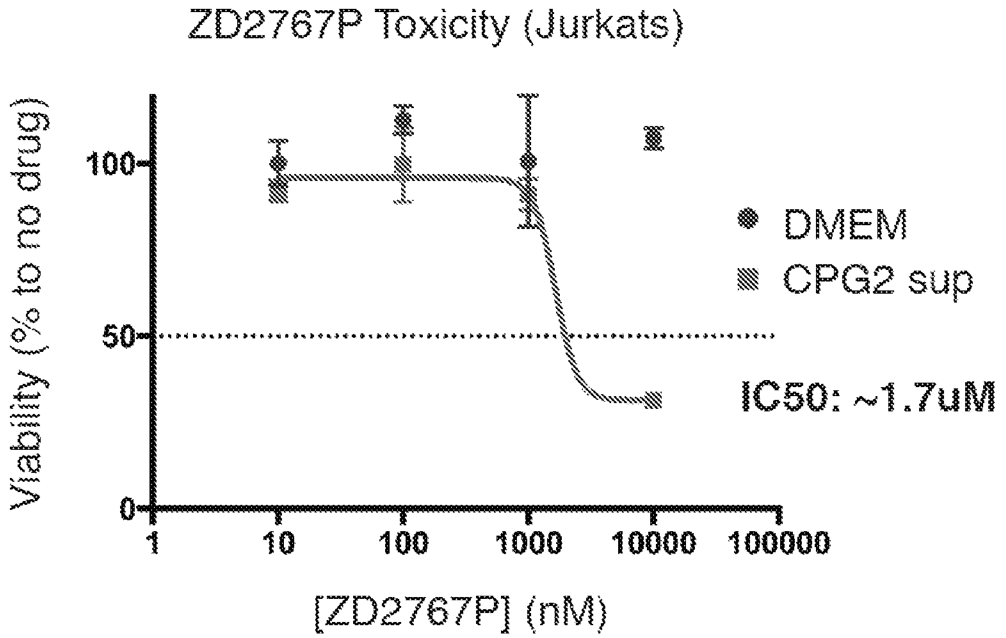
FIG. 14F shows a cell toxicity assay of Jurkat cells incubated in ZD2767P with or without recombinant CPG2.
Figure 15A:
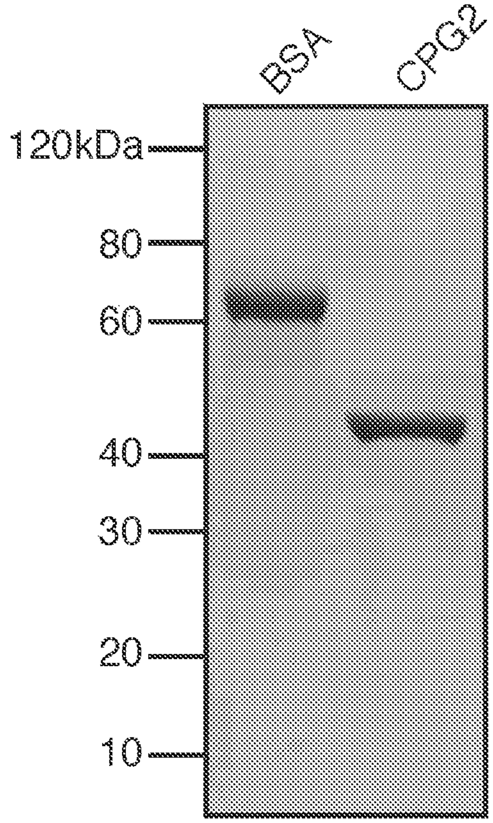
FIG. 15A shows Coomassie Blue staining of purified recombinant CPG2.
Figure 15B:
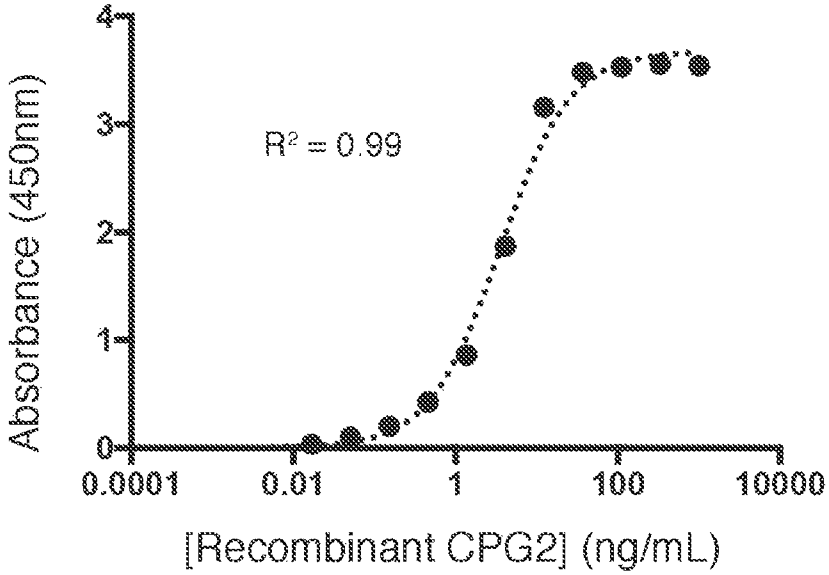
FIG. 15B shows a quantitative sandwich ELISA of purified recombinant CPG2.

Recombinant CPG2 protein was initially synthesized, purified (FIGS. 15A and 15B), and incubated with increasing concentrations of prodrug in a glutamate release assay (FIG. 14C). Mass spectrometry was used to determine that the glutamate moiety was released from all of the glutamate prodrugs. The in vitro cytotoxicity of the prodrugs (FIG. 14B) were tested against the myeloid leukemia cell line SET2 using a CellTitre Glo® assay (Promega, Madison, WI). As expected, the prodrugs were not cytotoxic to the SET2 cells, however, co-incubation of the prodrugs with the purified, recombinant CPG2 resulted in the subsequent death of SET2 cells, consistent with CPG2-mediated cleavage of the prodrug to release the active parent drug (FIGS. 14D-14F).

Figure 15C:
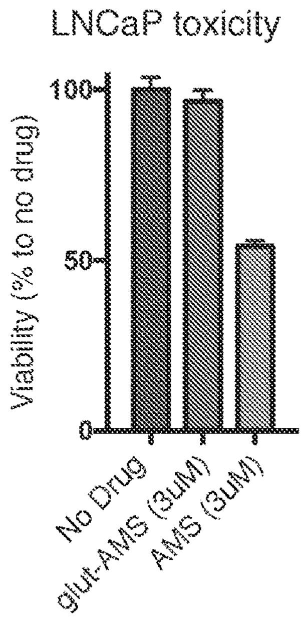
FIG. 15C shows a Cell Titer-Glo viability assay of LNCap cells incubated with the AMS-glut prodrug or AMS.

It was determined that the AMS prodrug expressed high (>100) selective indices for all cell types tested, and remained stable in the presence of the endogenous glutamate carboxypeptidase expressed in human prostate cells, confirming its specificity for the CPG2 carboxypeptidase (FIG. 15C, Table 1). This prodrug/drug combination was chosen for further development of the SEAKER systems.

Figure 16A:
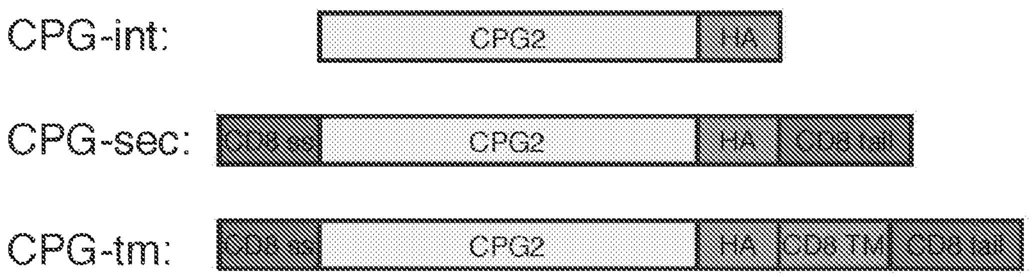
FIG. 16A provides a schematic of three forms of CPG2 (internal, secreted, membrane-bound) generated for optimal expression in mammalian cells.
Figure 16B:
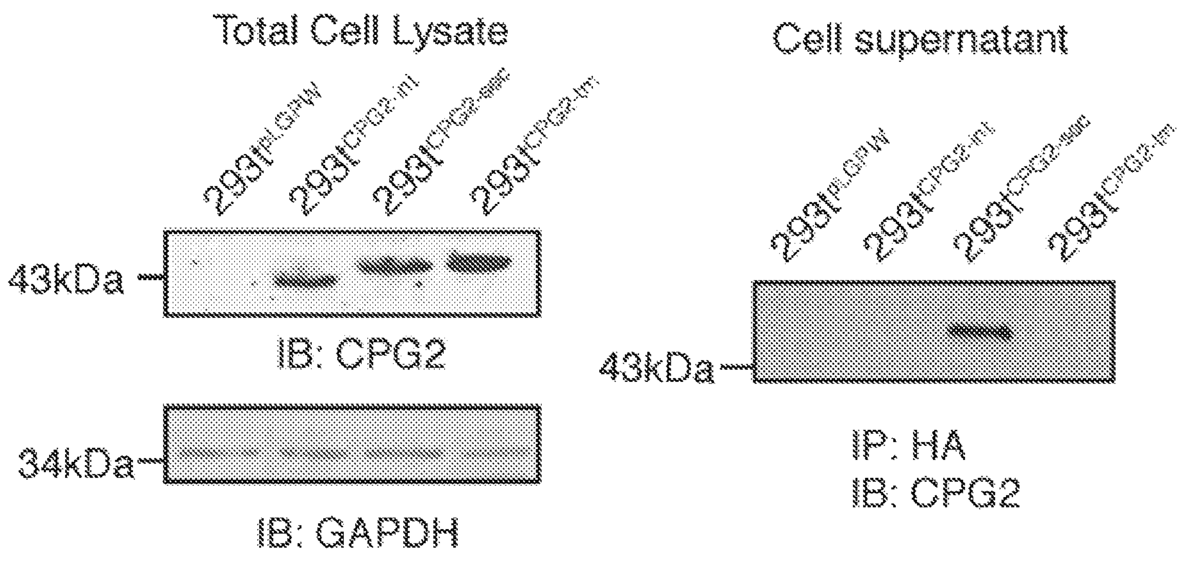
FIG. 16B provides immunoblots indicating expression of all three CPG2 isoforms in cell lysate (left panel) or secreted into the supernatant fluid (right panel) following transfection in Hek293t cells.

This example describes the generation of transmembrane and secreted forms of CPG and their characterization when expressed in bacteria or mammalian cells. Next, it was demonstrated that CPG2 could be genetically encoded and expressed in eukaryotic cells while maintaining enzymatic function and without harming the host cells. Transient transfection of HEK293t cells demonstrated that CPG2 tolerates various structural modifications, including the addition of an HA epitope tag, restriction to the cytoplasm, tethering to the cell surface, or routing through the secretory system to permit secretion into the extracellular milieu (FIGS. 16A and 16B). Immunoblot analysis determined that the addition of the CD8 cytosolic tail to the c-terminus of CPG2 increased secretion (FIG. 17A).

Figure 3C:
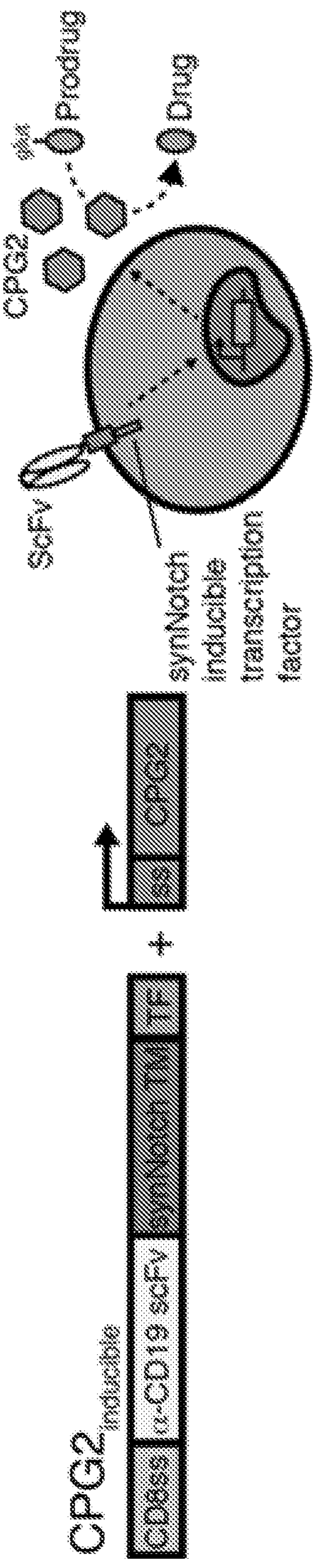
Figure 16C:
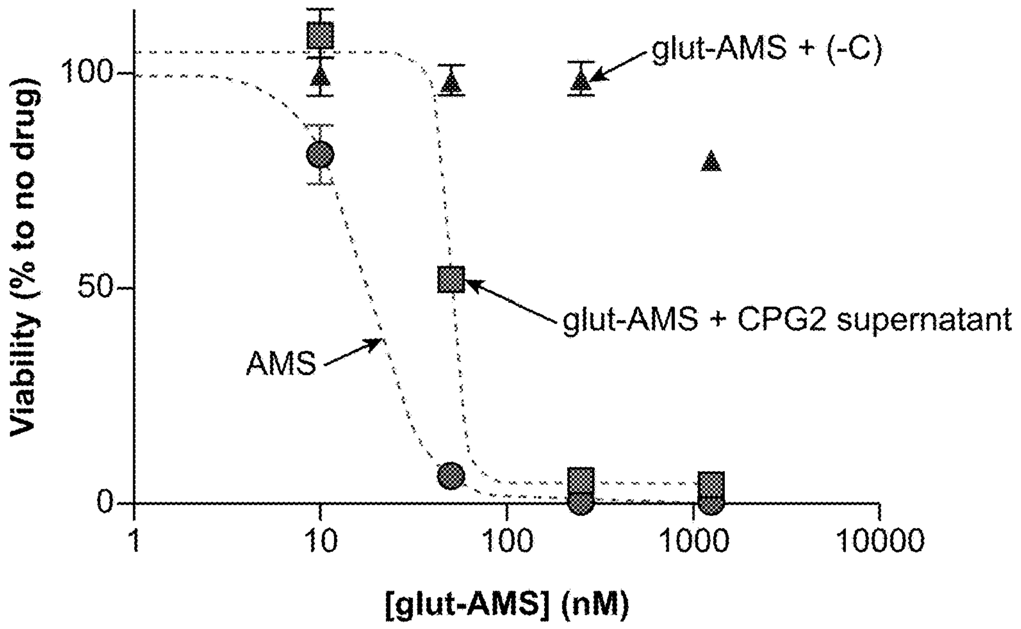
FIG. 16C shows a Cell Titer-Glo viability assay of SET2 cells incubated with AMS-glut prodrug in supernatant fluid from control Hek293t cells or supernatant from Hek293t cells expressing the secreted form of CPG2.
Figure 17A:
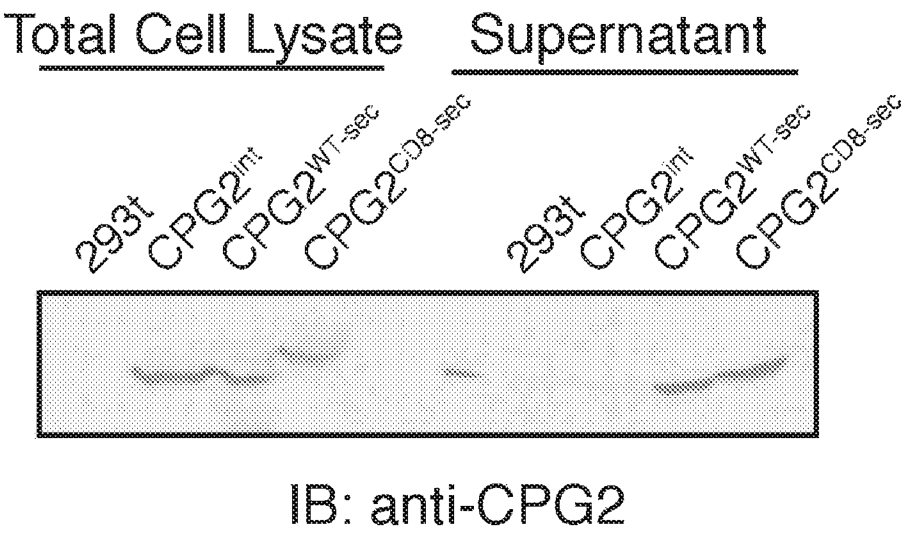
FIG. 17A shows an anti-CPG2 Immunoblot of lysate and supernatant fluid from Hek293t cells transduced with various forms of CPG2.
Figure 17B:
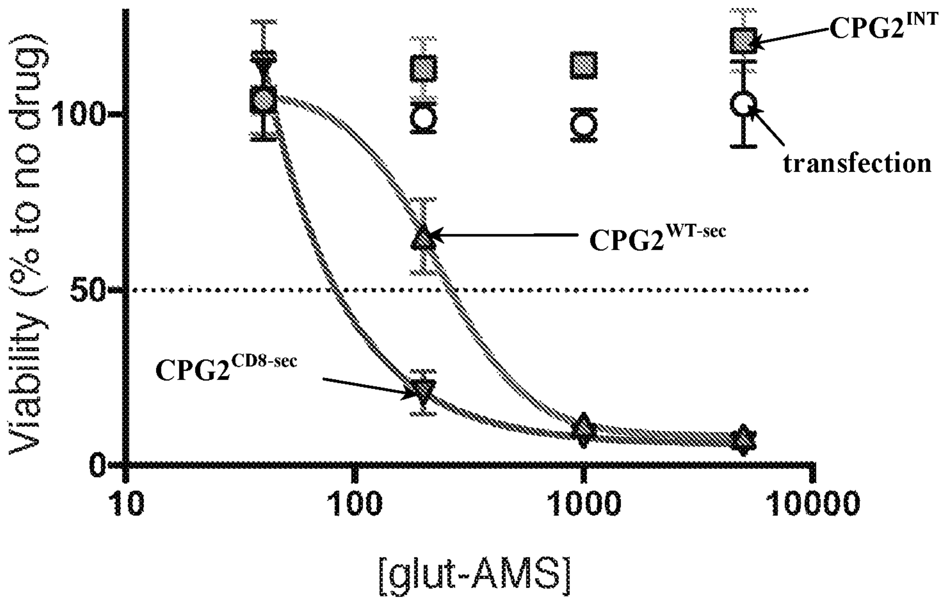
FIG. 17B shows a Cell Titer-Glo viability assay of SET2 cells incubated with AMS-glut prodrug in supernatant fluid from control Hek293t cells or supernatant from Hek293t cells expressing CPG2-int, CPG2WT-sec, or CPG2CD8-sec.
Figure 17C:
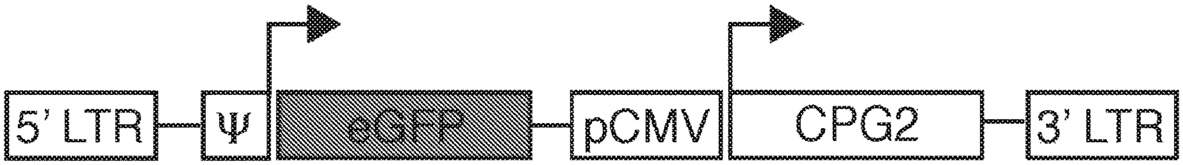
FIG. 17C shows a schematic of the pLGPW-CPG2 gene cassette.

FIGS. 16C and 17B-17C demonstrate that the secreted form of CPG2 expressed in HEK 293t cells has enzymatic activity in vitro. SET2 cells were exposed to increasing concentrations of AMS (square) or glut-AMS with media alone (−control, triangle) or supernatant from CPG2-secreting HEK293t cells (circle). Cell viability was measured by CellTitre-Glo® luminescence assay. As shown in FIG. 3C, increasing amount of the prodrug with the CPG2 supernatant resulted in a significant decrease in cell viability that was comparable to the AMS prodrug at around 100 nM, whereas control media did not.

Figure 16D:
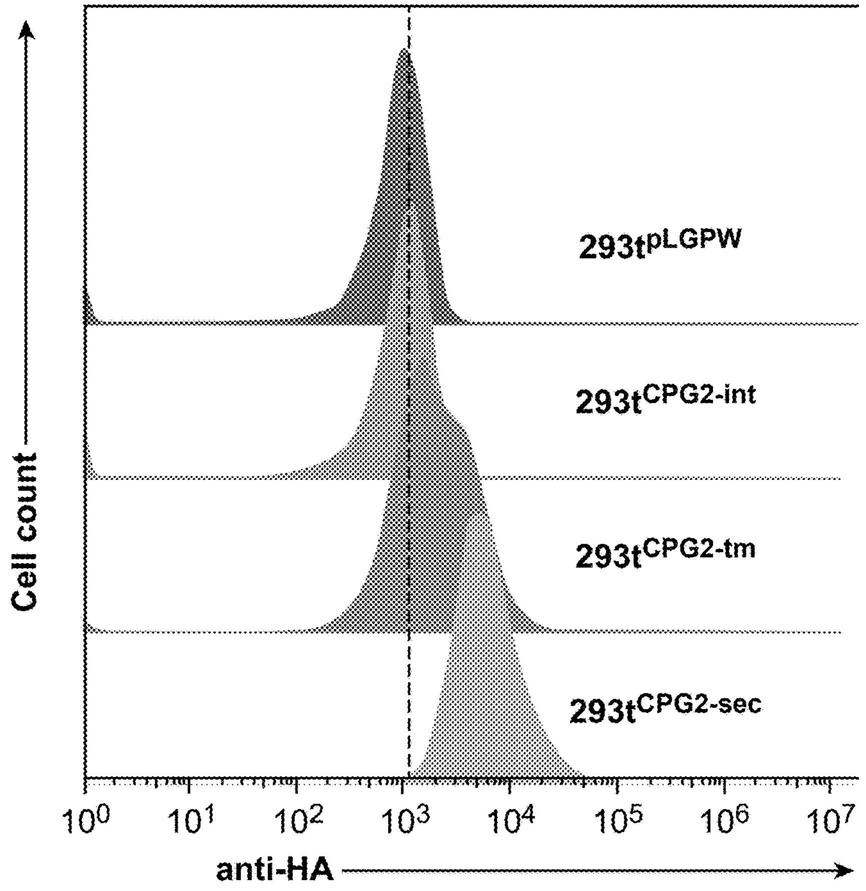
FIG. 16D demonstrated surface expression analysis of CPG2 proteins in Hek293t cells transduced to stably express the CPG2 gene.
Figure 16E:
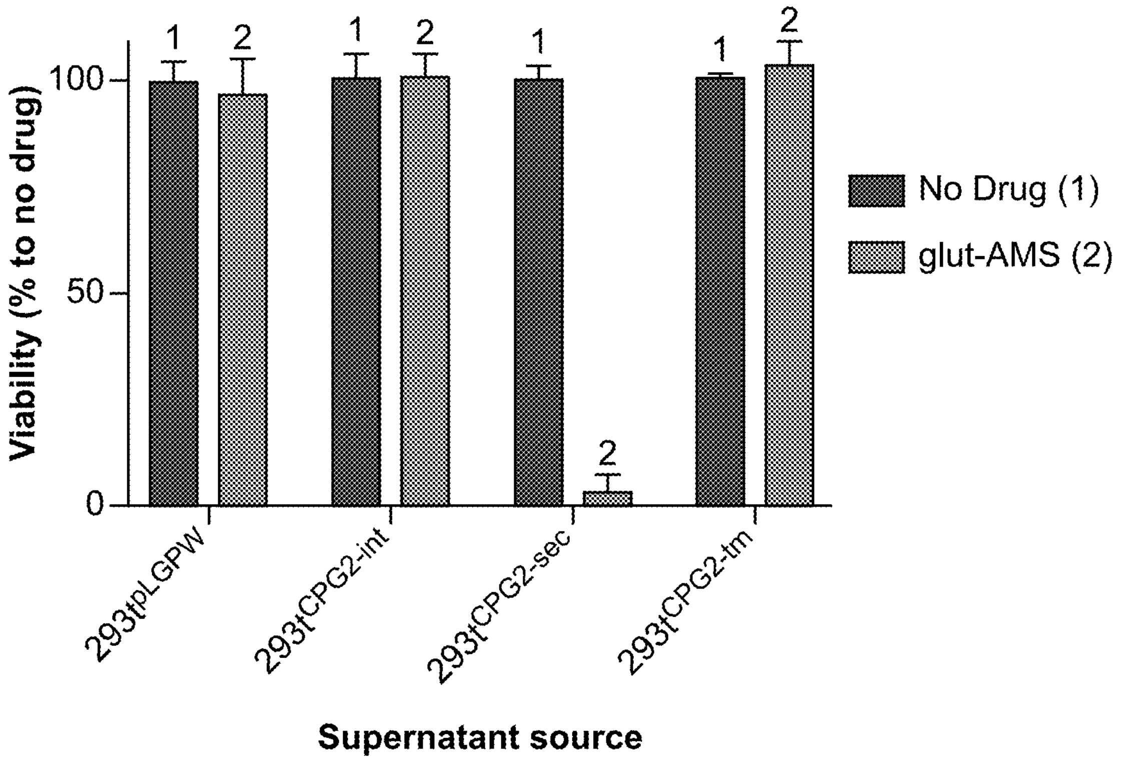
FIG. 16E shows a Cell Titer-Glo viability assay of SET2 cells incubated with AMS-glut supernatant fluid from Hek293t cells engineered to stably express CPG2.
Figure 16F:
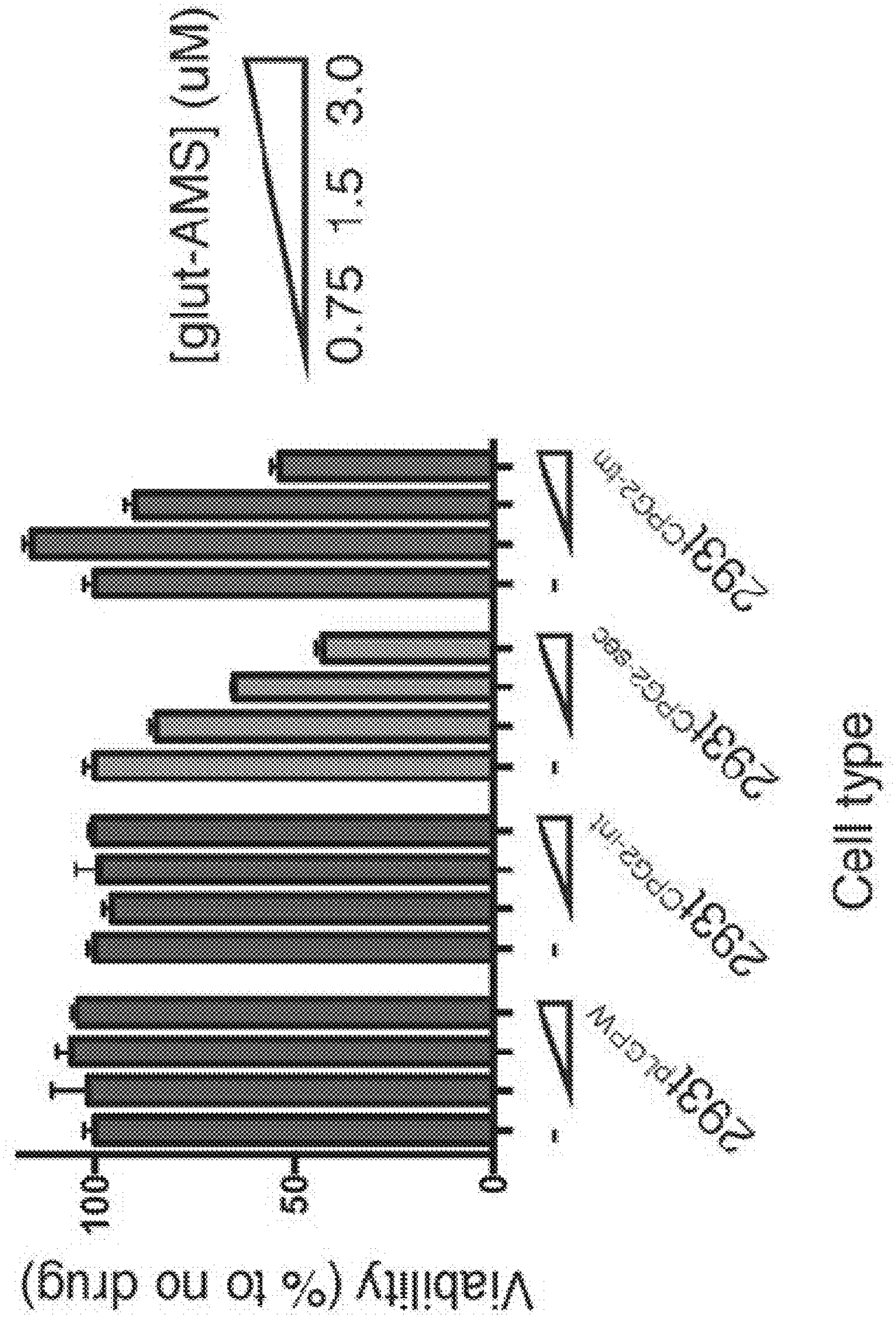
FIG. 16F shows a Cell Titer-Glo viability assay of Hek293t-CPG2 cells exposed to AMS-glut prodrug.
Figure 16G:
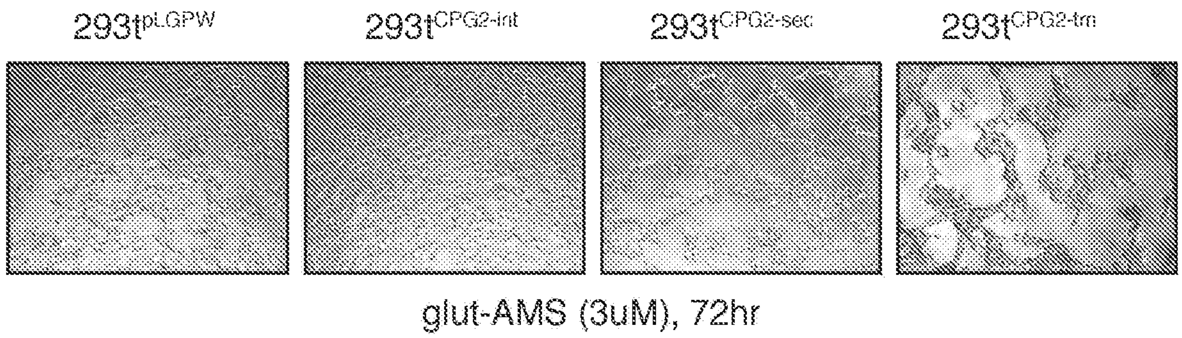
FIG. 16G provides a micrograph of Hek293t-CPG2 cells exposed to AMS-glut prodrug.

FIG. 17A demonstrates an immunoblot analysis of the stable expression of CPG2 and Beta-lactamase in HEK293t cells transduced with retrovirus, which were subsequently analyzed for enzyme expression and function. The HA epitope tag permitted staining of surface-level CPG2 in cells expressing either the secreted or transmembrane forms of the enzyme (FIG. 16D). Enzyme was detected in cell supernatant fluid and transfer of supernatant fluid from $293t^{CPG2\text{-}sec}$, but not the other forms of CPG2 or a GFP expressing control cell line in the presence of prodrug, resulted in death of SET2 cells (FIG. 16E). Cell viability was measured at 48 hours by CellTitre-Glo® luminescence. FIGS. 16F and 16G demonstrate that direct treatment of $293t^{CPG2}$ cell lines with prodrug resulted in cell death, indicating that cells expressing CPG2 are sensitized to prodrug treatment.

Figure 16H:
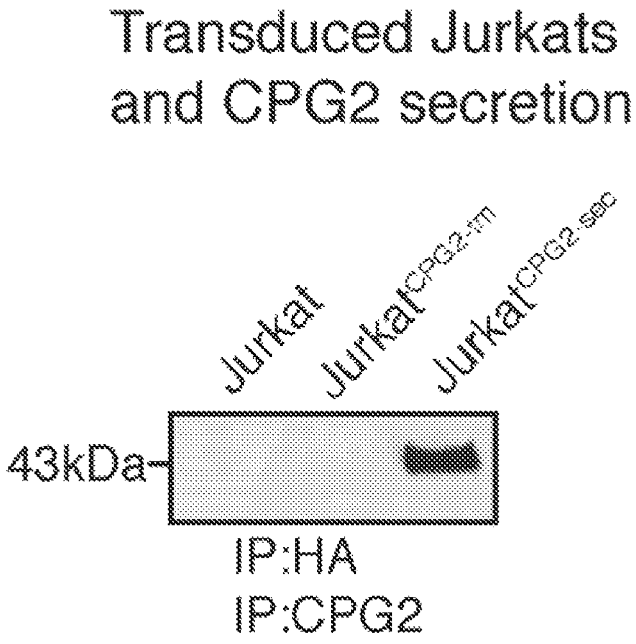
FIG. 16H shows an immunoblot analysis of supernatant fluid from Jurkat-CPG2 cells.

Retroviral constructs encoding the CPG2 enzyme described above were then introduced into T cell lines (e.g., Jurkat) to measure expression of CPG2 and characterize the activity. FIG. 16H shows an immunoblot analysis which demonstrates stable expression of CPG2 enzyme via retroviral transduction.

Figure 15D:
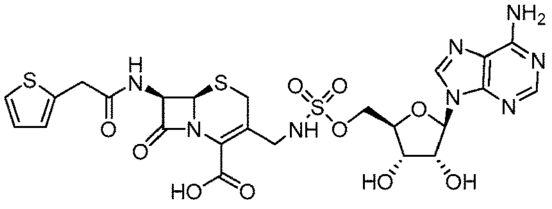
FIG. 15D provides a schematic of the classes of prodrug compounds synthesized for use with the Beta-lactamase enzyme platform.
Figure 15D:
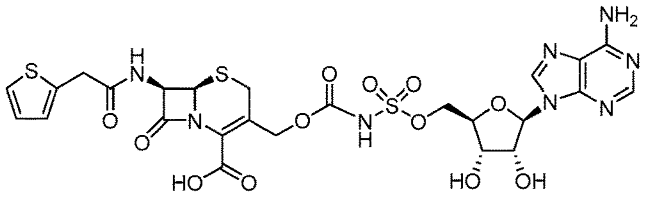
Figure 15D:
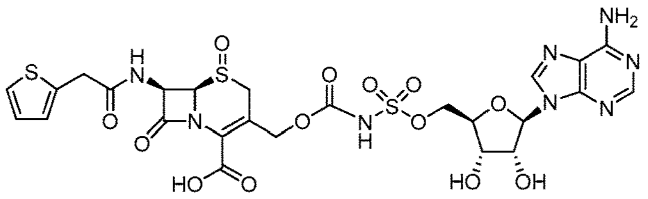
Figure 15D:
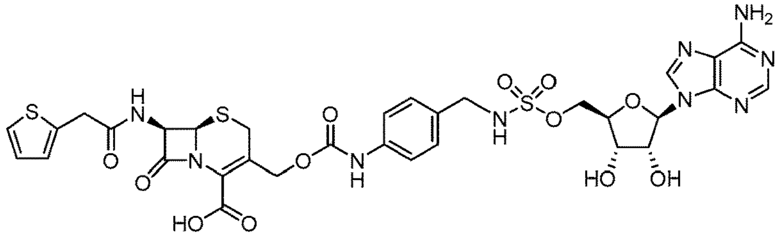
Figure 15E:
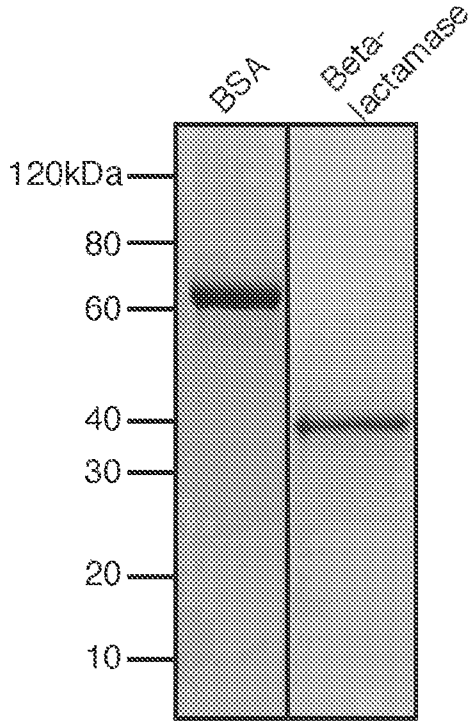
FIG. 15E shows Coomassie Blue staining of purified recombinant *E. cloacae* Beta-lactamase.

A second eukaryotic-adapted prodrug-activating enzyme was developed based on the *E. cloacae*-derived Beta-lactamase (B-lac), as well as a series of lactam prodrugs which were activated by recombinant B-lac (FIG. 15D). As with CPG2, B-lac was produced and secreted from stable 293t cells ($293t^{Beta\text{-}lac}$) and Jurkat cells (FIG. 15E). The secreted form of Beta lactamase displayed enzymatic activity in stable cell lines, and successfully activated various lactam prodrugs (FIG. 22C), which possessed high selective indices in various cell types (Table 3).

TABLE 3

Cell selectivity data for AMS prodrugs.

| | AMS (ng/mL) | glut-AMS (ng/mL) | glut-AMS Selective Index | ceph-AMS | ceph-AMS Selective Index |
|---|---|---|---|---|---|
| HEK293t | 666 | >5000 | >7.5 | 2000 | ~3 |
| Skov-3 | 350 | >5000 | >14.3 | >1250 | 3.6 |
| Jurkat (T-cell) | 17.7 | >1250 | >162.3 | | |
| Human T cell | 227.4 | >3000 | >13.2 | >1250 | >6 |
| Nalm6 | 36.9 | >3000 | >81.3 | | |
| Raji | 17.6 | >3000 | >170.5 | | |
| Set2 | 34.4 | >3000 | >87.2 | ~2200 | ~64 |

Figure 18A:
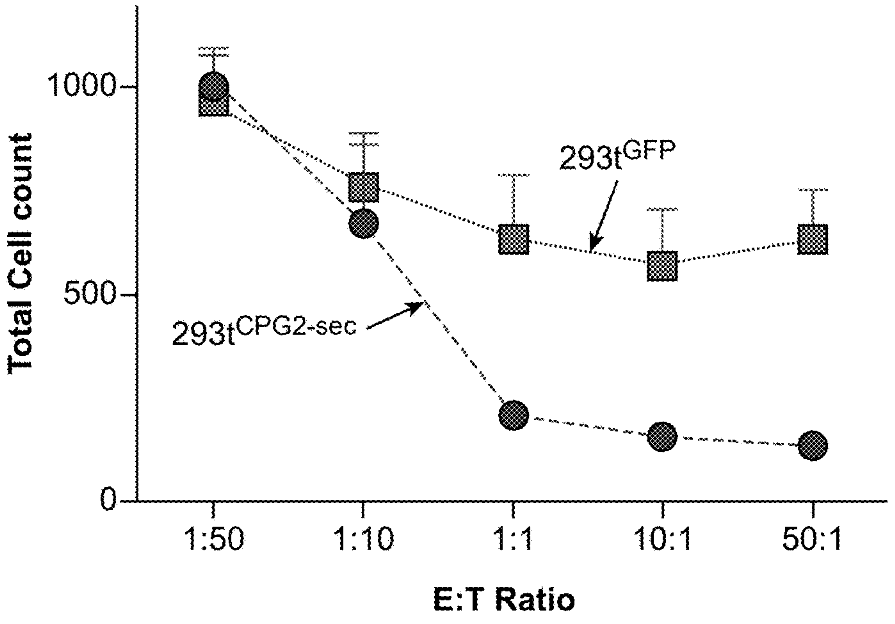
FIG. 18A provides a cell viability analysis of co-cultures with increasing ratio of Hek293t-GFP+/CPG2 or Hek293t-GFP+ cells (Effector cells) to Hek293t WT (Bystander cells) in the presence of AMS-glut prodrug.
Figure 18B:
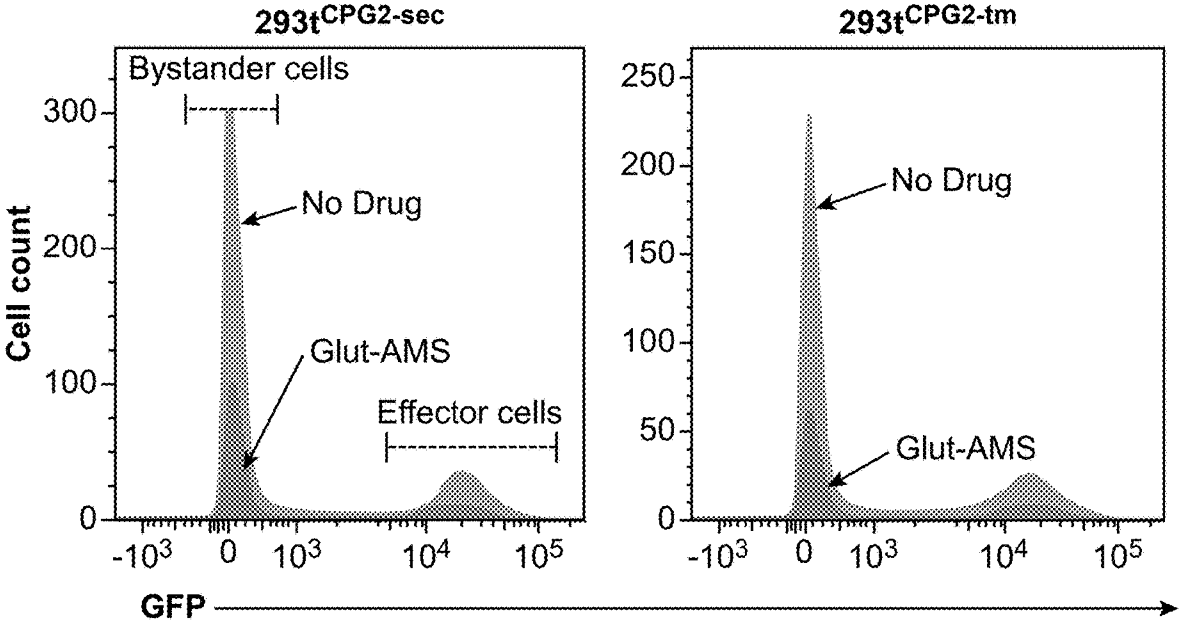
FIG. 18B shows GFP analysis of co-cultures with or without prodrug demonstrates equivalent depletion of both enzyme+ and enzyme− cell populations.
Figure 18C:
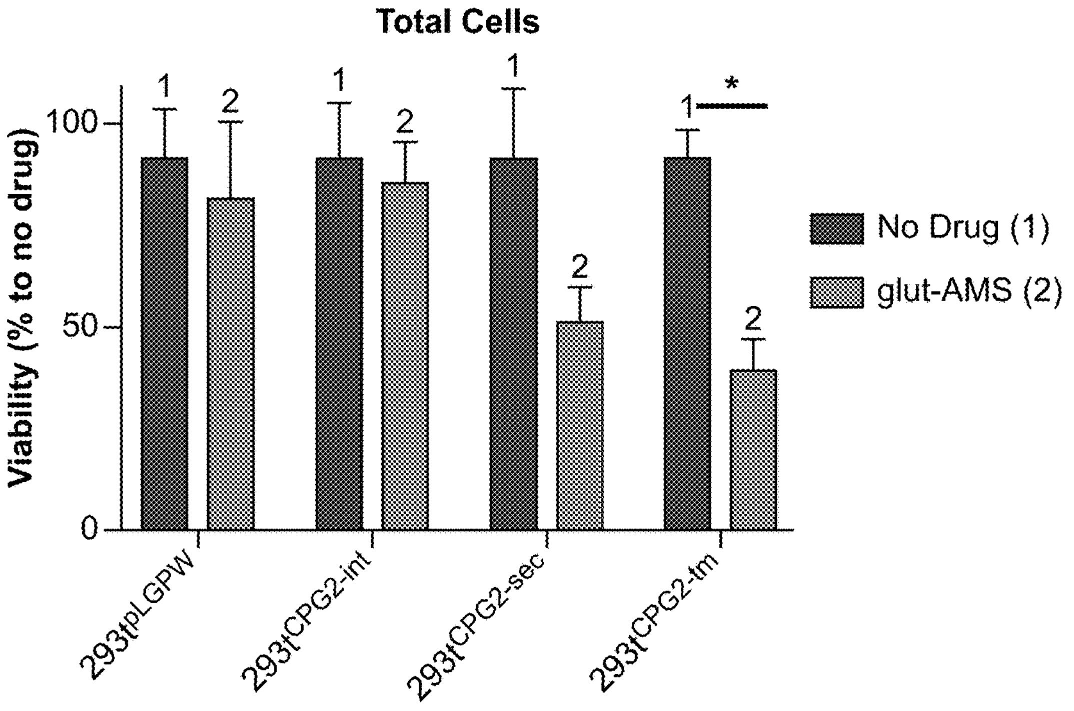
FIG. 18C shows quantification of total cell depletion in 1:1 E:T cocultures with or without prodrug.
Figure 18D:
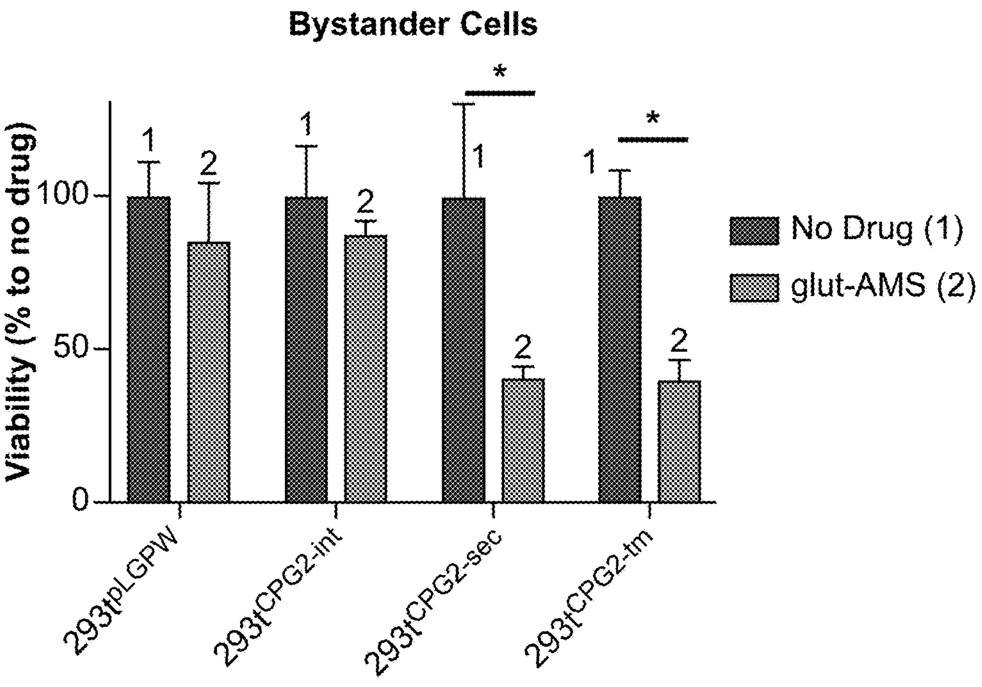
FIG. 18D shows quantification of enzyme-negative (bystander cell) depletion in 1:1 E:T cocultures with or without prodrug.

Cell permeability studies in human epithelial CACO-2 cells revealed that the glut-AMS prodrug exhibited no cell permeability and would thus not diffuse into CPG2-expressing cells prior to enzyme release (Table 4), however, the active drug could still kill the secreting cell after unmasking. To further investigate this effect, bystander toxicity assays were conducted in which enzyme-positive cells (effector cells) were cocultured with enzyme-negative cells (target cells), in the presence of prodrug. Cell counts following prodrug treatment demonstrated that increased effector:target ratios resulted in higher total cell death, with depletion of ~80% of cells when $293t^{CPG2\text{-}sec/GFP}$ or $293t^{Beta\text{-}lac/GFP}$ were cocultured at a 1:1 ratio with WT 293t cells (FIG. 18A). Analysis of cell fluorescence revealed equivalent depletion of both GFP+ (effector) and GFP− (target) cells, indicating that both cell populations (effector cells and target cells) are destroyed by the activated prodrug (FIG. 18B-18D).

TABLE 4

Cell permeability studies of prodrugs in human epithelial CACO-2 cells.

| S. No | Compounds | Papp ($10^{-6}$ cm/sec) | Efflux Ratio (B-A/A-B) |
|---|---|---|---|
| 1 | Loperamide (A-B) | 2.2 ± 0.3 | 7.7 |
| | Loperamide (B-A) | 16.9 ± 1.1 | |
| | Loperamide + Ver (A-B) | 10.5 ± 1.5 | 0.7 |
| | Loperamide + Ver (B-A) | 7.8 ± 0.5 | |
| 2 | Glutamate-AMS (A-B) | 0.0 ± 0.0 | NC |
| | Glutamate-AMS (B-A) | 0.0 ± 0.0 | |
| | Glutamate-AMS + Ver (A-B) | 0.0 ± 0.0 | NC |
| | Glutamate-AMS + Ver (B-A) | 0.0 ± 0.0 | |

Figure 15F:
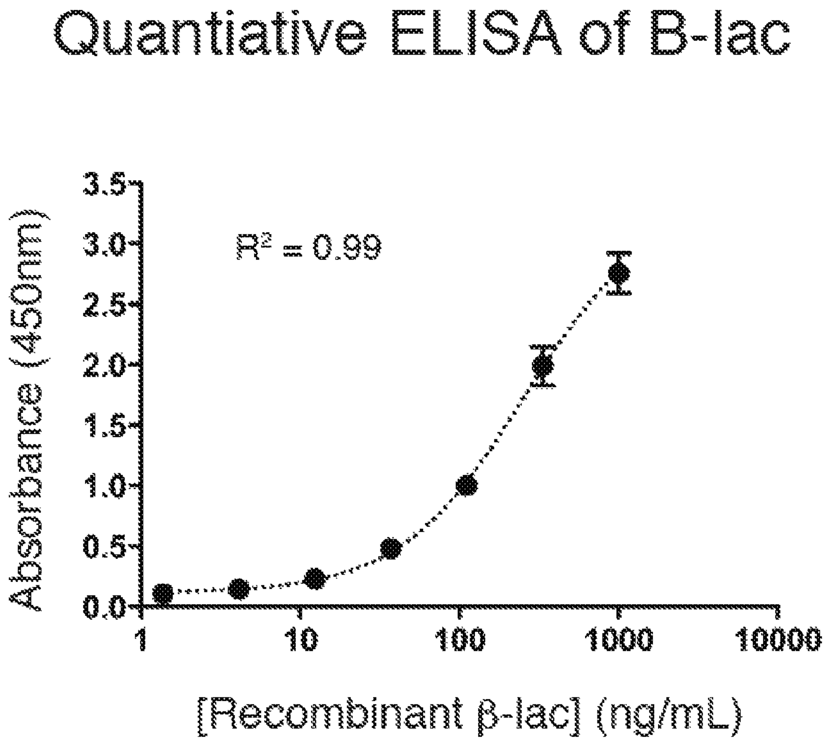
FIG. 15F shows a quantitative ELISA of purified recombinant Beta-lactamase.
Figure 19A:
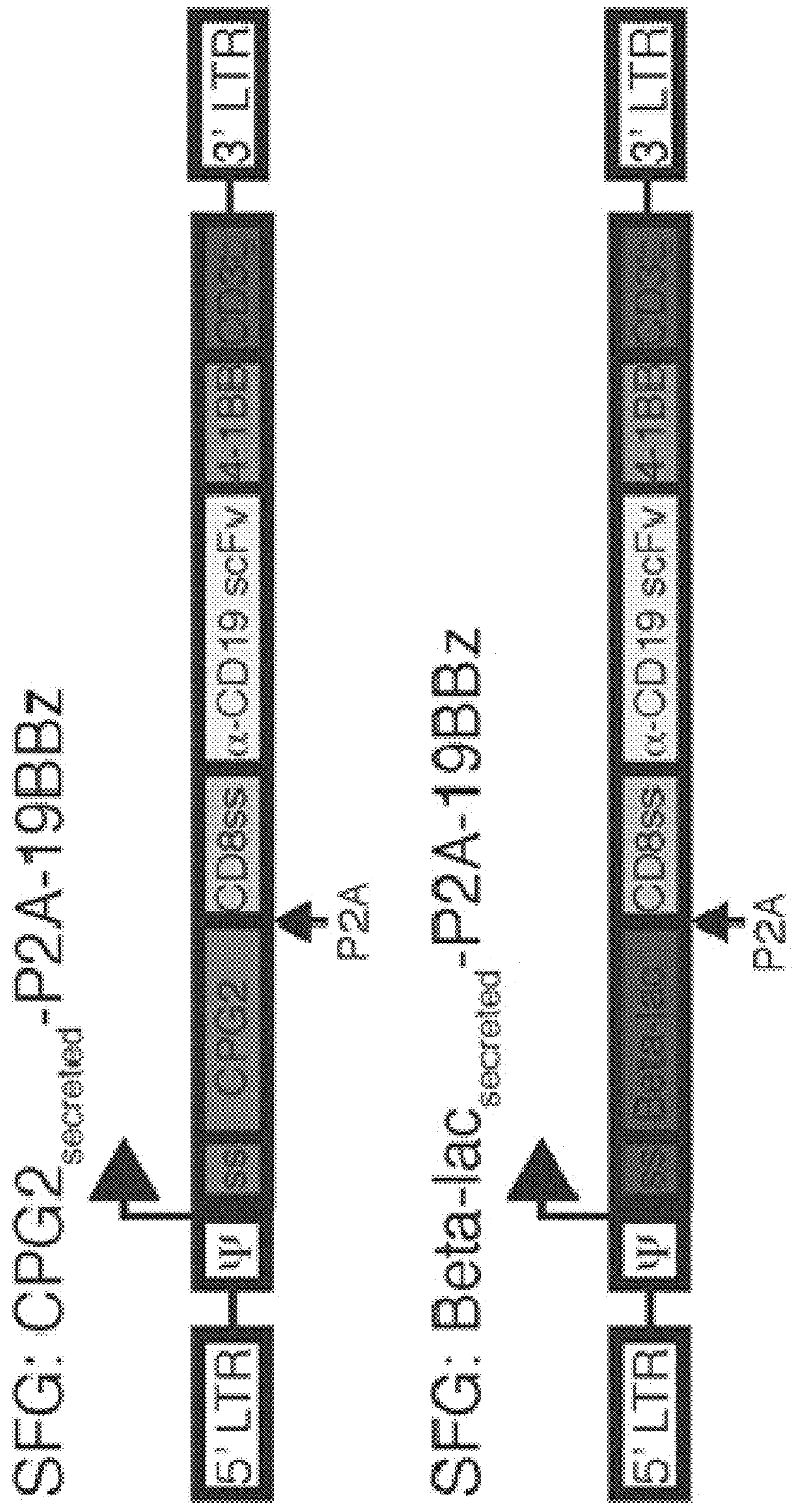
FIG. 19A provides a schematic of SFG retroviral vectors engineered to express CPG2 or Beta-lactamase upstream of the CD19-BBz gene cassette.
Figure 19B:
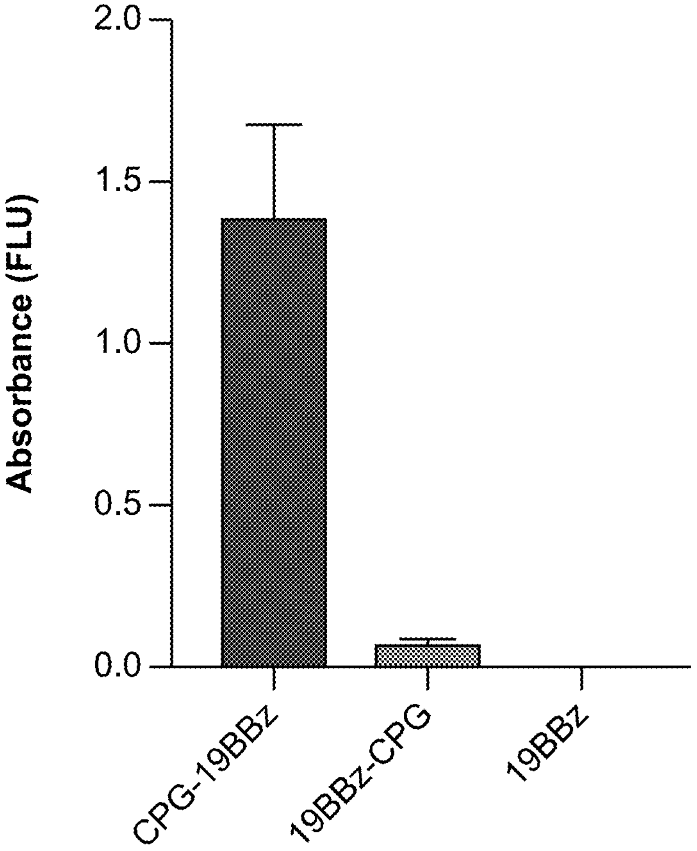
FIG. 19B shows an ELISA analysis of CPG2 secretion from primary human T cells transduced with a vector encoding CPG2 either before or after the CAR gene cassette.
Figure 20A:
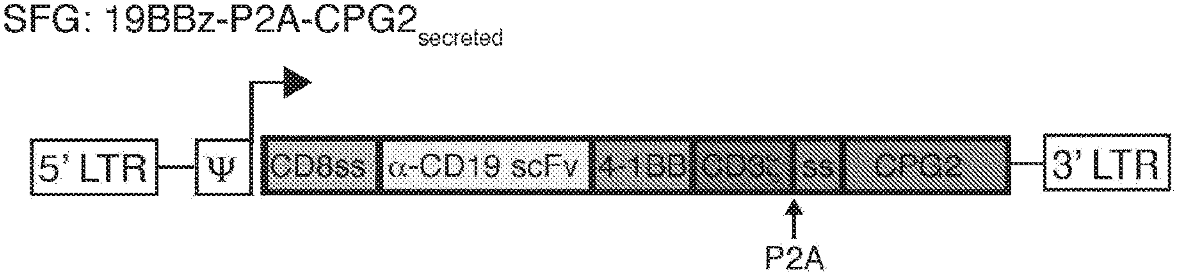
FIG. 20A provides a schematic of a 19BBz-CPG2 gene cassette in the SFG retroviral vector.
Figure 20B:
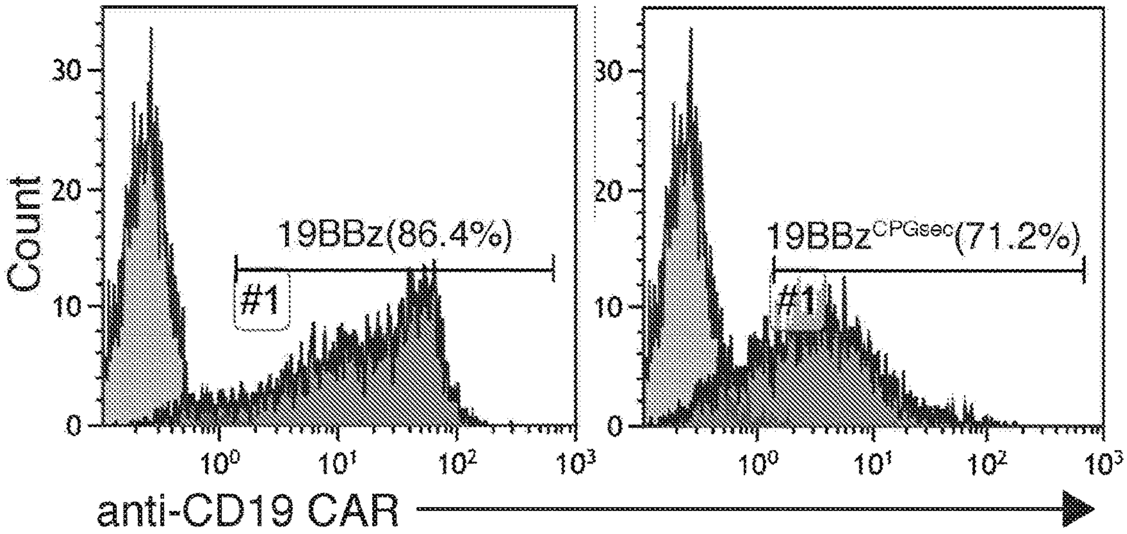
FIG. 20B shows the transduction of primary human T cells with 19BBz or 19BBz-CPG2 genes.
Figure 20C:
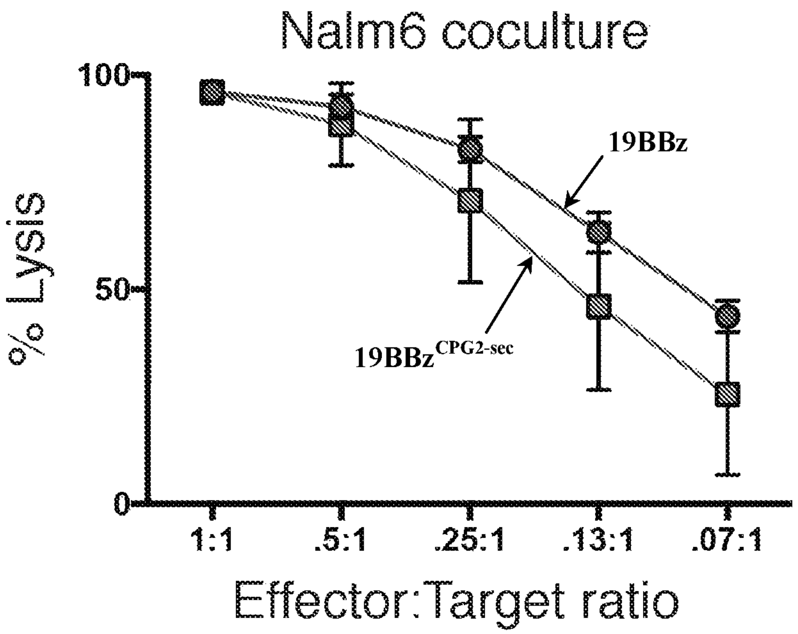
FIG. 20C shows the specific lysis of luc+/CD19+ Nalm6 cells following coculture with 19BBz or 19BBz-CPG2 CAR-T cells.
Figure 20D:
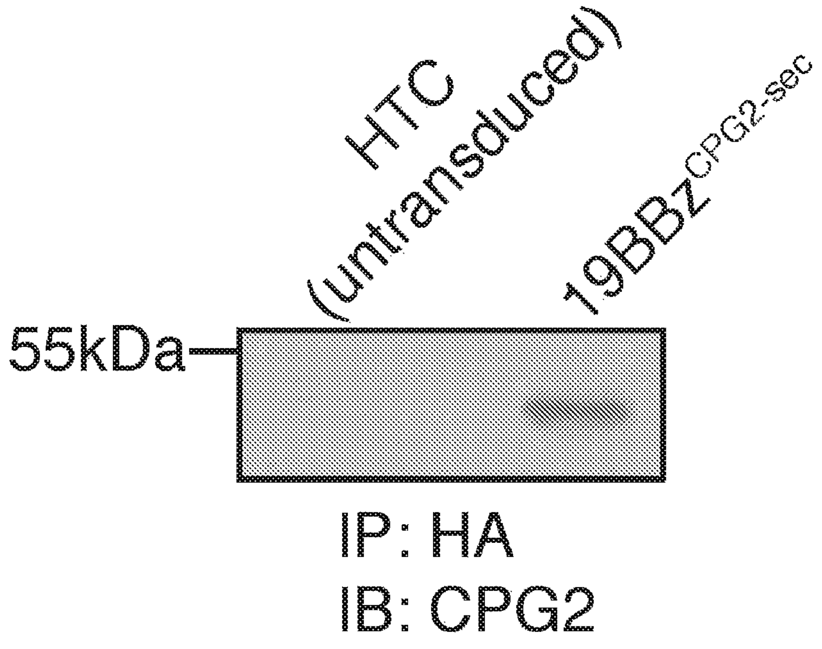
FIG. 20D shows an Anti-CPG2 immunoblot of anti-HA immunoprecipitation of supernatant fluid from 19BBz-CPG2 CAR-T cells.
Figure 20E:
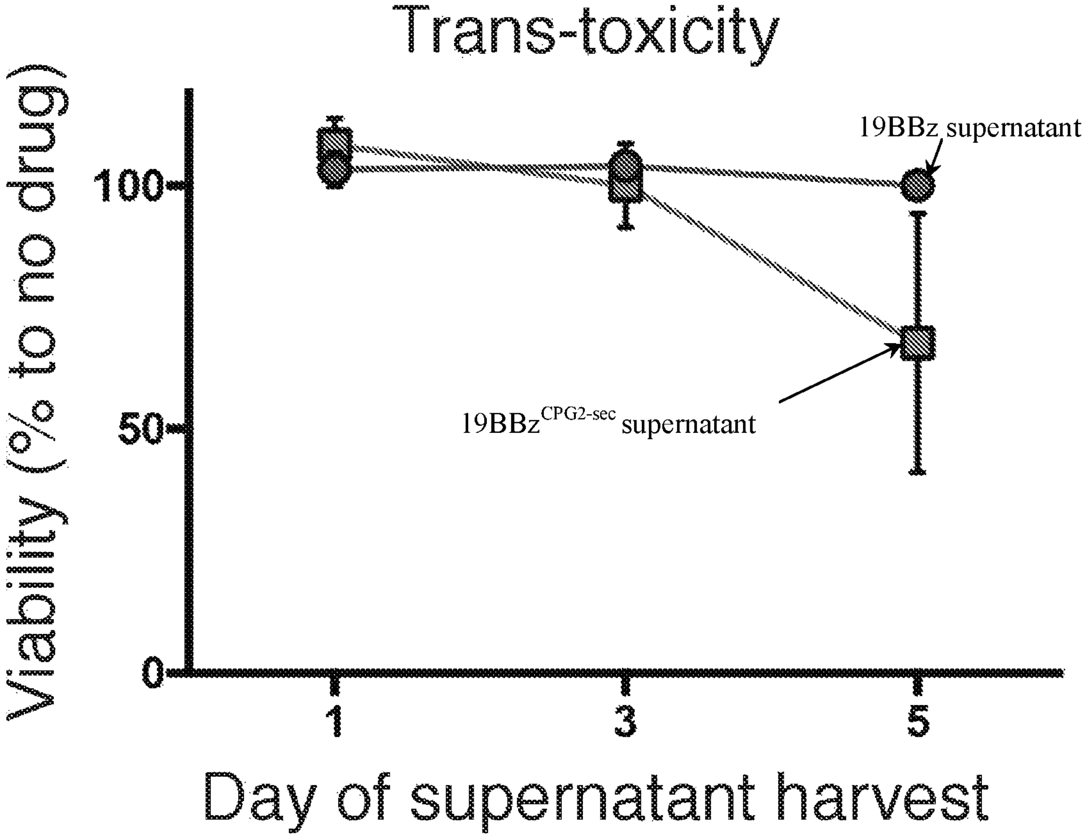
FIG. 20E shows a Cell Titer-Glo viability assay of SET cells incubated with prodrug and supernatant fluid from human T cells expressing the 19BBz or 19BBz-CPG2 constructs.

To integrate the enzyme prodrug systems with existing CAR-T cell platforms, a construct was created that positioned CPG2 or B-lac upstream of the 19BBz CAR cassette (FIG. 19A). A quantitative ELISA was also developed to determine the respective enzyme output of each construct (FIG. 15F). As a comparison, the secreted CPG2 construct was also cloned by introducing a P2A self-cleaving peptide sequence followed by CPG2 directly downstream of a prototypical anti CD-19 CAR containing the 4-1BB costimulatory element (19BBz) in the previously published SFG retroviral vector backbone (FIG. 20A). Supernatant fluid isolated from 19BBz-CPG2 CAR-T cells did not potently activate prodrug, as supernatant transfer experiments with prodrug did not cause death of SET2 cells (FIG. 20), despite high transduction levels of CPG2-sec-19BBz in primary human T cells, effective T-cell killing activity compared to a standard 19BBz CAR, and the detection of secreted CPG2 in the cellular supernatant fluid (FIG. 20). Unexpectedly, primary T cells expressing the CPG-19BBz construct expressed nearly 20-fold higher levels of CPG2 than cells transduced with the 19BBz-CPG2 construct (FIG. 19B). These data suggested that gene sequence was critical to the level of enzyme produced and allows for a second level of control of the amplitude of the system if needed. The higher amplitude configuration was chosen for all subsequent CAR-T cell studies, including a Beta-lac-19BBz CAR.

Figure 19C:
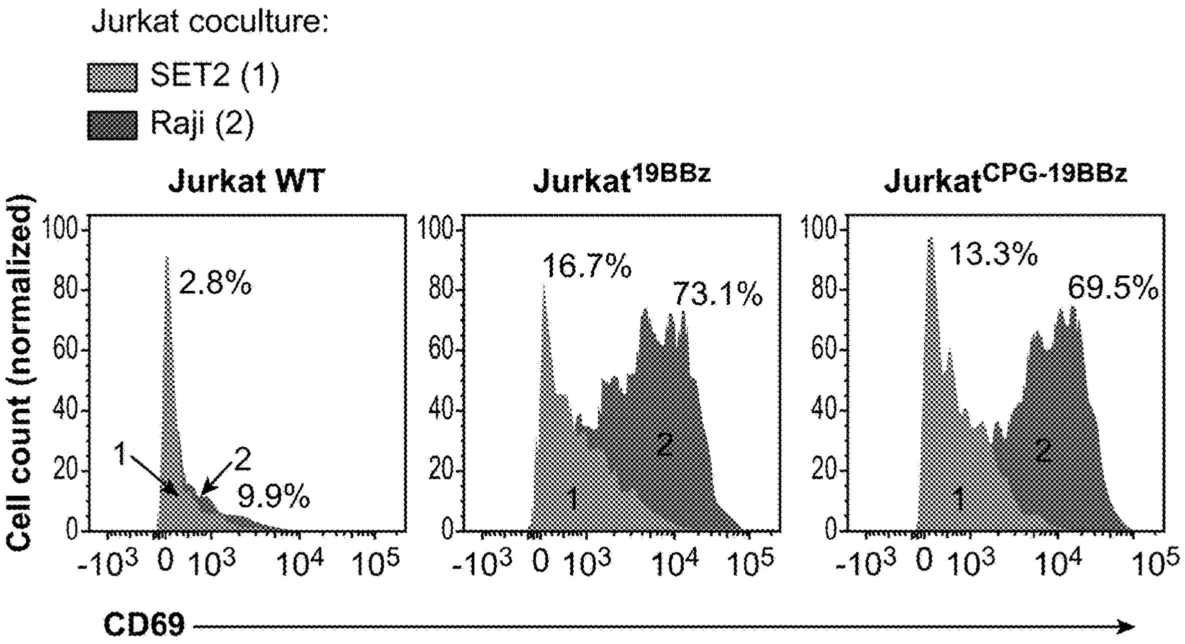
FIG. 19C shows a T cell activation analysis of 19BBz and CPG-19BBz Jurkat cells co-cultured with CD19+ (Raji) or CD19− (SET2) cells.
Figure 19D:
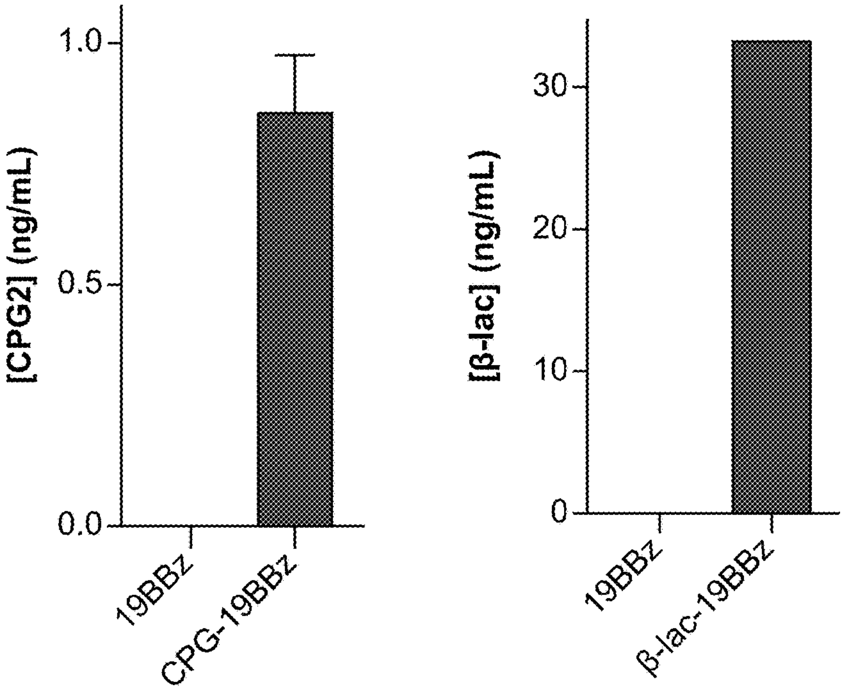
FIG. 19D shows enzyme secretion analysis of CPG2 Jurkats (left panel—ELISA), or Beta-lactamase Jurkats (right panel—nitrocefin).
Figure 19E:
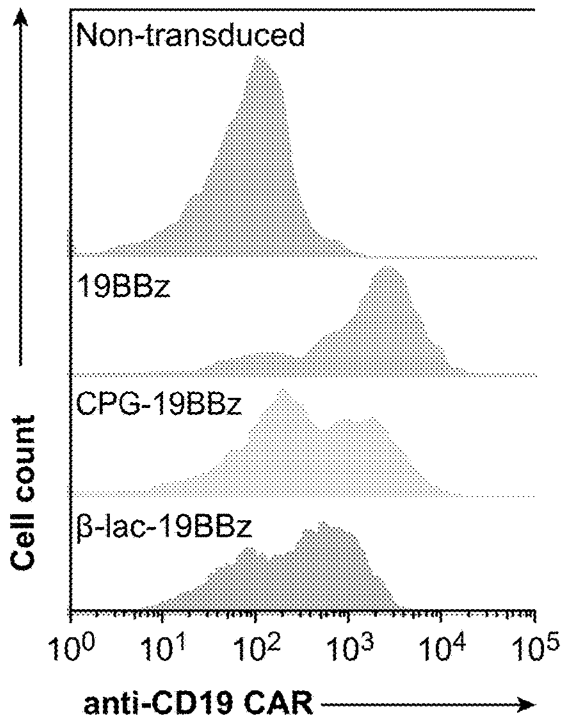
FIG. 19E shows the transduction of primary human T cells with 19BBz, CPG-19BBz, and Beta-lac-BBz CARs.
Figure 19F:
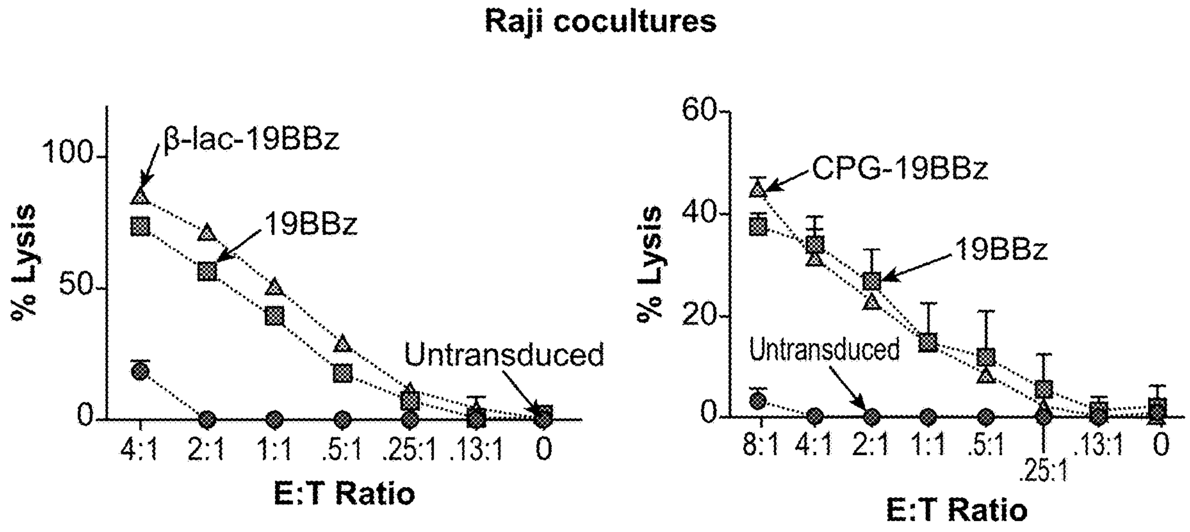
FIG. 19F shows specific lysis of luc+/CD19+ Raji cells following coculture with non-transduced, 19BBz, CPG-BBz, or Beta-lac-BBz CAR-T cells.
Figure 19G:
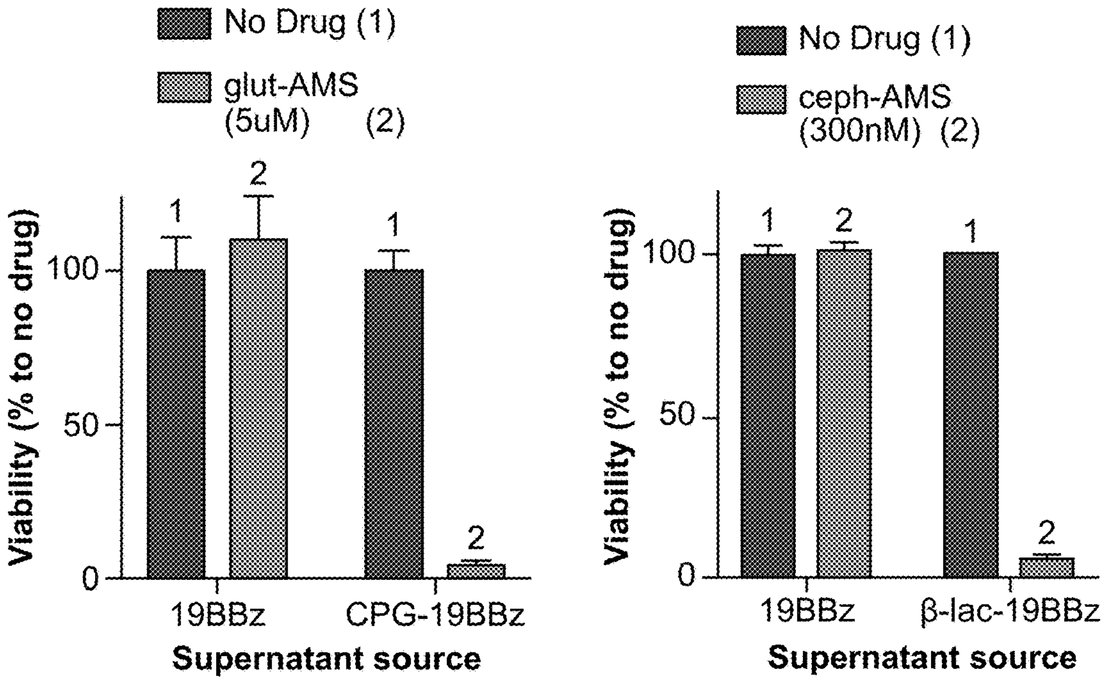
FIG. 19G shows a Cell Titer-Glo viability assay of SET cells incubated with prodrug and supernatant fluid from human T cells expressing the SEAKER constructs.
Figure 19H:
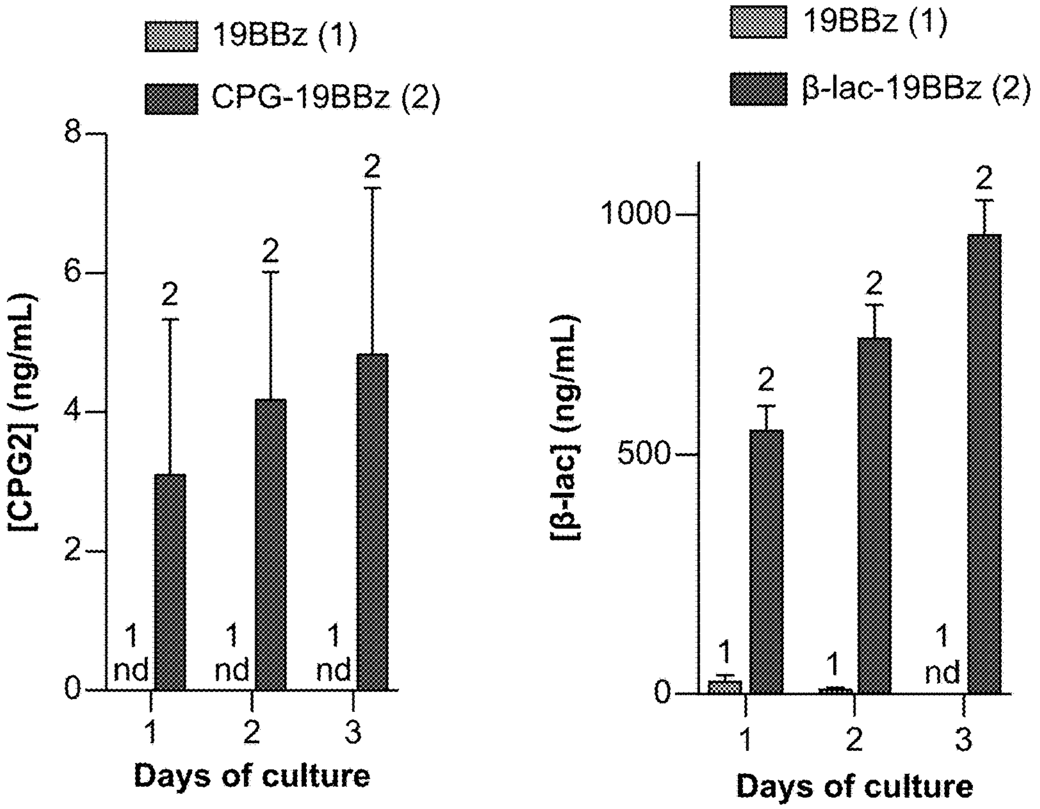
FIG. 19H shows an analysis of enzyme accumulation in supernatant fluid of CPG2-19BBz (left panel) and Beta-lac-19BBz (right panel) T cells compared to 19BBz T cells.

CPG-19BBz and Beta-lac-19BBz constructs were transduced at high efficiency in various T cell donors (FIG. 19C), which maintained equivalent antigen-dependent cytotoxic effect observed in WT 19BBz cells (FIG. 19D) and secreted robust levels of each respective enzyme (FIG. 19E). Further, supernatant fluid from the SEAKER CAR-T cells (19BBz, CPG-19BBz, and (Beta-lac-19BBz) converted prodrug and killed SET2 cells in a trans-toxicity assay, indicating that the SEAKER cells produce and secrete high enough levels of functional enzyme to achieve the aims (FIG. 19F). Time course analysis via CellTitre Glo® of CPG-19BBz and Beta-lac-19BBz T cells demonstrated accumulation of CPG2 in the supernatant of primary cells over 96 hours (FIG. 19G). To determine whether antigen-induced stimulation would cause expansion and increased secretion of CPG2 or Beta-lactamase enzymes, SEAKER T cells were co-cultured with CD19+ Raji cells, and the amount of enzyme secreted was significantly increased following 24 hours at a 1:1 coculture (FIG. 19H). Thus, antigen-dependent expansion of SEAKER T cells results in increased output of enzyme into the extracellular milieu.

Figure 19I:
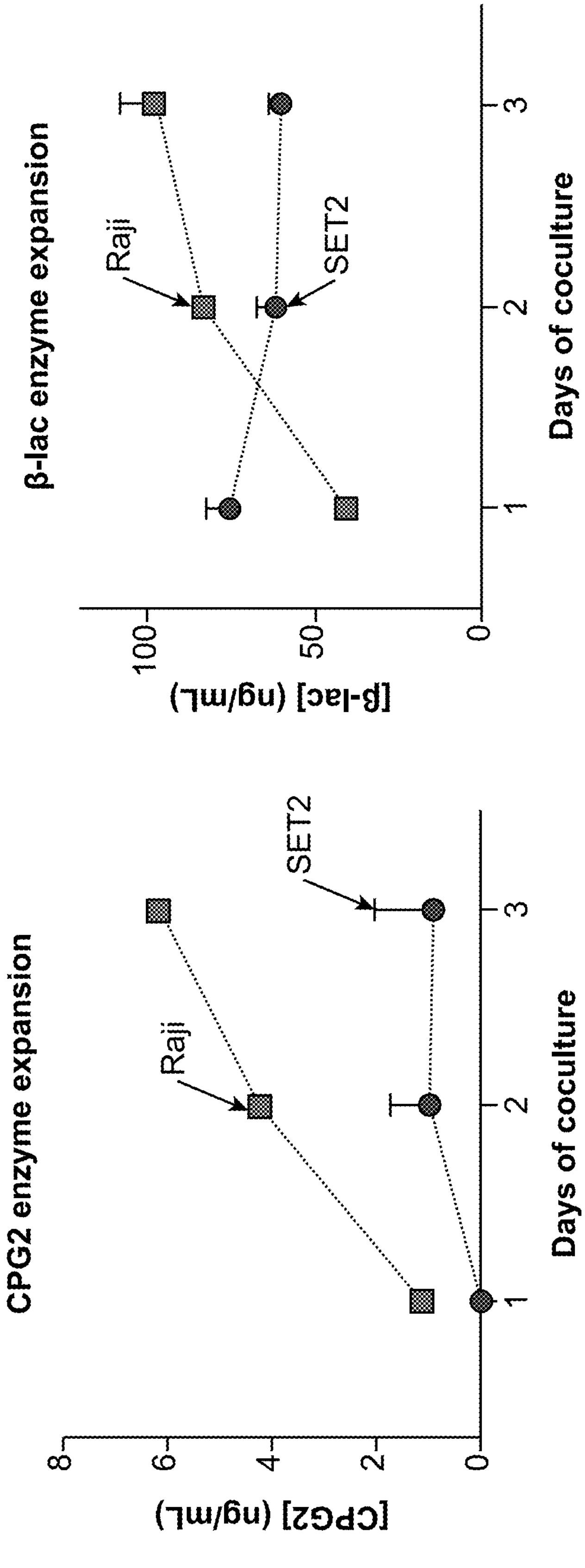
FIG. 19I shows an analysis of enzyme accumulation in supernatant fluid of CPG2-19BBz (left panel) and Beta-lac-19BBz (right panel) T cells cocultured with CD19+ Raji cells and CD19− SET2 cells.

To determine if a CAR-T cell functionalized to produce a small molecule drug will eliminate antigen-low or antigen-negative cells (antigen loss variants) as well as cell that the CAR T cell does not directly engage, the ability of CPG2 or Beta-lactamase expression by SEAKER T cells to eliminate antigen-negative cells in a coculture experiment was examined (FIG. 19H). SEAKER T cells were cocultured with CD19+ Raji cells and CD19− SET2 cells. Following 24 hours of coculture, glut-AMS was added to the wells, and total cell viability was measured following an additional 24-hr incubation period (FIG. 19I). While 19BBz CAR-T cells eliminated only the CD19+ Raji cells, SEAKER cells were able to eliminate both antigen+ and antigen− cell populations. The data demonstrate that functionalized CAR-T cells can eliminate antigen-low or antigen-negative cells.

This exemplary embodiment will describe the generation of SEAKER CAR-T cells capable of eliminating tumor populations in an antigen-loss variant tumor model in-vivo. An "on target" SKOV-3 human ovarian cancer cell line will be developed which will express the human CD19 ectodomain and the mCherry reporter (SKOV-$3^{CD19\text{-}ecto/mCherry}$), and an "off target" line expressing firefly luciferase and the GFP reporter (SKOV-$3^{luc/GFP}$). Cell viability studies will demonstrate that SKOV-3 cells will then be susceptible to killing by the active AMS drug, but not the glut-AMS prodrug. Co-culture experiments of the SKOV-3 cell lines and SEAKER T cells shall demonstrate that while standard 19BBz CAR T cells, or SEAKER T cells in the absence of prodrug will only deplete SKOV-$3^{CD19\text{-}ecto/mCherry}$ cells, both SKOV-3 cell types will be eliminated in cocultures with SEAKER T cells containing the glut-AMS prodrug.

The SKOV-3 cells will then be adapted for an in vivo mixed tumor model, where the IP cavity of NSG mice will be engrafted IP with a 1:1 ratio of SKOV-$3^{CD19\text{-}ecto/mCherry}$ and SKOV-$3^{luc/GFP}$. At 5 days post engraftment, the 19BBz CAR T cells or SEAKER CAR T cells will be administered via IP injection. Previously conducted pharmacokinetic and biodistribution studies conducted in Nod mice indicated that the glut-AMS prodrug is non-toxic and cleared rapidly with a half-life of 30-40 minutes (FIG. 25). Without wishing to be bound by theory, it is believed that daily IP dosing of high prodrug concentrations would be adequately converted into AMS. Three days post T cell injection, glut-AMS prodrug will be administered via IP injection daily for 3 consecutive days. Mice in the SEAKER CAR-T+ glut-AMS arm should demonstrate significantly enhanced survival.

Bioluminescent imaging studies should demonstrate the elimination of luc+ off-target tumor in mice that receive SEAKER CAR-T cells plus prodrug, but not in mice that receive no prodrug, or standard 19BBz CAR-T cells with prodrug. Flow cytometry analysis of tumors harvested from mice shall demonstrate the depletion of both tumor types in mice that receive SEAKER-T cells+prodrug, but not in mice from the other experimental groups. ELISA assays will be used to confirm high levels of CPG2 in fluid from the IP cavity of mice that received SEAKER CAR T cells. Tandem mass spectrometry will be used to identify the presence of active AMS in IP fluid from SEAKER-T cell+prodrug mice, which will confirm that secreted CPG2 successfully activated the prodrug. This data will demonstrate that SEAKER T cells possess increased functionality by eliminating both on and off target tumor cells in a solid tumor model of antigen escape.

Example 12

Figure 21A:
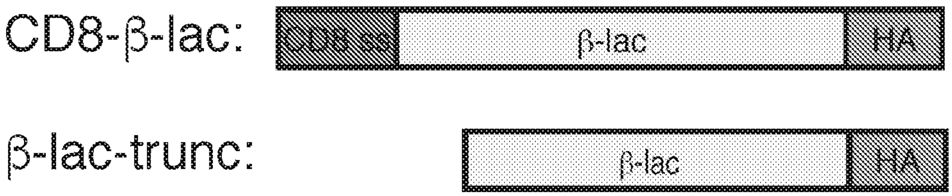
FIG. 21A shows a schematic of two forms of Beta-lactamase generated for optimal expression in mammalian cells.
Figure 21B:
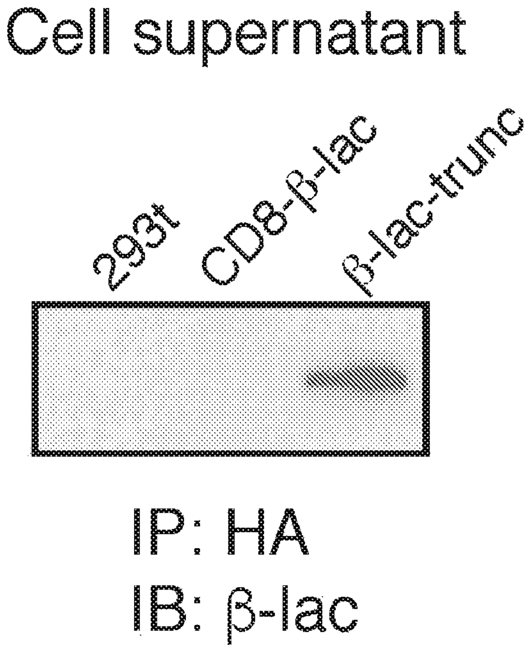
FIG. 21B shows an immunoblot indicating expression of only the truncated form of Beta-lactamase into the supernatant fluid of Hek293t cells transfected with the Beta-lactamase expression constructs.
Figure 21C:
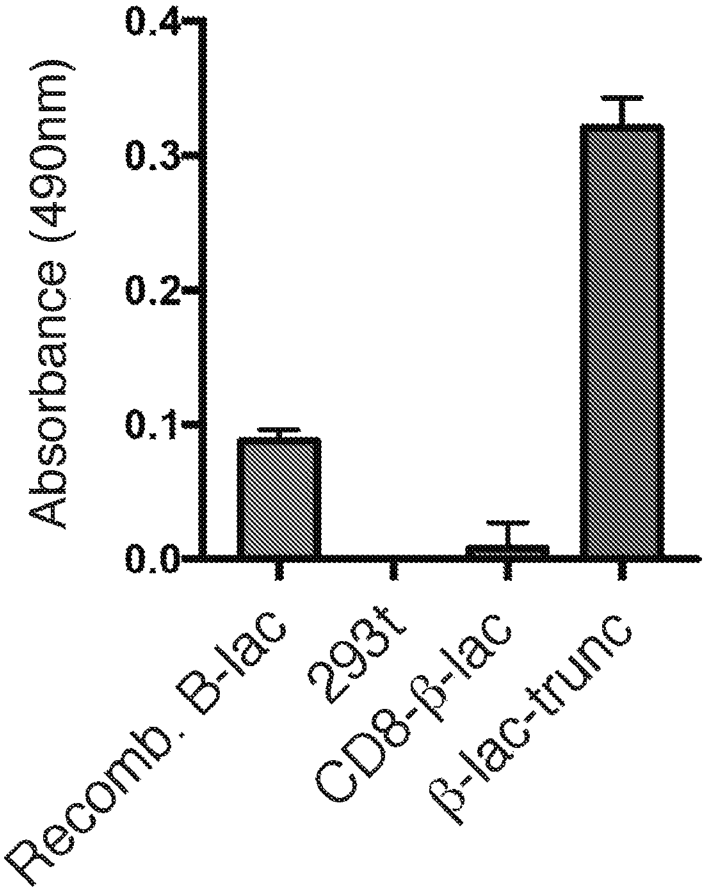
FIG. 21C provides a Nitrocefin analysis of Beta-lactamase activity in supernatant fluid from cells expressing the Beta-lactamase constructs.

This example describes the generation of transmembrane and secreted forms of Beta-lactamase and the characterization when expressed in mammalian cells. In this exemplary embodiment, transient transfection of HEK293t cells demonstrated that Beta-lactamase tolerates various structural modifications, including the routing of the enzyme through the secretory system to permit secretion into the extracellular milieu (FIGS. 21A and 21B). An immunoblot analysis of the supernatant of HEK293t cells expressing the various constructs (CD8-β-lac or β-lac-trunc) indicated the expression of only the truncated form of Beta-lactamase (β-lac-trunc), and not the membrane-tethered form of Beta-lactamase(CD8-β-lac) (FIG. 8B). Nitrocefin analysis of Beta-lactamase activity in the supernatant fluid from HEK293t cells expressing the various constructs (CD8-β-lac or β-lac-trunc) confirmed the expression and secretion of Beta-lactamase from Hek293t cells compared to supernatant fluid from control HEK293t cells or purified recombinant Beta-lactamase (FIG. 21C).

Figure 22A:
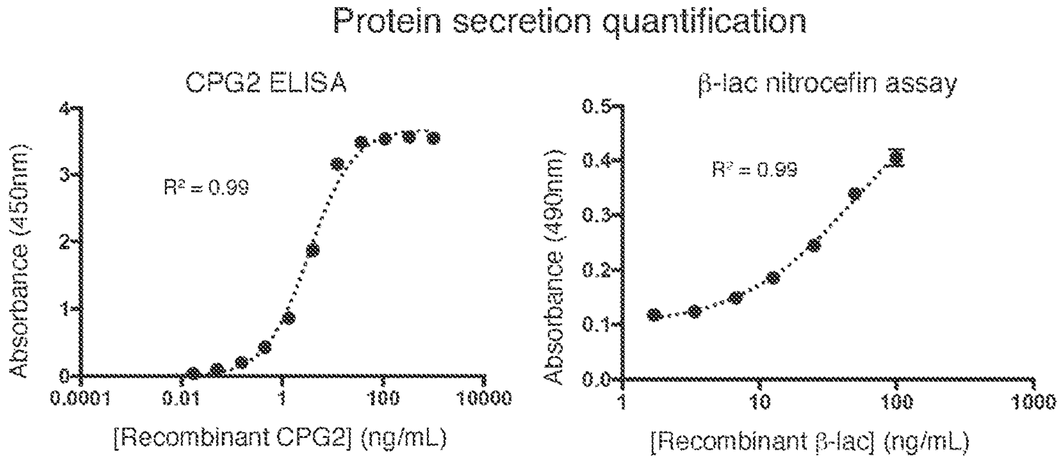
FIG. 22A shows a quantitative sandwich ELISA of purified recombinant CPG2 (left panel) and a quantitative nitrocefin assay of purified Beta-lactamase (right panel).
Figure 22B:
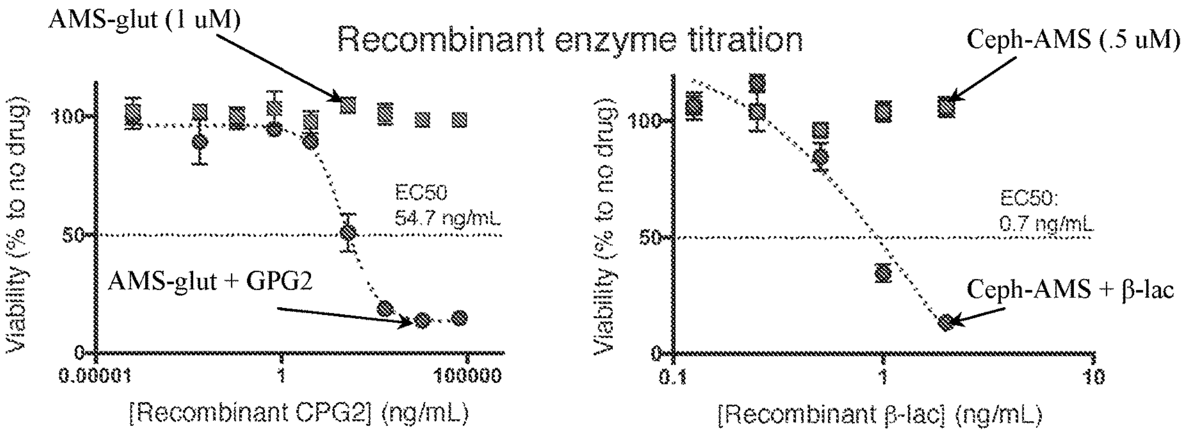
FIG. 22B shows a Cell Titer-Glo viability assay of SET cells incubated with prodrug and varying concentrations of purified recombinant CPG2 (left panel) or Beta-lactamase (right panel).
Figure 22C:
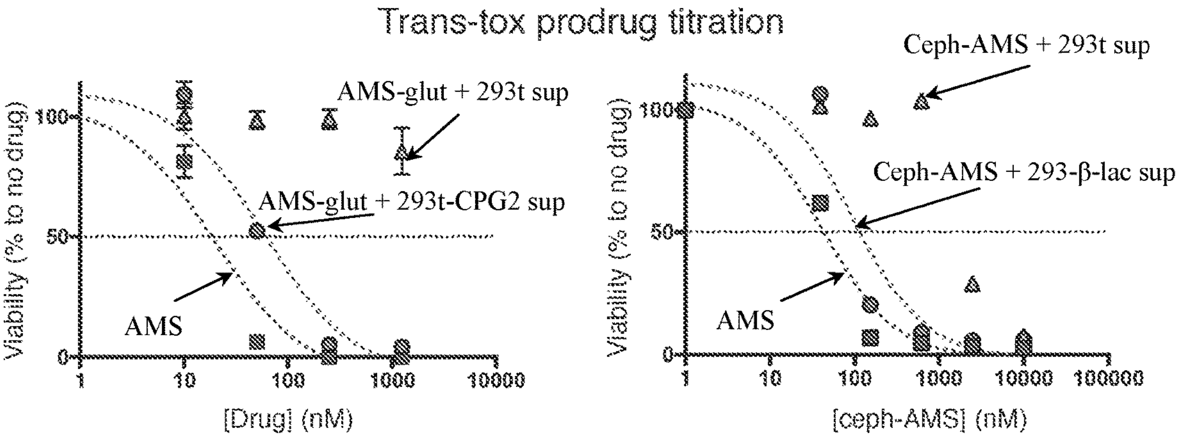
FIG. 22C shows a Cell Titer-Glo viability assay of SET cells incubated with prodrug and supernatant fluid from Hek293t cells transfected with CPG2 (left panel) or Beta-lactamase (right panel) expression constructs.

To determine to respective enzyme output of the Beta-lactamase constructs relative to the previous CPG2 constructs, a quantitative sandwich ELISA was used to determine the concentration (ng/mL) of purified recombinant CPG2, and a quantitative nitrocefin assay was used to determine the concentration (ng/mL) of purified recombinant Beta-lactamase (FIG. 22A). Cell viability was measured by CellTitre-Glo® luminescence in the presence of prodrug (glut-AMS or ceph-AMS) and varying concentrations of purified recombinant CPG2 or Beta-lactamase (FIG. 22B). To demonstrate that the secreted form of CPG2 or Beta-lactamase expressed in HEK 293t cells has enzymatic activity in vitro, SET2 cells were exposed to increasing concentrations of AMS (square) or glut-AMS/ceph-AMS (appropriate prodrug) with media alone (−control, triangle) or supernatant from CPG2-secreting HEK293t cells (circle). As shown in FIG. 22C, increasing amounts of the ceph-AMS prodrug with the Beta-lactamase supernatant resulted in a significant decrease in cell viability that was comparable to the AMS prodrug at around 100 nM, whereas control media did not.

Figure 22D:
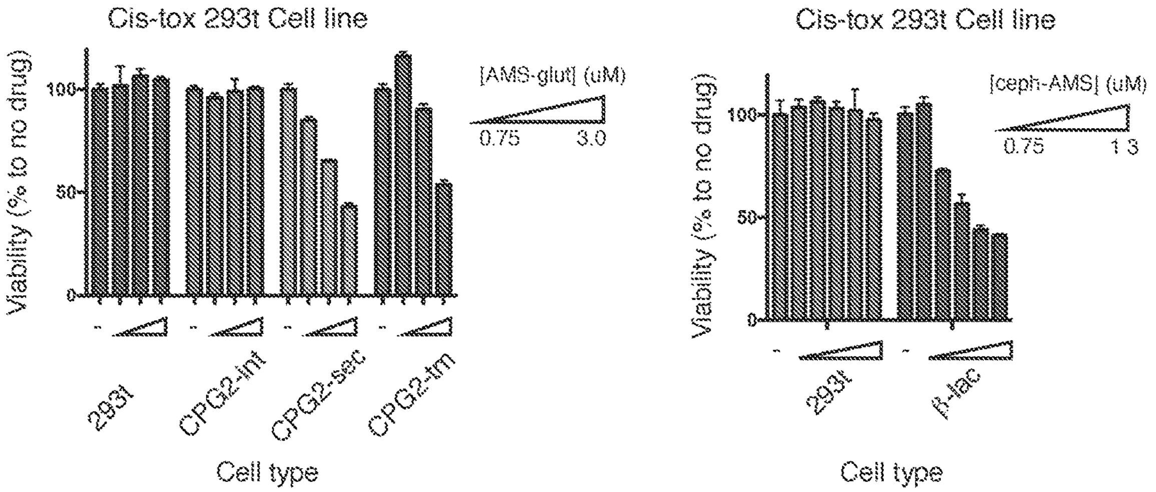
FIG. 22D shows a Cell Titer-Glo viability assay of Hek293t-CPG2 cells exposed to AMS-glut (left panel) or Hek293t-Beta-lac cells exposed to ceph-AMS (right panel).
Figure 22E:
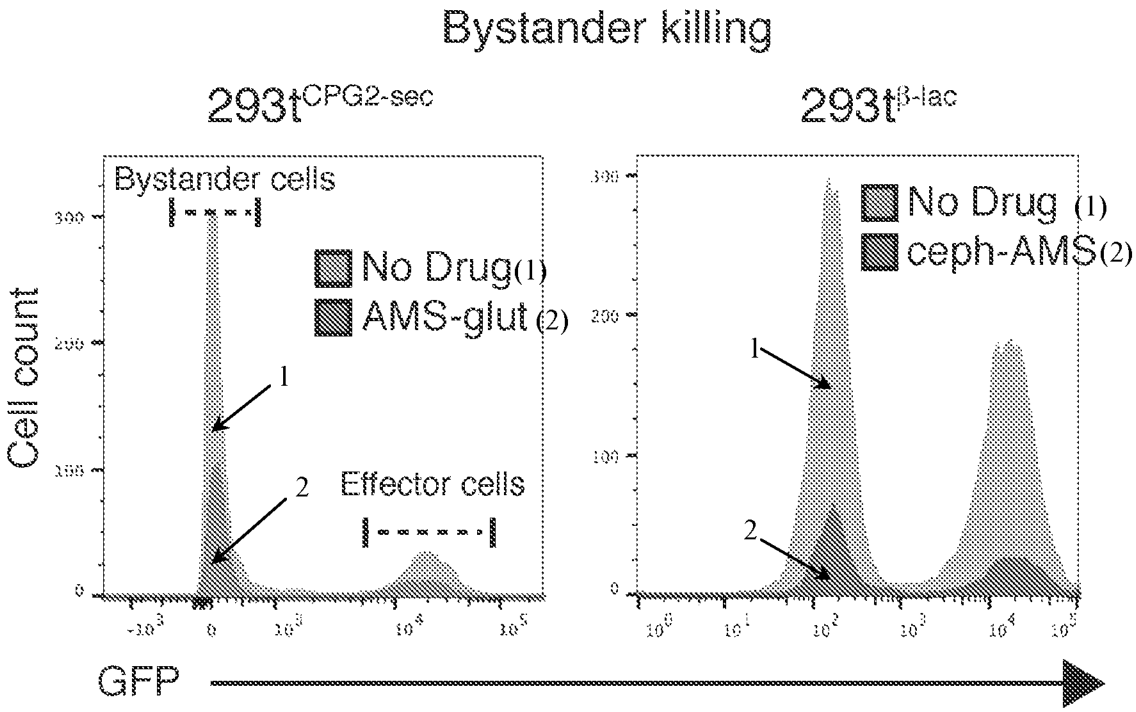
FIG. 22E shows GFP analysis of Hek293t-CPG2 or Hek293t-Beta-lac co-cultures with or without prodrug demonstrates equivalent depletion of both enzyme+ and enzyme− cell populations.

To assess the cis-toxicity of the HEK293t expressing the various constructs of CPG2 and Beta-lactamase, a CellTitre Glo® luminescence assay was carried out in which HEK293t, HEK293t-CPG2-int, HEK293t-CPG2-sec, or HEK293t-CPG2-trn cells were exposed to glut-AMS and HEK293t or HEK293t-Beta-lac cells were exposed to ceph-AMS. As shown in FIG. 22D, HEK293t-CPG2-sec, or HEK293t-CPG2-trn, and HEK293t-Beta-lac cells produce and secrete high enough levels of functional enzyme to induce cell death in bystander cells. To investigate this effect further, bystander toxicity assays were conducted in which enzyme-positive cells (effector cells) were cocultured with enzyme-negative cells (target cells), in the presence of the appropriate prodrug. Analysis of cell fluorescence demonstrated equivalent depletion of both GFP+ (effector) and GFP− (target) cells, indicating that both cell populations (effector cells and target cells) are destroyed by the activated prodrug (FIG. 22E).

The enzyme prodrug systems were incorporated into existing CAR-T cell platforms using a construct that positioned CPG2 or B-lac upstream of a 19BBz CAR cassette.

Figure 23A:
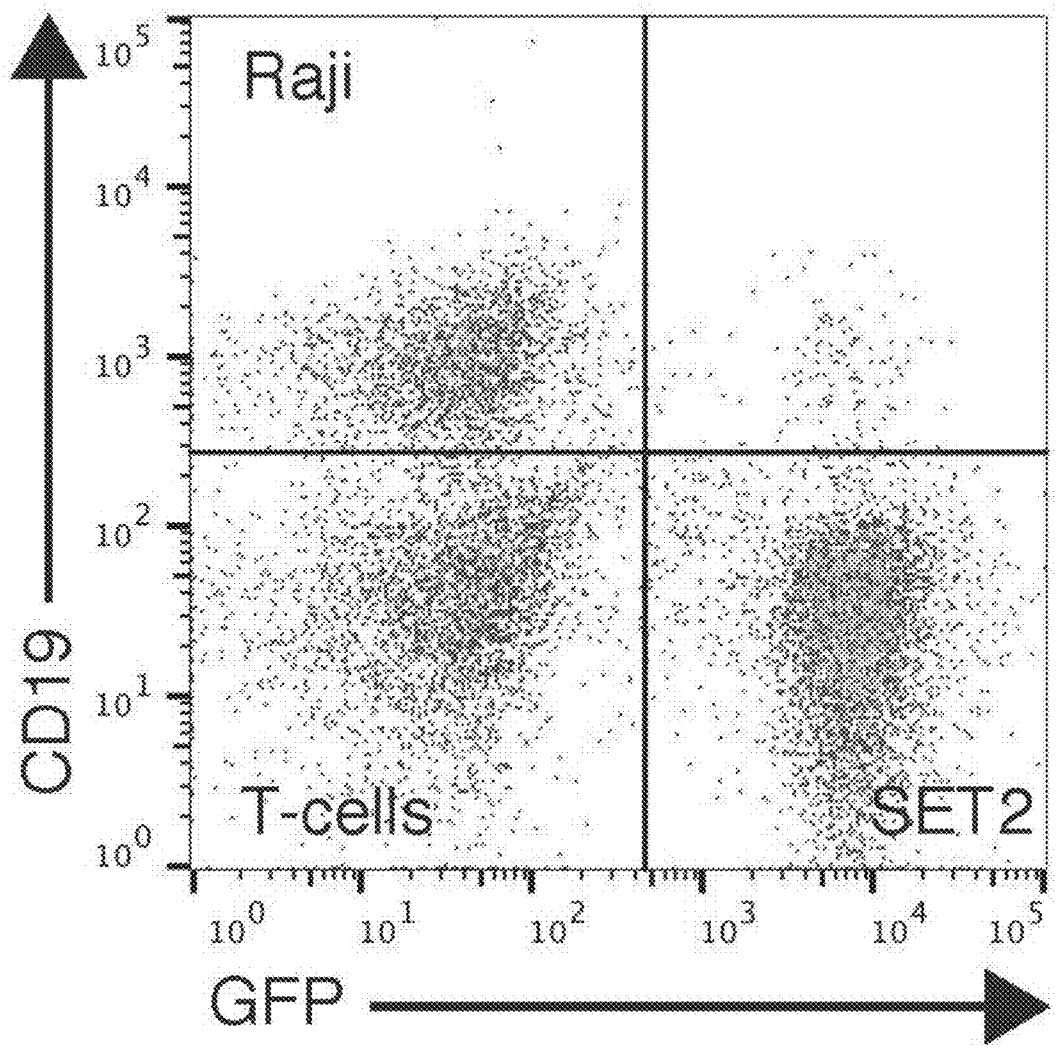
FIG. 23A shows a representation of on-target (Raji: GFP−/CD19+) and off-target (SET2: GFP+/CD19−) coculture with CAR-T cells at time zero.
Figure 23B:
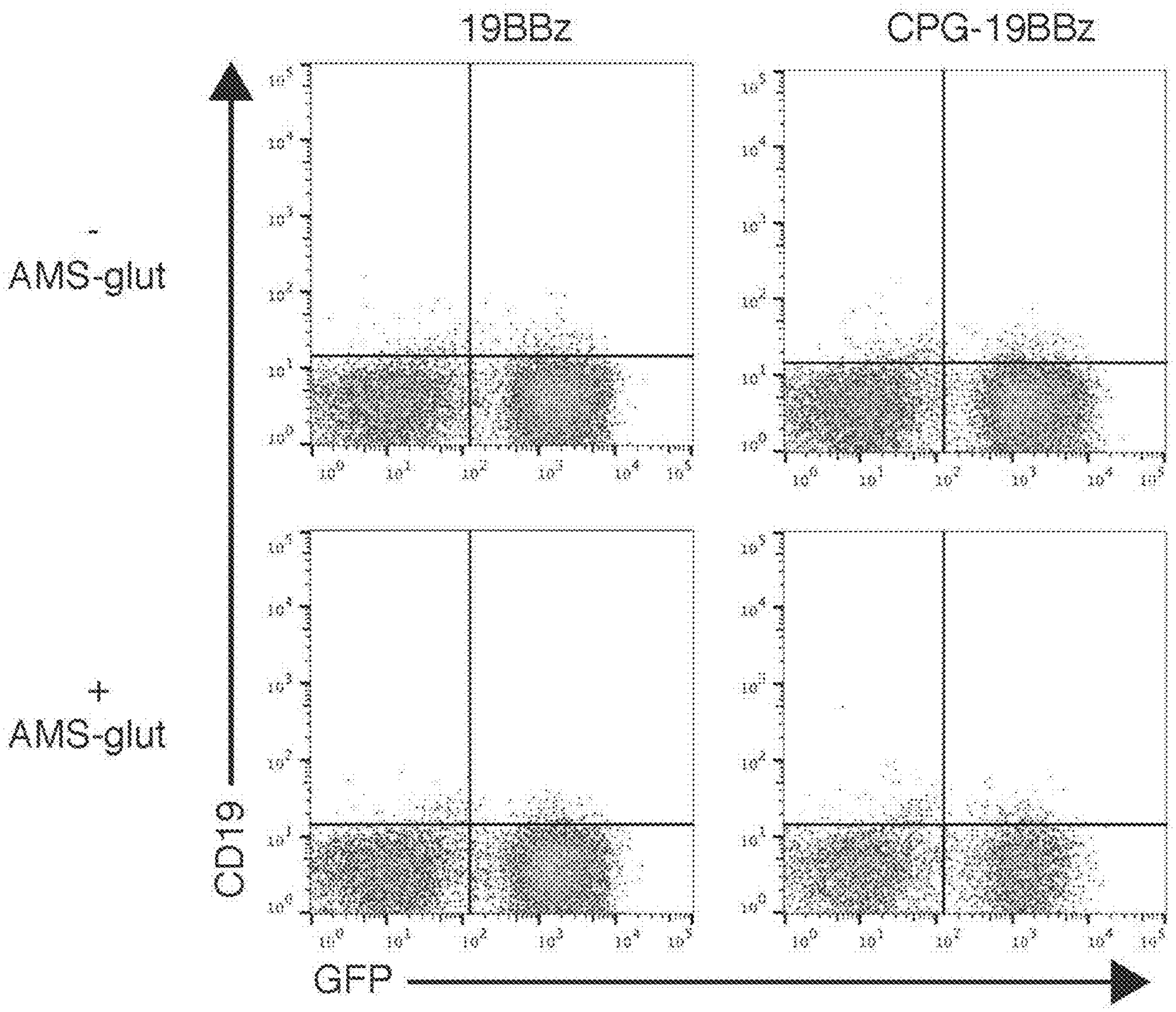
FIG. 23B shows a flow plot of 19BBz (left column) or CPG-19BBz (right column) T cells with SET2 and Raji cells with AMS-glut treatment (bottom row) or without AMS-glut treatment (top row), following 72 hr of coculture.
Figure 23C:
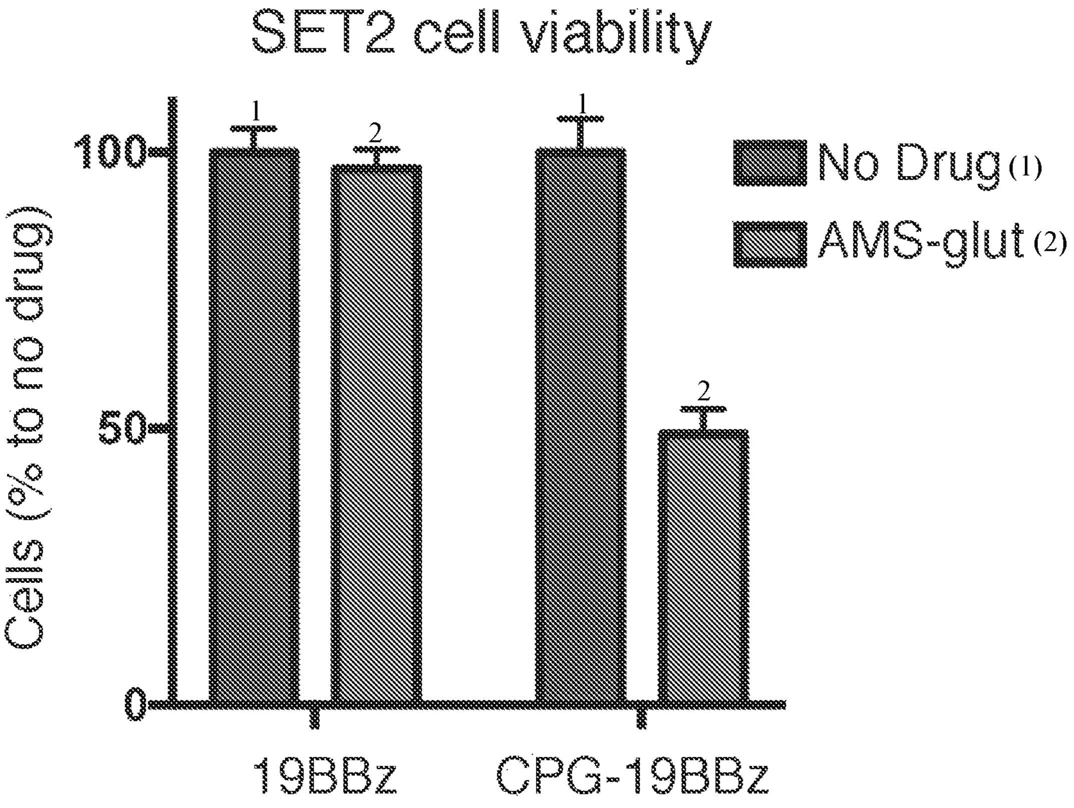
FIG. 23C shows the quantitation of off-target (SET2) cells following respective cocultures.
Figure 24A:
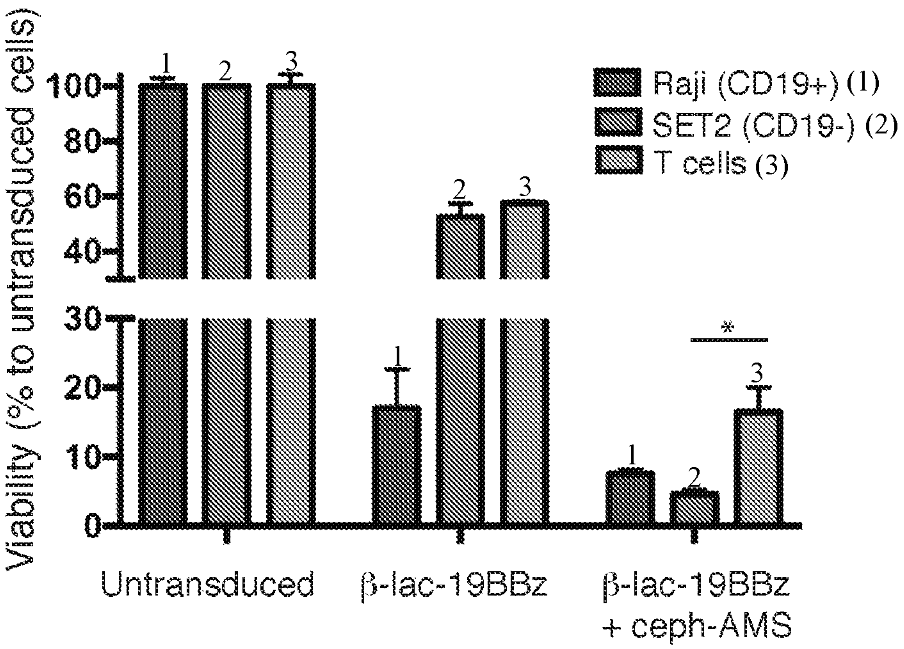
FIG. 24A shows the quantitation of cell number following Raji/SET2/Beta-lac-19BBz T-cells coculture (72 hr) with or without ceph-AMS prodrug. Respective cell populations are denoted by bar color.
Figure 24B:
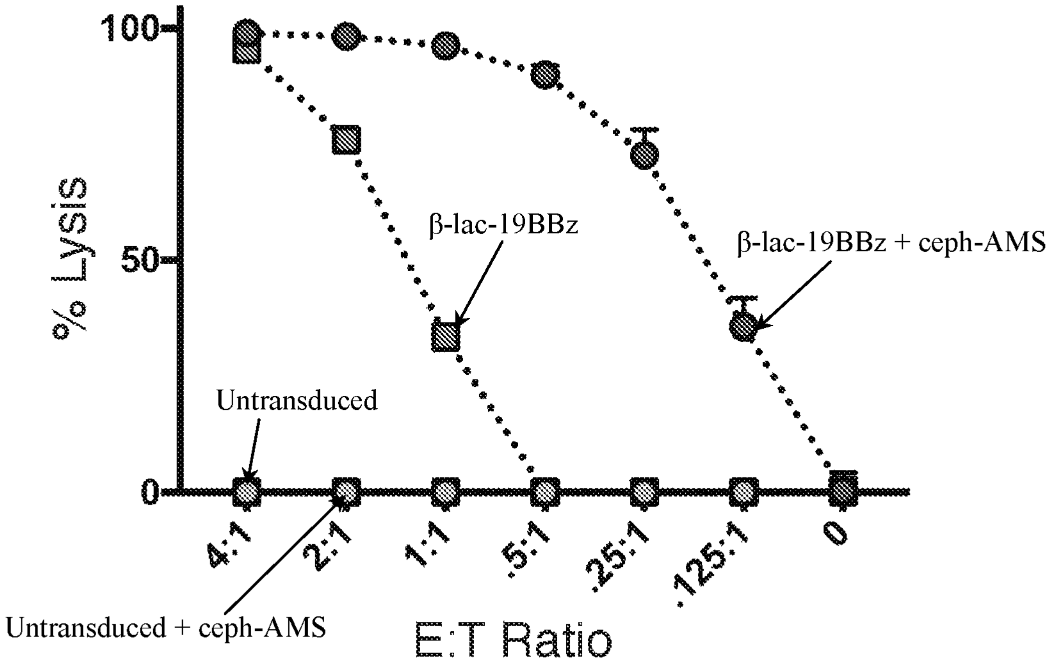
FIG. 24B shows the specific lysis of luc+/CD19+ Raji cells following coculture with Beta-lac 19BBz with or without ceph-AMS prodrug.

To determine if a CAR-T cell functionalized to produce a small molecule drug will eliminate antigen-low or antigen-negative cells (antigen loss variants) as well as cells that the CAR T cell does not directly engage, the ability of CPG2 expression by SEAKER T cells to eliminate antigen-negative cells in a coculture experiment was examined (FIGS. 23A-23C). SEAKER T cells (CPG-19BBz) were cocultured with (GFP−/CD19+) Raji cells and (GFP+/CD19−) SET2 cells. As shown in FIG. 23B, cocultures were treated with or without the glut-AMS prodrug following 72 hours of coculture. Flow cytometry was utilized to analyze the off target hits (SET2), which are quantified in FIG. 23C. FIG. 24A demonstrates the total cell viability of Raji (CD19+), SET2 (CD19−), and β-lac-19BBz T cells following a 72 hour coculture of the β-lac-19BBz T cells with either the Raji (CD19+) or SET2 (CD19−) cells with or without the ceph-AMS prodrug. FIG. 24B demonstrates that β-lac-19BBz T cells in the presence of the ceph-AMS prodrug were able to induce cell lysis in a luciferase assay in Raji cells expressing luciferase (Raji/Luc; CD19+/luc+) at a ratio of about 0.1:1.

Example 12

Scheme 4. Generation of Iodinated Cephalothin Derivative

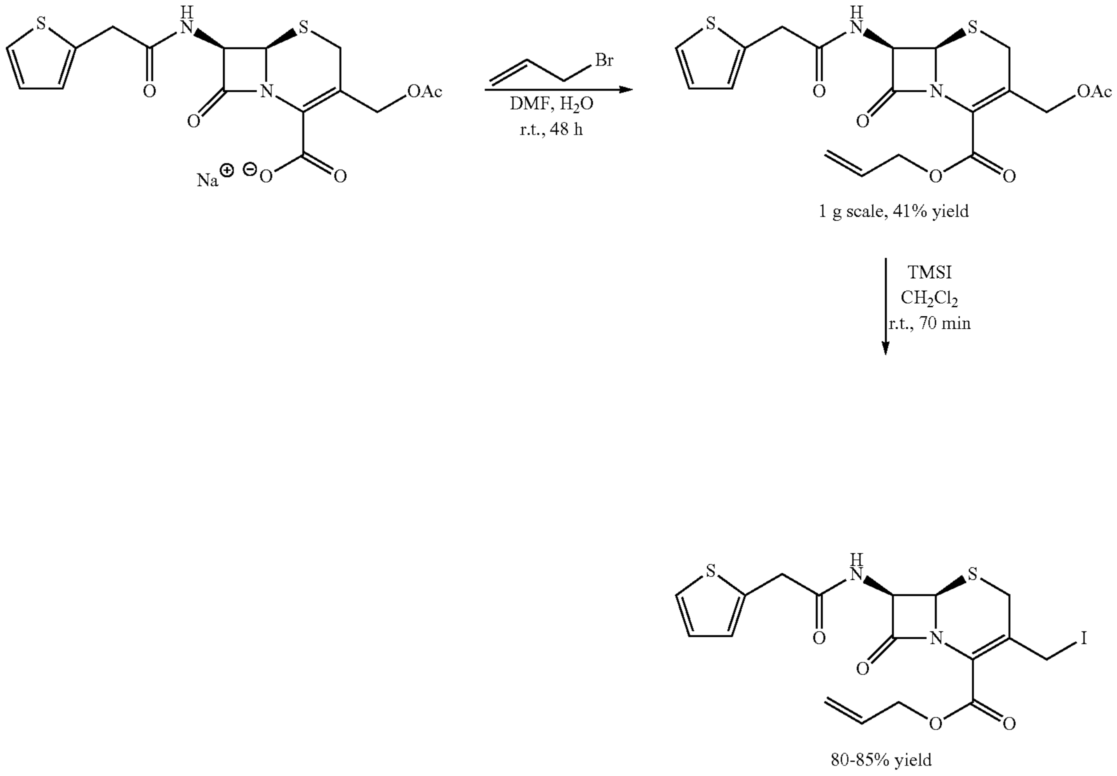

Scheme 5. Unoptimized Generation of an Exemplary β-Lactamase Prodrug Precursor of the Present Technology

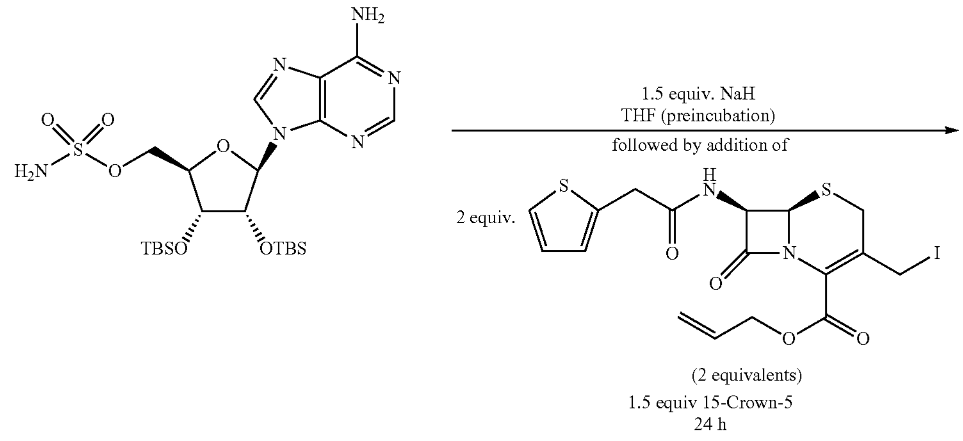

-continued

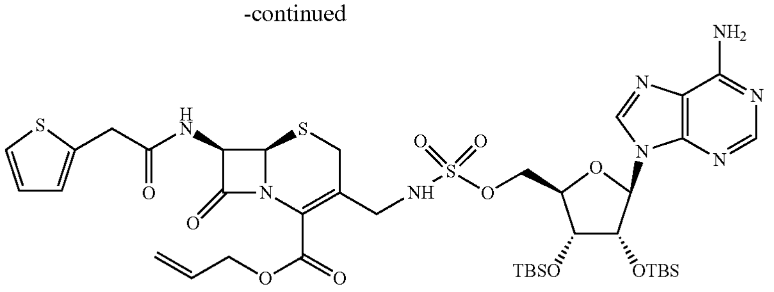

~ 50% yeild
(unoptimized)

The exemplary β-lactamase prodrug precursor of Scheme 5 may then be deprotected (such as by HF·pyridine and appropriate allyl deprotection conditions such as Pd(0)-catalyzed deprotection) to provide the exemplary β-lactamase prodrug illustrated below in Scheme 6. Greene et al. (1991) *Protective Groups in Organic Synthesis,* 3rd Ed. (John Wiley & Sons, Inc., New York), incorporated herein by reference, provides exemplary deprotection procedures.

Scheme 6.

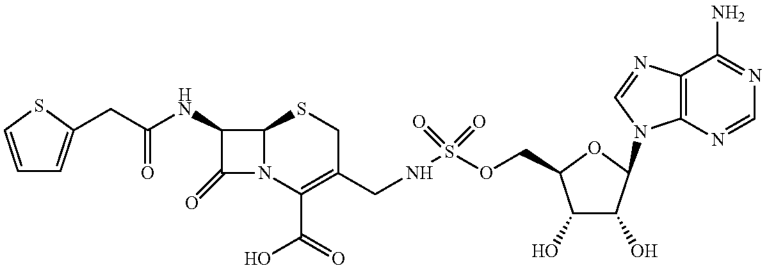

Scheme 7. Unoptimized Generation of an Exemplary Carbamate-Containing β-Lactamase Prodrug Precursor of the Present Technology

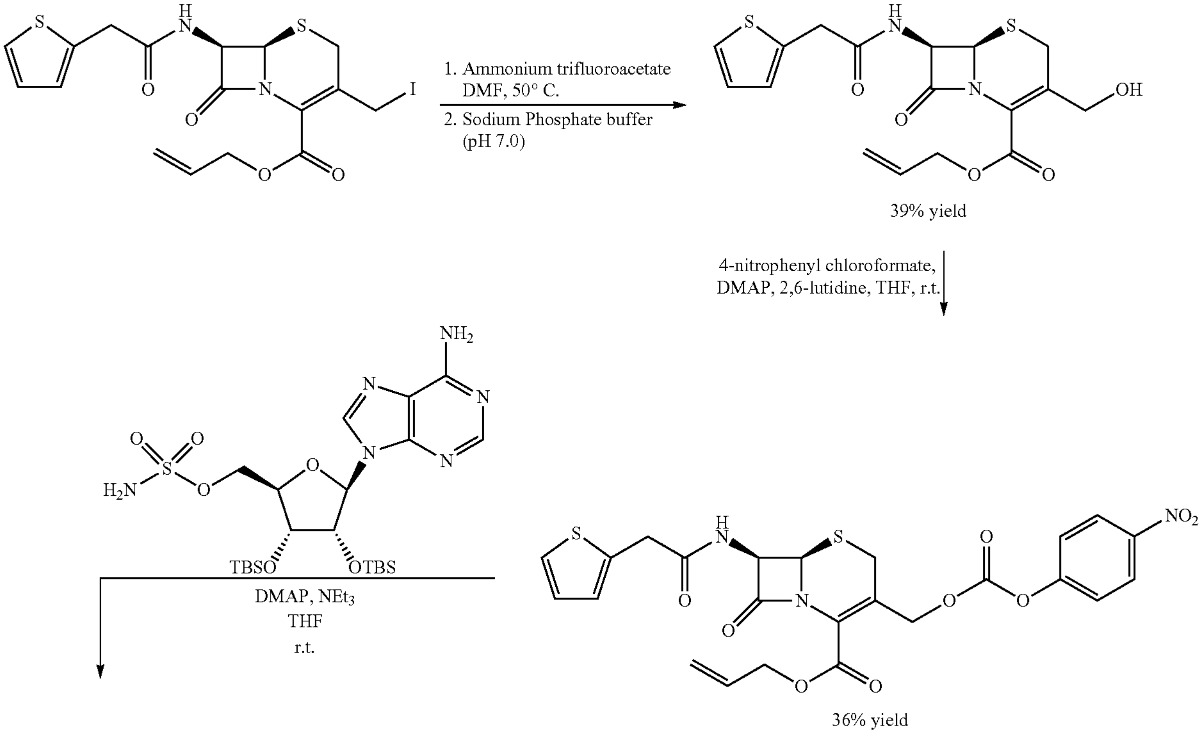

-continued

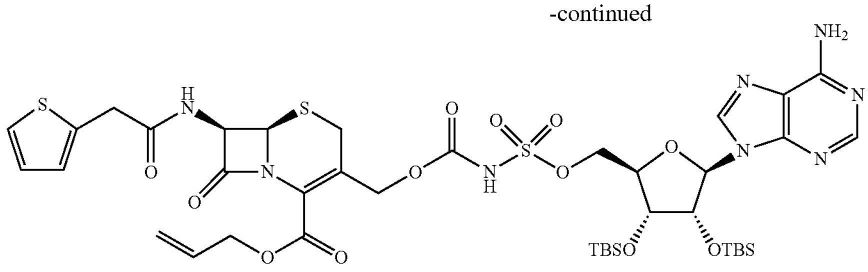

The sulfoxide variant illustrated below was also generated, where a similar synthesis as depicted in Scheme 7 may be utilized to generate this sulfoxide variant.

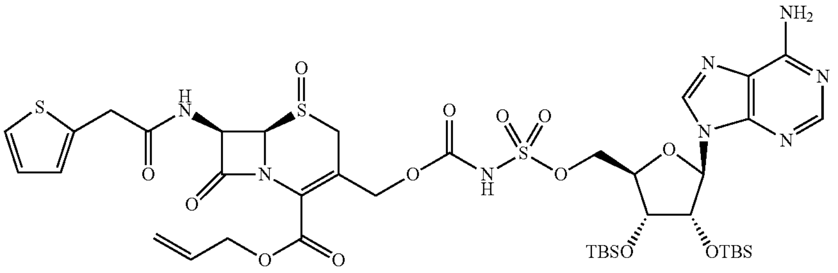

The exemplary β-lactamase prodrug precursor of Scheme 7 and the sulfoxide variant above may then be deprotected (such as by HF·pyridine and appropriate allyl deprotection conditions such as Pd(O)-catalyzed deprotection) to provide the exemplary β-lactamase prodrugs illustrated below in Scheme 8.

Scheme 8.

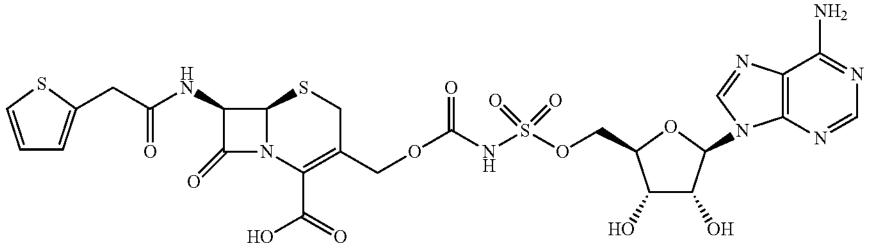

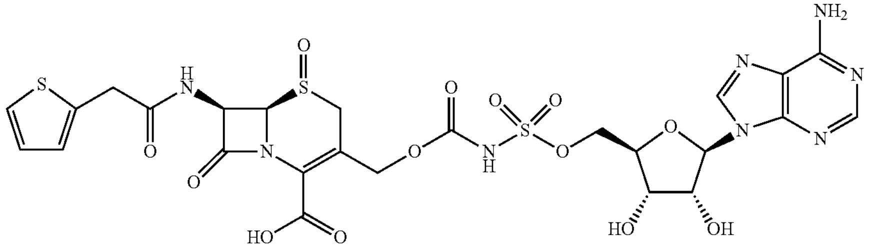

Scheme 9. Unoptimized Generation of an Exemplary PABA-Containing β-Lactamase Prodrug Precursor of the Present Technology

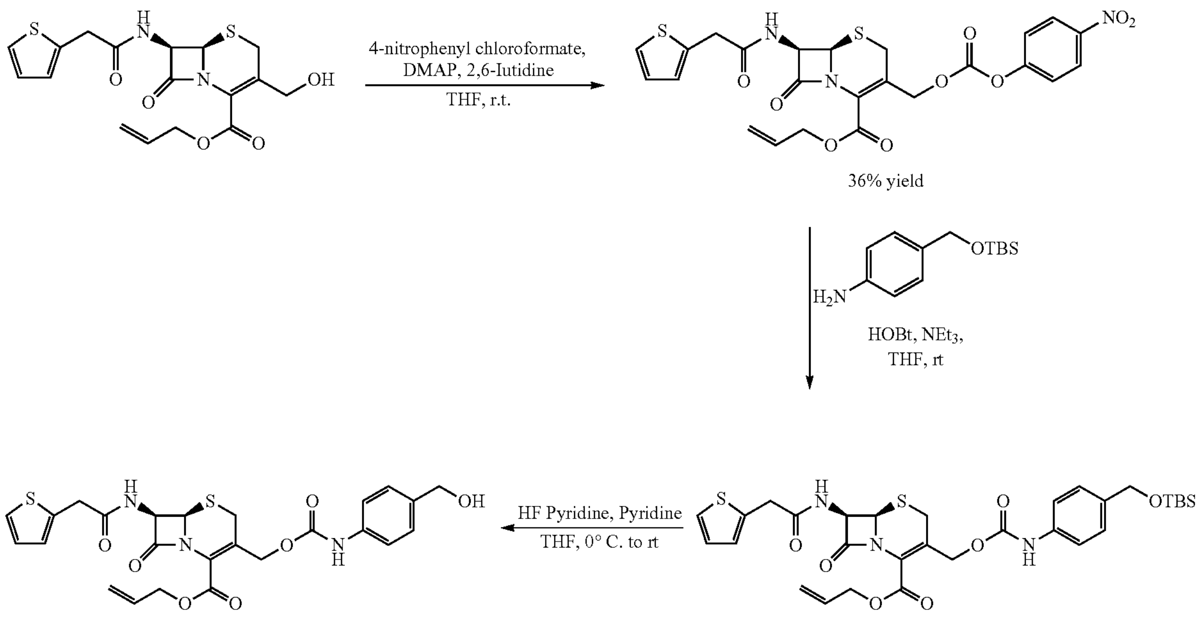

The precursor illustrated in Scheme 9 may be coupled via a Mitsunobu-type reaction with, e.g.,

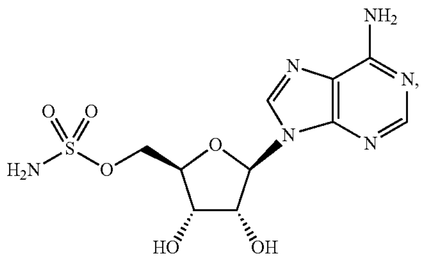 [SMILES: Nc1ncnc2c1ncn2[C@@H]1O[C@H](COS(N)(=O)=O)[C@@H](O)[C@H]1O]

and subsequently undergo deprotection (such as by HF·pyridine and appropriate allyl deprotection conditions such as Pd(0)-catalyzed deprotection) to afford the PABA-containing β-lactamase prodrug represented in Scheme 10.

Scheme 10.

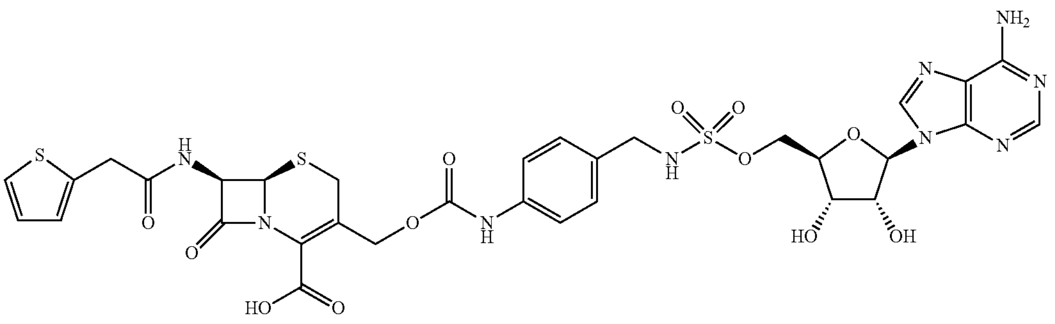

What is claimed is:

1. An engineered immune cell comprising:

(a) a prodrug converting enzyme and/or a nucleic acid encoding the prodrug converting enzyme, wherein the prodrug converting enzyme is *Pseudomonas* sp. Carboxypeptidase G2 (CPG2) or *Enterobacter cloacae* β-lactamase; and (b) a chimeric antigen receptor (CAR) comprising a first transmembrane domain, wherein the CAR is expressed on the surface of the engineered immune cell and binds to a target antigen, and/or a nucleic acid encoding the CAR, wherein the CAR targets the engineered immune cell to a site of pathogenic infection and wherein the target antigen is an antigen from a pathogen, wherein the prodrug converting enzyme is:

(i) secreted from the engineered immune cell, or (ii) expressed on the surface of the immune cell and is (A) fused to a second transmembrane domain; or (B) attached to the surface of the cell by a GPI anchor, wherein the first transmembrane domain of the CAR is separate from the second transmembrane domain of the prodrug converting enzyme, wherein the antigen from the pathogen is a bacterial antigen, a parasitic antigen, a HSV-1 protein antigen, a HSV-2 protein antigen, or an HIV-1 protein antigen.

2. The engineered immune cell of claim 1, wherein the nucleic acid encoding the prodrug converting enzyme is operably linked to a constitutive promoter or a conditional promoter and comprises a leader sequence for secretion of the prodrug converting enzyme.

3. The engineered immune cell of claim 1, wherein the CAR comprises (i) an extracellular antigen binding domain, (ii) the first transmembrane domain, and (iii) an intracellular domain.

4. The engineered immune cell of claim 3, wherein the extracellular antigen binding domain binds to the antigen from the pathogen, wherein the antigen from the pathogen is:

(i) a bacterial antigen selected from the group consisting of a *Pasteurella* species, Staphylococci species, *Streptococcus* species, *Escherichia coli, Pseudomonas species*, and *Salmonella* species bacteria, or wherein the bacterial antigen is at least one of a peptidoglycan antigen, a capsule antigen or a cell wall antigen; or (ii) a HSV-1 or HSV-2 protein antigen selected from the group consisting of gB, gD, gH, VP16, and VP22, or (iii) an HIV-1 protein antigen selected from the group consisting of gp120, gp41, gp160, gag, and pol.

5. The engineered immune cell of claim 3, wherein the extracellular antigen binding domain comprises a single chain variable fragment (scFv); or wherein the first transmembrane domain comprises a CD8 transmembrane domain, a CD28 transmembrane domain or an ICOS transmembrane domain; or wherein the intracellular domain comprises one or more costimulatory domains selected from a CD28 costimulatory domain, a CD32-chain, a 4-1BBL costimulatory domain, an OX40 costimulatory domain, an ICOS costimulatory domain, and a DAP10 costimulatory domain; or wherein a signal peptide is covalently joined to the N-terminus of the extracellular antigen binding domain.

6. The engineered immune cell of claim 1, wherein the engineered immune cell is a lymphocyte, a T cell, a B cell, or a natural killer cell, and wherein the T cell is a CD4+ T cell or a CD8+ T cell.

7. The engineered immune cell of claim 1, wherein the second transmembrane domain fused to the prodrug converting enzyme comprises a CD8 transmembrane domain.

* * * * *

SEQUENCE LISTING

<160> NUMBER OF SEQ ID NOS: 53

<210> SEQ ID NO 1
<211> LENGTH: 415
<212> TYPE: PRT
<213> ORGANISM: Homo sapiens

<400> SEQUENCE: 1

```
Met Arg Pro Ser Ile His Arg Thr Ala Ile Ala Ala Val Leu Ala Thr
1               5                   10                  15

Ala Phe Val Ala Gly Thr Ala Leu Ala Gln Lys Arg Asp Asn Val Leu
            20                  25                  30

Phe Gln Ala Ala Thr Asp Glu Gln Pro Ala Val Ile Lys Thr Leu Glu
        35                  40                  45

Lys Leu Val Asn Ile Glu Thr Gly Thr Gly Asp Ala Glu Gly Ile Ala
    50                  55                  60

Ala Ala Gly Asn Phe Leu Glu Ala Glu Leu Lys Asn Leu Gly Phe Thr
65                  70                  75                  80

Val Thr Arg Ser Lys Ser Ala Gly Leu Val Val Gly Asp Asn Ile Val
                85                  90                  95

Gly Lys Ile Lys Gly Arg Gly Gly Lys Asn Leu Leu Leu Met Ser His
            100                 105                 110

Met Asp Thr Val Tyr Leu Lys Gly Ile Leu Ala Lys Ala Pro Phe Arg
        115                 120                 125

Val Glu Gly Asp Lys Ala Tyr Gly Pro Gly Ile Ala Asp Asp Lys Gly
    130                 135                 140

Gly Asn Ala Val Ile Leu His Thr Leu Lys Leu Leu Lys Glu Tyr Gly
145                 150                 155                 160

Val Arg Asp Tyr Gly Thr Ile Thr Val Leu Phe Asn Thr Asp Glu Glu
                165                 170                 175

Lys Gly Ser Phe Gly Ser Arg Asp Leu Ile Gln Glu Glu Ala Lys Leu
            180                 185                 190

Ala Asp Tyr Val Leu Ser Phe Glu Pro Thr Ser Ala Gly Asp Glu Lys
        195                 200                 205

Leu Ser Leu Gly Thr Ser Gly Ile Ala Tyr Val Gln Val Asn Ile Thr
    210                 215                 220

Gly Lys Ala Ser His Ala Gly Ala Ala Pro Glu Leu Gly Val Asn Ala
225                 230                 235                 240

Leu Val Glu Ala Ser Asp Leu Val Leu Arg Thr Met Asn Ile Asp Asp
                245                 250                 255

Lys Ala Lys Asn Leu Arg Phe Asn Trp Thr Ile Ala Lys Ala Gly Asn
            260                 265                 270

Val Ser Asn Ile Ile Pro Ala Ser Ala Thr Leu Asn Ala Asp Val Arg
        275                 280                 285

Tyr Ala Arg Asn Glu Asp Phe Asp Ala Ala Met Lys Thr Leu Glu Glu
    290                 295                 300

Arg Ala Gln Gln Lys Lys Leu Pro Glu Ala Asp Val Lys Val Ile Val
305                 310                 315                 320

Thr Arg Gly Arg Pro Ala Phe Asn Ala Gly Glu Gly Gly Lys Lys Leu
                325                 330                 335

Val Asp Lys Ala Val Ala Tyr Tyr Lys Glu Ala Gly Gly Thr Leu Gly
            340                 345                 350

Val Glu Glu Arg Thr Gly Gly Gly Thr Asp Ala Ala Tyr Ala Ala Leu
        355                 360                 365
```

Ser Gly Lys Pro Val Ile Glu Ser Leu Gly Leu Pro Gly Phe Gly Tyr
    370                 375                 380

His Ser Asp Lys Ala Glu Tyr Val Asp Ile Ser Ala Ile Pro Arg Arg
385                 390                 395                 400

Leu Tyr Met Ala Ala Arg Leu Ile Met Asp Leu Gly Ala Gly Lys
                405                 410                 415

<210> SEQ ID NO 2
<211> LENGTH: 1248
<212> TYPE: DNA
<213> ORGANISM: Homo sapiens

<400> SEQUENCE: 2
atgcgtccct ctatccatcg tacggccatt gcggctgtat tagccacagc gtttgtagcg 60
ggcacggcct tggctcagaa acgtgacaac gtactgttcc aagcagctac tgacgagcaa 120
cccgccgtta ttaaaacatt agagaaattg gtaaatattg aaactgggac gggcgacgct 180
gaaggcattg ccgcggctgg gaacttcttg gaagccgaat taaaaaatct tgggtttaca 240
gtcactcgct cgaaatcagc ggggctggtc gttggtgata acatcgtcgg caaaattaaa 300
gggcgcgggg gtaaaaattt attgttgatg agccacatgg acaccgttta cctgaaaggg 360
atccttgcga aagccccctt tcgcgtcgag ggagacaagg cttacggtcc cggcatcgca 420
gatgataaag gtggaaatgc agtgatttta cacacactga aattgcttaa agagtacgga 480
gttcgcgatt acggcacgat cacagtattg ttcaatacgg acgaggaaaa gggatctttc 540
ggcagccgtg atcttatcca ggaagaagcg aaactggcgg attatgtgtt aagttttgaa 600
cccacaagcg ccggagatga gaagctttca ttaggtacat caggtattgc ctacgtacag 660
gtaaatatca caggtaaagc aagccacgca ggggcggcac cagagttagg cgttaatgca 720
ctggtagaag ctagtgacct ggtccttcgt actatgaata tcgatgataa agcgaaaaac 780
ttgcgcttta actggacgat cgccaaggcg ggtaatgtat cgaacattat tccagccagt 840
gcgacattaa atgctgatgt tcgttacgcg cgcaatgaag acttcgacgc tgctatgaaa 900
acacttgagg agcgcgctca acagaaaaaa cttccagagg ccgacgtaaa agttatcgtt 960
acacgtggac gtccggcctt taacgcgggt gaaggaggca agaagctggt agacaaagct 1020
gttgcttatt ataaagaagc gggggggaacc ttgggagtgg aggaacgtac cggtggaggg 1080
actgatgcgg cttacgccgc actttctgga aagcctgtaa tcgagagctt aggtttaccc 1140
ggttttgggt atcacagtga taaagcagag tacgtcgata tttcagcgat cccacgccgt 1200
ctttatatgg ctgcccgctt gattatggat ttgggggcgg ggaagtag 1248

<210> SEQ ID NO 3
<211> LENGTH: 393
<212> TYPE: PRT
<213> ORGANISM: Homo sapiens

<400> SEQUENCE: 3

Ala Leu Ala Gln Lys Arg Asp Asn Val Leu Phe Gln Ala Ala Thr Asp
1               5                   10                  15

Glu Gln Pro Ala Val Ile Lys Thr Leu Glu Lys Leu Val Asn Ile Glu
            20                  25                  30

Thr Gly Thr Gly Asp Ala Glu Gly Ile Ala Ala Ala Gly Asn Phe Leu
        35                  40                  45

Glu Ala Glu Leu Lys Asn Leu Gly Phe Thr Val Thr Arg Ser Lys Ser
    50                  55                  60

-continued

```
Ala Gly Leu Val Val Gly Asp Asn Ile Val Gly Lys Ile Lys Gly Arg
65                  70                  75                  80

Gly Gly Lys Asn Leu Leu Leu Met Ser His Met Asp Thr Val Tyr Leu
                85                  90                  95

Lys Gly Ile Leu Ala Lys Ala Pro Phe Arg Val Glu Gly Asp Lys Ala
            100                 105                 110

Tyr Gly Pro Gly Ile Ala Asp Asp Lys Gly Gly Asn Ala Val Ile Leu
        115                 120                 125

His Thr Leu Lys Leu Leu Lys Glu Tyr Gly Val Arg Asp Tyr Gly Thr
    130                 135                 140

Ile Thr Val Leu Phe Asn Thr Asp Glu Glu Lys Gly Ser Phe Gly Ser
145                 150                 155                 160

Arg Asp Leu Ile Gln Glu Glu Ala Lys Leu Ala Asp Tyr Val Leu Ser
                165                 170                 175

Phe Glu Pro Thr Ser Ala Gly Asp Glu Lys Leu Ser Leu Gly Thr Ser
            180                 185                 190

Gly Ile Ala Tyr Val Gln Val Gln Ile Thr Gly Lys Ala Ser His Ala
        195                 200                 205

Gly Ala Ala Pro Glu Leu Gly Val Asn Ala Leu Val Glu Ala Ser Asp
    210                 215                 220

Leu Val Leu Arg Thr Met Asn Ile Asp Asp Lys Ala Lys Asn Leu Arg
225                 230                 235                 240

Phe Gln Trp Thr Ile Ala Lys Ala Gly Gln Val Ser Asn Ile Ile Pro
                245                 250                 255

Ala Ser Ala Thr Leu Asn Ala Asp Val Arg Tyr Ala Arg Asn Glu Asp
            260                 265                 270

Phe Asp Ala Ala Met Lys Thr Leu Glu Glu Arg Ala Gln Gln Lys Lys
        275                 280                 285

Leu Pro Glu Ala Asp Val Lys Val Ile Val Thr Arg Gly Arg Pro Ala
    290                 295                 300

Phe Asn Ala Gly Glu Gly Gly Lys Lys Leu Val Asp Lys Ala Val Ala
305                 310                 315                 320

Tyr Tyr Lys Glu Ala Gly Gly Thr Leu Gly Val Glu Glu Arg Thr Gly
                325                 330                 335

Gly Gly Thr Asp Ala Ala Tyr Ala Ala Leu Ser Gly Lys Pro Val Ile
            340                 345                 350

Glu Ser Leu Gly Leu Pro Gly Phe Gly Tyr His Ser Asp Lys Ala Glu
        355                 360                 365

Tyr Val Asp Ile Ser Ala Ile Pro Arg Arg Leu Tyr Met Ala Ala Arg
    370                 375                 380

Leu Ile Met Asp Leu Gly Ala Gly Lys
385                 390
```

<210> SEQ ID NO 4
<211> LENGTH: 1182
<212> TYPE: DNA
<213> ORGANISM: Homo sapiens

<400> SEQUENCE: 4

```
gccctcgcgc aaaaacggga caatgtattg ttccaagcgg ctactgatga acagccagca     60

gtaattaaaa cgcttgaaaa acttgtcaac atcgagaccg ggacagggga tgctgaaggg    120

attgcagccg caggaaactt tcttgaagcc gaactcaaaa accttgggtt taccgtaacg    180

cgctctaagt cagccggttt ggtcgtaggt gacaacattg tgggaaagat caagggacgg    240
```

-continued

```
ggcggtaaaa acttgctttt gatgtctcat atggatactg tatatcttaa ggggatcctc    300

gcgaaggcgc cctttcgggt ggaaggcgat aaggcatatg gaccagggat agctgacgac    360

aagggggggta acgcggtcat tctccacaca ctgaaacttc ttaaagaata cggtgtgaga   420

gattatggga cgatcactgt actgttcaac accgatgagg aaaagggctc ttttggctct    480

agagatttga ttcaagaaga agcgaaactg gcagactacg tgttgtcctt cgaacccaca    540

tctgctggcg atgagaagct cagtcttgga acctctggga ttgcgtacgt ccaggtccaa    600

ataaccggaa aggcaagcca tgctggagca gccccagaac ttggcgtaaa tgcgctggtg    660

gaggcgagtg atctggtgct ccggaccatg aacatagatg acaaagccaa aaatctgagg    720

tttcaatgga ccatcgctaa agcagggcag gtctctaata tcatcccggc ttcagccact    780

ttgaacgccg atgttaggta cgcccggaat gaagattttg atgccgctat gaaaacattg    840

gaggaacgag cgcagcaaaa aaagctgcca gaagccgatg ttaaagtaat agtaactaga    900

ggacgacccg cgttcaatgc gggcgagggt ggaaagaagt tggtcgataa ggctgttgcg    960

tactataagg aagcgggggg tacgcttgga gttgaggaga ggaccggagg gggcactgac   1020

gcggcgtacg ccgccctctc aggcaagccc gtaattgagt cacttgggct tcctggtttt   1080

ggttatcact cagacaaggc cgagtacgtg gatatatcag ctatccctcg gcgattgtac   1140

atggcggcac gcttgataat ggatttgggg gctggaaagt aa                       1182
```

<210> SEQ ID NO 5
<211> LENGTH: 415
<212> TYPE: PRT
<213> ORGANISM: Homo sapiens

<400> SEQUENCE: 5

```
Met Arg Pro Ser Ile His Arg Thr Ala Ile Ala Ala Val Leu Ala Thr
1               5                   10                  15

Ala Phe Val Ala Gly Thr Ala Leu Ala Gln Lys Arg Asp Asn Val Leu
            20                  25                  30

Phe Gln Ala Ala Thr Asp Glu Gln Pro Ala Val Ile Lys Thr Leu Glu
        35                  40                  45

Lys Leu Val Asn Ile Glu Thr Gly Thr Gly Asp Ala Glu Gly Ile Ala
    50                  55                  60

Ala Ala Gly Asn Phe Leu Glu Ala Glu Leu Lys Asn Leu Gly Phe Thr
65                  70                  75                  80

Val Thr Arg Ser Lys Ser Ala Gly Leu Val Val Gly Asp Asn Ile Val
                85                  90                  95

Gly Lys Ile Lys Gly Arg Gly Gly Lys Asn Leu Leu Leu Met Ser His
            100                 105                 110

Met Asp Thr Val Tyr Leu Lys Gly Ile Leu Ala Lys Ala Pro Phe Arg
        115                 120                 125

Val Glu Gly Asp Lys Ala Tyr Gly Pro Gly Ile Ala Asp Asp Lys Gly
    130                 135                 140

Gly Asn Ala Val Ile Leu His Thr Leu Lys Leu Leu Lys Glu Tyr Gly
145                 150                 155                 160

Val Arg Asp Tyr Gly Thr Ile Thr Val Leu Phe Asn Thr Asp Glu Glu
                165                 170                 175

Lys Gly Ser Phe Gly Ser Arg Asp Leu Ile Gln Glu Glu Ala Lys Leu
            180                 185                 190

Ala Asp Tyr Val Leu Ser Phe Glu Pro Thr Ser Ala Gly Asp Glu Lys
        195                 200                 205
```

-continued

```
Leu Ser Leu Gly Thr Ser Gly Ile Ala Tyr Val Gln Val Gln Ile Thr
    210                 215                 220

Gly Lys Ala Ser His Ala Gly Ala Ala Pro Glu Leu Gly Val Asn Ala
225                 230                 235                 240

Leu Val Glu Ala Ser Asp Leu Val Leu Arg Thr Met Asn Ile Asp Asp
                245                 250                 255

Lys Ala Lys Asn Leu Arg Phe Gln Trp Thr Ile Ala Lys Ala Gly Gln
            260                 265                 270

Val Ser Asn Ile Ile Pro Ala Ser Ala Thr Leu Asn Ala Asp Val Arg
        275                 280                 285

Tyr Ala Arg Asn Glu Asp Phe Asp Ala Ala Met Lys Thr Leu Glu Glu
    290                 295                 300

Arg Ala Gln Gln Lys Lys Leu Pro Glu Ala Asp Val Lys Val Ile Val
305                 310                 315                 320

Thr Arg Gly Arg Pro Ala Phe Asn Ala Gly Glu Gly Gly Lys Lys Leu
                325                 330                 335

Val Asp Lys Ala Val Ala Tyr Tyr Lys Glu Ala Gly Gly Thr Leu Gly
            340                 345                 350

Val Glu Glu Arg Thr Gly Gly Gly Thr Asp Ala Ala Tyr Ala Ala Leu
        355                 360                 365

Ser Gly Lys Pro Val Ile Glu Ser Leu Gly Leu Pro Gly Phe Gly Tyr
    370                 375                 380

His Ser Asp Lys Ala Glu Tyr Val Asp Ile Ser Ala Ile Pro Arg Arg
385                 390                 395                 400

Leu Tyr Met Ala Ala Arg Leu Ile Met Asp Leu Gly Ala Gly Lys
                405                 410                 415
```

<210> SEQ ID NO 6
<211> LENGTH: 1248
<212> TYPE: DNA
<213> ORGANISM: Homo sapiens

<400> SEQUENCE: 6

```
atgcgaccga gtatccacag aacagcaata gctgctgtgc ttgcaacagc gtttgtagcg      60

ggcacggccc tcgcgcaaaa acgggacaat gtattgttcc aagcggctac tgatgaacag     120

ccagcagtaa ttaaaacgct tgaaaaactt gtcaacatcg agaccgggac aggggatgct     180

gaagggattg cagccgcagg aaactttctt gaagccgaac tcaaaaacct tgggtttacc     240

gtaacgcgct ctaagtcagc cggtttggtc gtaggtgaca acattgtggg aaagatcaag     300

ggacggggcg gtaaaaactt gcttttgatg tctcatatgg atactgtata tcttaagggg     360

atcctcgcga aggcgccctt tcgggtggaa ggcgataagg catatggacc agggatagct     420

gacgacaagg ggggtaacgc ggtcattctc cacacactga aacttcttaa agaatacggt     480

gtgagagatt atgggacgat cactgtactg ttcaacaccg atgaggaaaa gggctctttt     540

ggctctagag atttgattca agaagaagcg aaactggcag actacgtgtt gtccttcgaa     600

cccacatctg ctggcgatga gaagctcagt cttggaacct ctgggattgc gtacgtccag     660

gtccaaataa ccggaaaggc aagccatgct ggagcagccc cagaacttgg cgtaaatgcg     720

ctggtggagg cgagtgatct ggtgctccgg accatgaaca tagatgacaa agccaaaaat     780

ctgaggtttc aatggaccat cgctaaagca gggcaggtct ctaatatcat cccggcttca     840

gccactttga acgccgatgt taggtacgcc cggaatgaag attttgatgc cgctatgaaa     900

acattggagg aacgagcgca gcaaaaaaag ctgccagaag ccgatgttaa agtaatagta     960
```

-continued

```
actagaggac gacccgcgtt caatgcgggc gagggtggaa agaagttggt cgataaggct   1020

gttgcgtact ataaggaagc ggggggtacg cttggagttg aggagaggac cggagggggc   1080

actgacgcgg cgtacgccgc cctctcaggc aagcccgtaa ttgagtcact tgggcttcct   1140

ggttttggtt atcactcaga caaggccgag tacgtggata tatcagctat ccctcggcga   1200

ttgtacatgg cggcacgctt gataatggat ttgggggctg gaaagtaa                 1248


<210> SEQ ID NO 7
<211> LENGTH: 458
<212> TYPE: PRT
<213> ORGANISM: Homo sapiens

<400> SEQUENCE: 7

Met Ala Leu Pro Val Thr Ala Leu Leu Leu Pro Leu Ala Leu Leu Leu
1               5                   10                  15

His Ala Ala Arg Pro Ala Leu Ala Gln Lys Arg Asp Asn Val Leu Phe
            20                  25                  30

Gln Ala Ala Thr Asp Glu Gln Pro Ala Val Ile Lys Thr Leu Glu Lys
        35                  40                  45

Leu Val Asn Ile Glu Thr Gly Thr Gly Asp Ala Glu Gly Ile Ala Ala
    50                  55                  60

Ala Gly Asn Phe Leu Glu Ala Glu Leu Lys Asn Leu Gly Phe Thr Val
65                  70                  75                  80

Thr Arg Ser Lys Ser Ala Gly Leu Val Val Gly Asp Asn Ile Val Gly
                85                  90                  95

Lys Ile Lys Gly Arg Gly Gly Lys Asn Leu Leu Leu Met Ser His Met
            100                 105                 110

Asp Thr Val Tyr Leu Lys Gly Ile Leu Ala Lys Ala Pro Phe Arg Val
        115                 120                 125

Glu Gly Asp Lys Ala Tyr Gly Pro Gly Ile Ala Asp Asp Lys Gly Gly
    130                 135                 140

Asn Ala Val Ile Leu His Thr Leu Lys Leu Leu Lys Glu Tyr Gly Val
145                 150                 155                 160

Arg Asp Tyr Gly Thr Ile Thr Val Leu Phe Asn Thr Asp Glu Glu Lys
                165                 170                 175

Gly Ser Phe Gly Ser Arg Asp Leu Ile Gln Glu Glu Ala Lys Leu Ala
            180                 185                 190

Asp Tyr Val Leu Ser Phe Glu Pro Thr Ser Ala Gly Asp Glu Lys Leu
        195                 200                 205

Ser Leu Gly Thr Ser Gly Ile Ala Tyr Val Gln Val Gln Ile Thr Gly
    210                 215                 220

Lys Ala Ser His Ala Gly Ala Ala Pro Glu Leu Gly Val Asn Ala Leu
225                 230                 235                 240

Val Glu Ala Ser Asp Leu Val Leu Arg Thr Met Asn Ile Asp Asp Lys
                245                 250                 255

Ala Lys Asn Leu Arg Phe Gln Trp Thr Ile Ala Lys Ala Gly Gln Val
            260                 265                 270

Ser Asn Ile Ile Pro Ala Ser Ala Thr Leu Asn Ala Asp Val Arg Tyr
        275                 280                 285

Ala Arg Asn Glu Asp Phe Asp Ala Ala Met Lys Thr Leu Glu Glu Arg
    290                 295                 300

Ala Gln Gln Lys Lys Leu Pro Glu Ala Asp Val Lys Val Ile Val Thr
305                 310                 315                 320

Arg Gly Arg Pro Ala Phe Asn Ala Gly Glu Gly Gly Lys Lys Leu Val
```

```
                325                 330                 335

Asp Lys Ala Val Ala Tyr Tyr Lys Glu Ala Gly Gly Thr Leu Gly Val
            340                 345                 350

Glu Glu Arg Thr Gly Gly Gly Thr Asp Ala Ala Tyr Ala Ala Leu Ser
        355                 360                 365

Gly Lys Pro Val Ile Glu Ser Leu Gly Leu Pro Gly Phe Gly Tyr His
    370                 375                 380

Ser Asp Lys Ala Glu Tyr Val Asp Ile Ser Ala Ile Pro Arg Arg Leu
385                 390                 395                 400

Tyr Met Ala Ala Arg Leu Ile Met Asp Leu Gly Ala Gly Lys Tyr Pro
                405                 410                 415

Tyr Asp Val Pro Asp Tyr Ala Gly Gly Gly Leu Tyr Cys Asn His Arg
            420                 425                 430

Asn Arg Arg Arg Val Cys Lys Cys Pro Arg Pro Val Val Lys Ser Gly
        435                 440                 445

Asp Lys Pro Ser Leu Ser Ala Arg Tyr Val
    450                 455


<210> SEQ ID NO 8
<211> LENGTH: 1377
<212> TYPE: DNA
<213> ORGANISM: Homo sapiens

<400> SEQUENCE: 8

atggccttgc ccgttaccgc actcctgctg ccgctggcgc tgttgctgca cgcagctcga      60

ccggccctcg cgcaaaaacg ggacaatgta ttgttccaag cggctactga tgaacagcca     120

gcagtaatta aaacgcttga aaaacttgtc aacatcgaga ccgggacagg ggatgctgaa     180

gggattgcag ccgcaggaaa ctttcttgaa gccgaactca aaaaccttgg gtttaccgta     240

acgcgctcta agtcagccgg tttggtcgta ggtgacaaca ttgtgggaaa gatcaaggga     300

cggggcggta aaaacttgct tttgatgtct catatggata ctgtatatct taaggggatc     360

ctcgcgaagg cgccctttcg ggtggaaggc gataaggcat atggaccagg gatagctgac     420

gacaaggggg gtaacgcggt cattctccac acactgaaac ttcttaaaga atacggtgtg     480

agagattatg ggacgatcac tgtactgttc aacaccgatg aggaaaaggg ctcttttggc     540

tctagagatt tgattcaaga agaagcgaaa ctggcagact acgtgttgtc cttcgaaccc     600

acatctgctg gcgatgagaa gctcagtctt ggaacctctg ggattgcgta cgtccaggtc     660

caaataaccg gaaaggcaag ccatgctgga gcagccccag aacttggcgt aaatgcgctg     720

gtggaggcga gtgatctggt gctccggacc atgaacatag atgacaaagc caaaaatctg     780

aggtttcaat ggaccatcgc taaagcaggg caggtctcta atatcatccc ggcttcagcc     840

actttgaacg ccgatgttag gtacgcccgg aatgaagatt ttgatgccgc tatgaaaaca     900

ttggaggaac gagcgcagca aaaaaagctg ccagaagccg atgttaaagt aatagtaact     960

agaggacgac ccgcgttcaa tgcgggcgag ggtggaaaga agttggtcga taaggctgtt    1020

gcgtactata aggaagcggg gggtacgctt ggagttgagg agaggaccgg agggggcact    1080

gacgcggcgt acgccgccct ctcaggcaag cccgtaattg agtcacttgg gcttcctggt    1140

tttggttatc actcagacaa ggccgagtac gtggatatat cagctatccc tcggcgattg    1200

tacatggcgg cacgcttgat aatggatttg gggggctgga agtatcctta tgatgttcca    1260

gactacgcag gggcggact gtattgtaac caccgaaatc gacggcgagt atgcaagtgc     1320

cctcgaccag ttgttaaatc tggggataaa ccttcactgt ccgctagata cgtgtaa       1377
```

<210> SEQ ID NO 9
<211> LENGTH: 22
<212> TYPE: PRT
<213> ORGANISM: Homo sapiens

<400> SEQUENCE: 9

Met Arg Pro Ser Ile His Arg Thr Ala Ile Ala Ala Val Leu Ala Thr
1 5 10 15

Ala Phe Val Ala Gly Thr
20

<210> SEQ ID NO 10
<211> LENGTH: 66
<212> TYPE: DNA
<213> ORGANISM: Homo sapiens

<400> SEQUENCE: 10
atgcgaccga gtatccacag aacagcaata gctgctgtgc ttgcaacagc gtttgtagcg 60
ggcacg 66

<210> SEQ ID NO 11
<211> LENGTH: 21
<212> TYPE: PRT
<213> ORGANISM: Homo sapiens

<400> SEQUENCE: 11

Met Ala Leu Pro Val Thr Ala Leu Leu Leu Pro Leu Ala Leu Leu Leu
1 5 10 15

His Ala Ala Arg Pro
20

<210> SEQ ID NO 12
<211> LENGTH: 63
<212> TYPE: DNA
<213> ORGANISM: Homo sapiens

<400> SEQUENCE: 12
atggccttgc ccgttaccgc actcctgctg ccgctggcgc tgttgctgca cgcagctcga 60
ccg 63

<210> SEQ ID NO 13
<211> LENGTH: 32
<212> TYPE: PRT
<213> ORGANISM: Homo sapiens

<400> SEQUENCE: 13

Leu Tyr Cys Asn His Arg Asn Arg Arg Arg Val Cys Lys Cys Pro Arg
1 5 10 15

Pro Val Val Lys Ser Gly Asp Lys Pro Ser Leu Ser Ala Arg Tyr Val
20 25 30

<210> SEQ ID NO 14
<211> LENGTH: 99
<212> TYPE: DNA
<213> ORGANISM: Homo sapiens

<400> SEQUENCE: 14
ctgtattgta accaccgaaa tcgacggcga gtatgcaagt gccctcgacc agttgttaaa 60
tctggggata aaccttcact gtccgctaga tacgtgtaa 99

<210> SEQ ID NO 15
<211> LENGTH: 31
<212> TYPE: PRT
<213> ORGANISM: Homo sapiens

<400> SEQUENCE: 15

Leu Tyr Cys Asn His Arg Asn Arg Arg Arg Val Gly Gly Gly Arg Pro
1 5 10 15

Val Val Lys Ser Gly Asp Lys Pro Ser Leu Ser Ala Arg Tyr Val
20 25 30

<210> SEQ ID NO 16
<211> LENGTH: 96
<212> TYPE: DNA
<213> ORGANISM: Homo sapiens

<400> SEQUENCE: 16
ctgtattgta accaccgaaa tcgacggcga gtaggaggag gacgaccagt tgttaaatct 60
ggggataaac cttcactgtc cgctagatac gtgtaa 96

<210> SEQ ID NO 17
<211> LENGTH: 22
<212> TYPE: PRT
<213> ORGANISM: Homo sapiens

<400> SEQUENCE: 17

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 18
<211> LENGTH: 66
<212> TYPE: DNA
<213> ORGANISM: Homo sapiens

<400> SEQUENCE: 18
ggaagcggag ctactaactt cagcctgctg aagcaggctg gagacgtgga ggagaaccct 60
ggacct 66

<210> SEQ ID NO 19
<211> LENGTH: 245
<212> TYPE: PRT
<213> ORGANISM: Homo sapiens

<400> SEQUENCE: 19

Glu Val Lys Leu Gln Gln Ser Gly Ala Glu Leu Val Arg Pro Gly Ser
1 5 10 15

Ser Val Lys Ile Ser Cys Lys Ala Ser Gly Tyr Ala Phe Ser Ser Tyr
20 25 30

Trp Met Asn Trp Val Lys Gln Arg Pro Gly Gln Gly Leu Glu Trp Ile
35 40 45

Gly Gln Ile Tyr Pro Gly Asp Gly Asp Thr Asn Tyr Asn Gly Lys Phe
50 55 60

Lys Gly Gln Ala Thr Leu Thr Ala Asp Lys Ser Ser Ser Thr Ala Tyr
65 70 75 80

Met Gln Leu Ser Gly Leu Thr Ser Glu Asp Ser Ala Val Tyr Phe Cys
85 90 95

Ala Arg Lys Thr Ile Ser Ser Val Val Asp Phe Tyr Phe Asp Tyr Trp

-continued

```
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Glu Leu Thr Gln Ser
    130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
225                 230                 235                 240

Leu Glu Ile Lys Arg
                245


<210> SEQ ID NO 20
<211> LENGTH: 735
<212> TYPE: DNA
<213> ORGANISM: Homo sapiens

<400> SEQUENCE: 20

gaggtgaagc tgcagcagtc tggggctgag ctggtgaggc ctgggtcctc agtgaagatt     60

tcctgcaagg cttctggcta tgcattcagt agctactgga tgaactgggt gaagcagagg    120

cctggacagg gtcttgagtg gattggacag atttatcctg gagatggtga tactaactac    180

aatggaaagt tcaagggtca agccacactg actgcagaca aatcctccag cacagcctac    240

atgcagctca gcggcctaac atctgaggac tctgcggtct atttctgtgc aagaaagacc    300

attagttcgg tagtagattt ctactttgac tactggggcc aagggaccac ggtcaccgtc    360

tcctcaggtg gaggtggatc aggtggaggt ggatctggtg gaggtggatc tgacattgag    420

ctcacccagt ctccaaaatt catgtccaca tcagtaggag acagggtcag cgtcacctgc    480

aaggccagtc agaatgtggg tactaatgta gcctggtatc aacagaaacc aggacaatct    540

cctaaaccac tgatttactc ggcaacctac cggaacagtg gagtccctga tcgcttcaca    600

ggcagtggat ctgggacaga tttcactctc accatcacta acgtgcagtc taaagacttg    660

gcagactatt tctgtcaaca atataacagg tatccgtaca cgtccggagg ggggaccaag    720

ctggagatca aacgg                                                     735


<210> SEQ ID NO 21
<211> LENGTH: 15
<212> TYPE: PRT
<213> ORGANISM: Homo sapiens

<400> SEQUENCE: 21

Gly Gly Gly Gly Ser Gly Gly Gly Gly Ser Gly Gly Gly Gly Ser
1               5                   10                  15


<210> SEQ ID NO 22
<211> LENGTH: 45
<212> TYPE: DNA
<213> ORGANISM: Homo sapiens
```

<400> SEQUENCE: 22
ggcggcggcg gatctggagg tggtggctca ggtggcggag gctcc 45

<210> SEQ ID NO 23
<211> LENGTH: 10
<212> TYPE: PRT
<213> ORGANISM: Homo sapiens

<400> SEQUENCE: 23

Ala Leu Tyr Val Asp Ser Leu Phe Phe Leu
1 5 10

<210> SEQ ID NO 24
<211> LENGTH: 214
<212> TYPE: PRT
<213> ORGANISM: Homo sapiens

<400> SEQUENCE: 24

Met Leu Arg Leu Leu Leu Ala Leu Asn Leu Phe Pro Ser Ile Gln Val
1 5 10 15

Thr Gly Asn Lys Ile Leu Val Lys Gln Ser Pro Met Leu Val Ala Tyr
20 25 30

Asp Asn Ala Leu Ser Cys Lys Tyr Ser Tyr Asn Leu Phe Ser Arg Glu
35 40 45

Phe Arg Ala Ser Leu His Lys Gly Leu Asp Ser Ala Val Glu Val Cys
50 55 60

Trp Tyr Gly Asn Tyr Ser Gln Gln Leu Gln Val Tyr Ser Lys Thr Gly
65 70 75 80

Phe Asn Cys Asp Gly Lys Leu Gly Asn Glu Ser Val Thr Phe Tyr Leu
85 90 95

Gln Asn Leu Tyr Gln Thr Asp Ile Tyr Phe Cys Lys Ile Glu Val Met
100 105 110

Tyr Pro Pro Pro Tyr Leu Asp Asn Glu Lys Ser Asn Gly Thr Ile Ile
115 120 125

His Val Lys Gly Lys His Leu Cys Pro Ser Pro Leu Phe Pro Gly Pro
130 135 140

Ser Lys Pro Phe Trp Val Leu Val Trp Gly Gly Val Leu Ala Cys Tyr
145 150 155 160

Ser Leu Leu Val Thr Val Ala Phe Ile Ile Phe Trp Val Arg Ser Lys
165 170 175

Arg Ser Arg Leu Leu His Ser Asp Tyr Met Asn Met Thr Pro Arg Arg
180 185 190

Pro Gly Pro Thr Arg Lys His Tyr Gln Pro Tyr Ala Pro Pro Arg Asp
195 200 205

Phe Ala Ala Tyr Arg Ser
210

<210> SEQ ID NO 25
<211> LENGTH: 321
<212> TYPE: DNA
<213> ORGANISM: Homo sapiens

<400> SEQUENCE: 25
attgaagtta tgtatcctcc tccttaccta gacaatgaga agagcaatgg aaccattatc 60
catgtgaaag ggaaacacct ttgtccaagt cccctatttc ccggaccttc taagcccttt 120
tgggtgctgg tggtggttgg tggagtcctg gcttgctata gcttgctagt aacagtggcc 180

```
tttattattt tctgggtgag gagtaagagg agcaggctcc tgcacagtga ctacatgaac    240

atgactcccc gccgccccgg gcccacccgc aagcattacc agccctatgc cccaccacgc    300

gacttcgcag cctatcgctc c                                              321


<210> SEQ ID NO 26
<211> LENGTH: 234
<212> TYPE: PRT
<213> ORGANISM: Homo sapiens

<400> SEQUENCE: 26

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Trp Lys Ser Gly
    210                 215                 220

Asp Lys Pro Ser Leu Ser Ala Arg Tyr Val
225                 230


<210> SEQ ID NO 27
<211> LENGTH: 164
<212> TYPE: PRT
<213> ORGANISM: Homo sapiens

<400> SEQUENCE: 27

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60
```

```
Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 28
<211> LENGTH: 164
<212> TYPE: PRT
<213> ORGANISM: Homo sapiens

<400> SEQUENCE: 28

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 29
<211> LENGTH: 337
<212> TYPE: DNA
<213> ORGANISM: Homo sapiens

<400> SEQUENCE: 29

agagtgaagt tcagcaggag cgcagagccc cccgcgtacc agcagggcca gaaccagctc      60

tataacgagc tcaatctagg acgaagagag gagtacgatg ttttggacaa gagacgtggc     120

cgggaccctg agatgggggg aaagccgaga aggaagaacc ctcaggaagg cctgtacaat     180

gaactgcaga aagataagat ggcggaggcc tacagtgaga ttgggatgaa aggcgagcgc     240

cggaggggca aggggcacga tggcctttac cagggtctca gtacagccac caaggacacc     300
```

tacgacgccc ttcacatgca ggccctgccc cctcgcg 337

<210> SEQ ID NO 30
<211> LENGTH: 251
<212> TYPE: PRT
<213> ORGANISM: Homo sapiens

<400> SEQUENCE: 30

Met Gly Asn Ser Cys Tyr Asn Ile Val Ala Thr Leu Leu Leu Val Leu
1 5 10 15

Asn Phe Glu Arg Thr Arg Ser Leu Gln Asp Pro Cys Ser Asn Cys Pro
20 25 30

Ala Gly Thr Phe Cys Asp Asn Asn Arg Asn Gln Ile Cys Ser Pro Cys
35 40 45

Pro Pro Asn Ser Phe Ser Ser Ala Gly Gly Gln Arg Thr Cys Asp Ile
50 55 60

Cys Arg Gln Cys Lys Gly Val Phe Arg Thr Arg Lys Glu Cys Ser Ser
65 70 75 80

Thr Ser Asn Ala Glu Cys Asp Cys Thr Pro Gly Phe His Cys Leu Gly
85 90 95

Ala Gly Cys Ser Met Cys Glu Gln Asp Cys Lys Gln Gly Gln Glu Leu
100 105 110

Thr Lys Lys Gly Cys Lys Asp Cys Cys Phe Gly Thr Phe Asn Asp Gln
115 120 125

Lys Arg Gly Ile Cys Arg Pro Trp Thr Asn Cys Ser Leu Asp Gly Lys
130 135 140

Ser Val Leu Gly Thr Lys Glu Arg Asp Trp Cys Gly Pro Ser Pro Ala
145 150 155 160

Asp Leu Ser Pro Gly Ala Ser Ser Val Thr Pro Pro Ala Pro Ala Arg
165 170 175

Glu Pro Gly His Ser Pro Gln Ile Ile Ser Phe Phe Leu Ala Leu Thr
180 185 190

Ser Thr Ala Leu Leu Phe Leu Leu Phe Phe Leu Thr Leu Arg Phe Ser
195 200 205

Trp Lys Arg Gly Arg Lys Lys Leu Leu Tyr Ile Phe Lys Gln Pro Phe
210 215 220

Met Arg Pro Val Gln Thr Thr Gln Glu Glu Asp Gly Cys Ser Cys Arg
225 230 235 240

Phe Pro Glu Glu Glu Glu Gly Gly Cys Glu Leu
245 250

<210> SEQ ID NO 31
<211> LENGTH: 276
<212> TYPE: PRT
<213> ORGANISM: Homo sapiens

<400> SEQUENCE: 31

Met Cys Val Gly Ala Arg Arg Leu Gly Arg Gly Pro Cys Ala Ala Leu
1 5 10 15

Leu Leu Leu Gly Leu Gly Leu Ser Thr Val Thr Gly Leu His Cys Val
20 25 30

Gly Asp Thr Tyr Pro Ser Asn Asp Arg Cys Cys His Glu Cys Arg Pro
35 40 45

Gly Asn Gly Met Val Ser Arg Cys Ser Arg Ser Gln Asn Thr Val Cys
50 55 60

Arg Pro Cys Gly Pro Gly Phe Tyr Asn Asp Trp Ser Ser Lys Pro Cys

-continued

```
65                  70                  75                  80

Lys Pro Cys Thr Trp Cys Asn Leu Arg Ser Gly Ser Glu Arg Lys Gln
                85                  90                  95

Leu Cys Thr Ala Thr Gln Asp Thr Val Cys Arg Cys Arg Ala Gly Thr
            100                 105                 110

Gln Pro Leu Asp Ser Tyr Lys Pro Gly Val Asp Cys Ala Pro Cys Pro
        115                 120                 125

Pro Gly His Phe Ser Pro Gly Asp Asn Gln Ala Cys Lys Pro Trp Thr
    130                 135                 140

Asn Cys Thr Leu Ala Gly Lys His Thr Leu Gln Pro Ala Ser Asn Ser
145                 150                 155                 160

Ser Asp Ala Ile Cys Glu Asp Arg Asp Pro Pro Ala Thr Gln Pro Gln
                165                 170                 175

Glu Thr Gln Gly Pro Pro Ala Arg Pro Ile Thr Val Gln Pro Thr Glu
            180                 185                 190

Ala Trp Pro Arg Thr Ser Gln Gly Pro Ser Thr Arg Pro Val Glu Val
        195                 200                 205

Pro Gly Gly Arg Ala Val Ala Ala Ile Leu Gly Leu Gly Leu Val Leu
    210                 215                 220

Gly Leu Leu Gly Pro Leu Ala Ile Leu Leu Ala Leu Tyr Leu Leu Arg
225                 230                 235                 240

Arg Asp Gln Arg Leu Pro Pro Asp Ala His Lys Pro Pro Gly Gly Gly
                245                 250                 255

Ser Phe Arg Thr Pro Ile Gln Glu Glu Gln Ala Asp Ala His Ser Thr
            260                 265                 270

Leu Ala Lys Ile
        275


<210> SEQ ID NO 32
<211> LENGTH: 196
<212> TYPE: PRT
<213> ORGANISM: Homo sapiens

<400> SEQUENCE: 32

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Trp Cys Ile Leu Gly Cys Ile Leu Ile
145                 150                 155                 160
```

```
Cys Trp Leu Thr Lys Lys Lys Tyr Ser Ser Ser Val His Asp Pro Asn
                165                 170                 175

Gly Glu Tyr Met Phe Met Arg Ala Thr Ala Lys Lys Ser Arg Leu Thr
            180                 185                 190

Asp Val Thr Leu
        195


<210> SEQ ID NO 33
<211> LENGTH: 220
<212> TYPE: PRT
<213> ORGANISM: Homo sapiens

<400> SEQUENCE: 33

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Trp Leu Ala Ser
        35                  40                  45

Ser Arg Gly Ile Ala Ser Phe Val Cys Glu Tyr Ala Ser Pro Gly Lys
    50                  55                  60

Ala Thr Glu Val Arg Val Thr Val Leu Arg Gln Ala Asp Ser Gln Val
65                  70                  75                  80

Thr Glu Val Cys Ala Ala Thr Tyr Met Met Gly Asn Glu Leu Thr Phe
                85                  90                  95

Leu Asp Asp Ser Ile Cys Thr Gly Thr Ser Ser Gly Asn Gln Leu Thr
            100                 105                 110

Ile Gln Gly Leu Arg Ala Met Asp Thr Gly Leu Tyr Ile Cys Lys Val
        115                 120                 125

Glu Leu Met Tyr Pro Pro Pro Tyr Tyr Leu Gly Ile Gly Asn Gly Thr
    130                 135                 140

Gln Ile Tyr Val Ile Asp Pro Glu Pro Cys Pro Asp Ser Asp Phe Leu
145                 150                 155                 160

Leu Trp Ile Leu Ala Ala Val Ser Ser Gly Leu Phe Phe Tyr Ser Phe
                165                 170                 175

Leu Leu Thr Ala Val Ser Leu Ser Lys Met Leu Lys Lys Arg Ser Pro
            180                 185                 190

Leu Thr Thr Gly Val Tyr Val Lys Met Pro Pro Thr Glu Pro Glu Cys
        195                 200                 205

Glu Lys Gln Phe Gln Pro Tyr Phe Ile Pro Ile Asn
    210                 215                 220


<210> SEQ ID NO 34
<211> LENGTH: 286
<212> TYPE: PRT
<213> ORGANISM: Homo sapiens

<400> SEQUENCE: 34

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Trp Thr Glu Gly Asp Asn
        35                  40                  45

Ala Thr Phe Thr Cys Ser Phe Ser Asn Thr Ser Glu Ser Phe Val Leu
    50                  55                  60
```

```
Asn Trp Tyr Arg Met Ser Pro Ser Asn Gln Thr Asp Lys Leu Ala Ala
65                  70                  75                  80

Phe Pro Glu Asp Arg Ser Gln Pro Gly Gln Asp Cys Arg Phe Arg Val
                85                  90                  95

Thr Gln Leu Pro Asn Gly Arg Asp Phe His Met Ser Val Val Arg Ala
            100                 105                 110

Arg Arg Asn Asp Ser Gly Thr Tyr Leu Cys Gly Ala Ile Ser Leu Ala
        115                 120                 125

Pro Lys Ala Gln Ile Lys Glu Ser Leu Arg Ala Glu Leu Arg Val Thr
    130                 135                 140

Glu Arg Arg Ala Glu Val Pro Thr Ala His Pro Ser Pro Ser Pro Arg
145                 150                 155                 160

Pro Ala Gly Gln Phe Gln Thr Leu Val Val Gly Trp Gly Gly Leu Leu
                165                 170                 175

Gly Ser Leu Val Leu Leu Val Trp Val Leu Ala Val Ile Cys Ser Arg
            180                 185                 190

Ala Ala Arg Gly Thr Ile Gly Ala Arg Arg Thr Gly Gln Pro Leu Lys
        195                 200                 205

Glu Asp Pro Ser Ala Val Pro Val Phe Ser Val Asp Tyr Gly Glu Leu
    210                 215                 220

Asp Phe Gln Trp Arg Glu Lys Thr Pro Glu Pro Pro Val Pro Cys Val
225                 230                 235                 240

Pro Glu Gln Thr Glu Tyr Ala Thr Ile Val Phe Pro Ser Gly Met Gly
                245                 250                 255

Thr Ser Ser Pro Ala Arg Arg Gly Ser Ala Asp Gly Pro Arg Ser Ala
            260                 265                 270

Gln Pro Leu Arg Pro Glu Asp Gly His Cys Ser Trp Pro Leu
        275                 280                 285


<210> SEQ ID NO 35
<211> LENGTH: 524
<212> TYPE: PRT
<213> ORGANISM: Homo sapiens

<400> SEQUENCE: 35

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Trp Trp
            20                  25                  30

Ala Gln Glu Gly Ala Pro Ala Gln Leu Pro Cys Ser Pro Thr Ile Pro
        35                  40                  45

Leu Gln Asp Leu Ser Leu Leu Arg Arg Ala Gly Val Thr Trp Gln His
    50                  55                  60

Gln Pro Asp Ser Gly Pro Pro Ala Ala Ala Pro Gly His Pro Leu Ala
65                  70                  75                  80

Pro Gly Pro His Pro Ala Ala Pro Ser Ser Trp Gly Pro Arg Pro Arg
                85                  90                  95

Arg Tyr Thr Val Leu Ser Val Gly Pro Gly Gly Leu Arg Ser Gly Arg
            100                 105                 110

Leu Pro Leu Gln Pro Arg Val Gln Leu Asp Glu Arg Gly Arg Gln Arg
        115                 120                 125

Gly Asp Phe Ser Leu Trp Leu Arg Pro Ala Arg Arg Ala Asp Ala Gly
    130                 135                 140

Glu Tyr Arg Ala Ala Val His Leu Arg Asp Arg Ala Leu Ser Cys Arg
145                 150                 155                 160
```

```
Leu Arg Leu Arg Leu Gly Gln Ala Ser Met Thr Ala Ser Pro Pro Gly
                165                 170                 175

Ser Leu Arg Ala Ser Asp Trp Val Ile Leu Asn Cys Ser Phe Ser Arg
            180                 185                 190

Pro Asp Arg Pro Ala Ser Val His Trp Phe Arg Asn Arg Gly Gln Gly
        195                 200                 205

Arg Val Pro Val Arg Glu Ser Pro His His His Leu Ala Glu Ser Phe
    210                 215                 220

Leu Phe Leu Pro Gln Val Ser Pro Met Asp Ser Gly Pro Trp Gly Cys
225                 230                 235                 240

Ile Leu Thr Tyr Arg Asp Gly Phe Asn Val Ser Ile Met Tyr Asn Leu
                245                 250                 255

Thr Val Leu Gly Leu Glu Pro Pro Thr Pro Leu Thr Val Tyr Ala Gly
            260                 265                 270

Ala Gly Ser Arg Val Gly Leu Pro Cys Arg Leu Pro Ala Gly Val Gly
        275                 280                 285

Thr Arg Ser Phe Leu Thr Ala Lys Trp Thr Pro Pro Gly Gly Gly Pro
    290                 295                 300

Asp Leu Leu Val Thr Gly Asp Asn Gly Asp Phe Thr Leu Arg Leu Glu
305                 310                 315                 320

Asp Val Ser Gln Ala Gln Ala Gly Thr Tyr Thr Cys His Ile His Leu
                325                 330                 335

Gln Glu Gln Gln Leu Asn Ala Thr Val Thr Leu Ala Ile Ile Thr Val
            340                 345                 350

Thr Pro Lys Ser Phe Gly Ser Pro Gly Ser Leu Gly Lys Leu Leu Cys
        355                 360                 365

Glu Val Thr Pro Val Ser Gly Gln Glu Arg Phe Val Trp Ser Ser Leu
    370                 375                 380

Asp Thr Pro Ser Gln Arg Ser Phe Ser Gly Pro Trp Leu Glu Ala Gln
385                 390                 395                 400

Glu Ala Gln Leu Leu Ser Gln Pro Trp Gln Cys Gln Leu Tyr Gln Gly
                405                 410                 415

Glu Arg Leu Leu Gly Ala Ala Val Tyr Phe Thr Glu Leu Ser Ser Pro
            420                 425                 430

Gly Ala Gln Arg Ser Gly Arg Ala Pro Gly Ala Leu Pro Ala Gly His
        435                 440                 445

Leu Leu Leu Phe Leu Ile Leu Gly Val Leu Ser Leu Leu Leu Leu Val
    450                 455                 460

Thr Gly Ala Phe Gly Phe His Leu Trp Arg Arg Gln Trp Arg Pro Arg
465                 470                 475                 480

Arg Phe Ser Ala Leu Glu Gln Gly Ile His Pro Pro Gln Ala Gln Ser
                485                 490                 495

Lys Ile Glu Glu Leu Glu Gln Glu Pro Glu Pro Glu Pro Glu Pro Glu
            500                 505                 510

Pro Glu Pro Glu Pro Glu Pro Glu Pro Glu Gln Leu
        515                 520
```

<210> SEQ ID NO 36
<211> LENGTH: 368
<212> TYPE: PRT
<213> ORGANISM: Homo sapiens

<400> SEQUENCE: 36

```
Met Leu Gly Gln Trp Thr Leu Ile Leu Leu Leu Leu Leu Lys Val Tyr
```

```
1               5                   10                  15

Gln Gly Lys Gly Cys Gln Gly Ser Ala Asp His Trp Ser Ile Ser Gly
            20                  25                  30

Val Pro Leu Gln Leu Gln Pro Asn Ser Ile Gln Thr Lys Val Asp Ser
        35                  40                  45

Ile Ala Trp Lys Lys Leu Leu Pro Ser Gln Asn Gly Phe His His Ile
    50                  55                  60

Leu Lys Trp Glu Asn Gly Ser Leu Pro Ser Asn Thr Ser Asn Asp Arg
65                  70                  75                  80

Phe Ser Phe Ile Val Lys Asn Leu Ser Leu Leu Ile Lys Ala Ala Gln
                85                  90                  95

Gln Gln Asp Ser Gly Leu Tyr Cys Leu Glu Val Thr Ser Ile Ser Gly
            100                 105                 110

Lys Val Gln Thr Ala Thr Phe Gln Val Phe Val Phe Glu Ser Leu Leu
        115                 120                 125

Pro Asp Lys Val Glu Lys Pro Arg Leu Gln Gly Gln Gly Lys Ile Leu
    130                 135                 140

Asp Arg Gly Arg Cys Gln Val Ala Leu Ser Cys Leu Val Ser Arg Asp
145                 150                 155                 160

Gly Asn Val Ser Tyr Ala Trp Tyr Arg Gly Ser Lys Leu Ile Gln Thr
                165                 170                 175

Ala Gly Asn Leu Thr Tyr Leu Asp Glu Glu Val Asp Ile Asn Gly Thr
            180                 185                 190

His Thr Tyr Thr Cys Asn Val Ser Asn Pro Val Ser Trp Glu Ser His
        195                 200                 205

Thr Leu Asn Leu Thr Gln Asp Cys Gln Asn Ala His Gln Glu Phe Arg
    210                 215                 220

Phe Trp Pro Phe Leu Val Ile Ile Val Ile Leu Ser Ala Leu Phe Leu
225                 230                 235                 240

Gly Thr Leu Ala Cys Phe Cys Val Trp Arg Arg Lys Arg Lys Glu Lys
                245                 250                 255

Gln Ser Glu Thr Ser Pro Lys Glu Phe Leu Thr Ile Tyr Glu Asp Val
            260                 265                 270

Lys Asp Leu Lys Thr Arg Arg Asn His Glu Gln Glu Gln Thr Phe Pro
        275                 280                 285

Gly Gly Gly Ser Thr Ile Tyr Ser Met Ile Gln Ser Gln Ser Ser Ala
    290                 295                 300

Pro Thr Ser Gln Glu Pro Ala Tyr Thr Leu Tyr Ser Leu Ile Gln Pro
305                 310                 315                 320

Ser Arg Lys Ser Gly Ser Arg Lys Arg Asn His Ser Pro Ser Phe Asn
                325                 330                 335

Ser Thr Ile Tyr Glu Val Ile Gly Lys Ser Gln Pro Lys Ala Gln Asn
            340                 345                 350

Pro Ala Arg Leu Ser Arg Lys Glu Leu Glu Asn Phe Asp Val Tyr Ser
        355                 360                 365


<210> SEQ ID NO 37
<211> LENGTH: 289
<212> TYPE: PRT
<213> ORGANISM: Homo sapiens

<400> SEQUENCE: 37

Met Lys Thr Leu Pro Ala Met Leu Gly Thr Gly Lys Leu Phe Trp Val
1               5                   10                  15
```

```
Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser


<210> SEQ ID NO 38
<211> LENGTH: 21
<212> TYPE: PRT
<213> ORGANISM: Homo sapiens

<400> SEQUENCE: 38

Ile Tyr Ile Trp Ala Pro Leu Ala Gly Thr Cys Gly Val Leu Leu Leu
1               5                   10                  15

Ser Leu Val Ile Thr
            20


<210> SEQ ID NO 39
<211> LENGTH: 63
<212> TYPE: DNA
<213> ORGANISM: Homo sapiens

<400> SEQUENCE: 39

atctacatct gggcgcccct ggccgggact tgtggggtcc ttctcctgtc actggttatc     60

acc                                                                   63
```

<210> SEQ ID NO 40
<211> LENGTH: 478
<212> TYPE: PRT
<213> ORGANISM: Homo sapiens

<400> SEQUENCE: 40

Met Ala Leu Pro Val Thr Ala Leu Leu Leu Pro Leu Ala Leu Leu Leu
1 5 10 15

His Ala Ala Arg Pro Ala Leu Ala Gln Lys Arg Asp Asn Val Leu Phe
20 25 30

Gln Ala Ala Thr Asp Glu Gln Pro Ala Val Ile Lys Thr Leu Glu Lys
35 40 45

Leu Val Asn Ile Glu Thr Gly Thr Gly Asp Ala Glu Gly Ile Ala Ala
50 55 60

Ala Gly Asn Phe Leu Glu Ala Glu Leu Lys Asn Leu Gly Phe Thr Val
65 70 75 80

Thr Arg Ser Lys Ser Ala Gly Leu Val Val Gly Asp Asn Ile Val Gly
85 90 95

Lys Ile Lys Gly Arg Gly Gly Lys Asn Leu Leu Leu Met Ser His Met
100 105 110

Asp Thr Val Tyr Leu Lys Gly Ile Leu Ala Lys Ala Pro Phe Arg Val
115 120 125

Glu Gly Asp Lys Ala Tyr Gly Pro Gly Ile Ala Asp Asp Lys Gly Gly
130 135 140

Asn Ala Val Ile Leu His Thr Leu Lys Leu Leu Lys Glu Tyr Gly Val
145 150 155 160

Arg Asp Tyr Gly Thr Ile Thr Val Leu Phe Asn Thr Asp Glu Glu Lys
165 170 175

Gly Ser Phe Gly Ser Arg Asp Leu Ile Gln Glu Glu Ala Lys Leu Ala
180 185 190

Asp Tyr Val Leu Ser Phe Glu Pro Thr Ser Ala Gly Asp Glu Lys Leu
195 200 205

Ser Leu Gly Thr Ser Gly Ile Ala Tyr Val Gln Val Gln Ile Thr Gly
210 215 220

Lys Ala Ser His Ala Gly Ala Ala Pro Glu Leu Gly Val Asn Ala Leu
225 230 235 240

Val Glu Ala Ser Asp Leu Val Leu Arg Thr Met Asn Ile Asp Asp Lys
245 250 255

Ala Lys Asn Leu Arg Phe Gln Trp Thr Ile Ala Lys Ala Gly Gln Val
260 265 270

Ser Asn Ile Ile Pro Ala Ser Ala Thr Leu Asn Ala Asp Val Arg Tyr
275 280 285

Ala Arg Asn Glu Asp Phe Asp Ala Ala Met Lys Thr Leu Glu Glu Arg
290 295 300

Ala Gln Gln Lys Lys Leu Pro Glu Ala Asp Val Lys Val Ile Val Thr
305 310 315 320

Arg Gly Arg Pro Ala Phe Asn Ala Gly Glu Gly Gly Lys Lys Leu Val
325 330 335

Asp Lys Ala Val Ala Tyr Tyr Lys Glu Ala Gly Gly Thr Leu Gly Val
340 345 350

Glu Glu Arg Thr Gly Gly Gly Thr Asp Ala Ala Tyr Ala Ala Leu Ser
355 360 365

Gly Lys Pro Val Ile Glu Ser Leu Gly Leu Pro Gly Phe Gly Tyr His
370 375 380

-continued

```
Ser Asp Lys Ala Glu Tyr Val Asp Ile Ser Ala Ile Pro Arg Arg Leu
385                 390                 395                 400

Tyr Met Ala Ala Arg Leu Ile Met Asp Leu Gly Ala Gly Lys Tyr Pro
                405                 410                 415

Tyr Asp Val Pro Asp Tyr Ala Gly Gly Gly Ile Tyr Ile Trp Ala Pro
            420                 425                 430

Leu Ala Gly Thr Cys Gly Val Leu Leu Leu Ser Leu Val Ile Thr Leu
        435                 440                 445

Tyr Cys Asn His Arg Asn Arg Arg Arg Val Gly Gly Gly Arg Pro Val
    450                 455                 460

Val Lys Ser Gly Asp Lys Pro Ser Leu Ser Ala Arg Tyr Val
465                 470                 475
```

<210> SEQ ID NO 41
<211> LENGTH: 1437
<212> TYPE: DNA
<213> ORGANISM: Homo sapiens

<400> SEQUENCE: 41

```
atggccttgc ccgttaccgc actcctgctg ccgctggcgc tgttgctgca cgcagctcga     60

ccggccctcg cgcaaaaacg ggacaatgta ttgttccaag cggctactga tgaacagcca    120

gcagtaatta aaacgcttga aaaacttgtc aacatcgaga ccgggacagg ggatgctgaa    180

gggattgcag ccgcaggaaa ctttcttgaa gccgaactca aaaaccttgg gtttaccgta    240

acgcgctcta agtcagccgg tttggtcgta ggtgacaaca ttgtgggaaa gatcaaggga    300

cggggcggta aaaacttgct tttgatgtct catatggata ctgtatatct taaggggatc    360

ctcgcgaagg cgccctttcg ggtggaaggc gataaggcat atggaccagg gatagctgac    420

gacaaggggg gtaacgcggt cattctccac acactgaaac ttcttaaaga atacggtgtg    480

agagattatg ggacgatcac tgtactgttc aacaccgatg aggaaaaggg ctcttttggc    540

tctagagatt tgattcaaga agaagcgaaa ctggcagact acgtgttgtc cttcgaaccc    600

acatctgctg gcgatgagaa gctcagtctt ggaacctctg ggattgcgta cgtccaggtc    660

caaataaccg gaaaggcaag ccatgctgga gcagccccag aacttggcgt aaatgcgctg    720

gtggaggcga gtgatctggt gctccggacc atgaacatag atgacaaagc caaaaatctg    780

aggtttcaat ggaccatcgc taaagcaggg caggtctcta atatcatccc ggcttcagcc    840

actttgaacg ccgatgttag gtacgcccgg aatgaagatt ttgatgccgc tatgaaaaca    900

ttggaggaac gagcgcagca aaaaaagctg ccagaagccg atgttaaagt aatagtaact    960

agaggacgac ccgcgttcaa tgcgggcgag ggtggaaaga agttggtcga taaggctgtt   1020

gcgtactata aggaagcggg ggtacgctt ggagttgagg agaggaccgg agggggcact   1080

gacgcggcgt acgccgccct ctcaggcaag cccgtaattg agtcacttgg gcttcctggt   1140

tttggttatc actcagacaa ggccgagtac gtggatatat cagctatccc tcggcgattg   1200

tacatggcgg cacgcttgat aatggatttg gggctggaa agtatcctta tgatgttcca   1260

gactacgcag gggcggaat ctacatctgg gcgcccctgg ccgggacttg tggggtcctt   1320

ctcctgtcac tggttatcac cctgtattgt aaccaccgaa atcgacggcg agtaggagga   1380

ggacgaccag ttgttaaatc tggggataaa ccttcactgt ccgctagata cgtgtaa      1437
```

<210> SEQ ID NO 42
<211> LENGTH: 491
<212> TYPE: PRT

-continued

<213> ORGANISM: Homo sapiens

<400> SEQUENCE: 42

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Pro Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Asn Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

```
Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 43
<211> LENGTH: 381
<212> TYPE: PRT
<213> ORGANISM: Homo sapiens

<400> SEQUENCE: 43

Met Met Arg Lys Ser Leu Cys Cys Ala Leu Leu Leu Gly Ile Ser Cys
1               5                   10                  15

Ser Ala Leu Ala Thr Pro Val Ser Glu Lys Gln Leu Ala Glu Val Val
            20                  25                  30

Ala Asn Thr Ile Thr Pro Leu Met Lys Ala Gln Ser Val Pro Gly Met
        35                  40                  45

Ala Val Ala Val Ile Tyr Gln Gly Lys Pro His Tyr Tyr Thr Phe Gly
    50                  55                  60

Lys Ala Asp Ile Ala Ala Asn Lys Pro Val Thr Pro Gln Thr Leu Phe
65                  70                  75                  80

Glu Leu Gly Ser Ile Ser Lys Thr Phe Thr Gly Val Leu Gly Gly Asp
                85                  90                  95

Ala Ile Ala Arg Gly Glu Ile Ser Leu Asp Asp Ala Val Thr Arg Tyr
            100                 105                 110

Trp Pro Gln Leu Thr Gly Lys Gln Trp Gln Gly Ile Arg Met Leu Asp
        115                 120                 125

Leu Ala Thr Tyr Thr Ala Gly Gly Leu Pro Leu Gln Val Pro Asp Glu
    130                 135                 140

Val Thr Asp Asn Ala Ser Leu Leu Arg Phe Tyr Gln Asn Trp Gln Pro
145                 150                 155                 160

Gln Trp Lys Pro Gly Thr Thr Arg Leu Tyr Ala Asn Ala Ser Ile Gly
                165                 170                 175

Leu Phe Gly Ala Leu Ala Val Lys Pro Ser Gly Met Pro Tyr Glu Gln
            180                 185                 190

Ala Met Thr Thr Arg Val Leu Lys Pro Leu Lys Leu Asp His Thr Trp
        195                 200                 205

Ile Asn Val Pro Lys Ala Glu Glu Ala His Tyr Ala Trp Gly Tyr Arg
    210                 215                 220

Asp Gly Lys Ala Val Arg Val Ser Pro Gly Met Leu Asp Ala Gln Ala
225                 230                 235                 240

Tyr Gly Val Lys Thr Asn Val Gln Asp Met Ala Asn Trp Val Met Ala
                245                 250                 255

Asn Met Ala Pro Glu Asn Val Ala Asp Ala Ser Leu Lys Gln Gly Ile
            260                 265                 270

Ala Leu Ala Gln Ser Arg Tyr Trp Arg Ile Gly Ser Met Tyr Gln Gly
        275                 280                 285
```

```
Leu Gly Trp Glu Met Leu Asn Trp Pro Val Glu Ala Asn Thr Val Val
    290                 295                 300

Glu Gly Ser Asp Ser Lys Val Ala Leu Ala Pro Leu Pro Val Ala Glu
305                 310                 315                 320

Val Asn Pro Pro Ala Pro Pro Val Lys Ala Ser Trp Val His Lys Thr
                325                 330                 335

Gly Ser Thr Gly Gly Phe Gly Ser Tyr Val Ala Phe Ile Pro Glu Lys
            340                 345                 350

Gln Ile Gly Ile Val Met Leu Ala Asn Thr Ser Tyr Pro Asn Pro Ala
        355                 360                 365

Arg Val Glu Ala Ala Tyr His Ile Leu Glu Ala Leu Gln
    370                 375                 380


<210> SEQ ID NO 44
<211> LENGTH: 361
<212> TYPE: PRT
<213> ORGANISM: Homo sapiens

<400> SEQUENCE: 44

Thr Pro Val Ser Glu Lys Gln Leu Ala Glu Val Val Ala Asn Thr Ile
1               5                   10                  15

Thr Pro Leu Met Ala Ala Gln Ser Val Pro Gly Met Ala Val Ala Val
            20                  25                  30

Ile Tyr Gln Gly Lys Pro His Tyr Tyr Thr Phe Gly Lys Ala Asp Ile
        35                  40                  45

Ala Ala Asn Lys Pro Val Thr Pro Gln Thr Leu Phe Glu Leu Gly Ser
    50                  55                  60

Ile Ser Lys Thr Phe Thr Gly Val Leu Gly Gly Asp Ala Ile Ala Arg
65                  70                  75                  80

Gly Glu Ile Ser Leu Asp Asp Ala Val Thr Arg Tyr Trp Pro Gln Leu
                85                  90                  95

Thr Gly Lys Gln Trp Gln Gly Ile Arg Met Leu Asp Leu Ala Thr Tyr
            100                 105                 110

Thr Ala Gly Gly Leu Pro Leu Gln Val Pro Asp Glu Val Thr Asp Asn
        115                 120                 125

Ala Ser Leu Leu Arg Phe Tyr Gln Asn Trp Gln Pro Gln Trp Lys Pro
    130                 135                 140

Gly Thr Thr Arg Leu Tyr Ala Asn Ala Ser Ile Gly Leu Phe Gly Ala
145                 150                 155                 160

Leu Ala Val Lys Pro Ser Gly Met Pro Tyr Glu Gln Ala Met Thr Thr
                165                 170                 175

Arg Val Leu Lys Pro Leu Lys Leu Asp His Thr Trp Ile Asn Val Pro
            180                 185                 190

Lys Ala Glu Glu Ala His Tyr Ala Trp Gly Tyr Arg Asp Gly Lys Ala
        195                 200                 205

Val Arg Val Ser Pro Gly Met Leu Asp Ala Gln Ala Tyr Gly Val Lys
    210                 215                 220

Thr Asn Val Gln Asp Met Ala Asn Trp Val Met Ala Asn Met Ala Pro
225                 230                 235                 240

Glu Asn Val Ala Asp Ala Ser Leu Lys Gln Gly Ile Ala Leu Ala Gln
                245                 250                 255

Ser Arg Tyr Trp Arg Ile Gly Ser Met Tyr Gln Gly Leu Gly Trp Glu
            260                 265                 270

Met Leu Asn Trp Pro Val Glu Ala Asn Thr Val Val Glu Gly Ser Asp
```

```
        275                 280                 285

Ser Lys Val Ala Leu Ala Pro Leu Pro Val Ala Glu Val Asn Pro Pro
    290                 295                 300

Ala Pro Pro Val Lys Ala Ser Trp Val His Lys Thr Gly Ser Thr Gly
305                 310                 315                 320

Gly Phe Gly Ala Tyr Val Ala Phe Ile Pro Glu Lys Gln Ile Gly Ile
                325                 330                 335

Val Met Leu Ala Asn Thr Ser Tyr Pro Asn Pro Ala Arg Val Glu Ala
            340                 345                 350

Ala Tyr His Ile Leu Glu Ala Leu Gln
        355                 360


<210> SEQ ID NO 45
<211> LENGTH: 381
<212> TYPE: PRT
<213> ORGANISM: Homo sapiens

<400> SEQUENCE: 45

Met Met Arg Lys Ser Leu Cys Cys Ala Leu Leu Leu Gly Ile Ser Cys
1               5                   10                  15

Ser Ala Leu Ala Thr Pro Val Ser Glu Lys Gln Leu Ala Glu Val Val
            20                  25                  30

Ala Asn Thr Ile Thr Pro Leu Met Ala Ala Gln Ser Val Pro Gly Met
        35                  40                  45

Ala Val Ala Val Ile Tyr Gln Gly Lys Pro His Tyr Tyr Thr Phe Gly
    50                  55                  60

Lys Ala Asp Ile Ala Ala Asn Lys Pro Val Thr Pro Gln Thr Leu Phe
65                  70                  75                  80

Glu Leu Gly Ser Ile Ser Lys Thr Phe Thr Gly Val Leu Gly Gly Asp
                85                  90                  95

Ala Ile Ala Arg Gly Glu Ile Ser Leu Asp Asp Ala Val Thr Arg Tyr
            100                 105                 110

Trp Pro Gln Leu Thr Gly Lys Gln Trp Gln Gly Ile Arg Met Leu Asp
        115                 120                 125

Leu Ala Thr Tyr Thr Ala Gly Gly Leu Pro Leu Gln Val Pro Asp Glu
    130                 135                 140

Val Thr Asp Asn Ala Ser Leu Leu Arg Phe Tyr Gln Asn Trp Gln Pro
145                 150                 155                 160

Gln Trp Lys Pro Gly Thr Thr Arg Leu Tyr Ala Asn Ala Ser Ile Gly
                165                 170                 175

Leu Phe Gly Ala Leu Ala Val Lys Pro Ser Gly Met Pro Tyr Glu Gln
            180                 185                 190

Ala Met Thr Thr Arg Val Leu Lys Pro Leu Lys Leu Asp His Thr Trp
        195                 200                 205

Ile Asn Val Pro Lys Ala Glu Glu Ala His Tyr Ala Trp Gly Tyr Arg
    210                 215                 220

Asp Gly Lys Ala Val Arg Val Ser Pro Gly Met Leu Asp Ala Gln Ala
225                 230                 235                 240

Tyr Gly Val Lys Thr Asn Val Gln Asp Met Ala Asn Trp Val Met Ala
                245                 250                 255

Asn Met Ala Pro Glu Asn Val Ala Asp Ala Ser Leu Lys Gln Gly Ile
            260                 265                 270

Ala Leu Ala Gln Ser Arg Tyr Trp Arg Ile Gly Ser Met Tyr Gln Gly
        275                 280                 285
```

-continued

Leu Gly Trp Glu Met Leu Asn Trp Pro Val Glu Ala Asn Thr Val Val
    290                 295                 300

Glu Gly Ser Asp Ser Lys Val Ala Leu Ala Pro Leu Pro Val Ala Glu
305                 310                 315                 320

Val Asn Pro Pro Ala Pro Pro Val Lys Ala Ser Trp Val His Lys Thr
                325                 330                 335

Gly Ser Thr Gly Gly Phe Gly Ala Tyr Val Ala Phe Ile Pro Glu Lys
            340                 345                 350

Gln Ile Gly Ile Val Met Leu Ala Asn Thr Ser Tyr Pro Asn Pro Ala
        355                 360                 365

Arg Val Glu Ala Ala Tyr His Ile Leu Glu Ala Leu Gln
    370                 375                 380

<210> SEQ ID NO 46
<211> LENGTH: 391
<212> TYPE: PRT
<213> ORGANISM: Homo sapiens

<400> SEQUENCE: 46

Met Ala Leu Pro Val Thr Ala Leu Leu Leu Pro Leu Ala Leu Leu Leu
1               5                   10                  15

His Ala Ala Arg Pro Thr Pro Val Ser Glu Lys Gln Leu Ala Glu Val
            20                  25                  30

Val Ala Asn Thr Ile Thr Pro Leu Met Ala Ala Gln Ser Val Pro Gly
        35                  40                  45

Met Ala Val Ala Val Ile Tyr Gln Gly Lys Pro His Tyr Tyr Thr Phe
    50                  55                  60

Gly Lys Ala Asp Ile Ala Ala Asn Lys Pro Val Thr Pro Gln Thr Leu
65                  70                  75                  80

Phe Glu Leu Gly Ser Ile Ser Lys Thr Phe Thr Gly Val Leu Gly Gly
                85                  90                  95

Asp Ala Ile Ala Arg Gly Glu Ile Ser Leu Asp Asp Ala Val Thr Arg
            100                 105                 110

Tyr Trp Pro Gln Leu Thr Gly Lys Gln Trp Gln Gly Ile Arg Met Leu
        115                 120                 125

Asp Leu Ala Thr Tyr Thr Ala Gly Gly Leu Pro Leu Gln Val Pro Asp
    130                 135                 140

Glu Val Thr Asp Asn Ala Ser Leu Leu Arg Phe Tyr Gln Asn Trp Gln
145                 150                 155                 160

Pro Gln Trp Lys Pro Gly Thr Thr Arg Leu Tyr Ala Asn Ala Ser Ile
                165                 170                 175

Gly Leu Phe Gly Ala Leu Ala Val Lys Pro Ser Gly Met Pro Tyr Glu
            180                 185                 190

Gln Ala Met Thr Thr Arg Val Leu Lys Pro Leu Lys Leu Asp His Thr
        195                 200                 205

Trp Ile Asn Val Pro Lys Ala Glu Glu Ala His Tyr Ala Trp Gly Tyr
    210                 215                 220

Arg Asp Gly Lys Ala Val Arg Val Ser Pro Gly Met Leu Asp Ala Gln
225                 230                 235                 240

Ala Tyr Gly Val Lys Thr Asn Val Gln Asp Met Ala Asn Trp Val Met
                245                 250                 255

Ala Asn Met Ala Pro Glu Asn Val Ala Asp Ala Ser Leu Lys Gln Gly
            260                 265                 270

Ile Ala Leu Ala Gln Ser Arg Tyr Trp Arg Ile Gly Ser Met Tyr Gln
        275                 280                 285

```
Gly Leu Gly Trp Glu Met Leu Asn Trp Pro Val Glu Ala Asn Thr Val
    290                 295                 300

Val Glu Gly Ser Asp Ser Lys Val Ala Leu Ala Pro Leu Pro Val Ala
305                 310                 315                 320

Glu Val Asn Pro Pro Ala Pro Pro Val Lys Ala Ser Trp Val His Lys
                325                 330                 335

Thr Gly Ser Thr Gly Gly Phe Gly Ala Tyr Val Ala Phe Ile Pro Glu
            340                 345                 350

Lys Gln Ile Gly Ile Val Met Leu Ala Asn Thr Ser Tyr Pro Asn Pro
        355                 360                 365

Ala Arg Val Glu Ala Ala Tyr His Ile Leu Glu Ala Leu Gln Tyr Pro
    370                 375                 380

Tyr Asp Val Pro Asp Tyr Ala
385                 390


<210> SEQ ID NO 47
<211> LENGTH: 426
<212> TYPE: PRT
<213> ORGANISM: Homo sapiens

<400> SEQUENCE: 47

Met Ala Leu Pro Val Thr Ala Leu Leu Leu Pro Leu Ala Leu Leu Leu
1               5                   10                  15

His Ala Ala Arg Pro Thr Pro Val Ser Glu Lys Gln Leu Ala Glu Val
            20                  25                  30

Val Ala Asn Thr Ile Thr Pro Leu Met Ala Ala Gln Ser Val Pro Gly
        35                  40                  45

Met Ala Val Ala Val Ile Tyr Gln Gly Lys Pro His Tyr Tyr Thr Phe
    50                  55                  60

Gly Lys Ala Asp Ile Ala Ala Asn Lys Pro Val Thr Pro Gln Thr Leu
65                  70                  75                  80

Phe Glu Leu Gly Ser Ile Ser Lys Thr Phe Thr Gly Val Leu Gly Gly
                85                  90                  95

Asp Ala Ile Ala Arg Gly Glu Ile Ser Leu Asp Asp Ala Val Thr Arg
            100                 105                 110

Tyr Trp Pro Gln Leu Thr Gly Lys Gln Trp Gln Gly Ile Arg Met Leu
        115                 120                 125

Asp Leu Ala Thr Tyr Thr Ala Gly Gly Leu Pro Leu Gln Val Pro Asp
    130                 135                 140

Glu Val Thr Asp Asn Ala Ser Leu Leu Arg Phe Tyr Gln Asn Trp Gln
145                 150                 155                 160

Pro Gln Trp Lys Pro Gly Thr Thr Arg Leu Tyr Ala Asn Ala Ser Ile
                165                 170                 175

Gly Leu Phe Gly Ala Leu Ala Val Lys Pro Ser Gly Met Pro Tyr Glu
            180                 185                 190

Gln Ala Met Thr Thr Arg Val Leu Lys Pro Leu Lys Leu Asp His Thr
        195                 200                 205

Trp Ile Asn Val Pro Lys Ala Glu Glu Ala His Tyr Ala Trp Gly Tyr
    210                 215                 220

Arg Asp Gly Lys Ala Val Arg Val Ser Pro Gly Met Leu Asp Ala Gln
225                 230                 235                 240

Ala Tyr Gly Val Lys Thr Asn Val Gln Asp Met Ala Asn Trp Val Met
                245                 250                 255

Ala Asn Met Ala Pro Glu Asn Val Ala Asp Ala Ser Leu Lys Gln Gly
```

```
            260                 265                 270

Ile Ala Leu Ala Gln Ser Arg Tyr Trp Arg Ile Gly Ser Met Tyr Gln
        275                 280                 285

Gly Leu Gly Trp Glu Met Leu Asn Trp Pro Val Glu Ala Asn Thr Val
    290                 295                 300

Val Glu Gly Ser Asp Ser Lys Val Ala Leu Ala Pro Leu Pro Val Ala
305                 310                 315                 320

Glu Val Asn Pro Pro Ala Pro Pro Val Lys Ala Ser Trp Val His Lys
                325                 330                 335

Thr Gly Ser Thr Gly Gly Phe Gly Ala Tyr Val Ala Phe Ile Pro Glu
            340                 345                 350

Lys Gln Ile Gly Ile Val Met Leu Ala Asn Thr Ser Tyr Pro Asn Pro
        355                 360                 365

Ala Arg Val Glu Ala Ala Tyr His Ile Leu Glu Ala Leu Gln Tyr Pro
    370                 375                 380

Tyr Asp Val Pro Asp Tyr Ala Gly Gly Gly Leu Tyr Cys Asn His Arg
385                 390                 395                 400

Asn Arg Arg Arg Val Cys Lys Cys Pro Arg Pro Val Val Lys Ser Gly
                405                 410                 415

Asp Lys Pro Ser Leu Ser Ala Arg Tyr Val
            420                 425


<210> SEQ ID NO 48
<211> LENGTH: 970
<212> TYPE: PRT
<213> ORGANISM: Homo sapiens

<400> SEQUENCE: 48

Met Ala Leu Pro Val Thr Ala Leu Leu Leu Pro Leu Ala Leu Leu Leu
1               5                   10                  15

His Ala Ala Arg Pro Ala Leu Ala Gln Lys Arg Asp Asn Val Leu Phe
            20                  25                  30

Gln Ala Ala Thr Asp Glu Gln Pro Ala Val Ile Lys Thr Leu Glu Lys
        35                  40                  45

Leu Val Asn Ile Glu Thr Gly Thr Gly Asp Ala Glu Gly Ile Ala Ala
    50                  55                  60

Ala Gly Asn Phe Leu Glu Ala Glu Leu Lys Asn Leu Gly Phe Thr Val
65                  70                  75                  80

Thr Arg Ser Lys Ser Ala Gly Leu Val Val Gly Asp Asn Ile Val Gly
                85                  90                  95

Lys Ile Lys Gly Arg Gly Gly Lys Asn Leu Leu Leu Met Ser His Met
            100                 105                 110

Asp Thr Val Tyr Leu Lys Gly Ile Leu Ala Lys Ala Pro Phe Arg Val
        115                 120                 125

Glu Gly Asp Lys Ala Tyr Gly Pro Gly Ile Ala Asp Asp Lys Gly Gly
    130                 135                 140

Asn Ala Val Ile Leu His Thr Leu Lys Leu Leu Lys Glu Tyr Gly Val
145                 150                 155                 160

Arg Asp Tyr Gly Thr Ile Thr Val Leu Phe Asn Thr Asp Glu Glu Lys
                165                 170                 175

Gly Ser Phe Gly Ser Arg Asp Leu Ile Gln Glu Glu Ala Lys Leu Ala
            180                 185                 190

Asp Tyr Val Leu Ser Phe Glu Pro Thr Ser Ala Gly Asp Glu Lys Leu
        195                 200                 205
```

-continued

```
Ser Leu Gly Thr Ser Gly Ile Ala Tyr Val Gln Val Gln Ile Thr Gly
    210                 215                 220

Lys Ala Ser His Ala Gly Ala Ala Pro Glu Leu Gly Val Asn Ala Leu
225                 230                 235                 240

Val Glu Ala Ser Asp Leu Val Leu Arg Thr Met Asn Ile Asp Asp Lys
                245                 250                 255

Ala Lys Asn Leu Arg Phe Gln Trp Thr Ile Ala Lys Ala Gly Gln Val
            260                 265                 270

Ser Asn Ile Ile Pro Ala Ser Ala Thr Leu Asn Ala Asp Val Arg Tyr
        275                 280                 285

Ala Arg Asn Glu Asp Phe Asp Ala Ala Met Lys Thr Leu Glu Glu Arg
    290                 295                 300

Ala Gln Gln Lys Lys Leu Pro Glu Ala Asp Val Lys Val Ile Val Thr
305                 310                 315                 320

Arg Gly Arg Pro Ala Phe Asn Ala Gly Glu Gly Gly Lys Lys Leu Val
                325                 330                 335

Asp Lys Ala Val Ala Tyr Tyr Lys Glu Ala Gly Gly Thr Leu Gly Val
            340                 345                 350

Glu Glu Arg Thr Gly Gly Gly Thr Asp Ala Ala Tyr Ala Ala Leu Ser
        355                 360                 365

Gly Lys Pro Val Ile Glu Ser Leu Gly Leu Pro Gly Phe Gly Tyr His
    370                 375                 380

Ser Asp Lys Ala Glu Tyr Val Asp Ile Ser Ala Ile Pro Arg Arg Leu
385                 390                 395                 400

Tyr Met Ala Ala Arg Leu Ile Met Asp Leu Gly Ala Gly Lys Tyr Pro
                405                 410                 415

Tyr Asp Val Pro Asp Tyr Ala Gly Gly Leu Tyr Cys Asn His Arg
            420                 425                 430

Asn Arg Arg Arg Val Cys Lys Cys Pro Arg Pro Val Val Lys Ser Gly
        435                 440                 445

Asp Lys Pro Ser Leu Ser Ala Arg Tyr Val Gly Ser Gly Ala Thr Asn
    450                 455                 460

Phe Ser Leu Leu Lys Gln Ala Gly Asp Val Glu Glu Asn Pro Gly Pro
465                 470                 475                 480

Ala Leu Pro Val Thr Ala Leu Leu Leu Pro Leu Ala Leu Leu Leu His
                485                 490                 495

Ala Glu Val Lys Leu Gln Gln Ser Gly Ala Glu Leu Val Arg Pro Gly
            500                 505                 510

Ser Ser Val Lys Ile Ser Cys Lys Ala Ser Gly Tyr Ala Phe Ser Ser
        515                 520                 525

Tyr Trp Met Asn Trp Val Lys Gln Arg Pro Gly Gln Gly Leu Glu Trp
    530                 535                 540

Ile Gly Gln Ile Tyr Pro Gly Asp Gly Asp Thr Asn Tyr Asn Gly Lys
545                 550                 555                 560

Phe Lys Gly Gln Ala Thr Leu Thr Ala Asp Lys Ser Ser Ser Thr Ala
                565                 570                 575

Tyr Met Gln Leu Ser Gly Leu Thr Ser Glu Asp Ser Ala Val Tyr Phe
            580                 585                 590

Cys Ala Arg Lys Thr Ile Ser Ser Val Val Asp Phe Tyr Phe Asp Tyr
        595                 600                 605

Trp Gly Gln Gly Thr Thr Val Thr Val Ser Ser Gly Gly Gly Gly Ser
    610                 615                 620

Gly Gly Gly Gly Ser Gly Gly Gly Gly Ser Asp Ile Glu Leu Thr Gln
```

```
625                 630                 635                 640

Ser Pro Lys Phe Met Ser Thr Ser Val Gly Asp Arg Val Ser Val Thr
                645                 650                 655

Cys Lys Ala Ser Gln Asn Val Gly Thr Asn Val Ala Trp Tyr Gln Gln
            660                 665                 670

Lys Pro Gly Gln Ser Pro Lys Pro Leu Ile Tyr Ser Ala Thr Tyr Arg
        675                 680                 685

Asn Ser Gly Val Pro Asp Arg Phe Thr Gly Ser Gly Ser Gly Thr Asp
    690                 695                 700

Phe Thr Leu Thr Ile Thr Asn Val Gln Ser Lys Asp Leu Ala Asp Tyr
705                 710                 715                 720

Phe Cys Gln Gln Tyr Asn Arg Tyr Pro Tyr Thr Ser Gly Gly Gly Thr
                725                 730                 735

Lys Leu Glu Ile Lys Arg Ala Ala Ala Pro Thr Thr Thr Pro Ala Pro
            740                 745                 750

Arg Pro Pro Thr Pro Ala Pro Thr Ile Ala Ser Gln Pro Leu Ser Leu
        755                 760                 765

Arg Pro Glu Ala Cys Arg Pro Ala Ala Gly Gly Ala Val His Thr Arg
    770                 775                 780

Gly Leu Asp Phe Ala Cys Asp Ile Tyr Ile Trp Ala Pro Leu Ala Gly
785                 790                 795                 800

Thr Cys Gly Val Leu Leu Leu Ser Leu Val Ile Thr Leu Tyr Cys Asn
                805                 810                 815

Lys Arg Gly Arg Lys Lys Leu Leu Tyr Ile Phe Lys Gln Pro Phe Met
            820                 825                 830

Arg Pro Val Gln Thr Thr Gln Glu Glu Asp Gly Cys Ser Cys Arg Phe
        835                 840                 845

Pro Glu Glu Glu Glu Gly Gly Cys Glu Leu Arg Val Lys Phe Ser Arg
    850                 855                 860

Ser Ala Asp Ala Pro Ala Tyr Gln Gln Gly Gln Asn Gln Leu Tyr Asn
865                 870                 875                 880

Glu Leu Asn Leu Gly Arg Arg Glu Glu Tyr Asp Val Leu Asp Lys Arg
                885                 890                 895

Arg Gly Arg Asp Pro Glu Met Gly Gly Lys Pro Arg Arg Lys Asn Pro
            900                 905                 910

Gln Glu Gly Leu Tyr Asn Glu Leu Gln Lys Asp Lys Met Ala Glu Ala
        915                 920                 925

Tyr Ser Glu Ile Gly Met Lys Gly Glu Arg Arg Arg Gly Lys Gly His
    930                 935                 940

Asp Gly Leu Tyr Gln Gly Leu Ser Thr Ala Thr Lys Asp Thr Tyr Asp
945                 950                 955                 960

Ala Leu His Met Gln Ala Leu Pro Pro Arg
                965                 970


<210> SEQ ID NO 49
<211> LENGTH: 911
<212> TYPE: PRT
<213> ORGANISM: Homo sapiens

<400> SEQUENCE: 49

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30
```

```
Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Pro Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Asn Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
```

```
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Gln Pro Leu Glu Gly
                485                 490                 495

Ser Gly Ala Thr Asn Phe Ser Leu Leu Lys Gln Ala Gly Asp Val Glu
            500                 505                 510

Glu Asn Pro Gly Pro Met Ala Leu Ala Gln Lys Arg Asp Asn Val Leu
        515                 520                 525

Phe Gln Ala Ala Thr Asp Glu Gln Pro Ala Val Ile Lys Thr Leu Glu
    530                 535                 540

Lys Leu Val Asn Ile Glu Thr Gly Thr Gly Asp Ala Glu Gly Ile Ala
545                 550                 555                 560

Ala Ala Gly Asn Phe Leu Glu Ala Glu Leu Lys Asn Leu Gly Phe Thr
                565                 570                 575

Val Thr Arg Ser Lys Ser Ala Gly Leu Val Val Gly Asp Asn Ile Val
            580                 585                 590

Gly Lys Ile Lys Gly Arg Gly Gly Lys Asn Leu Leu Leu Met Ser His
        595                 600                 605

Met Asp Thr Val Tyr Leu Lys Gly Ile Leu Ala Lys Ala Pro Phe Arg
    610                 615                 620

Val Glu Gly Asp Lys Ala Tyr Gly Pro Gly Ile Ala Asp Asp Lys Gly
625                 630                 635                 640

Gly Asn Ala Val Ile Leu His Thr Leu Lys Leu Leu Lys Glu Tyr Gly
                645                 650                 655

Val Arg Asp Tyr Gly Thr Ile Thr Val Leu Phe Asn Thr Asp Glu Glu
            660                 665                 670

Lys Gly Ser Phe Gly Ser Arg Asp Leu Ile Gln Glu Glu Ala Lys Leu
        675                 680                 685

Ala Asp Tyr Val Leu Ser Phe Glu Pro Thr Ser Ala Gly Asp Glu Lys
    690                 695                 700

Leu Ser Leu Gly Thr Ser Gly Ile Ala Tyr Val Gln Val Gln Ile Thr
705                 710                 715                 720

Gly Lys Ala Ser His Ala Gly Ala Ala Pro Glu Leu Gly Val Asn Ala
                725                 730                 735

Leu Val Glu Ala Ser Asp Leu Val Leu Arg Thr Met Asn Ile Asp Asp
            740                 745                 750

Lys Ala Lys Asn Leu Arg Phe Gln Trp Thr Ile Ala Lys Ala Gly Gln
        755                 760                 765

Val Ser Asn Ile Ile Pro Ala Ser Ala Thr Leu Asn Ala Asp Val Arg
    770                 775                 780

Tyr Ala Arg Asn Glu Asp Phe Asp Ala Ala Met Lys Thr Leu Glu Glu
785                 790                 795                 800

Arg Ala Gln Gln Lys Lys Leu Pro Glu Ala Asp Val Lys Val Ile Val
                805                 810                 815

Thr Arg Gly Arg Pro Ala Phe Asn Ala Gly Glu Gly Gly Lys Lys Leu
            820                 825                 830

Val Asp Lys Ala Val Ala Tyr Tyr Lys Glu Ala Gly Gly Thr Leu Gly
        835                 840                 845

Val Glu Glu Arg Thr Gly Gly Gly Thr Asp Ala Ala Tyr Ala Ala Leu
    850                 855                 860

Ser Gly Lys Pro Val Ile Glu Ser Leu Gly Leu Pro Gly Phe Gly Tyr
865                 870                 875                 880
```

His Ser Asp Lys Ala Glu Tyr Val Asp Ile Ser Ala Ile Pro Arg Arg
885 890 895

Leu Tyr Met Ala Ala Arg Leu Ile Met Asp Leu Gly Ala Gly Lys
900 905 910

<210> SEQ ID NO 50
<211> LENGTH: 880
<212> TYPE: PRT
<213> ORGANISM: Homo sapiens

<400> SEQUENCE: 50

Met Thr Pro Val Ser Glu Lys Gln Leu Ala Glu Val Val Ala Asn Thr
1 5 10 15

Ile Thr Pro Leu Met Ala Ala Gln Ser Val Pro Gly Met Ala Val Ala
20 25 30

Val Ile Tyr Gln Gly Lys Pro His Tyr Tyr Thr Phe Gly Lys Ala Asp
35 40 45

Ile Ala Ala Asn Lys Pro Val Thr Pro Gln Thr Leu Phe Glu Leu Gly
50 55 60

Ser Ile Ser Lys Thr Phe Thr Gly Val Leu Gly Gly Asp Ala Ile Ala
65 70 75 80

Arg Gly Glu Ile Ser Leu Asp Asp Ala Val Thr Arg Tyr Trp Pro Gln
85 90 95

Leu Thr Gly Lys Gln Trp Gln Gly Ile Arg Met Leu Asp Leu Ala Thr
100 105 110

Tyr Thr Ala Gly Gly Leu Pro Leu Gln Val Pro Asp Glu Val Thr Asp
115 120 125

Asn Ala Ser Leu Leu Arg Phe Tyr Gln Asn Trp Gln Pro Gln Trp Lys
130 135 140

Pro Gly Thr Thr Arg Leu Tyr Ala Asn Ala Ser Ile Gly Leu Phe Gly
145 150 155 160

Ala Leu Ala Val Lys Pro Ser Gly Met Pro Tyr Glu Gln Ala Met Thr
165 170 175

Thr Arg Val Leu Lys Pro Leu Lys Leu Asp His Thr Trp Ile Asn Val
180 185 190

Pro Lys Ala Glu Glu Ala His Tyr Ala Trp Gly Tyr Arg Asp Gly Lys
195 200 205

Ala Val Arg Val Ser Pro Gly Met Leu Asp Ala Gln Ala Tyr Gly Val
210 215 220

Lys Thr Asn Val Gln Asp Met Ala Asn Trp Val Met Ala Asn Met Ala
225 230 235 240

Pro Glu Asn Val Ala Asp Ala Ser Leu Lys Gln Gly Ile Ala Leu Ala
245 250 255

Gln Ser Arg Tyr Trp Arg Ile Gly Ser Met Tyr Gln Gly Leu Gly Trp
260 265 270

Glu Met Leu Asn Trp Pro Val Glu Ala Asn Thr Val Val Glu Gly Ser
275 280 285

Asp Ser Lys Val Ala Leu Ala Pro Leu Pro Val Ala Glu Val Asn Pro
290 295 300

Pro Ala Pro Pro Val Lys Ala Ser Trp Val His Lys Thr Gly Ser Thr
305 310 315 320

Gly Gly Phe Gly Ala Tyr Val Ala Phe Ile Pro Glu Lys Gln Ile Gly
325 330 335

Ile Val Met Leu Ala Asn Thr Ser Tyr Pro Asn Pro Ala Arg Val Glu

-continued

```
            340                 345                 350

Ala Ala Tyr His Ile Leu Glu Ala Leu Gln Tyr Pro Tyr Asp Val Pro
        355                 360                 365

Asp Tyr Ala Ala Thr Asn Phe Ser Leu Leu Lys Gln Ala Gly Asp Val
    370                 375                 380

Glu Glu Asn Pro Gly Pro Ala Leu Pro Val Thr Ala Leu Leu Leu Pro
385                 390                 395                 400

Leu Ala Leu Leu Leu His Ala Glu Val Lys Leu Gln Gln Ser Gly Ala
                405                 410                 415

Glu Leu Val Arg Pro Gly Ser Ser Val Lys Ile Ser Cys Lys Ala Ser
            420                 425                 430

Gly Tyr Ala Phe Ser Ser Tyr Trp Met Asn Trp Val Lys Gln Arg Pro
        435                 440                 445

Gly Gln Gly Leu Glu Trp Ile Gly Gln Ile Tyr Pro Gly Asp Gly Asp
    450                 455                 460

Thr Asn Tyr Asn Gly Lys Phe Lys Gly Gln Ala Thr Leu Thr Ala Asp
465                 470                 475                 480

Lys Ser Ser Ser Thr Ala Tyr Met Gln Leu Ser Gly Leu Thr Ser Glu
                485                 490                 495

Asp Ser Ala Val Tyr Phe Cys Ala Arg Lys Thr Ile Ser Ser Val Val
            500                 505                 510

Asp Phe Tyr Phe Asp Tyr Trp Gly Gln Gly Thr Thr Val Thr Val Ser
        515                 520                 525

Ser Gly Gly Gly Gly Ser Gly Gly Gly Gly Ser Gly Gly Gly Gly Ser
    530                 535                 540

Asp Ile Glu Leu Thr Gln Ser Pro Lys Phe Met Ser Thr Ser Val Gly
545                 550                 555                 560

Asp Arg Val Ser Val Thr Cys Lys Ala Ser Gln Asn Val Gly Thr Asn
                565                 570                 575

Val Ala Trp Tyr Gln Gln Lys Pro Gly Gln Ser Pro Lys Pro Leu Ile
            580                 585                 590

Tyr Ser Ala Thr Tyr Arg Asn Ser Gly Val Pro Asp Arg Phe Thr Gly
        595                 600                 605

Ser Gly Ser Gly Thr Asp Phe Thr Leu Thr Ile Thr Asn Val Gln Ser
    610                 615                 620

Lys Asp Leu Ala Asp Tyr Phe Cys Gln Gln Tyr Asn Arg Tyr Pro Tyr
625                 630                 635                 640

Thr Ser Gly Gly Gly Thr Lys Leu Glu Ile Lys Arg Ala Ala Ala Pro
                645                 650                 655

Thr Thr Thr Pro Ala Pro Arg Pro Pro Thr Pro Ala Pro Thr Ile Ala
            660                 665                 670

Ser Gln Pro Leu Ser Leu Arg Pro Glu Ala Cys Arg Pro Ala Ala Gly
        675                 680                 685

Gly Ala Val His Thr Arg Gly Leu Asp Phe Ala Cys Asp Ile Tyr Ile
    690                 695                 700

Trp Ala Pro Leu Ala Gly Thr Cys Gly Val Leu Leu Leu Ser Leu Val
705                 710                 715                 720

Ile Thr Leu Tyr Cys Asn Lys Arg Gly Arg Lys Lys Leu Leu Tyr Ile
                725                 730                 735

Phe Lys Gln Pro Phe Met Arg Pro Val Gln Thr Thr Gln Glu Glu Asp
            740                 745                 750

Gly Cys Ser Cys Arg Phe Pro Glu Glu Glu Glu Gly Gly Cys Glu Leu
        755                 760                 765
```

```
Arg Val Lys Phe Ser Arg Ser Ala Asp Ala Pro Ala Tyr Gln Gln Gly
    770                 775                 780

Gln Asn Gln Leu Tyr Asn Glu Leu Asn Leu Gly Arg Arg Glu Glu Tyr
785                 790                 795                 800

Asp Val Leu Asp Lys Arg Arg Gly Arg Asp Pro Glu Met Gly Gly Lys
                805                 810                 815

Pro Arg Arg Lys Asn Pro Gln Glu Gly Leu Tyr Asn Glu Leu Gln Lys
            820                 825                 830

Asp Lys Met Ala Glu Ala Tyr Ser Glu Ile Gly Met Lys Gly Glu Arg
        835                 840                 845

Arg Arg Gly Lys Gly His Asp Gly Leu Tyr Gln Gly Leu Ser Thr Ala
    850                 855                 860

Thr Lys Asp Thr Tyr Asp Ala Leu His Met Gln Ala Leu Pro Pro Arg
865                 870                 875                 880


<210> SEQ ID NO 51
<211> LENGTH: 887
<212> TYPE: PRT
<213> ORGANISM: Homo sapiens

<400> SEQUENCE: 51

Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg Ala Ala Ala Pro Thr Thr Thr Pro Ala
```

```
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Asn Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Gln Pro Leu Glu Gly
                485                 490                 495

Ser Gly Ala Thr Asn Phe Ser Leu Leu Lys Gln Ala Gly Asp Val Glu
            500                 505                 510

Glu Asn Pro Gly Pro Thr Pro Val Ser Glu Lys Gln Leu Ala Glu Val
        515                 520                 525

Val Ala Asn Thr Ile Thr Pro Leu Met Ala Ala Gln Ser Val Pro Gly
    530                 535                 540

Met Ala Val Ala Val Ile Tyr Gln Gly Lys Pro His Tyr Tyr Thr Phe
545                 550                 555                 560

Gly Lys Ala Asp Ile Ala Ala Asn Lys Pro Val Thr Pro Gln Thr Leu
                565                 570                 575

Phe Glu Leu Gly Ser Ile Ser Lys Thr Phe Thr Gly Val Leu Gly Gly
            580                 585                 590

Asp Ala Ile Ala Arg Gly Glu Ile Ser Leu Asp Asp Ala Val Thr Arg
        595                 600                 605

Tyr Trp Pro Gln Leu Thr Gly Lys Gln Trp Gln Gly Ile Arg Met Leu
    610                 615                 620

Asp Leu Ala Thr Tyr Thr Ala Gly Gly Leu Pro Leu Gln Val Pro Asp
625                 630                 635                 640

Glu Val Thr Asp Asn Ala Ser Leu Leu Arg Phe Tyr Gln Asn Trp Gln
                645                 650                 655

Pro Gln Trp Lys Pro Gly Thr Thr Arg Leu Tyr Ala Asn Ala Ser Ile
            660                 665                 670

Gly Leu Phe Gly Ala Leu Ala Val Lys Pro Ser Gly Met Pro Tyr Glu
        675                 680                 685
```

```
Gln Ala Met Thr Thr Arg Val Leu Lys Pro Leu Lys Leu Asp His Thr
    690                 695                 700

Trp Ile Asn Val Pro Lys Ala Glu Glu Ala His Tyr Ala Trp Gly Tyr
705                 710                 715                 720

Arg Asp Gly Lys Ala Val Arg Val Ser Pro Gly Met Leu Asp Ala Gln
                725                 730                 735

Ala Tyr Gly Val Lys Thr Asn Val Gln Asp Met Ala Asn Trp Val Met
            740                 745                 750

Ala Asn Met Ala Pro Glu Asn Val Ala Asp Ala Ser Leu Lys Gln Gly
        755                 760                 765

Ile Ala Leu Ala Gln Ser Arg Tyr Trp Arg Ile Gly Ser Met Tyr Gln
    770                 775                 780

Gly Leu Gly Trp Glu Met Leu Asn Trp Pro Val Glu Ala Asn Thr Val
785                 790                 795                 800

Val Glu Gly Ser Asp Ser Lys Val Ala Leu Ala Pro Leu Pro Val Ala
                805                 810                 815

Glu Val Asn Pro Pro Ala Pro Pro Val Lys Ala Ser Trp Val His Lys
            820                 825                 830

Thr Gly Ser Thr Gly Gly Phe Gly Ala Tyr Val Ala Phe Ile Pro Glu
        835                 840                 845

Lys Gln Ile Gly Ile Val Met Leu Ala Asn Thr Ser Tyr Pro Asn Pro
    850                 855                 860

Ala Arg Val Glu Ala Ala Tyr His Ile Leu Glu Ala Leu Gln Tyr Pro
865                 870                 875                 880

Tyr Asp Val Pro Asp Tyr Ala
                885
```

<210> SEQ ID NO 52
<211> LENGTH: 263
<212> TYPE: PRT
<213> ORGANISM: Homo sapiens

<400> SEQUENCE: 52

```
Met Ala Leu Pro Val Thr Ala Leu Leu Leu Pro Leu Ala Leu Leu Leu
1               5                   10                  15

His Ala Glu Val Lys Leu Gln Gln Ser Gly Ala Glu Leu Val Arg Pro
            20                  25                  30

Gly Ser Ser Val Lys Ile Ser Cys Lys Ala Ser Gly Tyr Ala Phe Ser
        35                  40                  45

Ser Tyr Trp Met Asn Trp Val Lys Gln Arg Pro Gly Gln Gly Leu Glu
    50                  55                  60

Trp Ile Gly Gln Ile Tyr Pro Gly Asp Gly Asp Thr Asn Tyr Asn Gly
65                  70                  75                  80

Lys Phe Lys Gly Gln Ala Thr Leu Thr Ala Asp Lys Ser Ser Ser Thr
                85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
```

```
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg
            260


<210> SEQ ID NO 53
<211> LENGTH: 789
<212> TYPE: DNA
<213> ORGANISM: Homo sapiens

<400> SEQUENCE: 53

atggctctcc cagtgactgc cctactgctt cccctagcgc ttctcctgca tgcagaggtg     60

aagctgcagc agtctggggc tgagctggtg aggcctgggt cctcagtgaa gatttcctgc    120

aaggcttctg gctatgcatt cagtagctac tggatgaact gggtgaagca gaggcctgga    180

cagggtcttg agtggattgg acagatttat cctggagatg gtgatactaa ctacaatgga    240

aagttcaagg gtcaagccac actgactgca gacaaatcct ccagcacagc ctacatgcag    300

ctcagcggcc taacatctga ggactctgcg gtctatttct gtgcaagaaa gaccattagt    360

tcggtagtag atttctactt tgactactgg ggccaaggga ccacggtcac cgtctcctca    420

ggtggaggtg gatcaggtgg aggtggatct ggtggaggtg gatctgacat tgagctcacc    480

cagtctccaa aattcatgtc cacatcagta ggagacaggg tcagcgtcac ctgcaaggcc    540

agtcagaatg tgggtactaa tgtagcctgg tatcaacaga aaccaggaca atctcctaaa    600

ccactgattt actcggcaac ctaccggaac agtggagtcc ctgatcgctt cacaggcagt    660

ggatctggga cagatttcac tctcaccatc actaacgtgc agtctaaaga cttggcagac    720

tatttctgtc aacaatataa caggtatccg tacacgtccg gagggggggac caagctggag    780

atcaaacgg                                                            789
```